(12) United States Patent
Calvert et al.

(10) Patent No.: US 8,486,685 B2
(45) Date of Patent: *Jul. 16, 2013

(54) CELLULAR PERMISSIVITY FACTOR FOR VIRUSES AND USES THEREOF

(75) Inventors: Jay Gregory Calvert, Otsego, MI (US); Shelly Shields, Plainwell, MI (US); David E Slade, Portage, MI (US); Siao-Kun Welch, Kalamazoo, MI (US)

(73) Assignee: Zoetis P&U LLC, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/248,537

(22) Filed: Sep. 29, 2011

(65) Prior Publication Data
US 2012/0015425 A1    Jan. 19, 2012

Related U.S. Application Data

(63) Continuation of application No. 12/775,283, filed on May 6, 2010, now Pat. No. 8,058,050, which is a continuation of application No. 11/113,751, filed on Apr. 25, 2005, now Pat. No. 7,754,464.

(60) Provisional application No. 60/565,214, filed on Apr. 23, 2004, provisional application No. 60/634,736, filed on Dec. 9, 2004.

(51) Int. Cl.
*C12N 7/02* (2006.01)
*A61K 39/12* (2006.01)

(52) U.S. Cl.
USPC ..... 435/239; 435/69.1; 435/235.1; 424/204.1

(58) Field of Classification Search
None
See application file for complete search history.

(56) References Cited

U.S. PATENT DOCUMENTS

| | | | | |
|---|---|---|---|---|
| 4,366,241 | A | 12/1982 | Tom et al. | 435/7 |
| 4,376,110 | A | 3/1983 | David et al. | 436/613 |
| 4,517,288 | A | 5/1985 | Giegel et al. | 435/7 |
| 4,837,168 | A | 6/1989 | deJaeger et al. | 436/533 |
| 5,118,937 | A | 6/1992 | Hillenkamp et al. | 250/282 |
| 5,514,545 | A | 5/1996 | Eberwine | 435/6 |
| 5,591,645 | A | 1/1997 | Rosenstein | 436/514 |
| 5,622,871 | A | 4/1997 | May et al. | 436/514 |
| 5,698,203 | A | 12/1997 | Visser et al. | 424/218.1 |
| 5,719,060 | A | 2/1998 | Hutchens et al. | 436/174 |
| 5,840,563 | A | 11/1998 | Chladek et al. | 435/235.1 |
| 7,754,464 | B2* | 7/2010 | Calvert et al. | 435/235.1 |
| 8,058,050 | B2* | 11/2011 | Calvert et al. | 435/239 |
| 2003/0186236 | A1 | 10/2003 | Kapil et al. | 435/6 |

FOREIGN PATENT DOCUMENTS

| EP | A-0367566 | 6/1997 |
|---|---|---|
| WO | WO 91/09955 | 7/1991 |
| WO | WO 91/18982 | 12/1991 |
| WO | WO 92/20808 | 11/1992 |
| WO | WO 94/12650 | 6/1994 |
| WO | WO95/35505 | 12/1995 |
| WO | WO03/010200 | 2/2003 |

OTHER PUBLICATIONS

Calvert et al., J of Virology 2007, vol. 81, pp. 7371-7379.*
Asai, ed., Methods in Cell Biology vol. 37: Antibodies in Cell Biology,. Academic Press, Inc. New York (1993).
Ausubel et al., supra, [e.g., Chapter 11].
Ausubel et al., eds., Current Protocols in Molecular Biology, Section 10.11.8, John Wiley & Sons, New York , 1993.
Ausabel, et al. (Eds.), Protocols in Molecular Biology, John Wiley & Sons (1994), pp. 6.0.3 to 6.4.10.
Bolton and Hunter, Biochem. J. 133, 529 (1973).
Cole et al., p. 77-96 in Monoclonal Antibodies and Cancer Therapy, Alan R. Liss, Inc. (1985).
Cosman et al. *Mol. Immunol. 23*:935 (1986).
Cosman et al. *Nature 312*:768 (1984).
Creighton,T. E., Proteins-Structure and Molecular Properties, 2nd Ed., W. H. Freeman and Company, New York, 1993.
Dea,S., Gagnon,C.A., Mardassi,H., Pirzadeh,B., and Rogan,D. (2000). Arch. Virol. 145, 659-688.
Delputte,P.L.., Vanderheijden,N., Nauwynck,H.J., and Pensaert,M.B. (2002). J. Virol. 76, 4312-4320.
Duan,X., Nauwynck,H.J., and Pensaert,M.B. (1997a). Arch. Virol. 142, 2483-2497.
Duan,X., Nauwynck,H.J., and Pensaert,M.B. (1997b). Vet. Microbiol. 56, 9-19.
Duan,X.B., Nauwynck,H.J., Favoreel,H.W., and Pensaert,M.B. (1998). J. Virol. 72, 4520-4523.
Erlich, H. A. ed., PCR Technology, Stockton Press, New York, 1989; PCR Protocols: A Guide to Methods and Applications, M. A. Innis, David H. Gelfand, John J. Sninsky, and Thomas J. White, eds., Academic Press, Inc., New York, 1990.
Evan et al., Molecular and CellularBiology, 5:3610-3616 (1985).
Field et al., Mol. Cell. Biol., 8:2159-2165 (1988).
Graversaa,J.H., Madsen,M., and Moestrap,S.K. (2002). International Journal of Biochemistry & Cell Biology 34, 309-314.
Gronlund J. Vitved L. Lausen M. Skjodt K. Holmskov U. Journal of Immunology 165(11):6406-6415, 2000.
Harlow et al. (Eds), Antibodies A Laboratory Manual; Cold Spring Harbor Laboratory; Cold Spring Harbor, NY (1988), Chapter 6.
Harlow and Lane, supra [e.g., Chapter 14], 1988.
Henikoff and Henikoff (Proc. Nat. Acad. Sci. USA 89:10915-10919. 1992).
Hopp et al., BioTechnology, 6:1204-1210 (1988).
Kim,H.S., Kwang,J., Yoon,I.J., Joo,H.S., and Frey,M.L. (1993). Arch. Virol. 133, 477-483.
Kohler, G. and Milstein, C., Nature 256: 495-497 (1975).

(Continued)

*Primary Examiner* — Mary E Mosher
*Assistant Examiner* — Myron Hill
(74) *Attorney, Agent, or Firm* — Barbara L. Renda; E. Victor Donahue

(57) ABSTRACT

The present invention provides methods and compositions related to the generation of host cells permissive for virus growth, particularly Porcine Reproductive and Respiratory Syndrome (PRRS) virus.

9 Claims, 24 Drawing Sheets

OTHER PUBLICATIONS

Kozbor et al., Immunology Today 4: 72 (1983).
Kreutz,L.C. (1998). Virus Res. 53, 121-128.
Kreutz,L.C. and Ackermann,M.R. (1996). Virus Res. 42, 137-147.
Law, S.K., Micklem, K.J., Shaw, J.M., Zhang, X.P., Dong, Y., Willis, A.C. and Mason, D.Y. (1993) European Journal of Immunology 23 (9) 2320-2325).
Lutz-Freyermuth et al., Proc. Natl. Acad. Sci. USA, 87:6393-6397(1990).
Maddox et al., 1983, J. Exp. Med., 158:1211.
Martin et al., Science, 255:192-194 (1992).
Mengeling,W.L. and Lager,K.M. (2000). Veterinary Research 31, 61-69.
Meulenberg,J.J.M. (2000). PRRSV, the virus. Veterinary Research 31, 11-21.
Murtaugh,M.P., Xiao,Z.G., and Zuckermann,F. (2002). Viral Immunology 15, 533-547.
Morrison, Methods in Enzymology 32b, 103 (1974).
Nauwynck,H.J., Duan,X., Favoreel,H.W., Van Oostveldt,P., and Pensaert,M.B. (1999). J. Gen. Virol. 80, 297-305.
Nodelijk,G. (2002). Vet. Quart. 24, 95-100.
Okayama and Berg (*Mol. Cell. Biol.* 3:280 (1983).
Paborsky et al., Protein Engineering, 3(6):547-553(1990).
Philippidis,P., Mason,J.C., Evans,B.J., Nadra,I., Taylor,K.M., Haskard,D.O., and Landis,R.C. (2004). Circulation Research 94, 119-126.
Plagemann,P.G.W. (2003). Emerging Infectious Diseases 9, 903-908.
Rattan Et al., Ann NY Acad Sci (1992) 663:4842).
Ritter,M., Buechler,C, Langmann,T., and Schmitz,G. (1999). Biochemical & Biophysical Research Communications 260, 466-474.
Sambrook, et al., (Eds.), Molecular Cloning: A Laboratory Manual, Cold Spring Harbor Laboratory Press: Cold Spring Harbor, New York (1989), pp. 9.47 to 9.51.
Sanchez-Torres,C., Gomez-Puertas,P., Gomez-del-Moral,M., Alonso,F., Escribano,J.M., Ezquerra,A., and Dominguez,J. (2003). Arch. Virol. 148, 2307-2323.
Seifter et al., Meth Enzymol (1990) 182:626-646.
Shanmukhappa,K. and Kapil,S. (2001). Adv. Exp. Med. Biol. 494, 641-646.
Skinner et al.,J. Biol. Chem., 266:15163-15166 (1991).
Snijder,E.J. and Meulenberg,J.J.M. (2001). Arteriviruses. In Fields Virology, D.M.Knipe, P.M.Howley, D.E.Grifrm, M.A.Martin, R.A.Lamb, B.Roizman, and S.E.Straus, eds. (Philadelphia: Lippincott Williams & Wilkins), pp. 1205-1220.
Stites & Tar, eds. Basic and Clinical Immunology 7th Edition, (1991).
Syvanen et al., J. Biol. Chem. 284, 3762 (1973).
Tatusova TA and TL Madden, (1999) FEMS Microbiol Lett. 174:247-250.
Therrien,D., St Pierre,Y., and Dea,S. (2000). Arch. Virol. 145, 1099-1116.
Vanderheijden,N., Delputte,P.L., Favoreel,H.W., Vandekerckhove,J., Van Damme,J., van Woensel,P.A., and Nauwynck,H.J. (2003). J. Virol. 77, 8207-8215.
Weingartl,H.M., Sabara,M., Pasick,J., van Moorlehem,E., and Babiuk,L. (2002). J. Virol. Methods 104, 203-216.
Wissink,E.H.J., van Wijk,H.A.R., Pol,J.M.A., Godeke,G.J., van Rijn,P.A., Rottier,P.J.M., and Meulenberg,J.J.M. (2003). Arch. Virol. 148, 177-187.
Wold, F., Post-translational Protein Modifications: Perspectives and Prospects, pp. 1-12 in Postranslational Covalent Modification of Proteins, B. C. Johnson, Ed, Academic Press, New York, 1983.
AAH51281; Genbank Jun. 30, 2004.
AF274883; Genbank May 10, 2001.
AJ311716; Genbank Apr. 15, 2001.
BC051281; Genbank Jun. 30, 2004.
CAA80543; Genbank Apr. 18, 2005.
M96262; Genbank Nov. 8, 2000.
U87392; Genbank Nov. 17, 2000.
Z22968; Genbank Apr. 18, 2005.
Z22969; Genbank Apr. 18, 2005.
Bautista et al. Archives in Virology, 1999, vol. 144, pp. 117-134.
Lopez-Fuertes et al. Veterinary Research, 2000, vol. 31, pp. 42-43.
Frings et al. FEBS Letters, 2002, vol. 526, pp. 93-96.
Kristiansen et al. Nature, Jan. 2001, vol. 409, pp. 198-201.
Sanchez et al. The Journal of Immunology, 1999, vol. 162, pp. 5230-5237.
Seuberlich et al., Nucleocapsid Protein-Based Enzyme-Linked Immunosorbent Assay for Dection and Differentiation of Antibodies against European and North American Porcine Reproductive and Respiratory Syndrome Virus Clinical and Diagnostic Laboratory Immunology, 9(6): 1183-1191, 2002.

* cited by examiner

Figure 2A

```
                            1                                                               60
AJ311716(porcine)           .....MVLLEDSGSADFRRCSAHLSSFTFAVVAVLSACLVTSSLGGKDKELRLTGGENKC
Pfizer_susCD163v1           MDKLRMVLHENSGSAD............................................

61                                                              120
AJ311716(porcine)           SGRVEVKVQEEWGTVCNNGWDMDVVSVVCRQLGCPTAIKATGWANFSACSGRIWMDHVSC
Pfizer_susCD163v1           ............................................................

121                                                             180
AJ311716(porcine)           RGNESALWDCKHDGWGKHNCTHQQDAGVTCSDGSDLEMRLVNGGNRCLGRIEVKFQERWG
Pfizer_susCD163v1           ............................................................

181                                                             240
AJ311716(porcine)           TVCDDNFNINHASVVCKQLECGSAVSFSGSANFGEGSGPIWFDDLVCNGNESALWNCKHE
Pfizer_susCD163v1           ............................................................

241                                                             300
AJ311716(porcine)           GWGKHNCDHAEDAGVICLNGADLKLRVVDGLTECSGRLEVKFQGEWGTICDDGWDSDDAA
Pfizer_susCD163v1           ...........................LKLRVVDGVTECSGRLEVKFQGEWGTICDDGWDSDDAA 301                                                             360
AJ311716(porcine)           VACKQLGCPTAVTAIGRVNASECTGHIWLDSVSCHGHESALWCCRHHEWGKHYCNHNEDA
Pfizer_susCD163v1           VACKQLGCPTAVTAIGRVNASECTGHIWLDSVSCHGHESALWCCRHHEWGKHYCNHNEDA 361                                                             420
AJ311716(porcine)           GVTCSDGSDLELRLKGGGSHCAGTVEVEIQKLVGKVCDRSWGLKEADVVCRQLGCGSALK
Pfizer_susCD163v1           GVTCSDGSDLELRLKGGGSHCAGTVEVEIQKLVGKVCDRSWGLKEADVVCRQLGCGSALK 421                                                             480
AJ311716(porcine)           TSYQVYSKTKATNTWLFVSSCNGNETSLWDCKNMQWGGLSCDHYDEAKITCSAHRKPRLV
Pfizer_susCD163v1           TSYQVYSKTKATNTWLFVSSCNGNETSLWDCKNMQWGGLSCDHYDEAKITCSAHRKPRLV 481                                                             540
AJ311716(porcine)           GGDIPCSGRVEVQHGDTWGTVCDSDFSLEAASVLCRELQCGTVVSLLGGAHFGEGSGQIW
Pfizer_susCD163v1           GGDIPCSGRVEVQHGDTWGTVCDSDFSLEAASVLCRELQCGTVVSLLGGAHFGEGSGQIW
```

Figure 2B

```
                        541                                                          600
AJ311716(porcine)       AEEFQCEGHESHLSLCPVAPRPDGTCSHSRDVGVVCSRYTQIRLVNGKTPCEGRVELNIL
Pfizer_susCD163v1       AEEFQCEGHESHLSLCPVAPRPDGTCSHSRDVGVVCSRYTQIRLVNGKTPCEGRVELNIL 601                                                          660
AJ311716(porcine)       GSWGSLCNSHWDMEDAHVLCQQLKCGVALSIPGGAPFGKGSEQVWRHMFHCTGTEKHMGD
Pfizer_susCD163v1       GSWGSLCNSHWDMEDAHVLCQQLKCGVALSIPGGAPFGKGSEQVWRHMFHCTGTEKHMGD 661                                                          720
AJ311716(porcine)       CSVTALGASLCSSGQVASVICSGNQSQTLSPCNSSSSDPSSSIISESGVACIGSGQLRL
Pfizer_susCD163v1       CSVTALGASLCSSGQVASVICSGNQSQTLSPCNSSSSDPSSSIISENGVACIGSGQLRL 721                                                          780
AJ311716(porcine)       VDGGGRCAGRVEVYPGASWGTICDDSWDLNDAHVVCKQLSCGWAINATGSAHFGEGTGPI
Pfizer_susCD163v1       VDGGGRCAGRVEVYHEGSWGTICDDSWDLNDAHVVCKQLSCGWAINATGSAHFGEGTGPI
                        781                                                          840
AJ311716(porcine)       WLDEINCNGKESHIWQCHSHGWGRHNCRHKEDAGVICSEFMSLRLISENSRETCAGRLEV
Pfizer_susCD163v1       WLDEINCNGKESHIWQCHSHGWGRHNCRHKEDAGVICSEFMSLRLISENSRETCAGRLEV 841                                                          900
AJ311716(porcine)       FYNGAWGSVGRNSMSPATVGVVCRQLGCADRGDISPASSDKTVSRHMVVDNVQCPKGPDT
Pfizer_susCD163v1       FYNGAWGSVGKNSMSPATVGVVCRQLGCADRGDISPASSDKTVSRHMVVDNVQCPKGPDT 901                                                          960
AJ311716(porcine)       LWQCPSSPWKKRLASPSEETWITCANKIRLQEGNTNCSGRVEIWYGGSWGTVCDDSWDLE
Pfizer_susCD163v1       LWQCPSSPWKKRLASPSEETWITCANKIRLQEGNTNCSGRVEIWYGGSWGTVCDDSWDLE 961                                                          1020
AJ311716(porcine)       DAQVVCRQLGCGSALEAGKEPAFGQGTGPIWLNEVKCKGNEPSLWDCPARSWGHSDCGHK
Pfizer_susCD163v1       DAQVVCRQLGCGSALEAGKEAFGQGTGPIWLNEVKCKGNETSLWDCPARSWGHSDCGHK 1021                                                         1080
AJ311716(porcine)       EDAAVTCSEIAKSRESLHATGRSSFVALAIFGVILLACLIAFLIWTQKRRQRQRLSVFSG
Pfizer_susCD163v1       EDAAVTCSEIAKSRESLHATGRSSFVALAIFGVILLACLIAFLIWTQKRRQRQRLSVFSG 1081                                     1116
AJ311716(porcine)       GENSVHQIQYREMNSCLKADETDMLNPSGDHSEVQ.
Pfizer_susCD163v1       GENSVHQIQYREMNSCLKADETDMLNPSGDHSEVQ.
```

Figure 3A

```
Martinez/Needleman-Wunsch DNA Alignment
Minimum Match: 9; Gap Penalty: 1.10; Gap Length Penalty: 0.33

Genbank AJ311716 porcine CD163 cDNA          ------------------------------GTAATAATACAAGAAGATTTAAATGGGCATAAAACCTTGGAATGGACAAACTCAGA
Insert from plasmid pSport-susCD163d1        ATGGTGCTACTTGAAGACTCTGATCTGCACACTTTAGAAGATGTTCTGCCCATTTAAGTTCCTTCACTTTTGTGTAGTCGCTGTTCTCAGTGCCTGCT
                                             ATGGTGCTACAGAAAACTCTGGATCT--------------------------------------------------------------------

TGGTCACTAGTTCTCTTGGAGAAAAGACAAGGAGCTAACGGTGGTGAAAACAAGTGCTCTGAAGAGTGGAGGTGAAAGTGCAGGAGGAGTG

GGGAACTCTGTCTAATTAATGCCTGGACACATCCATCTGGTCTCTGTCTTCTTGTAGCCAGCCTGCGATGTCCAACTGCTATCAAAGCCACTGATCGCCTAAT

TTTAGTCAGGTTCTGGACGCATTTGGATGATCATGTTTCTGTCCAGGGAATGAATCTGATTTAGAGATGAGGCTGAGTCAGCTCTCTGGGACTGCAAACATGATGATGGGAAAGCATA

ACTGTACTCACCAACAGGATGCTGGAACAGTGTGTGATGATAACTTCAACATAAATCATGCTTCTCTGTGGTTTGTAAACAACTTGAGTCTGTC

AGTTTCTCTGGTTCAGCTAATTTTGGAGAAGGTTCTGGACCAATCTCGTTTGATGATCTTGTTTGCTTAAATGGAGCAGACCTGAAACTGAGAGTGATGAACTCAAAC
                                                                                                 GCAGACCTGAAACTGAGAGTGGTAGAGTCAC

ATGAAGGATGGGGAAGCACAATTGCGATCATGCTGGATGCTGAGGATGATGAGCAGACCTGAAACTGAGAGTGATGGCCATGTAAGCAA

TGAATGTTCAGGAAGATTGGAAGTGAAATTCCAAGGAGAATGGGGAACAATCTGTGATGATGCCTGGGATAGTGCTGGGATGCCGCTGTGGCATGTAAGCAA
TGAATGTTCAGGAAGATTGGAAGTGAAATTCCAAGGAGAATGGGGAACAATCTGTGATGATGCCTGGGATAGTGATGCCGCTGGCATGTAAGCAA

CTGGGATGTCCAACTGCTGTCACTGCCATTGTCCATTGCCATTGTCGAGTTAACGCGCCAGTGAGGGAACTGGACACATTGGCTTGACAGTGTTTCTTGCCATGGACACGAGT
CTGGGATGTCCAACTGCTGTCACTGCCATTGCCATTGTCGAGTTAACGCGCCAGTGAGGGAACTGGACACATTGGCTTGACAGTGTTTCTTGCCATGGACACGAGT

CTGCTCTCTGGCAGTGTAGACACCATGAATCGGGAAAGCATTATTGCAATCATAATGAAGATGCTGGTGTGACATGTTCTGATGATCAGATCTGAACT
CTGCTCTCTGGCAGTGTAGACACCATGAATCGGGAAAGCATTATTGCAATCATAATGAAGATGCTGGTGTGACATGTTCTGATGATCAGATCTGAACT
```

Figure 3B

```
GAGACTTAAAGGTGGAGGCAGCCACTCGTCGTCGGGACAGTGAGGTGGAAATTCAGAAACTGGTAGGAAAAGTGTGATAGAAGCTGGGACTGAAAGAA
GAGACTTAAAGGTGGAGGCAGCCACTCGTCGTCGGGACAGTGAGGTGGAAATTCAGAAACTGGTAGGAAAAGTGTGATAGAAGCTGGGACTGAAAGAA

GCTGATGTGGTTTGCAGGCAGCTGGGATGTGGATCTGCACTCAAAACATCATATCAAGTTTATTCCAAAACCAAGGCAACAACAACACATGCTGTTGTAA
GCTGATGTGGTTTGCAGGCAGCTGGGATGTGGATCTGCACTCAAAACATCATATCAAGTTTATTCCAAAACCAAGGCAACAACAACACATGCTGTTGTAA

GCAGCTCTAATGGAAATGAAACTTCTCTTTGGACTGCAAGAATTGGCAGTGGGGTGACTTAGTTGTGATCACTATGACGAAGCCAAAATTACCTGCTC
GCAGCTCTAATGGAAATGAAACTTCTCTTTGGACTGCAAGAATTGGCAGTGGGGTGACTTAGTTGTGATCACTATGACGAAGCCAAAATTACCTGCTC

AGCCCACAGGAAACCCAGGCTGGTTGAGGGGACATTCCCTCCTCTGGTCGTGTTGAAGTACAACATGGAGACACGTGGGGCACCGTCTGTGATTCTGAC
AGCCCACAGGAAACCCAGGCTGGTTGAGGGGACATTCCCTCCTCTGGTCGTGTTGAAGTACAACATGGAGACACGTGGGGCACCGTCTGTGATTCTGAC

TTCTCTCTGGAGGCGGCCAGCGTGCTGTGCAGGGAACTACAGTGCGGCCACTGTGGTTTCCCTCCTCGGGGAGCTCACTTTGGAGAAGAAGTGACAGA
TTCTCTCTGGAGGCGGCCAGCGTGCTGTGCAGGGAACTACAGTGCGGCCACTGTGGTTTCCCTCCTCGGGGAGCTCACTTTGGAGAAGAAGTGACAGA

TCTGGGCTGAAGAATTCCAGTGTGAGGGGCACAGAGTCCCACCTTTCACTCTGCCCAGTAGCACCCCGCCCTGACGGACATGTAGCCAAGCAGGACGT
TCTGGGCTGAAGAATTCCAGTGTGAGGGGCACAGAGTCCCACCTTTCACTCTGCCCAGTAGCACCCCGCCCTGACGGACATGTAGCCAAGCAGGACGT

CGGCGTAGTCTGCTCAAGATACACACAAAATCCGCTTGGTGAATGGCAAGACCCCATGTGAAGGAAGAGTGGAGCTCAACATTCTTGGGTCCTGGGGTCC
CGGCGTAGTCTGCTCAAGATACACACAAAATCCGCTTGGTGAATGGCAAGACCCCATGTGAAGGAAGAGTGGAGCTCAACATTCTTGGGTCCTGGGGTCC

CTCTGCAACTCTCACTGGACATGGAAGATGCCCATGTTTATGCCAGCAGCTTAAATGTGAGTTGCCCTTTCTATCCCGGAGGAGCACCTTTGGA
CTCTGCAACTCTCACTGGACATGGAAGATGCCCATGTTTATGCCAGCAGCTTAAATGTGAGTTGCCCTTTCTATCCCGGAGGAGCACCTTTGGA

AAGGAAGTGAGCAGGTCTGGAGGCACATGTTCACTGCACTGGACTGAGAAGCACATGGAGAATTGTTCCGTCACTGCTCTGGCGCATCACTCGTTC
AAGGAAGTGAGCAGGTCTGGAGGCACATGTTCACTGCACTGGACTGAGAAGCACATGGAGAATTGTTCCGTCACTGCTCTGGCGCATCACTCGTTC

TTCAGGCAAGTGCCCTCTGTAATCTGCTCAGGGAACCAGAGTCAGACACTATCCCCGCAATTCATCATCCTCCGACCCATCAAGCTCTATTATTCA
TTCAGGCAAGTGCCCTCTGTAATCTGCTCAGGGAACCAGAGTCAGACACTATCCCCGCAATTCATCATCCTCCGACCCATCAAGCTCTATTATTCA

GAAGAAAGTGGTGTTGCCTGCATAGGGAGTGGTCAACTTCGCCTGTCAATGAGGTGGTCGTTGTGCTGGAGAGTAGAGGTCTATCCTGGGCATCCT
GAAGAAAT̲GGTGTTGCCTGCATAGGGAGTGGTCAACTTCGCCTGTCAATGAGGTGGTCGTTGTGCTGGAGAGTAGAGGTCTATCA̲T̲AGGC̲TCCT

GGGGCACCACCATCTGTGATGACAGCTGGGACCTGGGACTGGAAACTGTGTGCAAACAGCTGAGCTGTGAAGGCCATTAATGCCACTGTTCTGCTCA
GGGGCACCACCATCTGTGATGACAGCTGGGACCTGGGACTGGAAACTGTGTGCAAACAGCTGAGCTGTGAAGGCCATTAATGCCACTGTTCTGCTCA

TTTTGGGAAGGAACACGGCCCATTTGGCTGATGCAGATAAACTGTAATGGAAAAGAATCTCATATTTGGCAATGCCACTGTTGGGCGCCCCAC
TTTTGGGAAGGAACACGGCCCATTTGGCTGATGAGATAAACTGTAATGGAAAAGAATCTCATATTTGGCAATGCCACTGTTGGGCGCCCCAC
```

Figure 3C

```
AATTGCAGGCATAAGGAGGATGCAGGAGTCATCTCCTCAGAGTTCATGTCTCTGAGACTGATCAGTGAAAACAGCAGAGAGACCTGTGCAGGCGCCTGG
AATTGCAGGCATAAGGAGGATGCAGGAGTCATCTCCTCAGAGTTCATGTCTCTGAGACTGATCAGTGAAAACAGCAGAGAGACCTGTGCAGGCGCCTGG

AAGTTTTTACAACCGGAGCTTGGGGCAGCGTTGGCAGGAATAGCATGTCTCCAGCCACCAGTGGGGTGGTATGCAGGCAGCTGGCCTGTGCAGACAGAGG
AAGTTTTTACAACCGGAGCTTGGGGCAGCGTTGGCAGGAATAGCATGTCTCCAGCCACCAGTGGGGTGGTATGCAGGCAGCTGGCCTGTGCAGACAGAGG

GGACATCAGCCCTGCATCTTCAGACAAGACAGTGTCCAGGCACATGTGGGTGGACAATGTTCAGTGTCCTAAAGGACCTGACACACTATGCCAGTGCCCC
GGACATCAGCCCTGCATCTTCAGACAAGACAGTGTCCAGGCACATGTGGGTGGACAATGTTCAGTGTCCTAAAGGACCTGACACCCTATGCCAGTGCCCA

TCATCTCCATGAAGAAGACTGGCCAGCCCCCTCAGAGAGGACATGGATCACATGTGCCAACAAAATAAGACTTCAAGAAGGAAACACTAATTGTTCTG
TCATCTCCATGAAGAAGACTGGCCAGCCCCCTCAGAGAGGACATGGATCACATGTGCCAACAAAATAAGACTTCAAGAAGGAAACACTAATTGTTCTG

GACCTGTGGAGATCTGTACGGACTCGGTGGGCCACGTTCCTGCCGAGCCACTGTGTCTGCACGACTCCTCCGGACCTTGAAGATCCTCAGCTGCTGTGCCCCACAGCTCGGCTGTGG
GACCTGTGGAGATCTGTACGGACTCGGTGGGCCACGTTCCTGCCGAGCCACTGTGTCTGCACGACTCCTCCGGACCTTGAAGATCCTCAGCTGCTGTGCCCCACAGCTCGGCTGTGG

CTCAGCTTTGGAGGCAGGAAAAGAGCCCGGCATTTGCCCAGGGACTGGGCCCATTGCCCAGGGACTGGGCCCATATGCCTCAATGAAGTGAAGTCCAAGGGAATGAACCCTCCTTGTGG
CTCAGCTTTGGAGGCAGGAAAAGAGCCCGGCATTTGCCCAGGGACTGGGCCCATTGCCCAGGGACTGGGCCCATATGCCTCAATGAAGTGAAGTCCAAGGGAATGAACCCTCCTTGTGG

GATTGTCTGCCAGATCCTGGGGCCCACAGTGACTGTGGACACAAGGAGATGCTCGTGACGTGCTCAGAAATTGCAAAGAGCCGAGAATCCCTACATG
GATTGTCTGCCAGATCCTGGGGCCCACAGTGACTGTGGACACAAGGAGATGCTCGTGACGTGCTCAGAAATTGCAAAGAGCCGAGAATCCCTACATG

CCACAGGTCGCTCATCTTTTGTTGCACTTGCACTTGCAATCTTTGGGGTCATTCTCTGTTGGCCCTGTCTCATCGCATTCCTCATTTGGACTCAGAAGGCGAAGACAGAG
CCACAGGTCGCTCATCTTTTGTTGCACTTGCACTTGCAATCTTTGGGGTCATTCTCTGTTGGCCCTGTCTCATCGCATTCCTCATTTGGACTCAGAAGGCGAAGACAGAG

GCAGCGGCTCTCAGTTTCTCAGGAGGAGAGAATTCTGTCCATCAAATTCAAATACCGGGAGATGAATTCTTGCCTGAAAGCAGATGAAACGGATATGCTA
GCAGCGGCTCTCAGTTTCTCAGGAGGAGAGAATTCTGTCCATCAAATTCAAATACCGGGAGATGAATTCTTGCCTGAAAGCAGATGAAACGGATATGCTA

AATCCCTCAGGAGACCACTCGAAGTACAATGAAGAATTACAATACAGTCCTCTGTCTCCTGGTATTCCAAAGACTGCTGTTGAATTTCTAAAATAGATT
AATCCCTCAGGAGACCACTCGAAGTACAATGAAGAATTACAATACAGTCCTCTGTCTCCTGGTATTCCAAAGACTGCTGTTGAATTTCTAAAATAGATT

TTGAATGAGCAAGAATCTGCCTCTTCACTGAACTTGTATGTAAGACTTTCAAGGCATTAAATAAAAAGATATTGCTGAAAAAAAAAAAAAAAAAAAAAA

GGTGAATGTGACTACTCAAGTTGTATGTAAGACTTTCAAGGCATTAAATAAAAAGATATTGCTGAAAAAAAAAAAAAAAAAAAAAA

AAAAAAAAAAA
```

Inhibition of PRRSV infection by anti-CD163 antibody

CELLULAR PERMISSIVITY FACTOR FOR VIRUSES AND USES THEREOF

CROSS REFERENCE TO RELATED APPLICATIONS

The present application is a continuation of U.S. application Ser. No. 12/775,283, field May 6, 2010, now U.S. Pat. 8,058,050, which is a continuation of U.S. application Ser. No. 11/113,751, filed Apr. 25, 2005, now U.S. Pat. 7,754,464, and claims benefit of U.S. Provisional Patent Application Ser. No. 60/565,214, filed Apr. 23, 2004, and 60/634,736, filed Dec. 9, 2004. The complete text and disclosure of the 12/775,283 parent application is incorporated by reference herein as if fully set forth.

FIELD OF THE INVENTION

The present invention provides methods and compositions related to the generation of host cells permissive for virus growth for viruses of the family Asfarviridae and Arteriviridae.

BACKGROUND OF THE INVENTION

Asfarviridae

Asfarviridae is a family of icosohedral enveloped viruses whose genome consists of a single molecule of linear double-stranded DNA of about 150000-190000 nucleotides long. The name of the family is derived from African Swine Fever and Releted Viruses. African Swine Fever Virus (ASFV) is the type species of the Asfivirus genus and is the sole member of the family Recently, porcine CD163 polypeptide has been surmised by implication to be the cellular receptor for African swine fever virus (ASFV) (Sanchez-Torres et al., 2003)

Arteriviridae

Viruses of the family of Arteriviridae includes equine arteritis virus (EAV), lactate dehydrogenase-elevating virus (LDV) and simian hemorrhagic fever virus (SHFV). The Arterivirus having the greatest economic importance is Porcine Reproductive and Respiratory Syndrome Virus (PRRSV).

PRRSV

Porcine Reproductive and Respiratory Syndrome (PRRS) is one of the most economically important diseases of swine. The syndrome appeared almost simultaneously in North America and in Western Europe in the late 1980s, and has since spread to become endemic in the major swine producing nations of Europe, Asia, and the Americas. The etiologic agent of PRRS is a virus that has been designated PRRS virus or PRRSV. For both European and North American PRRS, the disease is characterized by reproductive failure in sows and gilts (late term abortions, still births, and mummies), high mortality among nursery pigs, and respiratory disease in swine of all ages. The disease has been the subject of recent reviews (Mengeling and Lager, 2000; Murtaugh et al., 2002; Nodelijk, 2002; Plagemann, 2003).

In the pig, PRRSV infection is limited to a subset of cells of the monocyte/macrophage lineage. Fully differentiated porcine alveolar macrophage (PAM) cells are the primary target cells for viral replication (Duan et al., 1997a; Duan et al., 1997b). Immortalization of PAM cells is technically challenging, and when successful, has resulted in cell lines that are not permissive for PRRS virus growth (Weingartl et al., 2002). PRRS virions are specifically bound by macrophages and internalized in clathrin-coated pits by endocytosis. Release from endocytic vesicles requires acidic pH (Nauwynck et al., 1999). Initial binding of virions is mediated by interaction of the viral matrix protein with heparin sulfate glycosaminoglycans (Delputte et al., 2002). Internalization can be facilitated by a 210 or 220 kDa membrane glycoprotein, as incubation of PAM cells with monoclonal antibodies to this polypeptide blocks infection with PRRS virus (Duan et al., 1998; Wissink et al., 2003). The 210 kDa glycoprotein has recently been identified as sialoadhesin, a member of siglec family of sialic acid binding immunoglobulin-like lectins (Pensaert et al., 2003). Transfection of the non-permissive PK-15 (porcine kidney) cell line with porcine sialoadhesin conferred the ability to internalize PRRSV particles, but there remained an apparent block at the uncoating stage, as virions entered into cellular vesicles but did not undergo nucleocapsid disintegration and vesicle membrane fusion. Viral genes were not expressed, and the transfected PK-15 cells were not rendered permissive for the PRRS virus (Vanderheijden et al., 2003). To our knowledge, transfection with sialoadhesin has not been shown to be sufficient to convert any PRRSV non-permissive cell line to a PRRSV-permissive phenotype.

Apart from primary porcine cells of the monocyte/macrophage lineage, the only other cell type known to be permissive for the growth of PRRSV in cell culture is the immortalized monkey kidney cell line MA-104(Chladek et al., 1998) and derivatives such as MARC-145 (Kim et al., 1993) and CL-2621. It is not known why this one particular cell line is permissive, yet other mammalian cell lines are not. The PRRS virus binds specifically to a number of different cell types, but does not initiate infection (Kreutz, 1998; Therrien et al., 2000). In MARC-145 cells, the internalization of the virus by endocytosis and subsequent uncoating in low pH vesicles seems to mimic similar events in PAM cells (Kreutz and Ackermann, 1996). However, a number of monoclonal antibodies that bind to porcine sialoadhesin fail to detect a homologous protein on the surface of MARC-145 cells (Duan et al., 1998; Wissink et al., 2003), suggesting that MARC-145 cells may use a divergent member of the same protein family or a different receptor altogether.

Current PRRSV vaccines are propagated on simian cell lines, which is a potentially dangerous activity. The use of simian cell lines for vaccine production has the potential to introduce primate viruses of significance into swine lines intended for xenotransplant purposes. Because swine are being increasingly explored as a source of xenotransplanted organs for humans, the introduction of primate cell lines to swine populations may ultimately pose a risk to humans receiving xenotransplanted organs. Thus, it would be prudent to avoid the use of simian cell lines in swine vaccine preparations. It would be therefore desirable to identify or generate non-simian cells or cell lines capable of supporting PRRSV replication. Towards this goal, it is essential to identify the gene product(s) which may be responsible for conferring the permissivity for PRRSV replication as seen in certain simian cells lines as well as PAM cells. Once such gene products are identified, non-permissive cells might be rendered permissive by, for example, transfection of the essential gene into them, thereby affording a wider array of production lines for a vaccine.

One lab has reported that the tetraspanin protein CD151 from MARC-145 cells, when transfected into non-permissive BHK-21 cells, confers permissivity to the PRRS virus (Kapil and Shanmukhappa, 2003; Shanmukhappa and Kapil, 2001). This observation has yet to be confirmed by an independent lab.

We describe here an unrelated polypeptide, which when introduced into non-permissive cells, confers permissivity to the PRRS virus.

References Cited

Chladek, D. W., Harris, L. L., and Gorcyca, D. E. Method of growing and attenuating a viral agent associated with mystery swine disease. Boehringer Ingelheim Animal Health, Inc. 677,585 [U.S. Pat. No. 5,840,563], 1-24. Nov. 24, 1998. USA. Jul. 9, 1996. Ref Type: patent Dea, S., Gagnon, C. A., Mardassi, H., Pirzadeh, B., and Rogan, D. (2000). Current knowledge on the structural proteins of porcine reproductive and respiratory syndrome (PRRS) virus: comparison of the North American and European isolates [Review]. Arch. Virol. 145, 659-688.

Delputte, P. L., Vanderheijden, N., Nauwynck, H. J., and Pensaert, M. B. (2002). Involvement of the matrix protein in attachment of porcine reproductive and respiratory syndrome virus to a heparinlike receptor on porcine alveolar macrophages. J. Virol. 76, 4312-4320.

Duan, X., Nauwynck, H. J., and Pensaert, M. B. (1997a). Effects of origin and state of differentiation and activation of monocytes/macrophages on their susceptibility to porcine reproductive and respiratory syndrome virus (PRRSV). Arch. Virol. 142, 2483-2497.

Duan, X., Nauwynck, H. J., and Pensaert, M. B. (1997b). Virus quantification and identification of cellular targets in the lungs and lymphoid tissues of pigs at different time intervals after inoculation with porcine reproductive and respiratory syndrome virus (PRRSV). Vet. Microbiol. 56, 9-19.

Duan, X. B., Nauwynck, H. J., Favoreel, H. W., and Pensaert, M. B. (1998). Identification of a putative receptor for porcine reproductive and respiratory syndrome virus on porcine alveolar macrophages. J. Virol. 72, 4520-4523.

Graversen, J. H., Madsen, M., and Moestrup, S. K. (2002). CD163: a signal receptor scavenging haptoglobin-hemoglobin complexes from plasma. [Review][19 refs]. International Journal of Biochemistry & Cell Biology 34, 309-314.

Gronlund J. Vitved L. Lausen M. Skjodt K. Holmskov U. Cloning of a novel scavenger receptor cysteine-rich type I transmembrane molecule (M160) expressed by human macrophages. Journal of Immunology 165(11):6406-6415, 2000.

Kapil, S, and Shanmukhappa, K. Host susceptibility factor(s) for porcine reproductive and respiratory syndrome virus and uses in swine breeding, as a target for antiviral compounds, and development of a non-simian recombinant cell line for propagation of the virus. none. US 2003/0186236 A1, 1-45. Oct. 2, 2003. USA. Jan. 28, 2002. Ref Type: patent Kim, H. S., Kwang, J., Yoon, I. J., Joo, H. S., and Frey, M. L. (1993). Enhanced replication of porcine reproductive and respiratory syndrome (PRRS) virus in a homogenous subpopulation of MA-104 cell line. Arch. Virol. 133, 477-483.

Kreutz, L. C. (1998). Cellular membrane factors are the major determinants of porcine reproductive and respiratory syndrome virus tropism. Virus Res. 53, 121-128.

Kreutz, L. C. and Ackermann, M. R. (1996). Porcine reproductive and respiratory syndrome virus enters cells through a low pH-dependent endocytic pathway. Virus Res. 42, 137-147.

Mengeling, W. L. and Lager, K. M. (2000). A brief review of procedures and potential problems associated with the diagnosis of porcine reproductive and respiratory syndrome. Veterinary Research 31, 61-69.

Meulenberg, J. J. M. (2000). PRRSV, the virus. Veterinary Research 31, 11-21.

Murtaugh, M. P., Xiao, Z. G., and Zuckermann, F. (2002). Immunological responses of swine to porcine reproductive and respiratory syndrome virus infection [Review]. Viral Immunology 15, 533-547.

Nauwynck, H. J., Duan, X., Favoreel, H. W., Van Oostveldt, P., and Pensaert, M. B. (1999). Entry of porcine reproductive and respiratory syndrome virus into porcine alveolar macrophages via receptor-mediated endocytosis. J. Gen. Virol. 80, 297-305.

Nodelijk, G. (2002). Porcine Reproductive and Respiratory Syndrome (PRRS) with special reference to clinical aspects and diagnosis—A review [Review]. Vet. Quart. 24, 95-100.

Pensaert, M., Nauwynck, H., and Vanderheijden, N. Nucleic acid encoding polypeptide involved in cellular entrance of the PRRS virus. Akzo Nobel N.V. and Universiteit Gent. WO 03/010200 A2, 1-24. Feb. 6, 2003. Jul. 18, 2002. Ref Type: patent Philippidis, P., Mason, J. C., Evans, B. J., Nadra, I., Taylor, K. M., Haskard, D. O., and Landis, R. C. (2004). Hemoglobin scavenger receptor CD163 mediates interleukin-10 release and heme oxygenase-1 synthesis—Antiinflammatory monocyte-macrophage responses in vitro, in resolving skin blisters in vivo, and after cardiopulmonary bypass surgery. Circulation Research 94, 119-126.

Plagemann, P. G. W. (2003). Porcine reproductive and respiratory syndrome virus: Origin hypothesis. Emerging Infectious Diseases 9, 903-908.

Ritter, M., Buechler, C., Langmann, T., and Schmitz, G. (1999). Genomic organization and chromosomal localization of the human CD163 (M130) gene: a member of the scavenger receptor cysteine-rich superfamily. Biochemical & Biophysical Research Communications 260, 466-474.

Sanchez-Torres, C., Gomez-Puertas, P., Gomez-del-Moral, M., Alonso, F., Escribano, J. M., Ezquerra, A., and Dominguez, J. (2003). Expression of porcine CD163 on monocytes/macrophages correlates with permissiveness to African swine fever infection. Arch. Virol. 148, 2307-2323.

Shanmukhappa, K. and Kapil, S. (2001). Cloning and identification of MARC-145 cell proteins binding to 3'UTR and partial nucleoprotein gene of porcine reproductive and respiratory syndrome virus. Adv. Exp. Med. Biol. 494, 641-646.

Snijder, E. J. and Meulenberg, J. J. M. (2001). Arteriviruses. In Fields Virology, D. M. Knipe, P. M. Howley, D. E. Griffin, M. A. Martin, R. A. Lamb, B. Roizman, and S. E. Straus, eds. (Philadelphia: Lippincott Williams & Wilkins), pp. 1205-1220.

Therrien, D., St Pierre, Y., and Dea, S. (2000). Preliminary characterization of protein binding factor for porcine reproductive and respiratory syndrome virus on the surface of permissive and non-permissive cells. Arch. Virol. 145, 1099-1116.

Vanderheijden, N., Delputte, P. L., Favoreel, H. W., Vandekerckhove, J., Van Damme, J., van Woensel, P. A., and Nauwynck, H. J. (2003). Involvement of sialoadhesin in entry of porcine reproductive and respiratory syndrome virus into porcine alveolar macrophages. J. Virol. 77, 8207-8215.

Weingartl, H. M., Sabara, M., Pasick, J., van Moorlehem, E., and Babiuk, L. (2002). Continuous porcine cell lines developed from alveolar macrophages—Partial characterization and virus susceptibility. J. Virol. Methods 104, 203-216.

Wissink, E. H. J., van Wijk, H. A. R., Pol, J. M. A., Godeke, G. J., van Rijn, P. A., Rottier, P. J. M., and Meulenberg, J. J. M. (2003). Identification of porcine alveolar macrophage glycoproteins involved in infection of porcine respiratory and reproductive syndrome virus. Arch. Virol. 148, 177-187.

SUMMARY OF THE INVENTION

The invention includes a method of facilitating infection of one or more cells by a virus that is selected from the group consisting of Arteriviridae and Asfarviridae, which comprises the step of increasing expression of a CD163 polypeptide within said cell. In a preferred embodiment the CD163 is membrane bound. In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

Increased expression of a CD163 polypeptide may be accomplished by methods such as introduction of exogenous nucleic acids encoding CD163 polypeptides. Such methods include but are not limited to transfection, electroporation and fusion with a carrier of a polynucleotide comprising a polynucleotide encoding a CD163 polypeptide. Increased expression may also be accomplished by induction of expression of endogenous CD163 by chemical treatment.

The method may render previously non PRRSV-permissive cells to be PRRSV permissive. The method may render a cell that was previously PRRSV permissive to be more PRRSV permissive. The method also includes rendering one or more cells that previously did not express a CD163 polypeptide into cells that are induced to express a CD163 polypeptide. The method also includes rendering one or more cells that previously expressed a CD163 polypeptide to express a higher level of CD163 polypeptide.

The cells in a preferred embodiment are animal cells. They may be vertebrate or invertebrate cells. The cells may be mammalian. The cells or cell line may be an insect cell line. The cells may be BHK21 cells. The cells may be derived from porcine kidney cells. The cells or cell line may be derived from feline kidney cells. The cells or cell line may be but are not limited to BHK-21, NLST-1, NLFK-1, Vero, swine testicle, or rabbit lung cells. The cells or cell line may be derived from avian cells. The PRRSV may be of the European or North American genotype.

As noted above, increased expression of a CD163 polypeptide may be accomplished by methods which include but are not limited to: transfection, electroporation and fusion with a carrier of a polynucleotide comprising a polynucleotide encoding a CD163 polypeptide. In addition, viral vectors may be used to introduce a polynucleotide encoding a CD163 polypeptide. Any CD163 polypeptides are contemplated. Those containing a transmembrane region are preferred. Exemplary polynucleotide encoding CD163 polypeptides that may be used in the method are selected from the group consisting of the polynucleotides listed below.

One such polynucleotide comprises a polynucleotide encoding a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 2 or fragments thereof.

One such polynucleotide comprises a polynucleotide encoding a polypeptide differing from SEQ ID NO: 2 by no more than 20 conservative amino acid substitutions.

One such polynucleotide comprises a polynucleotide encoding a polypeptide differing from SEQ ID NO: 2 by no more than 10 conservative amino acid substitutions.

One such polynucleotide comprises a polynucleotide encoding a polypeptide comprising SEQ ID NO: 2.

One such polynucleotide comprises a polynucleotide with the sequence set forth in SEQ ID NO: 1.

One such polynucleotide comprises a polynucleotide encoding a polypeptide that has at least 70% identity to a polypeptide set forth in SEQ ID NO: 14 or fragments thereof.

One such polynucleotide comprises a polynucleotide encoding a polypeptide that has at least 90% identity to a polypeptide set forth in SEQ ID NO: 14 or fragments thereof.

One such polynucleotide comprises a polynucleotide encoding a polypeptide that has at least 99% identity to a polypeptide set forth in SEQ ID NO: 14 or fragments thereof.

One such polynucleotide comprises a polynucleotide encoding a polypeptide differing from SEQ ID NO: 14 by no more than 15 conservative amino acid substitutions.

One such polynucleotide comprises a polynucleotide encoding a polypeptide differing from SEQ ID NO: 14 by no more than 10 conservative amino acid substitutions.

One such polynucleotide comprises a polynucleotide encoding a polypeptide comprising SEQ ID NO: 14.

One such polynucleotide comprises a polynucleotide with the sequence set forth in SEQ ID NO: 13.

One such polynucleotide comprises a polynucleotide encoding a polypeptide that has at least 90% identity to a polypeptide set forth in SEQ ID NO: 19 or fragments thereof.

One such polynucleotide comprises a polynucleotide encoding a polypeptide differing from SEQ ID NO: 19 by no more than 2 conservative amino acid substitutions.

One such polynucleotide comprises a polynucleotide encoding a polypeptide comprising SEQ ID NO: 19.

One such polynucleotide comprises a polynucleotide with the sequence set forth in SEQ ID NO: 18.

One such polynucleotide comprises a polynucleotide encoding a polypeptide differing from SEQ ID NO: 24 by no more than 2 conservative amino acid substitutions.

One such polynucleotide comprises a polynucleotide encoding a polypeptide comprising SEQ ID NO: 24.

One such polynucleotide comprises a polynucleotide with the sequence set forth in SEQ ID NO: 23.

One such polynucleotide comprises a polynucleotide encoding a polypeptide having at least 96%, 97%, 98%, or 99% identity to a polypeptide set forth in SEQ ID NO: 27 or fragments thereof.

One such polynucleotide comprises a polynucleotide encoding a polypeptide differing from SEQ ID NO: 27 by no more than 20 conservative amino acid substitutions.

One such polynucleotide comprises a polynucleotide encoding a polypeptide differing from SEQ ID NO: 27 by no more than 10 conservative amino acid substitutions.

One such polynucleotide comprises a polynucleotide encoding a polypeptide comprising SEQ ID NO: 27.

One such polynucleotide comprises a polynucleotide with the sequence set forth in SEQ ID NO: 26.

One such polynucleotide comprises a polynucleotide encoding a polypeptide that has at least 98% or 99% identity to a polypeptide set forth in SEQ ID NO: 32 or fragments thereof.

One such polynucleotide comprises a polynucleotide encoding a polypeptide differing from SEQ ID NO: 32 by no more than 15 conservative amino acid substitutions.

One such polynucleotide comprises a polynucleotide encoding a polypeptide differing from SEQ ID NO: 32 by no more than 10 conservative amino acid substitutions.

One such polynucleotide comprises a polynucleotide encoding a polypeptide comprising SEQ ID NO: 32.

One such polynucleotide comprises a polynucleotide with the sequence set forth in SEQ ID NO: 31.

One such polynucleotide comprises a polynucleotide encoding a polypeptide that has at least 95%, 96%, 97%, 98%, or 99% identity to a polypeptide set forth in SEQ ID NO: 34 or fragments thereof.

One such polynucleotide comprises a polynucleotide encoding a polypeptide differing from SEQ ID NO: 34 by no more than 15 conservative amino acid substitutions.

One such polynucleotide comprises a polynucleotide encoding a polypeptide differing from SEQ ID NO: 34 by no more than 10 conservative amino acid substitutions.

One such polynucleotide comprises a polynucleotide encoding a polypeptide comprising SEQ ID NO: 34.

One such polynucleotide comprises a polynucleotide with the sequence set forth in SEQ ID NO: 33.

One such polynucleotide comprises a polynucleotide encoding a polypeptide that has at least 95%, 96%, 97%, 98%, or 99% identity to a polypeptide set forth in SEQ ID NO: 36 or fragments thereof.

One such polynucleotide comprises a polynucleotide encoding a polypeptide differing from SEQ ID NO: 36 by no more than 15 conservative amino acid substitutions.

One such polynucleotide comprises a polynucleotide encoding a polypeptide differing from SEQ ID NO: 36 by no more than 10 conservative amino acid substitutions.

One such polynucleotide comprises a polynucleotide encoding a polypeptide comprising SEQ ID NO: 36.

One such polynucleotide comprises a polynucleotide with the sequence set forth in SEQ ID NO: 35.

One such polynucleotide comprises a polynucleotide encoding a polypeptide that has at least 90%, 91%, 92%, 93%, 94%, 95%, 96%, 97%, 98%, or 99% identity to a polypeptide set forth in SEQ ID NO: 42 or fragments thereof.

One such polynucleotide comprises a polynucleotide encoding a polypeptide differing from SEQ ID NO: 42 by no more than 15 conservative amino acid substitutions.

One such polynucleotide comprises a polynucleotide encoding a polypeptide differing from SEQ ID NO: 42 by no more than 10 conservative amino acid substitutions.

One such polynucleotide comprises a polynucleotide encoding a polypeptide comprising SEQ ID NO: 42.

One such polynucleotide comprises a polynucleotide with the sequence set forth in SEQ ID NO: 41.

One such polynucleotide comprises a polynucleotide encoding a polypeptide that has at least 90%, 91%, 92%, 93%, 94%, 95%, 96%, 97%, 98%, or 99% identity to a polypeptide set forth in SEQ ID NO: 44 or fragments thereof.

One such polynucleotide comprises a polynucleotide encoding a polypeptide differing from SEQ ID NO: 44 by no more than 15 conservative amino acid substitutions.

One such polynucleotide comprises a polynucleotide encoding a polypeptide differing from SEQ ID NO: 44 by no more than 10 conservative amino acid substitutions.

One such polynucleotide comprises a polynucleotide encoding a polypeptide comprising SEQ ID NO: 44.

One such polynucleotide comprises a polynucleotide with the sequence set forth in SEQ ID NO: 43.

One such polynucleotide comprises a polynucleotide encoding a polypeptide that has at least 95%, 96%, 97%, 98%, or 99% identity to a polypeptide set forth in SEQ ID NO: 46 or fragments thereof.

One such polynucleotide comprises a polynucleotide encoding a polypeptide differing from SEQ ID NO: 46 by no more than 15 conservative amino acid substitutions.

One such polynucleotide comprises a polynucleotide encoding a polypeptide differing from SEQ ID NO: 46 by no more than 10 conservative amino acid substitutions.

One such polynucleotide comprises a polynucleotide encoding a polypeptide comprising SEQ ID NO: 46.

One such polynucleotide comprises a polynucleotide with the sequence set forth in SEQ ID NO: 45.

One such polynucleotide comprises a polynucleotide encoding a polypeptide that has at least 90%, 91%, 92%, 93%, 94%, 95%, 96%, 97%, 98%, or 99% identity to a polypeptide set forth in SEQ ID NO: 48 or fragments thereof.

One such polynucleotide comprises a polynucleotide encoding a polypeptide differing from SEQ ID NO: 48 by no more than 15 conservative amino acid substitutions.

One such polynucleotide comprises a polynucleotide encoding a polypeptide differing from SEQ ID NO: 48 by no more than 10 conservative amino acid substitutions.

One such polynucleotide comprises a polynucleotide encoding a polypeptide comprising SEQ ID NO: 48.

One such polynucleotide comprises a polynucleotide with the sequence set forth in SEQ ID NO: 47.

The method of facilitating infection described above may further comprise the step of producing a culture of virus. The invention also comprises the step of isolating the virus from said culture.

The invention further comprises the culture isolated by the method described above.

The invention further comprises the virus isolated by the method described above.

Any of the methods described above may further comprise the step of producing a PRRSV or other viral vaccine. The vaccine may comprise killed or live attenuated virus. The invention further comprises the vaccines produced by said method.

The invention also comprises a cell or cell line wherein the ability of one or more cells to be infected by a virus selected from the group consisting of Arteriviridae and Asfarviridae has been modified by increasing expression of a CD163 polypeptide within said cells. In another embodiment the virus is PRRSV. In another embodiment said virus is equine arteritis virus (EAV). In yet another embodiment said virus is African Swine Fever virus (ASFV).

In a preferred embodiment the CD163 polypeptide comprises a transmembrane region. In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

The cell or cell line of the invention may have been previously PRRSV non-permissive and is rendered PRRSV permissive by directing increased expression of a CD163 polypeptide within said cell or cell line. The cell or cell line of the invention may have been previously PRRSV permissive and is rendered to be more PRRSV permissive by directing increased expression of a CD163 polypeptide within said cell or cell line.

The cell or cell line of the invention includes cells or cell lines that did not express a CD163 polypeptide and is induced to express a CD163 polypeptide. The cell or cell line of the invention includes cells or cell lines that previously expressed a CD163 polypeptide and is induced to express a higher level of CD163 polypeptide.

The cells in a preferred embodiment are animal cells. They may be vertebrate or invertebrate cells. The cells may be mammalian. The cell or cell line may be an insect cell or cell line. The cells may be BHK21 cells. The cells may be derived from porcine kidney cells. The cell or cell line may be derived from feline kidney cells. The cells may be, but are not limited to, BHK-21, NLST-1, NLFK-1, Vero, swine testicle (ST), or rabbit lung (RL) cells. The PRRSV may be North American or European.

The invention includes a method for measuring the propensity of a test cell or cell line to allow infection by a virus selected from the group consisting of Arteriviridae and Asfarviridae comprising:
a) providing a sample containing nucleic acids from the test cell or cell line;
b) determining the amount of polynucleotide encoding a CD163 polypeptide or its complement in said sample;
wherein an increased amount of polynucleotide encoding a CD163 polypeptide relative to a control sample derived from a control cell or cell line known not to support the growth of said virus indicates a propensity of the test cell or cell line to support the replication of said virus.

In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

The amount of polynucleotide encoding a CD163 polypeptide may be determined by hybridization.

The amount of polynucleotide encoding a CD163 polypeptide may be determined by PCR.

The invention also includes a method for measuring the propensity of a test cell or cell line to allow infection by a virus selected from the group consisting of Arteriviridae and Asfarviridae comprising:
(a) providing a sample containing polypeptides from the test cell or cell line;
(b) determining the amount of CD163 polypeptide in said sample;
wherein an increased amount of a CD163 polypeptide relative to a control sample derived from a control cell or cell line known not to support the growth of said virus indicates a propensity of the test cell or cell line to support the replication of said virus.

In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

In one embodiment the determining is accomplished by contacting a CD163 polypeptide with an antibody specific for the CD163 polypeptide, under conditions wherein the antibody binds the CD163 polypeptide.

The invention includes a method for measuring the propensity of a first pig to become infected by a virus selected from the group consisting of Arteriviridae and Asfarviridae comprising:
a) providing a sample containing nucleic acids from the pig to be tested;
b) determining the amount of polynucleotide encoding a CD163 polypeptide or its complement in said sample;
wherein an increased amount of polynucleotide encoding a CD163 polypeptide relative to the amount of polynucleotide encoding a CD163 polypeptide in a sample from a second pig indicates a greater propensity of the first pig to be infected by said virus.

In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

In one embodiment the determining is accomplished by hybridization. In another embodiment the determining is accomplished by PCR.

The invention also includes a method for measuring the propensity of a first pig to become infected by a virus selected from the group consisting of Arteriviridae and Asfarviridae comprising:
(a) providing a sample containing polypeptides from pig to be tested;
(b) determining the amount of CD163 polypeptide in said sample;
wherein an increased amount of a CD163 polypeptide relative to the amount of CD163 polypeptide in a sample from a second pig indicates a greater propensity of the first pig to be infected by said virus.

In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

In one embodiment the determining is accomplished by contacting a CD163 polypeptide with an antibody specific for the CD163 polypeptide, under conditions wherein the antibody binds the CD163 polypeptide.

The invention also includes an isolated polypeptide wherein the polypeptide is selected from the group consisting of the polypeptides described below.

Therefore the invention also includes an isolated polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 2 or fragments thereof.

One such polypeptide is a polypeptide differing from SEQ ID NO: 2 by no more than 20 conservative amino acid substitutions.

One such polypeptide is a polypeptide differing from SEQ ID NO: 2 by no more than 10 conservative amino acid substitutions.

One such polypeptide comprises SEQ ID NO: 2.

The invention also includes an isolated polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a polypeptide set forth in SEQ ID NO: 14 or fragments thereof.

One such polypeptide is a polypeptide differing from SEQ ID NO: 14 by no more than 15 conservative amino acid substitutions.

One such polypeptide is a polypeptide differing from SEQ ID NO: 14 by no more than 10 conservative amino acid substitutions.

One such polypeptide comprises SEQ ID NO: 14.

The invention also includes an isolated polypeptide having at least 90%, 91%, 92%, 93%, 94%, 95%, 96%, 97%, 98%, or 99% identity to a polypeptide set forth in SEQ ID NO: 19 or fragments thereof.

The invention also includes an isolated polypeptide differing from SEQ ID NO: 19 by no more than 2 conservative amino acid substitutions.

One such polypeptide comprises SEQ ID NO: 19.

The invention also includes an isolated polypeptide having at least 90%, 91%, 92%, 93%, 94%, 95%, 96%, 97%, 98%, or 99% identity to a polypeptide set forth in SEQ ID NO: 24 or fragments thereof.

The invention also includes an isolated polypeptide differing from SEQ ID NO: 24 by no more than 2 conservative amino acid substitutions.

One such polypeptide comprises SEQ ID NO: 24.

The invention also includes an isolated polypeptide having at least 96%, 97%, 98%, or 99% identity to a polypeptide set forth in SEQ ID NO: 27.

One such polypeptide is a polypeptide differing from SEQ ID NO: 27 by no more than 20 conservative amino acid substitutions.

One such polypeptide is a polypeptide differing from SEQ ID NO: 27 by no more than 10 conservative amino acid substitutions.

One such polypeptide is a polypeptide comprising SEQ ID NO: 27.

The invention also includes an isolated polypeptide having at least 90%, 91%, 92%, 93%, 94%, 95%, 96%, 97%, 98% or 99% identity to a polypeptide set forth in SEQ ID NO: 32 or fragments thereof.

One such polypeptide is a polypeptide differing from SEQ ID NO: 32 by no more than 15 conservative amino acid substitutions.

One such polypeptide is a polypeptide differing from SEQ ID NO: 32 by no more than 10 conservative amino acid substitutions.

One such polypeptide is a polypeptide comprising SEQ ID NO: 32.

The invention also includes an isolated polypeptide having at least 95%, 96%, 97%, 98%, or 99% identity to a polypeptide set forth in SEQ ID NO: 34 or fragments thereof.

One such polypeptide is a polypeptide differing from SEQ ID NO: 34 by no more than 15 conservative amino acid substitutions.

One such polypeptide is a polypeptide differing from SEQ ID NO: 34 by no more than 10 conservative amino acid substitutions.

One such polypeptide is a polypeptide comprising SEQ ID NO: 34.

The invention also includes an isolated polypeptide having at least 95%, 96%, 97%, 98%, or 99% identity to a polypeptide set forth in SEQ ID NO: 36 or fragments thereof.

One such polypeptide is a polypeptide differing from SEQ ID NO: 36 by no more than 15 conservative amino acid substitutions.

One such polypeptide is a polypeptide differing from SEQ ID NO: 36 by no more than 10 conservative amino acid substitutions.

One such polypeptide is a polypeptide comprising SEQ ID NO: 36.

The invention also includes an isolated polypeptide having at least 95%, 96%, 97%, 98%, or 99% identity to a polypeptide set forth in SEQ ID NO: 38 or fragments thereof.

One such polypeptide is a polypeptide differing from SEQ ID NO: 38 by no more than 15 conservative amino acid substitutions.

One such polypeptide is a polypeptide differing from SEQ ID NO: 38 by no more than 10 conservative amino acid substitutions.

One such polypeptide is a polypeptide comprising SEQ ID NO: 38.

The invention also includes an isolated polypeptide having at least 95%, 96%, 97%, 98%, or 99% identity to a polypeptide set forth in SEQ ID NO: 40 or fragments thereof.

One such polypeptide is a polypeptide differing from SEQ ID NO: 40 by no more than 15 conservative amino acid substitutions.

One such polypeptide is a polypeptide differing from SEQ ID NO: 40 by no more than 10 conservative amino acid substitutions.

One such polypeptide is a polypeptide comprising SEQ ID NO: 40.

The invention also includes an isolated polypeptide having at 90%, 91%, 92%, 93%, 94%, 95%, 96%, 97%, 98%, or 99% identity to a polypeptide set forth in SEQ ID NO: 42 or fragments thereof.

One such polypeptide is a polypeptide differing from SEQ ID NO: 42 by no more than 15 conservative amino acid substitutions.

One such polypeptide is a polypeptide differing from SEQ ID NO: 42 by no more than 10 conservative amino acid substitutions.

One such polypeptide is a polypeptide comprising SEQ ID NO: 42.

The invention also includes an isolated polypeptide having at least 90%, 91%, 92%, 93%, 94%, 95%, 96%, 97%, 98%, or 99% identity to a polypeptide set forth in SEQ ID NO: 44 or fragments thereof.

One such polypeptide is a polypeptide differing from SEQ ID NO: 44 by no more than 15 conservative amino acid substitutions.

One such polypeptide is a polypeptide differing from SEQ ID NO: 44 by no more than 10 conservative amino acid substitutions.

One such polypeptide is a polypeptide comprising SEQ ID NO: 44.

The invention also includes an isolated polypeptide having at least 90%, 91%, 92%, 93%, 94%, 95%, 96%, 97%, 98%, or 99% identity to a polypeptide set forth in SEQ ID NO: 46 or fragments thereof.

One such polypeptide is a polypeptide differing from SEQ ID NO: 46 by no more than 15 conservative amino acid substitutions.

One such polypeptide is a polypeptide differing from SEQ ID NO: 46 by no more than 10 conservative amino acid substitutions.

One such polypeptide is a polypeptide comprising SEQ ID NO: 46.

Therefore the invention also includes an isolated polypeptide having at least 90%, 91%, 92%, 93%, 94%, 95%, 96%, 97%, 98%, or 99% identity to a polypeptide set forth in SEQ ID NO: 48 or fragments thereof.

One such polypeptide is a polypeptide differing from SEQ ID NO: 48 by no more than 15 conservative amino acid substitutions.

One such polypeptide is a polypeptide differing from SEQ ID NO: 48 by no more than 10 conservative amino acid substitutions.

One such polypeptide is a polypeptide comprising SEQ ID NO: 48.

The invention also includes an isolated CD163 polynucleotide wherein said polynucleotide is selected from the group consisting of the polynucleotides enumerated below.

Therefore the invention also includes an isolated polynucleotide comprising:

(a) a polynucleotide sequence set forth in SEQ ID NOs: 1 or 5;
(b) a polynucleotide that encodes a polypeptide that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity and/or similarity to a polypeptide set forth in SEQ ID NO: 2 or fragments thereof;
(c) a polynucleotide encoding a polypeptide of SEQ ID NO: 2;
(d) a polynucleotide which is the complement of any of (a), (b), or (c).

Therefore the invention also includes an isolated polynucleotide comprising:
(a) a polynucleotide sequence set forth in SEQ ID NOs: 12 or 13;
(b) a polynucleotide that encodes a polypeptide that has at least 99% identity and/or similarity to a polypeptide set forth in SEQ ID NO: 14 or fragments thereof;
(c) a polynucleotide encoding a polypeptide of SEQ ID NO: 14;
(d) a polynucleotide that is the complement of any of (a), (b), or (c).

Therefore the invention also includes an isolated polynucleotide comprising:
(a) a polynucleotide sequence set forth in SEQ ID NOs: 17 or 18;
(b) a polynucleotide encoding a polypeptide of SEQ ID NO: 19 or fragments thereof;
(c) a polynucleotide which is the complement of (a) or (b).

Therefore the invention also includes an isolated polynucleotide comprising:
(a) a polynucleotide sequence set forth in SEQ ID NOs: 22 or 23;
(b) a polynucleotide that encodes a polypeptide that has at least 99%, 99.9% identity to a polypeptide set forth in SEQ ID NO: 24 or fragments thereof;
(c) a polynucleotide encoding a polypeptide of SEQ ID NO: 24;
(d) a polynucleotide which is the complement of any of (a), (b), or (c).

Therefore the invention also includes an isolated polynucleotide comprising:
(a) a polynucleotide sequence set forth in SEQ ID NOs: 25 or 26;
(b) a polynucleotide that encodes a polypeptide that has at least 96%, 97%, 98%, or 99% identity and/or similarity to a polypeptide set forth in SEQ ID NO: 27 or fragments thereof;
(c) a polynucleotide encoding a polypeptide of SEQ ID NO: 27;
(d) a polynucleotide which is the complement of any of (a), (b), or (c).

Therefore the invention also includes an isolated polynucleotide comprising:
(a) polynucleotide sequence set forth in SEQ ID NOs: 30 or 31;
(b) a polynucleotide that encodes a polypeptide that has at least 96%, 96.2%, 97%, 98% or 99% identity and/or similarity to a polypeptide set forth in SEQ ID NO: 32 or fragments thereof;
(c) a polynucleotide encoding a polypeptide of SEQ ID NO: 32;
(d) a polynucleotide which is the complement of any of (a), (b), or (c).

Therefore the invention also includes an isolated polynucleotide comprising:
(a) polynucleotide sequence set forth in SEQ ID NO: 33;
(b) a polynucleotide that encodes a polypeptide that has at least 95%, 96%, 97%, 98%, or 99% identity and/or similarity to a polypeptide set forth in SEQ ID NO: 34 or fragments thereof;
(c) a polynucleotide encoding a polypeptide of SEQ ID NO: 34;
(d) a polynucleotide which is the complement of any of (a), (b), or (c).

Therefore the invention also includes an isolated polynucleotide comprising:
(a) polynucleotide sequence set forth in SEQ ID NO: 35;
(b) a polynucleotide that encodes a polypeptide that has at least 95%, 96%, 97%, 98%, or 99% identity and/or similarity to a polypeptide set forth in SEQ ID NO: 36 or fragments thereof;
(c) a polynucleotide encoding a polypeptide of SEQ ID NO: 36;
(d) a polynucleotide which is the complement of any of (a), (b), or (c).

Therefore the invention also includes an isolated polynucleotide comprising:
(a) polynucleotide sequence set forth in SEQ ID NO: 37;
(b) a polynucleotide that encodes a polypeptide that has at least 95%, 96%, 97%, 98%, or 99% identity and/or similarity to a polypeptide set forth in SEQ ID NO: 38 or fragments thereof;
(c) a polynucleotide encoding a polypeptide of SEQ ID NO: 38;
(d) a polynucleotide that is the complement of any of (a), (b), or (c).

Therefore the invention also includes an isolated polynucleotide comprising:
(a) polynucleotide sequence set forth in SEQ ID NO: 39;
(b) a polynucleotide that encodes a polypeptide that has at least 95%, 96%, 97%, 98%, or 99% identity and/or similarity to a polypeptide set forth in SEQ ID NO: 40 or fragments thereof;
(c) a polynucleotide encoding a polypeptide of SEQ ID NO: 40;
(d) a polynucleotide that is the complement of any of (a), (b), or (c).

Therefore the invention also includes an isolated polynucleotide comprising:
(a) polynucleotide sequence set forth in SEQ ID NO: 41;
(b) a polynucleotide that encodes a polypeptide that has at least 95%, 96%, 97%, 98%, or 99% identity and/or similarity to a polypeptide set forth in SEQ ID NO: 42 or fragments thereof;
(c) a polynucleotide encoding a polypeptide of SEQ ID NO: 42;
(d) a polynucleotide that is the complement of any of (a), (b), or (c).

Therefore the invention also includes an isolated polynucleotide comprising:
(a) polynucleotide sequence set forth in SEQ ID NO: 43;
(b) a polynucleotide that encodes a polypeptide that has at least 95%, 96%, 97%, 98%, or 99% identity and/or similarity to a polypeptide set forth in SEQ ID NO: 44 or fragments thereof;
(c) a polynucleotide encoding a polypeptide of SEQ ID NO: 44;
(d) a polynucleotide that is the complement of any of (a), (b), or (c).

Therefore the invention also includes an isolated polynucleotide comprising:
(a) polynucleotide sequence set forth in SEQ ID NO: 45;
(b) a polynucleotide that encodes a polypeptide that has at least 85%, 85.5%, 86%, 87%, 88%, 89%, 90%, 91%, 92%, 93%, 94%, 95%; 96%, 97%, 98%; or 99% identity and/or similarity to a polypeptide set forth in SEQ ID NO: 46 or fragments thereof;

(c) a polynucleotide encoding a polypeptide of SEQ ID NO: 46;
(d) a polynucleotide which is the complement of any of (a), (b), or (c).

The invention also includes an isolated polynucleotide comprising:
(a) polynucleotide sequence set forth in SEQ ID NO: 47;
(b) a polynucleotide that encodes a polypeptide that has at least 90%, 91%, 92%, 93%, 94%, 95%, 96%, 97%, 98%, or 99% identity and/or similarity to a polypeptide set forth in SEQ ID NO: 48 or fragments thereof;
(c) a polynucleotide encoding a polypeptide of SEQ ID NO: 49;
(d) a polynucleotide which is the complement of any of (a), (b), or (c).

Therefore the invention also includes a CD163 polypeptide in which the transmembrane region is deleted.

Therefore the invention also includes a polynucleotide encoding a CD163 polypeptide in which the transmembrane region is deleted.

In addition to the foregoing, the invention includes, as an additional aspect, all embodiments of the invention narrower in scope in any way than the variations specifically mentioned above.

Brief Description of the Sequence Listings

SEQ ID NO: 1—cDNA sequence encoding porcine susCD163v1
SEQ ID NO: 2—predicted amino acid sequence of porcine susCD163v1
SEQ ID NO: 3—cDNA sequence, Genbank accession number AJ311716
SEQ ID NO: 4—predicted amino acid sequence derived from Genbank accession number AJ311716
SEQ ID NO: 5—cDNA sequence of susCD163v1 containing flanking (non-coding) sequence
SEQ ID NO: 6-11—primer sequences
SEQ ID NO: 12—cDNA sequence encoding porcine susCD163v2 containing flanking (non-coding) sequence
SEQ ID NO: 13—cDNA sequence encoding porcine susCD163v2
SEQ ID NO: 14—predicted amino acid sequence of porcine susCD163v2
SEQ ID NO: 15-16—primer sequences
SEQ ID NO: 17—cDNA sequence encoding human CD163v2 containing flanking (non-coding) sequence
SEQ ID NO: 18—cDNA sequence encoding human CD163v2
SEQ ID NO: 19—predicted amino acid sequence of human CD163v2
SEQ ID NO: 20-21—primer sequences
SEQ ID NO: 22—cDNA sequence encoding murine CD163v2 containing flanking (non-coding) sequence
SEQ ID NO: 23—cDNA sequence encoding murine CD163v2
SEQ ID NO: 24—predicted amino acid sequence of murine CD163v2
SEQ ID NO: 25—cDNA sequence encoding murine CD163v3 containing flanking (non-coding) sequence
SEQ ID NO: 26—cDNA sequence encoding murine CD163v3
SEQ ID NO: 27—predicted amino acid sequence of murine CD163v3
SEQ ID NO: 28-29—primer sequences
SEQ ID NO: 30—cDNA sequence encoding MARC-145 CD163v2 containing flanking (non-coding) sequence
SEQ ID NO: 31—cDNA sequence encoding MARC-145 CD163v2
SEQ ID NO: 32—predicted amino acid sequence of MARC-145 CD163v2
SEQ ID NO: 33—cDNA sequence encoding Vero cell CD163v2 transcript
SEQ ID NO: 34—predicted amino acid sequence of Vero cell CD163v2
SEQ ID NO: 35—cDNA sequence encoding Vero cell CD163v3 transcript
SEQ ID NO: 36—predicted amino acid sequence of Vero cell CD163v3
SEQ ID NO: 37—cDNA sequence encoding Vero cell CD163v4 transcript
SEQ ID NO: 38—predicted amino acid sequence of Vero cell CD163v4
SEQ ID NO: 39—cDNA sequence encoding Vero cell CD163v5 transcript
SEQ ID NO: 40—predicted amino acid sequence of Vero cell CD163v5
SEQ ID NO: 41—cDNA sequence encoding Vero cell CD163v6 transcript
SEQ ID NO: 42—predicted amino acid sequence of Vero cell CD163v6
SEQ ID NO: 43—cDNA sequence encoding Vero cell CD163v7 transcript
SEQ ID NO: 44—predicted amino acid sequence of Vero cell CD163v7
SEQ ID NO: 45—cDNA sequence encoding canine CD163v2 transcript
SEQ ID NO: 46—predicted amino acid sequence of canine CD163v2
SEQ ID NO: 47—cDNA sequence encoding canine CD163v3 transcript
SEQ ID NO: 48—predicted amino acid sequence of canine CD163v3

BRIEF DESCRIPTION OF THE DRAWINGS

FIG. 2 Amino acid sequence alignment of susCD163v1 (SEQ ID NO: 2) with AJ311716 (SEQ ID NO: 4)

FIG. 3 Nucleotide sequence alignment of susCD163v1 (SEQ ID NO:1) with AJ311716(SEQ ID NO:3).

FIG. 14 The amount of progeny PRRSV produced by four recombinant cell lines stably expressing susCD163v1, and by MARC-145 cells, was determined in a growth curve experiment using the NVSL 94-3 isolate of PRRSV. Samples harvested at 12-hour intervals were titrated on MARC-145 cell monolayers.

FIG. 16 Flow cytometry analysis of PRRSV infection in the presence of CD163 specific antibody. NLFK cells stably expressing human CD163 were incubated with either CD163 specific antibody or normal goat IgG (NGS) and infected with a GFP expressing PRRSV. At 24 hours post infection the percentage of GFP expressing infected cells was determined. Each data point represents the result from a single well of cells.

DETAILED DESCRIPTION OF THE INVENTION

General Definitions

Figure 1:
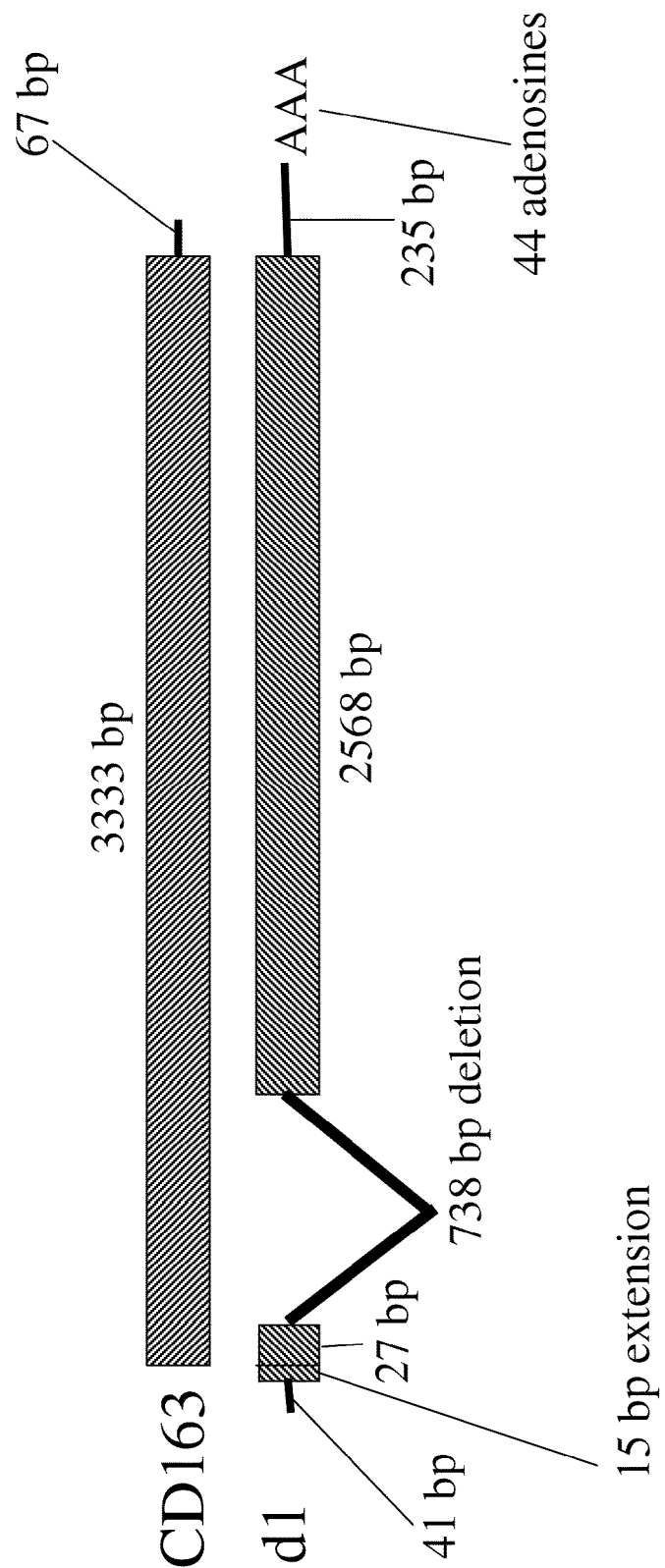
FIG. 1 Schematic comparison of susCD163v1 with AJ311716

Cells and cell lines can be either "virus permissive" or "virus non-permissive". For example, a cell or cell line that is virus permissive is capable of allowing virus infection, subsequent replication, and virus production. A cell or cell line that is virus non-permissive is incapable of allowing virus infection, subsequent replication, and virus production. A cell line that is already somewhat permissive may be rendered more permissive by the methods of the invention.

Arteriviridae refers to a family of enveloped, positive-stranded RNA viruses belonging to the order Nidovirales. The family includes lactate dehydrogenase-elevating virus (LDV) of mice, equine arteritis virus (EAV), simian hemorrhagic fever virus (SHFV), and PRRSV.

Asfarviridae is a family of icosohedral, enveloped viruses whose genomes consist of single molecules of linear double-stranded DNA about 150000-190000 nucleotides long. The name of the family is derived from African Swine Fever And Releted Viruses. African Swine Fever Virus (ASFV) is the type species of the Asfivirus genus and is the sole member of the family.

The term "PRRSV" or PRRS virus refers to both European and North American PRRS virus genotypes. Within each genotype, isolates typically share 85% or higher nucleotide identity. Between genotypes, however, the level of sequence identity is only about 60%. The North American genotype of PRRSV is exemplified by the prototype isolate VR2332. The genomic sequence of VR2332 is found in Genbank accession number U87392, which is incorporated herein by reference. The European genotype of PRRSV is exemplified by the prototype isolate "Lelystad virus". The genomic sequence of Lelystad virus is found in Genbank accession number M96262, which is incorporated herein by reference.

The PRRS virus is a member of the family Arteriviridae. The genome of the arteriviruses is single-stranded RNA of positive polarity between 12 and 16 kb in length, capped at the 5' end and polyadenylated at the 3' end. Over two-thirds of the genome is dedicated to open reading frames (ORFs) 1a and 1b, which encode the non-structural functions of the virus. ORF1b is an extension of ORF1a, and is the result of a ribosomal frameshift. ORFs 1a and 1b are translated directly from the genomic RNA. These large polypeptide products are cleaved by viral proteases to yield 12 or 13 discrete smaller peptides. The remaining ORFs, which encode viral structural proteins, are expressed from a series of 3' co-terminal subgenomic RNAs (sgRNAs). The sgRNAs are produced by discontinuous transcription of negative-stranded RNA, such that a common 5' leader sequence becomes fused to each transcript. The major structural proteins are the nucleocapsid (N, encoded by ORF7), the matrix protein (M, encoded by ORF6), and the major envelope glycoprotein (GP5, encoded by ORF5). The remaining proteins, GP4 (ORF4), GP3 (ORF3), GP2 (ORF2a), and E (ORF2b) are minor structural components of the virion, whose functions have not yet been elucidated. The molecular biology of PRRSV has been the subject of recent review articles (Dea et al., 2000; Meulenberg, 2000; Snijder and Meulenberg, 2001).

As used herein, the term "CD163 polypeptide" means a protein encoded by a mammalian CD163 gene, including allelic variants containing conservative or non-conservative changes. A cDNA sequence that encodes a porcine CD163 polypeptide has been reported (Genbank accession number AJ311716). A murine CD163 polypeptide has also been reported (Genbank access number AF274883), as well as multiple human variants, exemplified by Genbank access numbers AAH151281 and CAA80543. We report herein polynucleotides that encode porcine, human, murine, canine, and african green monkey CD163 polypeptides and which comprise the sequences set forth in SEQ ID NO: 1, 5, 12, 13, 17, 18, 22, 23, 25, 26, 30, 31, 33, 35, 37, 39, 41, 43, 45, and 47. A "CD163 polypeptide" is a member of the scavenger receptor cysteine-rich (SRCR) family of transmembrane glycoproteins, and is thought to be expressed exclusively on monocytes and macrophages. One identified role of CD163 is to inhibit oxidative tissue damage following hemolysis by consuming hemoglobin:haptoglobin complexes by endocytosis. The subsequent release of interleukin-10 and synthesis of heme oxygenase-1 results in antiinflammatory and cytoprotective effects (Philippidis et al., 2004; Graversen et al., 2002). The human CD163 gene spans 35 kb on chromosome 12, and consists of 17 exons and 16 introns. A number of isoforms of the CD163 polypeptide, including membrane bound, cytoplasmic and secreted types, are known to be generated by alternative splicing (Ritter et al., 1999). Isoforms that comprise a transmembrane domain are particularly preferred.

A transmembrane domain is characterized by a polypeptide segment of a larger sequence that is exposed on both sides of a membrane. The cytoplasmic and extracellular domains are separated by at least one membrane-spanning segment that traverses the hydrophobic environment of the lipid bilayer. The membrane-spanning segment is composed of amino acid residues with nonpolar side chains, usually in the form of an alpha helix. Segments that contain about 20-30 hydrophobic residues are long enough to span a membrane as an alpha helix, and they can often be identified by means of a hydropathy plot. The predicted transmembrane domain of SEQ ID NOs:2 and 14 are indicated by bolding in the specification. To determine whether other CD163 sequences contain a similar sequence feature is easily determined by inspection of the sequence or hydropathy plots. SEQ ID NOs: 37-40 are representative of variant CD163 proteins which do not contain a transmembrane domain and their encoding nucleic acids.

As used hereinafter, "polynucleotide" generally refers to any polyribonucleotide or polydeoxyribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides. Polynucleotide and nucleic acid are used synonymously herein.

As used hereinafter, "polypeptide" refers to any peptide or protein comprising amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications or modified forms include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation prenylation, racemization, selenoylation, sulfation, transfer-RNA mediated addition of amino acids to proteins such as arginylation, and ubiquitination (see, for instance, Proteins-Structure and Molecular Properties, 2nd Ed., T. E. Creighton, W. H. Freeman and Company, New York, 1993; Wold, F., Post-translational Protein Modifications: Perspectives and Prospects, pgs. 1-12 in Postranslational Covalent Modification of Proteins, B. C. Johnson, Ed., Academic Press, New York, 1983; Seifter et al., "Analysis for protein modifications and nonprotein cofactors", Meth Enzymol (1990) 182:626-646 and Rattan et al., "Protein Synthesis: Post-translational Modifications and Aging", Ann NY Acad Sci (1992) 663:4842).

A "fragment" of a polypeptide as used herein means a segment of at least about 25 consecutive amino acids of a polypeptide of the invention. In another embodiment, a "fragment" as used herein means a segment of at least about 50 consecutive amino acids of a polypeptide of the invention. In another embodiment, a "fragment" as used herein means a segment of at least about 100 consecutive amino acids of a polypeptide of the invention.

As used hereinafter, "isolated" means altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Therefore "isolated" as used herein and as understood in the art, whether referring to "isolated" polynucleotides or polypeptides, is taken to mean separated from the original cellular environment in which the polypeptide or nucleic acid is normally found. As used herein therefore, by way of example only, a transgenic animal or a recombinant cell line constructed with a polynucleotide of the invention makes use of the "isolated" nucleic acid. Specifically excluded from the definition of isolated polynucleotides of the invention are entire isolated chromosomes from native host cells from which the polynucleotide was originally derived.

In the disclosure to follow we will often make use of the term "identity" or similarity as applied to the amino acid sequences of polypeptides. Percent amino acid sequence "identity" with respect to polypeptides is defined herein as the percentage of amino acid residues in the candidate sequence that are identical with the residues in the target sequences after aligning both sequences and introducing gaps, if necessary, to achieve the maximum percent sequence identity, and not considering any conservative substitutions as part of the sequence identity. Percent sequence identity is determined by conventional methods. For example, BLASTP 2.2.6 [Tatusova TA and TL Madden, "BLAST 2 sequences—a new tool for comparing protein and nucleotide sequences." (1999) FEMS Microbiol Lett. 174:247-250.]

Briefly, as noted above, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 89:10915-10919. 1992).

The percent identity is then calculated as:

$$\frac{\text{Total number of identical matches}}{[\text{length of the longer sequence} + \text{number of gaps introduced into the longer sequence to align the two sequences}]} \times 100$$

Percent sequence "similarity" (often referred to as "homology") with respect to a polypeptide of the invention is defined herein as the percentage of amino acid residues in the candidate sequence that are identical with the residues in the target sequences after aligning the sequences and introducing gaps, if necessary, to achieve the maximum percent sequence identity (as described above), and also considering any conservative substitutions as part of the sequence identity.

$$\frac{\text{Total number of identical matches and conservative substitutions}}{[\text{length of the longer sequence} + \text{number of gaps introduced into the longer sequence to align the two sequences}]} \times 100$$

Amino acids can be classified according to physical properties and contribution to secondary and tertiary protein structure. A conservative substitution is recognized in the art as a substitution of one amino acid for another amino acid that has similar properties.

Exemplary conservative substitutions are set out in Tables 1, 2, and 3 below.

TABLE 1

Conservative Substitutions I

| SIDE CHAIN CHARACTERISTIC | AMINO ACID |
|---|---|
| Aliphatic | |
| Non-polar | G A P I L V |
| Polar - uncharged | C S T M N Q |
| Polar - charged | D E K R |
| Aromatic | H F W Y |
| Other | N Q D E |

Alternatively, conservative amino acids can be grouped as described in Lehninger, [Biochemistry, Second Edition; Worth Publishers, Inc. NY:NY (1975), pp. 71-77] as set out in Table 2, immediately below

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |

TABLE 2-continued

Conservative Substitutions II

| SIDE CHAIN CHARACTERISTIC | AMINO ACID |
|---|---|
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, immediately below.

TABLE 3

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Methods Directed to the Production of Virus and Host Cells of the Invention

The invention provides a method of modifying production of a virus that is a member of the family Arteriviridae and Asfarviridae in a cell comprising the step of directing said cell to express a CD163 polypeptide. This may include rendering a virus non-permissive cell into a virus permissive cell, or may involve rendering a cell more permissive to the virus.

In one embodiment, the virus that is a member of the family Arteriviridae or Asfarviridae is selected from the group consisting of LDV of mice, equine arteritis virus (EAV), simian hemorrhagic fever virus (SHFV), PRRSV of swine, and ASFV of swine.

In a preferred embodiment the virus is PPRSV.

The invention further provides a method of preparing a culture of a virus that is a member of the family Arteriviridae or Asfarviridae comprising the steps of providing a cell line; directing said cell line to express a CD163 polypeptide; infecting said cell line with virus; and causing said cell line to produce viral progeny.

In one embodiment, the virus that is a member of the family Arteriviridae is selected from the group consisting of LDV of mice, equine arteritis virus (EAV), simian hemorrhagic fever virus (SHFV), PRRSV of swine and ASFV of swine.

In a preferred embodiment the virus is PRRSV.

All of the above methods utilize cells and cell lines expressing a CD163 polypeptide. Expression of CD163 may be facilitated or increased by methods that involve the introduction of exogenous nucleic acid into the cell. Such a cell may comprise a polynucleotide or vector in a manner that permits expression of an encoded CD163 polypeptide.

Polynucleotides that encode CD163 may be introduced into the host cell as part of a circular plasmid, or as linear DNA comprising an isolated protein-coding region, or in a viral vector. Methods for introducing exogenous nucleic acid into the host cell are well known and routinely practiced in the art, including transformation, transfection, electroporation, nuclear injection, or fusion with carriers such as liposomes, micelles, ghost cells, and protoplasts. Host cell systems of the invention include invertebrate and vertebrate cells systems. Hosts may include, but are not limited to, the following: insect cells, porcine kidney (PK) cells, feline kidney (FK) cells, swine testicular (ST) cells, African green monkey kidney cells (MA-104, MARC-145, VERO, and COS cells), Chinese hamster ovary (CHO) cells, baby hampster kidney cells, human 293 cells, and murine 3T3 fibroblasts. Insect host cell culture systems may also be used for the expression of CD163 polypeptides. In another embodiment, the CD163 polypeptides are expressed using a *drosophila* expression system.

The choice of a suitable expression vector for expression of the CD163 polypeptides will of course depend upon the specific host cell to be used, and is within the skill of the ordinary artisan. Examples of suitable expression vectors include pSport and pcDNA3 (Invitrogen), pCMV-Script (Stratagene), and pSVL (Pharmacia Biotech). Expression vectors for use in mammalian host cells may include transcriptional and translational control sequences derived from viral genomes. Commonly used promoter sequences and modifier sequences which may be used in the present invention include, but are not limited to, those derived from human cytomegalovirus (CMV), Rous sarcoma virus (RSV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO 91/18982.

Because CD163 sequences are known to exist in cells from various species, the endogenous gene may be modified to permit, or increase, expression of the CD163 polypeptide. Cells can be modified (e.g., by homologous recombination) to provide increased expression by replacing, in whole or in part, the naturally occurring CD163 promoter with all or part of a heterologous promoter, so that the cells express CD163 polypeptide at higher levels. The heterologous promoter is inserted in such a manner that it is operatively linked to endogenous CD163 encoding sequences. [See, for example, PCT International Publication No. WO 94/12650, PCT International Publication No. WO 92/20808, and PCT International Publication No. WO 91/09955.] It is also contemplated that, in addition to heterologous promoter DNA, amplifiable marker DNA (e.g., ada, dhfr, and the multifunctional cad gene, which encodes for carbamyl phosphate synthase, aspartate transcarbamylase, and dihydroorotase) and/or intron DNA may be inserted along with the heterologous promoter DNA. If linked to the CD163 coding sequence, amplification of the marker DNA by standard selection methods results in co-amplification of the CD163 coding sequences in the cells.

CD163 expression may also be induced by chemical treatment. Phorbol esters, especially phorbol myristyl acetate (PMA), activate one or more isozymes of the ubiquitous membrane receptor, protein kinase C (PKC) and are particularly preferred means of increasing CD163 expression. Other methods of intracellular calcium mobilization are also contemplated.

Vaccine Production

The methods described above may be used to produce any virus that is a member of the family Arteriviridae or Asfarviridae for the purpose of vaccine production or diagnostics.

In one embodiment the virus that is a member of the family Arteriviridae is selected from the group consisting of LDV of mice, equine arteritis virus (EAV), simian hemorrhagic fever virus (SHFV), and PRRSV of swine.

In a preferred embodiment the virus is PRRSV.

Vaccine Production

The methods described above may be used to produce virus for the purpose of vaccine production or diagnostics.

Killed (inactivated) or live vaccines can be produced. Therefore, to make a live vaccine, a viral isolate, or an attenuated or mutated variant thereof, is grown in cell culture. The virus is harvested according to methods well known in the art. The virus may then be concentrated, frozen, and stored at −70° C., or freeze-dried and stored at 4° C. Prior to vaccination the virus is mixed at an appropriate dosage, (which is from about $10^3$ to $10^8$ tissue culture infectious doses per ml ($TCID_{50}$/ml)), with a pharmaceutically acceptable carrier such as a saline solution, and optionally an adjuvant.

The vaccine produced might also comprise an inactivated or killed virus comprising a virus grown by the methods of the invention. The inactivated vaccine is made by methods well known in the art. For example, once the virus is propagated to high titers, it would be readily apparent by those skilled in the art that the virus antigenic mass could be obtained by methods well known in the art. For example, the virus antigenic mass may be obtained by dilution, concentration, or extraction. All of these methods have been employed to obtain appropriate viral antigenic mass to produce vaccines. The virus is then inactivated by treatment with formalin, betapropriolactone (BPL), binary ethyleneimine (BEI), or other methods known to those skilled in the art. The inactivated virus is then mixed with a pharmaceutically acceptable carrier such as a saline solution, and optionally an adjuvant. Examples of adjuvants include, but not limited to, aluminum hydroxide, oil-in-water and water-in-oil emulsions, AMPHIGEN, saponins such as QuilA, and polypeptide adjuvants including interleukins, interferons, and other cytokines.

Inactivation by formalin is performed by mixing the viral suspension with 37% formaldehyde to a final formaldehyde concentration of 0.05%. The virus-formaldehyde mixture is mixed by constant stirring for approximately 24 hours at room temperature. The inactivated virus mixture is then tested for residual live virus by assaying for growth on a suitable cell line.

Inactivation by BEI is performed by mixing the viral suspension of the present invention with 0.1 M BEI (2-bromo-ethylamine in 0.175 N NaOH) to a final BEI concentration of 1 mM. The virus-BEI mixture is mixed by constant stirring for approximately 48 hours at room temperature, followed by the addition of 1.0 M sodium thiosulfate to a final concentration of 0.1 mM. Mixing is continued for an additional two hours. The inactivated virus mixture is tested for residual live virus by assaying for growth on a suitable cell line.

Virus permissive cells that have been directed to express CD163 can also be used to quantify live virus. Two common methods, which are well known to those skilled in the art, are the plaque assay and the limiting dilution assay.

CD163-expressing cell lines of the present invention can be used to grow virus for the purpose of producing viral antigen for diagnostic kits. For example lysates from infected cells (with optional purification of viral particles or extraction of selected viral proteins) may be coated on ELISA plates in order to detect and quantify antibodies to the virus in swine sera.

Live or inactivated virus grown in CD163-expressing cells can be used after optional separation of the viral proteins to immunize animals in order to generate polyclonal, monospecific or monoclonal antibodies. These in turn can be used as the basis of diagnostic assays for the detection and quantification of virus in swine serum and other biological samples.

Assays of the Invention

The invention provides methods for determining the propensity of an animal to be infected by a virus that is a member of the family Arteriviridae or Asfarviridae, or of a cell line to support the replication of a virus that is a member of the family Arteriviridae or Asfarviridae. Samples from either source are obtained and assayed for expression of CD163. The level of CD163 gene expression can be compared with levels of controls known not to support replication of the virus, where an increased amount of CD163 gene expression relative to levels from the controls indicates a greater propensity of the non-control to be infected by said virus.

In the case of an animal, samples can be any sample comprising sample nucleic acid molecules or proteins, and obtained from any bodily tissue expressing CD163, including, but not limited to, alveolar macrophages, cultured cells, biopsies, or other tissue preparations. The level of expression can be assessed at the level of genomic DNA, messenger RNA, and/or protein produced. In a preferred embodiment the member of the virus of the family Arteriviridae or Asfarviridae is selected from the group consisting of LDV of mice, equine arteritis virus (EAV), simian hemorrhagic fever virus (SHFV), PRRSV of swine, and ASFV of swine.

Nucleic Acid Based Assays

Methods of determining CD163 levels may be nucleic acid based as noted above. CD163-derived nucleic acids may be in solution or on a solid support. In some embodiments, they may be employed as array elements in microarrays alone or in combination with other array element molecules. Nucleic acid based methods generally require the isolation of DNA or RNA from the sample and subsequent hybridization or PCR amplification using specific primers derived from any known CD163 encoding sequences in the art or those specifically disclosed as SEQ ID NOs: 1, 3, 5, 12, 13, 17, 18, 22, 23, 25, 26, 30, 31, 33, 35, 37, 39, 41, 43, 45, and 47. DNA or RNA can be isolated from the sample according to any of a number of methods well known to those of skill in the art. For example, methods of purification of nucleic acids are described in Tijssen, P. (1993) Laboratory Techniques in Biochemistry and Molecular Biology Hybridization With Nucleic Acid Probes, Part I. Theory and Nucleic Acid Preparation, Elsevier, New York, N.Y. In one preferred embodiment, total RNA is isolated using the TRIZOL total RNA isolation reagent (Life Technologies, Inc., Gaithersburg Md.) and mRNA is isolated using oligo d(T) column chromatography or glass beads. When sample nucleic acid molecules are amplified it is desirable to amplify the sample nucleic acid molecules and maintain the relative abundances of the original sample, including low abundance transcripts. RNA can be amplified in vitro, in situ, or in vivo (See Eberwine U.S. Pat. No. 5,514,545).

It is also advantageous to include controls within the sample to assure that amplification and labeling procedures do not change the true distribution of nucleic acid molecules in a sample. For this purpose, a sample is spiked with an amount of a control nucleic acid molecule predetermined to be detectable upon hybridization to its complementary arrayed nucleic acid molecule and the composition of nucleic acid molecules includes reference nucleic acid molecules which specifically hybridize with the control arrayed nucleic acid molecules. After hybridization and processing, the hybridization signals obtained should reflect accurately the amounts of control arrayed nucleic acid molecules added to the sample.

Prior to hybridization, it may be desirable to fragment the sample nucleic acid molecules. Fragmentation improves hybridization by minimizing secondary structure and cross-hybridization to other sample nucleic acid molecules in the sample or noncomplementary nucleic acid molecules. Fragmentation can be performed by mechanical or chemical means.

Labeling

The sample nucleic acid molecules or probes may be labeled with one or more labeling moieties to allow for detection of hybridized arrayed/sample nucleic acid molecule complexes. The labeling moieties can include compositions that can be detected by spectroscopic, photochemical, biochemical, bioelectronic, immunochemical, electrical, optical, or chemical means. The labeling moieties include radio-isotopes, such as (32)P, (33)P or (35)S, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like. Preferred fluorescent markers include Cy3 and Cy5 fluorophores (Amersham Pharmacia Biotech, Piscataway N.J.).

Hybridization

The nucleic acid molecule sequence of SEQ ID NOs: 1, 3, 5, 12, 13, 17, 18, 22, 23, 25, 26, 30, 31, 33, 35, 37, 39, 41, 43, 45, and 47 or other CD163 encoding sequences in the art and fragments thereof can be used in various hybridization technologies for various purposes. Hybridization probes may be designed or derived from any mammalian CD163 sequence but may make use of those sequences disclosed in SEQ ID NOs: 1, 3, 5, 12, 13, 17, 18, 22, 23, 25, 26, 30, 31, 33, 35, 37, 39, 41, 43, 45, and 47. Such probes may be made from a highly specific region or from a conserved motif, and used in protocols to quantify CD163 message, allelic variants, or related sequences. The hybridization probes of the subject invention may be DNA or RNA and may be derived from any mammalian CD163 sequence known in the art or from those sequences disclosed herein as SEQ ID NOs: 1, 3, 5, 12, 13, 17, 18, 22, 23, 25, 26, 30, 31, 33, 35, 37, 39, 41, 43, 45, and 47 or from genomic sequences including promoters, enhancers, and introns of the mammalian gene. Hybridization or PCR probes may be produced using oligolabeling, nick translation, end-labeling, or PCR amplification in the presence of the labeled nucleotide. A vector containing the nucleic acid sequence may be used to produce an mRNA probe in vitro by addition of an RNA polymerase and labeled nucleic acid molecules. These procedures may be conducted using commercially available kits such as those provided by Amersham Pharmacia Biotech.

The stringency of hybridization is determined by the G+C content of the probe, salt concentration, and temperature. In particular, stringency can be increased by reducing the concentration of salt or raising the hybridization temperature. In solutions used for some membrane-based hybridizations, additions of an organic solvent such as formamide allows the reaction to occur at a lower temperature. Hybridization can be performed at low stringency with buffers, such as 5× saline sodium citrate (SSC) with 1% sodium dodecyl sulfate (SDS) at 60° C., which permits the formation of a hybridization complex between nucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid sequences are almost completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or Triton X-100 and a blocking agent such as salmon sperm DNA. Selection of components and conditions for hybridization are well known to those skilled in the art and are reviewed in Ausubel (supra) and Sambrook et al. (1989) Molecular Cloning, A Laboratory Manual, Cold Spring Harbor Press, Plainview N.Y.

Exemplary highly stringent hybridization conditions are as follows: hybridization at 42° C. in a hybridization solution comprising 50% formamide, 1% SDS, 1M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described in Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51.

Hybridization specificity can be evaluated by comparing the hybridization of specificity-control nucleic acid molecules to specificity-control sample nucleic acid molecules that are added to a sample in a known amount. The specificity-control arrayed nucleic acid molecules may have one or more sequence mismatches compared with the corresponding arrayed nucleic acid molecules. In this manner, it is possible to determine whether only complementary arrayed nucleic acid molecules are hybridizing to the sample nucleic acid molecules or whether mismatched hybrid duplexes are forming is determined.

Hybridization reactions can be performed in absolute or differential hybridization formats. In the absolute hybridization format, nucleic acid molecules from one sample are hybridized to the molecules in a microarray format and signals detected after hybridization complex formation correlate to nucleic acid molecule levels in a sample. In the differential hybridization format, the differential expression of a set of genes in two biological samples is analyzed. For differential hybridization, nucleic acid molecules from both biological samples are prepared and labeled with different labeling moieties. A mixture of the two labeled nucleic acid molecules is added to a microarray. The microarray is then examined under conditions in which the emissions from the two different labels are individually detectable. Molecules in the microarray that are hybridized to substantially equal numbers of nucleic acid molecules derived from both biological samples give a distinct combined fluorescence (Shalon et al.; PCT publication WO95/35505). In a preferred embodiment, the labels are fluorescent markers with distinguishable emission spectra, such as Cy3 and Cy5 fluorophores.

After hybridization, the microarray is washed to remove nonhybridized nucleic acid molecules and complex formation between the hybridizable array elements and the nucleic acid molecules is detected. Methods for detecting complex formation are well known to those skilled in the art. In a preferred embodiment, the nucleic acid molecules are labeled with a fluorescent label and measurement of levels and patterns of fluorescence indicative of complex formation is accomplished by fluorescence microscopy, preferably confocal fluorescence microscopy.

In a differential hybridization experiment, nucleic acid molecules from two or more different biological samples are labeled with two or more different fluorescent labels with different emission wavelengths. Fluorescent signals are detected separately with different photomultipliers set to detect specific wavelengths. The relative abundances/expression levels of the nucleic acid molecules in two or more samples are obtained.

Typically, microarray fluorescence intensities can be normalized to take into account variations in hybridization intensities when more than one microarray is used under similar test conditions. In a preferred embodiment, individual arrayed-sample nucleic acid molecule complex hybridization intensities are normalized using the intensities derived from internal normalization controls contained on each microarray.

Polypeptide Based Assays

The present invention provides methods and reagents for detecting and quantifying CD163 polypeptides. These methods include analytical biochemical methods such as electrophoresis, mass spectroscopy, chromatographic methods and the like, or various immunological methods such as radioimmunoassay (RIA), enzyme-linked immunosorbent assays (ELISAs), immunofluorescent assays, western blotting, affinity capture mass spectrometry, biological activity, and others described below and apparent to those of skill in the art upon review of this disclosure.

Immunoassays

The present invention also provides methods for detection of CD163 polypeptides employing one or more anti-CD163 antibody reagents (i.e., immunoassays). As used herein, an immunoassay is an assay that utilizes an antibody (as broadly defined herein and specifically includes fragments, chimeras and other binding agents) that specifically binds a CD163 polypeptide or epitope.

A number of well-established immunological binding assay formats suitable for the practice of the invention are known (see, e.g., U.S. Pat. Nos. 4,366,241; 4,376,110; 4,517,288; and 4,837,168). See, e.g., Methods in Cell Biology Volume 37: Antibodies in Cell Biology, Asai, ed. Academic Press, Inc. New York (1993); Basic and Clinical Immunology 7th Edition, Stites & Ten, eds. (1991); Harlow and Lane, supra [e.g., Chapter 14], and Ausubel et al., supra, [e.g., Chapter 11]. Typically, immunological binding assays (or immunoassays) utilize a "capture agent" to specifically bind to and, often, immobilize the analyte to a solid phase. In one embodiment, the capture agent is a moiety that specifically binds to a CD163 polypeptide or subsequence, such as an anti-CD163 antibody.

Usually the CD163 gene product being assayed is detected directly or indirectly using a detectable label. The particular label or detectable group used in the assay is usually not a critical aspect of the invention, so long as it does not significantly interfere with the specific binding of the antibody or antibodies used in the assay. The label may be covalently attached to the capture agent (e.g., an anti-CD163 antibody), or may be attached to a third moiety, such as another antibody, that specifically binds to the CD163 polypeptide.

The present invention provides methods and reagents for competitive and noncompetitive immunoassays for detecting CD163 polypeptides. Noncompetitive immunoassays are assays in which the amount of captured analyte (in this case CD163) is directly measured. One such assay is a two-site, monoclonal-based immunoassay utilizing monoclonal antibodies reactive to two non-interfering epitopes on the CD163 polypeptide. See, e.g., Maddox et al., 1983, J. Exp. Med., 158:1211 for background information. In one "sandwich" assay, the capture agent (e.g., an anti-CD163 antibody) is bound directly to a solid substrate where it is immobilized. These immobilized antibodies then capture any CD163 polypeptide present in the test sample. The CD163 polypeptide thus immobilized can then be labeled, e.g., by binding to a second anti-CD163 antibody bearing a label. Alternatively, the second CD163 antibody may lack a label, but be bound by a labeled third antibody specific to antibodies of the species from which the second antibody is derived. The second antibody alternatively can be modified with a detectable moiety, such as biotin, to which a third labeled molecule can specifically bind, such as enzyme-labeled streptavidin.

In competitive assays, the amount of CD163 polypeptide present in the sample is measured indirectly by measuring the amount of an added (exogenous) CD163 polypeptide displaced (or competed away) from a capture agent (e.g., CD163 antibody) by the CD163 polypeptide present in the sample. A hapten inhibition assay is another example of a competitive assay. In this assay CD163 polypeptide is immobilized on a solid substrate. A known amount of CD163 antibody is added to the sample, and the sample is then contacted with the immobilized CD163 polypeptide. In this case, the amount of anti-CD163 antibody bound to the immobilized CD163 polypeptide is inversely proportional to the amount of CD163 polypeptide present in the sample. The amount of immobilized antibody may be detected by detecting either the immobilized fraction of antibody or the fraction of the antibody that remains in solution. In this aspect, detection may be direct, where the antibody is labeled, or indirect where the label is bound to a molecule that specifically binds to the antibody as described above.

Other Antibody-Based Assay Formats

The invention also provides reagents and methods for detecting and quantifying the presence of CD163 polypeptide in the sample by using an immunoblot (Western blot) format. Another immunoassay is the so-called "lateral flow chromatography." In a non-competitive version of lateral flow chromatography, a sample moves across a substrate by, e.g., capillary action, and encounters a mobile-labeled antibody that binds the analyte forming a conjugate. The conjugate then moves across the substrate and encounters an immobilized second antibody that binds the analyte. Thus, immobilized analyte is detected by detecting the labeled antibody. In a competitive version of lateral flow chromatography a labeled version of the analyte moves across the carrier and competes with unlabeled analyte for binding with the immobilized antibody. The greater the amount of the analyte in the sample, the less the binding by labeled analyte and, therefore, the weaker the signal. See, e.g., May et al., U.S. Pat. No. 5,622,871; and Rosenstein, U.S. Pat. No. 5,591,645.

Depending upon the assay, various components, including the antigen, target antibody, or anti-cathepsin S antibody, may be bound to a solid surface or support (i.e., a substrate, membrane, or filter paper). Many methods for immobilizing biomolecules to a variety of solid surfaces are known in the art. For instance, the solid surface may be a membrane (e.g., nitrocellulose), a microliter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly (4-methylbutene), polystyrene, polymethacrylate, poly(ethylene terephthalate), rayon, nylon, poly(vinylbutyrate), polyvinylidene difluoride (PVDF), silicones, polyformaldehyde, cellulose, cellulose acetate, nitrocellulose, and the like. Other materials that may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

Mass Spectrometry

The mass of a molecule frequently can be used as an identifier of the molecule. Therefore, methods of mass spectrometry can be used to identify a protein analyte. Mass spectrometers can measure mass by determining the time required for an ionized analyte to travel down a flight tube and to be detected by an ion detector. One method of mass spectrometry for proteins is matrix-assisted laser desorption ionization mass spectrometry ("MALDI"). In MALDI the analyte is mixed with an energy absorbing matrix material that absorbs energy of the wavelength of a laser and placed on the surface of a probe. Upon striking the matrix with the laser, the analyte is desorbed from the probe surface, ionized, and detected by the ion detector. See, for example, Hillenkamp et al., U.S. Pat. No. 5,118,937.

Other methods of mass spectrometry for proteins are described in Hutchens and Yip, U.S. Pat. No. 5,719,060. In one such method referred to as Surfaces Enhanced for Affinity Capture ("SEAC") a solid phase affinity reagent that binds the analyte specifically or non-specifically, such as an antibody or a metal ion, is used to separate the analyte from other materials in a sample. Then the captured analyte is desorbed from the solid phase by, e.g., laser energy, ionized, and detected by the detector.

Nucleic Acids of the Invention

The examples below disclose our discovery of several novel CD163 polynucleotides. The invention includes these novel CD163 polynucleotides. The present invention provides several isolated novel polynucleotides (e.g., DNA sequences and RNA transcripts, both sense and complementary antisense strands, both single and double-stranded, including splice variants thereof, which encode novel CD163 polypeptides. We report herein isolated novel polynucleotides which encode porcine, murine, human, canine, and african green monkey CD163 polypeptides and which comprise the sequences set forth in SEQ ID NOs: 1, 5, 12, 13, 22, 23, 25, 26, 30, 31, 33, 35, 37, 39, 41, 43, 45, and 47.

It should be recognized that by disclosing SEQ ID NOs: 1, 5, 12, 13, 22, 23, 25, 26, 30, 31, 33, 35, 37, 39, 41, 43, 45, and 47 it provides one skilled in the art a multitude of methods of obtaining these sequences. By way of example, it would be possible to generate probes from the sequences disclosed in SEQ ID NOs: 1, 5, 12, 13, 22, 23, 25, 26, 30, 31, 33, 35, 37, 39, 41, 43, 45, and 47 and screen porcine, murine, human, canine, and african green monkey cDNA or genomic libraries and thereby obtain the entire sequence disclosed in SEQ ID NOs: 1, 3, 5, 12, 13, 17, 18, 22, 23, 25, 26, 30, 31, 33, 35, 37, 39, 41, 43, 45 and 47, or its genomic equivalent. Sambrook, et al., (Eds.), *Molecular Cloning: A Laboratory Manual*, Cold Spring Harbor Laboratory Press: Cold Spring Harbor, N.Y. (1989). Also by way of example, one skilled in the art would immediately recognize that given the sequence disclosed in SEQ ID NO: 1, 5, 12, 13, 22, 23, 25, 26, 30, 31, 33, 35, 37, 39, 41, 43, 45, and 47 it is then possible to generate the appropriate primers for PCR amplification to obtain the entire sequence represented by these sequences. (See e.g., PCR Technology, H. A. Erlich, ed., Stockton Press, New York, 1989; PCR Protocols: A Guide to Methods and Applications, M. A. Innis, David H. Gelfand, John J. Sninsky, and Thomas J. White, eds., Academic Press, Inc., New York, 1990.)

DNA polynucleotides of the invention include cDNA, and DNA that has been chemically synthesized in whole or in part and is also intended to include allelic variants thereof. Allelic variants are modified forms of a wild type gene sequence, the modification resulting from recombination during chromosomal segregation, or exposure to conditions which give rise to genetic mutation. Allelic variants, like wild type genes, are naturally occurring sequences (as opposed to non-naturally occurring variants which arise from in vitro manipulation).

DNA sequences encoding the novel CD163 polypeptides are set forth in SEQ ID NOs: 1, 5, 12, 13, 22, 23, 25, 26, 30, 31, 33, 35, 37, 39, 41, 43, 45, and 47. The worker of skill in the art will readily appreciate that the DNA of the invention comprises a double stranded molecule, for example the molecule having the sequence set forth in SEQ ID NO: 1, 5, 12, 13, 22, 23, 25, 26, 30, 31, 33, 35, 37, 39, 41, 43, 45, and 47 along with the complementary molecule (the "non-coding strand" or "complement") having a sequence deducible from the sequences of SEQ ID NOs: 1, 5, 12, 13, 22, 23, 25, 26, 30, 31, 33, 35, 37, 39, 41, 43, 45, and 47 according to Watson-Crick base pairing rules for DNA. Also contemplated by the invention are other polynucleotides encoding for the porcine, murine, and african green monkey CD163 polypeptides of SEQ ID NOS: 2, 14, 24, 27, 32, 34, 36, 38, 40, 42, 44, 46, and 48 which differ in sequence from the polynucleotide of SEQ ID NOs: 1, 3, 5, 12, 13, 17, 18, 22, 23, 25, 26, 30, 31, 33, 35, 37, 39, 41, 43, 45, and 47 by virtue of the well-known degeneracy of the universal genetic code, as is well known in the art. The present invention, therefore, contemplates those other DNA and RNA molecules that, on expression, encode the polypeptides of SEQ ID NO: 2, 14, 24, 27, 32, 34, 36, 38, 40, 42, 44, 46, and 48. Having identified the amino acid residue sequence encoded the porcine CD163 polypeptide, and with the knowledge of all triplet codons for each particular amino acid residue, it is possible to describe all such encoding RNA and DNA sequences. DNA and RNA molecules other than those specifically disclosed herein characterized simply by a change in a codon for a particular amino acid, are, therefore, within the scope of this invention.

A table of amino acids and their representative abbreviations, symbols and codons is set forth below in the following Table 4.

TABLE 4

| Amino acid | Abbrev. | Symbol | Codon(s) |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

As is well known in the art, codons constitute triplet sequences of nucleotides in mRNA and their corresponding cDNA molecules. Codons are characterized by the base uracil (U) when present in an mRNA molecule but are characterized by the base thymidine (T) when present in DNA. A simple change in a codon for the same amino acid residue within a polynucleotide will not change the sequence or structure of the encoded polypeptide. It is apparent that when a phrase stating that a particular 3 nucleotide sequence "encode(s)" any particular amino acid, the ordinarily skilled artisan would recognize that the table above provides a means of identifying the particular nucleotides at issue. By way of example, if a particular three-nucleotide sequence encodes theonine the table above discloses that the posible triplet sequences are ACA, ACG, ACC, and ACU (ACT if in DNA).

The invention includes therefore, an isolated polynucleotide comprising:
(a) a susCD163v1 polynucleotide sequence set forth in SEQ ID NOs: 1 and 5;
(b) a polynucleotide that encodes a polypeptide that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity and/or similarity to a polypeptide set forth in SEQ ID NO: 2;
(c) a polynucleotide encoding a polypeptide of SEQ ID NO: 2;
(d) a polynucleotide that is the complement of any of (a), (b), or (c).

The invention also includes an isolated polynucleotide comprising:
(a) a susCD163v2 polynucleotide sequence set forth in SEQ ID NOs: 12 or 13;
(b) a polynucleotide that encodes a polypeptide that has at least 99% identity and/or similarity to a polypeptide set forth in SEQ ID NO: 14;
(c) a polynucleotide encoding a polypeptide of SEQ ID NO: 14;
(d) a polynucleotide that is the complement of any of (a), (b), or (c).

The invention also includes an isolated polynucleotide comprising:
(a) a susCD163v2 polynucleotide sequence set forth in SEQ ID NOs: 17 or 18;
(b) a polynucleotide encoding a polypeptide of SEQ ID NO: 19;
(d) a polynucleotide that is the complement of any of (a) or (b).

The invention also includes an isolated polynucleotide comprising:
(a) a CD63v2 polynucleotide sequence set forth in SEQ ID NOs: 22 or 23;
(b) a polynucleotide encoding a polypeptide of SEQ ID NO: 24;
(c) a polynucleotide that is the complement of (a) or (b).

The invention also includes an isolated polynucleotide comprising:
(a) a CD163v3 polynucleotide sequence set forth in SEQ ID NOs: 25 or 26;

(b) a polynucleotide that encodes a polypeptide that has at least 96%, 97%, 98%, or 99% identity and/or similarity to a polypeptide set forth in SEQ ID NO: 27;
(c) a polynucleotide encoding a polypeptide of SEQ ID NO: 27;
(d) a polynucleotide that is the complement of any of (a), (b), or (c).

The invention also includes an isolated polynucleotide comprising:
(a) a CD163v2 polynucleotide sequence set forth in SEQ ID NOs: 30 or 31;
(b) a polynucleotide that encodes a polypeptide that has at least 98% or 99% identity and/or similarity to a polypeptide set forth in SEQ ID NO: 32;
(c) a polynucleotide encoding a polypeptide of SEQ ID NO: 32;
(d) a polynucleotide that is the complement of any of (a), (b), or (c).

The invention also includes an isolated polynucleotide comprising:
(a) a polynucleotide sequence set forth in SEQ ID NO: 33;
(b) a polynucleotide that encodes a polypeptide that has at least 95%, 96%, 97%, 98%, or 99% identity and/or similarity to a polypeptide set forth in SEQ ID NO: 34;
(c) a polynucleotide encoding a polypeptide of SEQ ID NO: 34;
(d) a polynucleotide that is the complement of any of (a), (b), or (c).

The invention also includes an isolated polynucleotide comprising:
(a) a polynucleotide sequence set forth in SEQ ID NO: 35;
(b) a polynucleotide that encodes a polypeptide that has at least 95%, 96%, 97%, 98%, or 99% identity and/or similarity to a polypeptide set forth in SEQ ID NO: 36;
(c) a polynucleotide encoding a polypeptide of SEQ ID NO: 36;
(d) a polynucleotide that is the complement of any of (a), (b), or (c).

The invention also includes an isolated polynucleotide comprising:
(a) a polynucleotide sequence set forth in SEQ ID NO: 37;
(b) a polynucleotide that encodes a polypeptide that has at least 95%, 96%, 97%, 98%, or 99% identity and/or similarity to a polypeptide set forth in SEQ ID NO: 38
(c) a polynucleotide encoding a polypeptide of SEQ ID NO: 38;
(d) a polynucleotide that is the complement of any of (a), (b), or (c).

The invention also includes an isolated polynucleotide comprising:
(a) a polynucleotide sequence set forth in SEQ ID NO: 39;
(b) a polynucleotide that encodes a polypeptide that has at least 95%, 96%, 97%, 98%, or 99% identity and/or similarity to a polypeptide set forth in SEQ ID NO: 40;
(c) a polynucleotide encoding a polypeptide of SEQ ID NO: 40;
(d) a polynucleotide that is the complement of any of (a), (b), or (c).

The invention also includes an isolated polynucleotide comprising:
(a) a polynucleotide sequence set forth in SEQ ID NO: 41;
(b) a polynucleotide that encodes a polypeptide that has at least 95%, 96%, 97%, 98%, or 99% identity and/or similarity to a polypeptide set forth in SEQ ID NO: 42;
(c) a polynucleotide encoding a polypeptide of SEQ ID NO: 42;
(d) a polynucleotide that is the complement of any of (a), (b), or (c).

The invention also includes an isolated polynucleotide comprising:
(a) a polynucleotide sequence set forth in SEQ ID NO: 43;
(b) a polynucleotide that encodes a polypeptide that has at least 95%, 96%, 97%, 98%, or 99% identity and/or similarity to a polypeptide set forth in SEQ ID NO: 44;
(c) a polynucleotide encoding a polypeptide of SEQ ID NO: 44;
(d) a polynucleotide that is the complement of any of (a), (b), or (c).

The invention also includes an isolated polynucleotide comprising:
(a) a polynucleotide sequence set forth in SEQ ID NO: 45;
(b) a polynucleotide that encodes a polypeptide that has at least 90%, 91%, 92%, 93%, 94%, 95%, 96%, 97%, 98%, or 99% identity and/or similarity to a polypeptide set forth in SEQ ID NO: 46;
(c) a polynucleotide encoding a polypeptide of SEQ ID NO: 46;
(d) a polynucleotide that is the complement of any of (a), (b), or (c).

The invention also includes an isolated polynucleotide comprising:
(a) a polynucleotide sequence set forth in SEQ ID NO: 47;
(b) a polynucleotide that encodes a polypeptide that has at least 90%, 91%, 92%, 93%, 94%, 95%, 96%, 97%, 98%, or 99% identity and/or similarity to a polypeptide set forth in SEQ ID NO: 48;
(c) a polynucleotide encoding a polypeptide of SEQ ID NO: 49;
(d) a polynucleotide that is the complement of any of (a), (b), or (c).

The polynucleotide sequence information provided by the invention makes possible large-scale expression of the encoded polypeptide by techniques well known and routinely practiced in the art. Polynucleotides of the invention also permit identification and isolation of polynucleotides encoding related porcine CD163v1 polypeptides, such as human allelic variants and species homologs, by well-known techniques including Southern and/or Northern hybridization, and the polymerase chain reaction (PCR).

Knowledge of the sequence of any of the CD163 sequences disclosed herein also makes possible through use of Southern hybridization or polymerase chain reaction (PCR), the identification of genomic DNA sequences encoding CD163 regulatory sequences, such as promoters, operators, enhancers, repressors, and the like.

As noted in the section above entitled "Assays of the Invention" polynucleotides of the invention are also useful in hybridization assays to detect the capacity of cells to express CD163, or to measure levels of CD163 expression. Polynucleotides of the invention may also be the basis for diagnostic methods useful for determining the susceptibility of an animal to virus infection as described above.

The disclosure herein of the full-length polynucleotides encoding a CD163 polypeptide makes readily available to the worker of ordinary skill in the art fragments of the full length polynucleotide. The invention therefore provides unique fragments of the CD163 encoding polynucleotides comprising at least 15 through the length of the full-length sequence (including each and every integer value between) consecutive nucleotides of a polynucleotide encoding a CD163 disclosed herein. Because polynucleotides of the invention (including fragments) comprise sequences unique to the particular CD163-encoding polynucleotide sequence, they therefore would hybridize under highly stringent or moderately stringent conditions only (i.e., "specifically") to polynucleotides encoding the various CD163 polypeptides. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

One or more unique fragment polynucleotides (or other CD163 polynucleotides as discussed above) can be included in kits that are used to detect the presence of a polynucleotide encoding for CD163, or used to detect variations in a polynucleotide sequence encoding for CD163. Also made available by the invention are anti-sense polynucleotides that recognize and hybridize to polynucleotides encoding CD163. Full length and fragment anti-sense polynucleotides are provided. Fragment anti-sense molecules of the invention include (i) those that specifically recognize and hybridize to the CD163 variants disclosed herein (as determined by sequence comparison of DNA encoding CD163s to DNA encoding other known molecules). Identification of sequences unique to the novel CD163-encoding polynucleotides can be deduced through the use of any publicly available sequence database, and/or through the use of commercially available sequence comparison programs. The uniqueness of selected sequences in an entire genome can be further verified by hybridization analyses. After identification of the desired sequences, isolation through restriction digestion or amplification using any of the various polymerase chain reaction techniques well known in the art can be performed. Anti-sense polynucleotides are particularly relevant to regulating expression of CD163 by those cells expressing CD163 mRNA.

Antisense nucleic acids (preferably 10 to 20 base pair oligonucleotides) capable of specifically binding to CD163 expression control sequences or CD163 RNA are introduced into cells (e.g., by a viral vector or colloidal dispersion system such as a liposome). The antisense nucleic acid binds to the porcine CD163 target nucleotide sequence in the cell and prevents transcription or translation of the target sequence. Phosphorothioate and methylphosphonate antisense oligonucleotides are specifically contemplated for therapeutic use by the invention. The antisense oligonucleotides may be further modified by poly-L-lysine, transferrin polylysine, or cholesterol moieties at their 5' end. Suppression of porcine CD163 expression at either the transcriptional or translational level is useful to generate cellular or animal models for diseases characterized by aberrant porcine CD163 expression or as a therapeutic modality.

As noted above in more detail, the nucleic acids of the invention include vectors comprising a polynucleotide of the invention. Such vectors are useful, e.g., for amplifying the polynucleotides in host cells to create useful quantities thereof. In other embodiments, the vector is an expression vector wherein the polynucleotide of the invention is operatively linked to a polynucleotide comprising an expression control sequence. Such vectors are useful for recombinant production of polypeptides of the invention.

Also as noted above the invention provides host cells that are transformed or transfected (stably or transiently) with polynucleotides of the invention or vectors of the invention.

As stated above, such host cells are useful for the production of virus and the production of vaccines.

The invention also provides isolated CD163 polypeptides encoded by a novel polynucleotide of the invention.

Polypeptides of the Invention

The examples disclose our discovery of several novel CD163 polypeptides. The invention includes these novel CD163 polypeptide which are set forth in SEQ ID NOs: 2, 14, 19, 24, 27, 32, 34, 36, 38, 40, 42, 44, 46, and 48.

The invention includes therefore, an isolated polynucleotide comprising a susCD163v1 polypeptide with the sequence set forth in SEQ ID NO: 2.

The invention also includes a polypeptide that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity and/or similarity to a polypeptide set forth in SEQ ID NO: 2.

The invention includes therefore, an isolated polynucleotide comprising a susCD163v2 polypeptide with the sequence set forth in SEQ ID NO: 14.

The invention also includes a polypeptide that has at least 99%, identity and/or similarity to a sus CD163v2 polypeptide set forth in SEQ ID NO: 14.

The invention also includes a CD163v2 polypeptide having the sequence set forth in SEQ ID NO: 24.

The invention also includes a CD163v3 polypeptide having the sequence set forth in SEQ ID NO: 27.

The invention also includes a polypeptide having at least 96%, 97% 98%, or 99% identity and/or similarity to a polypeptide set forth in SEQ ID NO: 27.

The invention also includes a polypeptide having the sequence set forth in SEQ ID NO: 32.

The invention also includes a polypeptide that has at least 98% or 99% identity and/or similarity to a polypeptide set forth in SEQ ID NO: 32.

The invention also includes a polypeptide having the sequence set forth in SEQ ID NO: 34.

The invention also includes a polypeptide that has at least 95%, 96%, 97%, 98%, or 99% identity and/or similarity to a polypeptide set forth in SEQ ID NO: 34.

The invention also includes a polypeptide having the sequence set forth in SEQ ID NO: 36.

The invention also includes a polypeptide that has at least 95%, 96%, 97%, 98%, or 99% identity and/or similarity to a polypeptide set forth in SEQ ID NO: 36.

The invention also includes a polypeptide having the sequence set forth in SEQ ID NO: 38.

The invention also includes a polypeptide that has at least 95%, 96%, 97%, 98%, or 99% identity and/or similarity to a polypeptide set forth in SEQ ID NO: 39.

The invention also includes a polypeptide having the sequence set forth in SEQ ID NO: 40.

The invention also includes a polypeptide that has at least 95%, 96%, 97%, 98%, or 99% identity and/or similarity to a polypeptide set forth in SEQ ID NO: 40.

The invention also includes a polypeptide having the sequence set forth in SEQ ID NO: 42.

The invention also includes a polypeptide that has at least 90%, 91%, 92%, 93%, 94%, 95%, 96%, 97%, 98%, or 99% identity and/or similarity to a polypeptide set forth in SEQ ID NO: 42.

The invention also includes a polypeptide having the sequence set forth in SEQ ID NO: 44.

The invention also includes a polypeptide that has at least 90%, 91%, 92%, 93%, 94%, 95%, 96%, 97%, 98%, or 99% identity and/or similarity to a polypeptide set forth in SEQ ID NO: 44.

The invention also includes a polypeptide having the sequence set forth in SEQ ID NO: 46.

The invention also includes a polypeptide that has at least 90%, 91%, 92%, 93%, 94%, 95%, 96%, 97%, 98%, or 99% identity and/or similarity to a polypeptide set forth in SEQ ID NO: 46.

The invention also includes a polypeptide having the sequence set forth in SEQ ID NO: 48.

The invention also includes a polypeptide that has at least 90%, 91%, 92%, 93%, 94%, 95%, 96%, 97%, 98%, or 99% identity and/or similarity to a polypeptide set forth in SEQ ID NO: 48.

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms of the novel CD163 polypeptides are embraced.

Overexpression in eukaryotic and prokaryotic hosts as described above facilitates the isolation of CD163 polypeptides. The invention therefore includes isolated CD163 polypeptides as set out in SEQ ID NOs: 2, 14, 19, 24, 27, 32, 34, 36, 38, 40, 42, 44, 46, and 48 and variants and conservative amino acid substitutions therein including labeled and tagged polypeptides.

The invention includes novel CD163 polypeptides that are "labeled". The term "labeled" is used herein to refer to the conjugating or covalent bonding of any suitable detectable group, including enzymes (e.g., horseradish peroxidase, beta-glucuronidase, alkaline phosphatase, and beta-D-galactosidase), fluorescent labels (e.g., fluorescein, luciferase), and radiolabels (e.g., $^{14}C$, $^{125}I$, $^{3}H$, $^{32}P$, and $^{35}S$) to the compound being labeled. Techniques for labeling various compounds, including proteins, peptides, and antibodies, are well known. See, e.g., Morrison, Methods in Enzymology 32b, 103 (1974); Syvanen et al., J. Biol. Chem. 284, 3762 (1973); Bolton and Hunter, Biochem. J. 133, 529 (1973). The termed labeled may also encompass a polypeptide which has covalently attached an amino acid tag as discussed below.

In addition, the novel CD163 polypeptides of the invention may be indirectly labeled. This involves the covalent addition of a moiety to the polypeptide and subsequent coupling of the added moiety to a label or labeled compound that exhibits specific binding to the added moiety. Possibilities for indirect labeling include biotinylation of the peptide followed by binding to avidin coupled to one of the above label groups. Another example would be incubating a radiolabeled antibody specific for a histidine tag with a CD163s polypeptide comprising a polyhistidine tag. The net effect is to bind the radioactive antibody to the polypeptide because of the considerable affinity of the antibody for the tag.

The invention also embraces variants (or analogs) of the novel CD163 protein. In one example, insertion variants are provided wherein one or more amino acid residues supplement a novel CD163 amino acid sequence. Insertions may be located at either or both termini of the protein, or may be positioned within internal regions of the novel CD163 protein amino acid sequence. Insertional variants with additional residues at either or both termini can include for example, fusion proteins and proteins including amino acid tags or labels. Insertion variants include novel CD163 polypeptides wherein one or more amino acid residues are added to a CD163 acid sequence, or to a biologically active fragment thereof.

Insertional variants therefore can also include fusion proteins wherein the amino and/or carboxy termini of the novel CD163 polypeptide is fused to another polypeptide. Various tag polypeptides and their respective antibodies are well known in the art. Examples include poly-histidine (poly-his) or poly-histidine-glycine (poly-his-gly) tags; the influenza HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and CellularBiology, 5:3610-3616 (1985)], and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; an alpha-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)]. In addition, the CD163 polypeptide can be tagged with enzymatic proteins such as peroxidase and alkaline phosphatase.

In another aspect, the invention provides deletion variants wherein one or more amino acid residues in a novel CD163 polypeptide is removed. Deletions can be effected at one or both termini of the novel CD163 polypeptide, or with removal of one or more residues within the novel CD163 amino acid sequence. Deletion variants, therefore, include all fragments of the novel CD163 polypeptide.

CD163 polypeptides contain a transmembrane or membrane anchor region. It should be recognized that such transmembrane domains are useful when expressed in the context of a heterologous protein to aid in the targeting of the heterologous protein to membranes. It should also be recognized that it may be advantageous to delete some transmembrane domains to enhance the purification or solubility of the protein. Transmembrane deleted variants of CD163 and polynucleotides encoding them are of potential value as antiviral therapeutics. Such variants are specifically disclosed here as SEQ ID NOs: 37-40.

The present invention also includes variants of the aforementioned polypeptides, that is, polypeptides that vary from the reference sequence by conservative amino acid substitutions, Exemplary conservative substitutions are set out in Tables 1, 2 and 3 in the section above entitled "Definitions".

In those situations where it is preferable to partially or completely isolate the novel CD163 polypeptides, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

Purification of novel CD163 polypeptides can be accomplished using a variety of techniques. If the polypeptide has been synthesized such that it contains a tag such as Hexahistidine (CD163/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing CD163). For example, polyhistidine binds with great affinity and specificity to nickel, thus an affinity column of nickel (such as the Qiagen Registered TM nickel columns) can be used for purification of CD163/polyHis. (See for example, Ausubel et al., eds., Current Protocols in Molecular Biology, Section 10.11.8, John Wiley & Sons, New York [1993]).

Even if the novel CD163 polypeptide is prepared without a label or tag to facilitate purification, the novel CD163 of the invention may be purified by immunoaffinity chromatography. To accomplish this, antibodies specific for CD163 polypeptides must be prepared by means well known in the art.

Antibodies generated against the novel CD163 polypeptides of the invention can be obtained by administering the polypeptides or epitope-bearing fragments, analogues, or cells to an animal, preferably a non-human, using routine protocols. For preparation of monoclonal antibodies, any technique known in the art that provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in Monoclonal Antibodies and Cancer Therapy, Alan R. Liss, Inc. (1985).

Where the novel CD163 polypeptides are prepared without a tag attached, and no antibodies are available, other well-known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties.

Antibodies

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for novel CD163 or fragments thereof.

The term "specific for," when used to describe antibodies of the invention, indicates that the variable regions of the antibodies of the invention recognize and bind CD163s polypeptides exclusively (i.e., able to distinguish CD163s polypeptides from other known polypeptides by virtue of measurable differences in binding affinity, despite the possible existence of localized sequence identity, homology, or similarity between the novel CD163 and such polypeptides). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the CD163s polypeptides of the invention are also contemplated, provided that the antibodies are, first and foremost, specific for novel CD163 polypeptides. Antibodies of the invention can be produced using any method well known and routinely practiced in the art. Non-human antibodies may be humanized by any methods known in the art. In one method, the non-human CDRs are inserted into a human antibody or consensus antibody framework sequence. Further changes can then be introduced into the antibody framework to modulate affinity or immunogenicity.

Antibodies of the invention are useful for, diagnostic purposes to detect or quantitate CD163s, as well as purification of CD163s. Kits comprising an antibody of the invention for any of the purposes described herein are also contemplated. In general, a kit of the invention also includes a control antigen for which the antibody is immunospecific.

The present invention is further illustrated, but not limited, by the following examples.

Example 1

Transient Transfection with Porcine CD163 Confers Permissivity to PRRS Virus Infection to a Non-Permissive Cell Line Total mRNA from primary porcine alveolar macrophage cells was used to construct a cDNA library in the plasmid pCMV-Sport6.1 (Invitrogen), with the cDNA cloned between the EcoRV and NotI sites. A member of this library, when isolated and transiently transfected into the BHK-21 (baby hamster kidney) cell line, conferred a PRRS-permissive phenotype. Cells were grown in Dulbecco's modified Eagle medium (DMEM) supplemented with 5% fetal bovine serum (FBS) in a 5% $CO_2$ atmosphere at 37° C. Cell cultures were transiently transfected using 10.0 uL of Lipofectamine 2000 (Invitrogen) and 2.0 ug of plasmid. A duplicate monolayer was transfected with negative control plasmid pPAMB. This plasmid is pCMV-Sport6.1 lacking an insert. Transfection efficiency was monitored with a plasmid expressing green fluorescent protein (GFP). Approximately 24 hours post-transfection, monolayers were infected with either North American (isolate P129) or European (isolate 96V198) genotypes of PRRS virus. For detection of PRRS replication, the monolayers were fixed using 80% acetone approximately 24 hours post-infection and incubated for approximately 1 hour with FITC-conjugated monoclonal antibody SDOW17 (Rural Technologies Inc.). This monoclonal antibody is specific for PRRS viral nucleocapsid expressed from open reading frame 7. A Nikon TE 300 inverted fluorescent microscope with a 10× objective was used to photograph a monolayer containing FITC positive cells and a negative control monolayer.

It was confirmed that transfected cells became permissive to both the North American (isolate P129) and European (isolate 96V198) genotypes of PRRSV. Expression of viral genes could be detected in many of the transfected BHK cells, and progeny virus was readily detectable in the supernatant. Control transfections using vector without insert or irrelevant plasmids did not confer permissivity.

Sequencing of the insert in the functional plasmid, using the Big Dye Terminator Version 1.0 Sequence Reaction kit (Applied Biosystems, Foster City, Calif.) and the Applied Biosystems 3730 DNA Analyzer (Applied Biosystems), revealed a gene that was highly homologous to the published porcine CD163 gene cDNA (Genbank accession number AJ311716). The cDNA we identified contained additional 5' and 3' untranslated regions relative to AJ311716, and the open reading frame differed in three ways: (1) a 738 by internal deletion near the 5' end, (2) a 15 by extension of the 5' end to an upstream ATG codon, and (3) sixteen nucleotide changes predicted to cause 10 amino acid changes. Nucleotide sequence identity between the sequences was 99.4%. Alignments of the newly discovered porcine CD163 sequence with the previously reported sequence AJ311716 are shown in FIGS. 1 and 2. The novel porcine CD163 variant was designated "susCD163v1".

| SEQUENCE | | | | | | ID NO |
|---|---|---|---|---|---|---|
| gtaataatac | aagaagattt | aaatgggcat | aaaaccttgg | aatggacaaa | ctcagaatgg | 60 SEQ ID |
| tgctacatga | aaactctgga | tctgcagacc | tgaaactgag | agtggtagat | ggagtcactg | 120 NO: 5 |
| aatgttcagg | aagattggaa | gtgaaattcc | aaggagaatg | gggaacaatc | tgtgatgatg | 180 |
| gctgggatag | tgatgatgcc | gctgtggcat | gtaagcaact | gggatgtcca | actgctgtca | 240 |
| ctgccattgg | tcgagttaac | gccagtgagg | gaactggaca | catttggctt | gacagtgttt | 300 |
| cttgccatgg | acacgagtct | gctctctggc | agtgtagaca | ccatgaatgg | ggaaagcatt | 360 |
| attgcaatca | taatgaagat | gctggtgtga | catgttctga | tggatcagat | ctggaactga | 420 |
| gacttaaagg | tggaggcagc | cactgtgctg | ggacagtgga | ggtggaaatt | cagaaactgg | 480 |
| taggaaaagt | gtgtgataga | agctggggac | tgaaagaagc | tgatgtggtt | tgcaggcagc | 540 |
| tgggatgtgg | atctgcactc | aaaacatcat | atcaagttta | ttccaaaacc | aaggcaacaa | 600 |
| acacatggct | gtttgtaagc | agctgtaatg | gaaatgaaac | ttctctttgg | gactgcaaga | 660 |
| attggcagtg | gggtggactt | agttgtgatc | actatgacga | agccaaaatt | acctgctcag | 720 |
| cccacaggaa | acccaggctg | gttggagggg | acattccctg | ctctggtcgt | gttgaagtac | 780 |
| aacatggaga | cacgtggggc | accgtctgtg | attctgactt | ctctctggag | gcggccagcg | 840 |
| tgctgtgcag | ggaactacag | tgcggcactg | tggtttccct | cctgggggga | gctcactttg | 900 |
| gagaaggaag | tggacagatc | tgggctgaag | aattccagtg | tgaggggcac | gagtcccacc | 960 |
| tttcactctg | cccagtagca | ccccgccctg | acgggacatg | tagccacagc | agggacgtcg | 1020 |
| gcgtagtctg | ctcaagatac | acacaaatcc | gcttggtgaa | tggcaagacc | ccatgtgaag | 1080 |
| gaagagtgga | gctcaacatt | cttgggtcct | gggggtccct | ctgcaactct | cactgggaca | 1140 |
| tggaagatgc | ccatgtttta | tgccagcagc | ttaaatgtgg | agttgccctt | tctatcccgg | 1200 |
| gaggagcacc | ttttgggaaa | ggaagtgagc | aggtctggag | gcacatgttt | cactgcactg | 1260 |
| ggactgagaa | gcacatggga | gattgttccg | tcactgctct | gggcgcatca | ctctgttctt | 1320 |
| cagggcaagt | ggcctctgta | atctgctcag | ggaaccagag | tcagacacta | tccccgtgca | 1380 |
| attcatcatc | ctcggaccca | tcaagctcta | ttatttcaga | agaaaatggt | gttgcctgca | 1440 |
| tagggagtgg | tcaacttcgc | ctggtcgatg | gaggtggtcg | ttgtgctggg | agagtagagg | 1500 |
| tctatcatga | gggctcctgg | ggcaccatct | gtgatgacag | ctgggacctg | aatgatgccc | 1560 |
| atgtggtgtg | caaacagctg | agctgtggat | gggccattaa | tgccactggt | tctgctcatt | 1620 |
| ttggggaagg | aacagggccc | atttggctgg | atgagataaa | ctgtaatgga | aagaatctc | 1680 |
| atatttggca | atgccactca | catggttggg | ggcggcacaa | ttgcaggcat | aaggaggatg | 1740 |
| caggagtcat | ctgctcggag | ttcatgtctc | tcagactgat | cagtgaaaac | agcagagaga | 1800 |
| cctgtgcagg | gcgcctggaa | gttttttaca | acggagcttg | gggcagcgtt | ggcaagaata | 1860 |
| gcatgtctcc | agccacagtg | ggggtggtat | gcaggcagct | gggctgtgca | gacagagggg | 1920 |
| acatcagccc | tgcatcttca | gacaagacag | tgtccaggca | catgtgggtg | gacaatgttc | 1980 |
| agtgtcctaa | aggacctgac | accctatggc | agtgcccatc | atctccatgg | aagaagagac | 2040 |
| tggccagccc | ctcagaggag | acatggatca | catgtgccaa | caaaataaga | cttcaagaag | 2100 |

| SEQUENCE | | ID NO |
|---|---|---|
| gaaacactaa ttgttctgga cgtgtggaga tctggtacgg aggttcctgg ggcactgtgt | 2160 | |
| gtgacgactc ctgggacctt gaagatgctc aggtggtgtg ccgacagctg ggctgtggct | 2220 | |
| cagctttgga ggcaggaaaa gaggccgcat ttggccaggg gactgggccc atatggctca | 2280 | |
| atgaagtgaa gtgcaagggg aatgaaacct ccttgtggga ttgtcctgcc agatcctggg | 2340 | |
| gccacagtga ctgtggacac aaggaggatg ctgctgtgac gtgttcagaa attgcaaaga | 2400 | |
| gccgagaatc cctacatgcc acaggtcgct catcttttgt tgcacttgca atctttgggg | 2460 | |
| tcattctgtt ggcctgtctc atcgcattcc tcatttggac tcagaagcga agacagaggc | 2520 | |
| agcggctctc agttttctca ggaggagaga attctgtcca tcaaattcaa taccgggaga | 2580 | |
| tgaattcttg cctgaaagca gatgaaacgg atatgctaaa tccctcagga gaccactctg | 2640 | |
| aagtacaatg aaaaggaaaa tgggaattat aacctggtga gttcagcctt taagatacct | 2700 | |
| tgatgaagac ctggactatt gaatgagcaa gaatctgcct cttacactga agattacaat | 2760 | |
| acagtcctct gtctcctggt attccaaaga ctgctgttga atttctaaaa aatagattgg | 2820 | |
| tgaatgtgac tactcaaagt tgtatgtaag actttcaagg gcattaaata aaaagaata | 2880 | |
| ttgctgaaaa aaaaaaaaaa aaaaaaaaaa aaaaaaaaaa aaaaaaaaaa | 2930 | |
|    1   M  D  K  L  R  M  V  L  H  E  N  S  G  S  A  D  L  K  L  R<br>   1   atggacaaactcagaatggtgctacatgaaaactctggatctgcagacctgaaactgaga | | SEQ ID NO: 1 |
|   21   V  V  D  C  V  T  E  C  S  G  R  L  E  V  K  F  Q  G  E  W<br>  61   gtggtagatggagtcactgaatgttcaggaagattggaagtgaaattccaaggagaatgg | | and 2 |
|   41   G  T  I  C  D  D  G  W  D  S  D  D  A  A  V  A  C  K  Q  L<br> 121   ggaacaatctgtgatgatggctgggatagtgatgatgccgctgtggcatgtaagcaactg | | |
|   61   G  C  P  T  A  V  T  A  I  G  R  V  N  A  S  E  G  T  G  H<br> 181   ggatgtccaactgctgtcactgccattggtcgagttaacgccagtgagggaactggacac | | |
|   81   I  W  L  D  S  V  S  C  H  G  H  E  S  A  L  W  Q  C  R  H<br> 241   atttggcttgacagtgtttcttgccatggacacgagtctgctctctggcagtgtagacac | | |
|  101   H  E  W  G  K  H  Y  C  N  H  N  E  D  A  G  V  T  C  S  D<br> 301   catgaatggggaaagcattattgcaatcataatgaagatgctggtgtgacatgttctgat | | |
|  121   G  S  D  L  E  L  R  L  K  G  G  S  H  C  A  G  T  V  E<br> 361   ggatcagatctggaactgagacttaaaggtggaggcagccactgtgctgggacagtggag | | |
|  141   V  E  I  Q  K  L  V  G  K  V  C  D  N  S  W  G  L  K  E  A<br> 421   gtggaaattcagaaactggtaggaaaagtgtgtgatagaagctggggactgaaagaagct | | |
|  161   D  V  V  C  R  Q  L  G  C  G  S  A  L  K  T  S  Y  Q  V  Y<br> 481   gatgtggtttgcaggcagctgggatgtggatctgcactccaaaacatcatatcaagtttat | | |
|  181   S  K  T  K  A  T  N  T  W  L  F  V  S  S  C  N  G  N  E  T<br> 541   tccaaaaccaaggcaacaaacacatggctgtttgtaagcagctgtaatggaaatgaaact | | |
|  201   S  L  W  D  C  K  N  W  Q  W  G  G  L  S  C  D  H  Y  D  E<br> 601   tctctttgggactgcaagaattggcagtgggtggacttagttgtgatcactatgacgaa | | |
|  221   A  K  I  T  C  S  A  H  R  K  P  R  L  V  G  G  D  I  P  C<br> 661   gccaaaattacctgctcagcccacaggaaacccaggctggttggaggggacattccctgc | | |
|  241   S  G  R  V  E  V  Q  H  G  D  T  W  G  T  V  C  D  S  D  F<br> 721   tctggtcgtgttgaagtacaacatggagacacgtgggcaccgtctgtgattctgacttc | | |
|  261   S  L  E  A  A  S  V  L  C  R  E  L  Q  C  G  T  V  V  S  L<br> 781   tctctggaggcggccagcgtgctgtgcagggaactacagtgcggcactgtggtttccctc | | |
|  281   L  G  G  A  H  F  G  E  G  S  G  Q  I  W  A  E  E  F  Q  C<br> 841   ctgggggagctcactttggagaaggaagtggacagatctgggctgaagaattccagtgt | | |
|  301   E  G  H  E  S  H  L  S  L  C  P  V  A  P  R  P  D  G  T  C<br> 901   gaggggcacgagtccaccctttcactctgcccagtagcacccgccctgacgggacatgt | | |
|  321   S  H  S  R  D  V  G  V  V  C  S  R  Y  T  Q  I  R  L  V  N<br> 961   agccacagcagggacgtcggcgtagtctgctcaagatacacacaaatccgcttggtgaat | | |

```
SEQUENCE                                                                    ID NO

341  G  K  T  S  C  E  G  R  V  E  L  N  I  L  G  S  W  G  S  L
1021  ggcaagacccatgtgaaggaagagtggagctcaacattcttgggtcctgggggtccctc 361  C  N  S  H  W  D  M  E  D  A  H  V  L  C  Q  Q  L  K  C  G
1081  tgcaactctcactgggacatggaagatgcccatgttttatgccagcagcttaaatgtgga 381  V  A  L  S  I  P  G  G  A  P  F  G  K  G  S  E  Q  V  W  R
1141  gttgccctttctatcccgggaggagcaccttttgggaaaggaagtgagcaggtctggagg 401  H  M  F  H  C  T  G  T  E  K  H  M  G  D  C  S  V  T  A  L
1201  cacatgtttcactgcactgggactgagaagcacatgggagattgttccgtcactgctctg 421  G  A  S  L  C  S  S  G  Q  V  A  S  V  I  C  S  G  N  Q  S
1261  ggcgcatcactctgttcttcagggcaagtggcctctgtaatctgctcagggaaccagagt 441  Q  T  L  S  P  C  N  S  S  S  S  D  P  S  S  S  I  I  S  E
1321  cagacactatccccgtgcaattcatcatcctcggacccatcaagctctattatttcagaa 461  E  N  G  V  A  C  I  G  S  G  Q  L  R  L  V  D  G  G  G  R
1381  gaaaatggtgttgcctgcatagggagtggtcaacttcgcctggtcgatggaggtggtcgt 481  C  A  G  R  V  E  V  Y  H  E  G  S  W  G  T  I  C  D  D  S
1441  tgtgctgggagagtagaggtctatcatgagggctcctggggcaccatctgtgatgacagc 501  W  D  L  N  D  A  H  V  V  C  K  Q  L  S  C  G  W  A  I  N
1501  tgggacctgaatgatgcccatgtggtgtgcaaacagctgagctgtggatgggccattaat 521  A  T  G  S  A  H  F  G  E  G  T  G  P  I  W  L  D  E  I  N
1561  gccactggttctgctcattttggggaaggaacagggcccatttggctggatgagataaac 541  C  N  G  K  E  S  H  I  W  Q  C  H  S  H  G  W  G  R  H  N
1621  tgtaatggaaaagaatctcatatttggcaatgccactcacatggttgggggcggcacaat 561  C  R  H  K  E  D  A  G  V  I  C  S  E  F  M  S  L  R  L  I
1681  tgcaggcataaggaggatgcaggagtcatctgctcggagttcatgtctctcagactgatc 581  S  E  N  S  R  E  T  C  A  G  R  L  E  V  F  Y  N  G  A  W
1741  agtgaaaacagcagagagacctgtgcagggcgcctggaagttttttacaacggagcttgg 601  G  S  V  G  K  N  S  M  S  P  A  T  V  G  V  V  C  R  Q  L
1801  ggcagcgttggcaagaatagcatgtctccagccacagtgggggtggtatgcaggcagctg 621  G  C  A  D  R  G  D  I  S  P  A  S  S  D  K  T  V  S  R  H
1861  ggctgtgcagacagaggggacatcagccctgcatcttcagacaagacagtgtccaggcac 641  M  W  V  D  N  V  Q  C  P  K  G  P  D  T  L  W  Q  C  P  S
1921  atgtgggtggacaatgttcagtgtcctaaaggacctgacacccctatggcagtgcccatca 661  S  P  W  K  K  R  L  A  S  P  S  E  E  T  W  I  T  C  A  N
1981  tctccatggaagaagagactggccagcccctcagaggagacatggatcacatgtgccaac 681  K  I  R  L  Q  E  G  N  T  N  C  S  G  R  V  E  I  W  Y  G
2041  aaaataagacttcaagaaggaaacactaattgttctggacgtgtggagatctggtacgga 701  G  S  W  G  T  V  C  D  D  S  W  D  L  E  D  A  Q  V  V  C
2101  ggttcctggggcactgtgtgtgacgactcctgggacctgaagatgctcaggtggtgtgc 721  R  Q  L  G  C  G  S  A  L  E  A  G  K  E  A  A  F  G  Q  G
2161  cgacagctgggctgtggctcagctttggaggcaggaaaagaggccgcatttggccagggg 741  T  G  P  I  W  L  N  E  V  K  C  K  G  N  E  T  S  L  W  D
2221  actgggcccatatggctcaatgaagtgaagtgcaaggggaatgaaacctccttgtgggat 761  C  P  A  R  S  W  G  H  S  D  C  G  H  K  E  D  A  A  V  T
2281  tgtcctgccagatcctggggccacagtgactgtggacacaaggaggatgctgctgtgacg 781  C  S  E  I  A  K  S  R  E  S  L  H  A  T  G  R  S  S  F  V
2341  tgttcagaaattgcaaagagccgagaatccctacatgccacaggtcgctcatctttgtt 801  A  L  A  I  F  G  V  I  L  L  A  C  L  I  A  F  L  I  W  T
2401  gcacttgcaatctttggggtcattctgttggcctgtctcatcgcattcctcatttggact 821  Q  K  R  R  Q  R  Q  R  L  S  V  F  S  G  G  E  N  S  V  H
2461  cagaagcgaagacagaggcagcggctctcagttttctcaggaggagagaattctgtccat 841  Q  I  Q  Y  R  E  M  N  S  C  L  K  A  D  E  T  D  M  L  N
2521  caaattcaataccgggagatgaattcttgcctgaaagcagatgaaacggatatgctaaat
```

-continued

| SEQUENCE | | | | | | | | ID NO |
|---|---|---|---|---|---|---|---|---|
| 861 | P | S | G | D | H | S | E V Q | |
| 2581 | ccctcaggagaccactctgaagtacaa | | | | | | | |
| | | | | | | | | |
| 1 | MDKLRMVLHE | NSGSADLKLR | VVDGVTECSG | RLEVKFQGEW | GTICDDGWDS | | | SEQ ID |
| 51 | DDAAVACKQL | GCPTAVTAIG | RVNASEGTGH | IWLDSVSCHG | HESALWQCRH | | | NO: 2 |
| 101 | HEWGKHYCNH | NEDAGVTCSD | GSDLELRLKG | GGSHCAGTVE | VEIQKLVGKV | | | |
| 151 | CDRSWGLKEA | DVVCRQLGCG | SALKTSYQVY | SKTKATNTWL | FVSSCNGNET | | | |
| 201 | SLWDCKNWQW | GGLSCDHYDE | AKITCSAHRK | PRLVGGDIPC | SGRVEVQHGD | | | |
| 251 | TWGTVCDSDF | SLEAASVLCR | ELQCGTVVSL | LGGAHFGEGS | GQIWAEEFQC | | | |
| 301 | EGHESHLSLC | PVAPRPDGTC | SHSRDVGVVC | SRYTQIRLVN | GKTPCEGRVE | | | |
| 351 | LNILGSWGSL | CNSHWDMEDA | HVLCQQLKCG | VALSIPGGAP | FGKGSEQVWR | | | |
| 401 | HMFHCTGTEK | HMGDCSVTAL | GASLCSSGQV | ASVICSGNQS | QTLSPCNSSS | | | |
| 451 | SDPSSSIISE | ENGVACIGSG | QLRLVDGGGR | CAGRVEVYHE | GSWGTICDDS | | | |
| 501 | WDLNDAHVVC | KQLSCGWAIN | ATGSAHFGEG | TGPIWLDEIN | CNGKESHIWQ | | | |
| 551 | CHSHGWGRHN | CRHKEDAGVI | CSEFMSLRLI | SENSRETCAG | RLEVFYNGAW | | | |
| 601 | GSVGKNSMSP | ATVGVVCRQL | GCADRGDISP | ASSDKTVSRH | MWVDNVQCPK | | | |
| 651 | GPDTLWQCPS | SPWKKRLASP | SEETWITCAN | KIRLQEGNTN | CSGRVEIWYG | | | |
| 701 | GSWGTVCDDS | WDLEDAQVVC | RQLGCGSALE | AGKEAAFGQG | TGPIWLNEVK | | | |
| 751 | CKGNETSLWD | CPARSWGHSD | CGHKEDAAVT | CSEIAKSRES | LHATGASSFV | | | |
| 801 | ALAIFGVILL | ACLIAFLIWT | QKRRQRQRLS | VFSGGENSVH | QIQYREMNSC | | | |
| 851 | LKADETDMLN | PSGDHSEVQ | | | | | | |

Example 2

Construction of Plasmid pCMVsusCD163v1

Construction of the plasmid pCMVsusCD163v1 was performed as follows. The functional clone identified in the primary porcine macrophage cDNA library as conferring PRRSV permissivity served as template for PCR amplification of the CD163 insert, including the 5' and 3' untranslated regions, using the primers 5'DS-CD163 (SEQ ID NO:6) (5'-CGGAATTCCGCGGATGTAATAATACAAGAAGA-3') and 3'CD163 (SEQ ID NO:7) (5'CCG CTCGAGTAGTCCAGGTCTTCATCAAGGTATCTT-3'). Primer 5'DS-CD163 incorporates a SacII restriction site at the 5' end of the CD163 insert, while primer 3'CD163 incorporates an XhoI restriction site at the 3' end of the insert (underlined). Reactions containing 190 ng of plasmid template were amplified using Platinum Pfx DNA polymerase (Invitrogen cat #11708-013) following the manufacture's instructions. Reactions were heated to 94° for 2 minutes then cycled 35 times through 94° for 20 seconds, 55° for 30 seconds, and 68° for 3.5 minutes followed by a terminal extension at 72° for 7 minutes. The resulting PCR products were purified using the Qiaquick PCR purification kit (Qiagen cat #28104), digested with restriction enzymes SacII and XhoI, and the resulting fragments were gel purified using the Qiaquick Gel Extraction kit (Qiagen cat #28704). The CD163 PCR fragment was then ligated into the plasmid pCMV-Script (Stratagene cat #212220) prepared to accept the digested PCR fragment by digestion with SacII and XhoI followed by gel purification as described above. The ligated material was transformed into *E. coli* strain DH5α and recombinants were selected by growth in 50 µg/ml kanamycin and identified by restriction analysis. The resulting plasmid, "pCMVsusCD163v1", contains the internally deleted porcine CD163 insert described in Example 1 under the transcriptional control of the eukaryotic CMV promoter and the neomycin/kanamycin resistance gene under the control of both eukaryotic and prokaryotic promoters.

Example 3

Construction of the pRSV-Script Expression Vector and pRSVsusCD163v1

The plasmid pRc/RSV (Invitrogen) was used as a template for PCR amplification of the RSV promoter. RSV promoter sequence was contained within nucleotides 209 through 604 of pRc/RSV. Forward primer PCIRSVLTR (SEQ ID NO:8) (5'-ACACTCG ACATGTCGATGTACGGGCCAGATATACGCGT-3') and reverse primer VSRRTLSAC (SEQ ID NO: 9) (5'TTCCT-TACAGAGCTCGAGGTGCACACCAATGTGGTGAA-3') were synthesized. Restriction endonuclease Pci I and Sac I recognition sites (underlined) were incorporated into the 5' and 3' primers, respectively, for future cloning. PCR was performed using the HotMaster Taq DNA Polymerase kit (Eppendorf) following the manufacturer's instructions. The reactions contained 0.9 ng of pRc/RSV plasmid template and 0.3 µM of each primer described above. The reactions were heated to 94° for 2 minutes then cycled 30 times through 94° for 20 seconds, 52° for 10 seconds, and 65° for 1 minute. The resulting PCR fragment was digested with restriction enzymes Pci I and Sac I, gel purified, and cloned into the plasmid pCMV-Script (Stratagene) that had been similarly digested to remove the CMV promoter sequence. The final construct placed the RSV promoter immediately upstream of the multiple cloning site, and was named "pRSV-Script".

The susCD163v1 insert was cloned behind the RSV promoter as follows. The susCD163v1 sequence was excised from plasmid pCMVsusCD163v1 by restriction digestion (Kpn I and Sac II) and gel purified. This fragment was ligated into pRSV-Script which had also been digested with the same enzymes and gel purified. The ligation mixture was transformed into DH5α E. coli and transformants selected using kanamycin at 50 µg/ml. The clone contained the correct insert was designed "pRSVsusCD163v1".

Example 4

Cloning and Characterization of a Longer Variant of Porcine CD163 cDNA

Based on the porcine CD163v1 sequence, a forward primer 5'CD163NotIlong (SEQ ID NO:10) (5'CGGTCCGGA GCGGCCGCGATGTAATAATACAAGAAGATTTAAATGG-3') and a reverse primer 3'CD163 KpnI (SEQ ID NO:11) (5'-CG-GTT GGTACCCAGCAATATTCTTTTTTATTTAATGCC-3') were designed using the Lasergene PrimerSelect program (DNASTAR Inc., Madison Wis.) for amplification of a full-length porcine CD163 gene. Restriction endonuclease sites for Not I and Kpn I (underlined) were included in 5' and 3' primers, respectively, to allow for convenient cloning. Total cellular RNA was prepared from primary alveolar macrophages (PAM) harvested from lung lavages of healthy pigs. RNA preparation was done using the RNeasy mini kit (Qiagen, Valencia, Calif.). RT-PCR reactions were prepared using the SuperScript one-step RT-PCR for Long Templates kit (Invitrogen, Carlsbad, Calif.) and RT-PCR parameters were set as follows: 50° C. for 30 min, 94° C. for 2 min, (94° C. 30 sec, 55° C. 30 sec and 68° C. 4 min) for 35 cycles, 72° C. for 10 min. PCR products were analyzed on 0.8% SeaKem GTG agarose gels. RT-PCR products of various sizes were cut from agarose gels and DNA was extracted using the GeneClean kit (QBiogene). These RT-PCR products were cloned into the pCR2.1-TOPO cloning vector (Invitrogen). Clones were analyzed by restriction enzyme digestion for the presence of an insert. Colonies containing inserts were sequenced using Big Dye Terminator Version 1.0 Sequence Reaction kit (Applied Biosystems, Foster City, Calif.) and Applied Biosystems 3730 DNA Analyzer (Applied Biosystems) to confirm sequence authenticity. Sequences were edited and assembled using the Lasergene EditSeq and SeqMan programs (DNASTAR Inc., Madison Wis.). One plasmid with a large insert was designated "pCRsusCD163v2" (pCR2.1 containing porcine CD163 variant 2 which we have designated SEQ ID NO:12). The coding sequence contained within SEQ ID NO:12 is reproduced below and is designated SEQ ID NO:13. Sequence analysis showed that this porcine CD163 encodes an amino acid sequence of 1115 amino acids which we have designated SEQ ID NO:14. When compared to the porcine CD163 sequence in GenBank (Accession No. AJ311716), our CD163v2 sequence is 98.9% identical at the amino acid level. CD163v2 also has an additional 5 amino acid residues at the extreme 5' end, extending the open reading frame to an in-frame upstream ATG initiation codon (as in the porcine CD163v1 sequence described in example 1). Porcine CD163 is 84.3% identical to human CD163 (GenBank Accession No. Z22968), and 73.7% identical to mouse CD163 (GenBank Accession No. AF274883) at the amino acid level. The predicted signal sequence and transmembrane region of SEQ ID NO:14 are indicated by underlining and bolding respectively. To determine whether other CD163 sequences contain similar sequence features is easily determined by inspection of the sequence.

| SEQUENCE | | | | | | ID NO |
|---|---|---|---|---|---|---|
| gtaataatac | aagaagattt | aaatggcata | aaaccttgga | atggacaaac | tcagaatggt | 60 | SEQ ID |
| gctacatgaa | aactctggat | ctgcagactt | tagaagatgt | tctgcccatt | taagttcctt | 120 | NO: 12 |
| cacttttgct | gtagtcgctg | ttctcagtgc | ctgcttggtc | actagttctc | ttggaggaaa | 180 | |
| agacaaggag | ctgaggctaa | cggtggtga | aaacaagtgc | tctggaagag | tggaggtgaa | 240 | |
| agtgcaggag | gagtggggaa | ctgtgtgtaa | taatggctgg | gacatggatg | tggtctctgt | 300 | |
| tgtttgtagg | cagctgggat | gtccaactgc | tatcaaagcc | actggatggg | ctaattttag | 360 | |
| tgcaggttct | ggacgcattt | ggatggatca | tgtttcttgt | cgagggaatg | agtcagctct | 420 | |
| ctgggactgc | aaacatgatg | gatggggaaa | gcataactgt | actcaccaac | aggatgctgg | 480 | |
| agtaacctgc | tcagatggat | ctgatttaga | gatggggctg | gtgaatggag | gaaaccggtg | 540 | |
| cttaggaaga | atagaagtca | aatttcaagg | acggtgggga | acagtgtgtg | atgataactt | 600 | |
| caacataaat | catgcttctg | tggtttgtaa | acaacttgaa | tgtggaagtg | ctgtcagttt | 660 | |
| ctctggttca | gctaattttg | gagaaggttc | tggaccaatc | tggtttgatg | atcttgtatg | 720 | |
| caatggaaat | gagtcagctc | tctggaactg | caaacatgaa | ggatggggaa | agcacaattg | 780 | |
| cgatcatgct | gaggatgctg | gagtgatttg | cttaaatgga | gcagacctga | aactgagagt | 840 | |
| ggtagatgga | gtcactgaat | gttcaggaag | attggaagtg | aaattccaag | gagaatgggg | 900 | |

| SEQUENCE | ID NO |
|---|---|
| aacaatctgt gatgatggct gggatagtga tgatgccgct gtggcatgta agcaactggg | 960 |
| atgtccaact gctgtcactg ccattggtcg agttaacgcc agtgagggaa ctggacacat | 1020 |
| ttggcttgac agtgtttctt gccatggaca cgagtctgct ctctggcagt gtagacacca | 1080 |
| tgaatgggga agcattatt gcaatcatga tgaagatgct ggtgtgacat gttctgatgg | 1140 |
| atcagatctg gaactgagac ttaaaggtgg aggcagccac tgtgctggga cagtggaggt | 1200 |
| ggaaattcag aaactggtag gaaaagtgtg tgatagaagc tggggactga agaagctga | 1260 |
| tgtggtttgc aggcagctgg gatgtggatc tgcactcaaa acatcatatc aagtttattc | 1320 |
| caaaaccaag gcaacaaaca catggctgtt tgtaagcagc tgtaatggaa atgaaacttc | 1380 |
| tctttgggac tgcaagaatt ggcagtgggg tggacttagt tgtgatcact atgacgaagc | 1440 |
| caaaattacc tgctcagccc acaggaaacc caggctggtt ggaggggaca ttccctgctc | 1500 |
| tggtcgtgtt gaagtacaac atggagacac gtggggcacc gtctgtgatt ctgacttctc | 1560 |
| tctggaggcg gccagcgtgc tgtgcaggga actacagtgc ggcactgtgg tttccctcct | 1620 |
| gggggggagct cactttggag aaggaagtgg acagatctgg gctgaagaat tccagtgtga | 1680 |
| ggggcacgag tcccaccttt cactctgccc agtagcaccc cgccctgacg ggacatgtag | 1740 |
| ccacagcagg gacgtcggcg tagtctgctc aagatacaca caaatccgct tggtgaatgg | 1800 |
| caagacccca tgtgaaggaa gagtggagct caacattctt gggtcctggg ggtccctctg | 1860 |
| caactctcac tgggacatgg aagatgccca tgttttatgc cagcagctta aatgtggagt | 1920 |
| tgcccttctt atcccgggag gagcaccttt tgggaaagga agtgagcagg tctggaggca | 1980 |
| catgttttcac tgcactggga ctgagaagca catgggagat tgttccgtca ctgctctggg | 2040 |
| cgcatcactc tgttcttcag ggcaagtggc ctctgtaatc tgctcaggga accagagtca | 2100 |
| gacactatct ccgtgcaatt catcatcctc ggacccatca agctctatta tttcagaaga | 2160 |
| aaatggtgtt gcctgcatag ggagtggtca acttcgcctg gtcgatggag gtggtcgttg | 2220 |
| tgctgggaga gtagaggtct atcatgaggg ctcctggggc accatctgtg atgacagctg | 2280 |
| ggacctgaat gatgcccatg tggtgtgcaa acagctgagc tgtggatggg ccattaatgc | 2340 |
| cactggttct gctcattttg gggaaggaac agggcccatt tggctggatg agataaactg | 2400 |
| taatggaaaa gaatctctata tttggcaatg ccactcacat ggttggggc ggcacaattg | 2460 |
| caggcataag gaggatgcag gagtcatctg ctcagagttc atgtctctga gactgatcag | 2520 |
| tgaaaacagc agagagacct gtgcaggcg cctggaagtt ttttacaacg gagcttgggg | 2580 |
| cagcgttggc aggaatagca tgtctccagc cacagtgggg gtggtatgca ggcagctggg | 2640 |
| ctgtgcagag agaggggaca tcagccctgc atcttcagac aagacagtgt ccaggcacat | 2700 |
| gtgggtggac aatgttcagt gtcctaaagg acctgacaca ctatggcagt gcccatcatc | 2760 |
| tccatggaag aagagactgg ccagcccctc agaggagaca tggatcacat gtgccaacaa | 2820 |
| aataagactt caagaaggaa acactaattg ttctggacgt gtggagatct ggtacggagg | 2880 |
| ttcctggggc actgtgtgtg acgactcctg ggacttgaa gatgctcagg tggtgtgccg | 2940 |
| acagctgggc tgtggctcag ctttggaggc aggaaaagag gccgcatttg ccaggggac | 3000 |
| tgggcccata tggctcaatg aagtgaagtg caagggaat gaaacctcct tgtgggattg | 3060 |
| tcctgccaga tcctggggcc acagtgactg tggacacaag gaggatgctg ctgtgacgtg | 3120 |
| ctcagaaatt gcaaagagcc gagaatccct acatgccaca ggtcgctcat cttttgttgc | 3180 |
| acttgcaatc tttgggggtca ttctgttggc ctgtctcatc gcattcctca tttggactca | 3240 |

-continued

| SEQUENCE | | ID NO |
|---|---|---|
| gaagcgaaga cagaggcagc ggctctcagt tttctcagga ggagagaatt ctgtccatca | 3300 | |
| aattcaatac cgggagatga attcttgcct gaaagcagat gaaacggata tgctaaatcc | 3360 | |
| ctcaggagac cactctgaag tacaatgaaa aggaaaatgg gaattataac ctggtgagtt | 3420 | |
| cagcctttaa gataccttga tgaagacctg gactattgaa tgagcaagaa tctgcctctt | 3480 | |
| acactgaaga ttacaataca gtcctctgtc tcctggtatt ccaaagactg ctgctgaatt | 3540 | |
| tctaaagaat agattggtga atgtgactac tcaaagttgt atgtaagact ttcaagggca | 3600 | |
| ttaaataaaa aagaatattg ctg | 3623 | |

```
  1  M  D  K  L  R  M  V  L  H  E  N  S  G  S  A  D  F  R  R  C
  1  atggacaaactcagaatggtgctacatgaaaactctggatctgcagactttagaagatgt 21  S  A  H  L  S  S  F  T  F  A  V  V  A  V  L  S  A  C  L  V
 61  tctgcccatttaagttccttcacttttgctgtagtcgctgttctcagtgcctgcttggtc 41  T  S  S  L  G  G  K  D  K  E  L  R  L  T  G  G  E  N  K  C
121  actagttctcttggaggaaaagacaaggagctgaggctaacggggtggtgaaaacaagtgc 61  S  G  R  V  E  V  K  V  Q  E  E  W  G  T  V  C  N  N  G  W
181  tctggaagagtggaggtgaaagtgcaggaggagtggggaactgtgtgtaataatggctgg 81  D  M  D  V  V  S  V  V  C  R  Q  L  G  C  P  T  A  I  K  A
241  gacatggatgtggtctctgttgtttgtaggcagctgggatgtccaactgctatcaaagcc 101  T  G  W  A  N  F  S  A  G  S  G  R  I  W  M  D  H  V  S  C
301  actggatgggctaatttttagtgcaggttctggacgcatttggatggatcatgtttcttgt 121  R  G  N  E  S  A  L  W  D  C  K  H  D  G  W  K  H  N  C
361  cgagggaatgagtcagctctctgggactgcaaacatgatggatggggaaagcataactgt 141  T  H  Q  Q  D  A  G  V  T  C  S  D  G  S  D  L  E  M  G  L
421  actcaccaacaggatgctggagtaacctgctcagatggatctgatttagagatggggctg 161  V  N  G  G  N  R  C  L  G  R  I  E  V  K  F  Q  G  K  W  G
481  gtgaatggaggaaaccggtgcttaggaagaatagaagtcaaatttcaaggacggtgggga 181  T  V  C  D  D  N  F  N  I  N  H  A  S  V  V  C  K  Q  L  E
541  acagtgtgtgatgataacttcaacataaatcatgcttctgtggtttgtaaacaacttgaa 201  C  G  S  A  V  S  F  S  G  S  A  N  F  G  E  G  S  G  P  I
601  tgtggaagtgctgtcagtttctctggttcagctaattttggagaaggttctggaccaatc 221  W  F  D  D  L  V  C  N  G  N  E  S  A  L  W  N  C  K  H  E
661  tggtttgatgatcttgtatgcaatggaaatgagtcagctctctggaactgcaaacatgaa 241  G  W  G  K  H  N  C  D  H  A  E  D  A  G  V  I  C  L  N  G
721  ggatggggaaagcacaattgcgatcatgctgaggatgctggagtgatttgcttaaatgga 261  A  D  L  K  L  R  V  V  D  G  V  T  E  C  S  G  R  L  E  V
781  gcagacctgaaactgagagtggtagatggagtcactgaatgttcaggaagattggaagtg 281  K  F  Q  G  E  W  G  T  I  C  D  D  G  W  D  S  D  D  A  A
841  aaattccaaggagaatggggaacaatctgtgatgatggctgggatagtgatgatgccgct 301  V  A  C  K  Q  L  G  C  P  T  A  V  T  A  I  G  R  V  N  A
901  gtggcatgtaagcaactgggatgtccaactgctgtcactgccattggtcgagttaacgcc 321  S  E  G  T  G  H  I  W  L  D  S  V  S  C  H  G  H  E  S  A
961  agtgagggaactggacacatttggcttgacagtgtttcttgccatggacacgagtctgct 341  L  W  Q  C  R  H  H  E  W  G  K  H  Y  C  N  H  D  E  D  A
1021 ctctggcagtgtagacaccatgaatggggaaagcattattgcaatcatgatgaagatgct 361  G  V  T  C  S  D  G  S  D  L  E  L  R  L  K  G  G  G  S  H
1081 ggtgtgacatgttctgatggatcagatctggaactgagacttaaaggtggaggcagccac 381  C  A  G  T  V  E  V  E  I  Q  K  L  V  G  K  V  C  D  R  S
1141 tgtgctgggacagtggaggtggaaattcagaaactggtaggaaaagtgtgtgatagagc 401  W  G  L  K  E  A  D  V  V  C  R  Q  L  G  C  G  S  A  L  K
1201 tgggactgaaagaagctgatgtggtttgcaggcagctgggatgtggatctgcactcaaa
```

SEQ ID NO: 13 and 14

-continued

| SEQUENCE | ID NO |
|---|---|
| 421  T S Y Q V Y S K T K A T N T W L F V S S<br>1261 acatcatatcaagtttattccaaaaccaaggcaacaaacacatggctgtttgtaagcagc | |
| 441  C N G N E T S L W D C K N W Q W G G L S<br>1321 tgtaatggaaatgaaacttctctttgggactgcaagaattggcagtggggtggacttagt | |
| 461  C D H Y D E A K I T C S A H R K P R L V<br>1381 tgtgatcactatgacgaagccaaaattacctgctcagcccacaggaaacccaggctggtt | |
| 481  G G D I P C S G R V E V Q H G D T W G T<br>1441 ggaggggacattccctgctctggtcgtgttgaagtacaacatggagacacgtgggcacc | |
| 501  V C D S D F S L E A A S V L C R E L Q C<br>1501 gtctgtgattctgacttctctctggaggcggccagcgtgctgtgcagggaactacagtgc | |
| 521  G T V V S L L G G A H F G E G S G Q I W<br>1561 ggcactgtggtttccctcctggggggagctcactttggagaaggaagtggacagatctgg | |
| 541  A E E F Q C E G H E S H L S L C P V A P<br>1621 gctgaagaattccagtgtgaggggcacgagtcccacctttcactctgcccagtagcaccc | |
| 561  R P D G T C S H S R D V G V V C S R Y T<br>1681 cgccctgacgggacatgtagccacagcagggacgtcggcgtagtctgctcaagatacaca | |
| 581  Q I R L V N G K T P C E G R V E L N I L<br>1741 caaatccgcttggtgaatggcaagacccccatgtgaaggaagagtggagctcaacattctt | |
| 601  G S W G S L C N S H W D M E D A H V L C<br>1801 gggtcctgggggtccctctgcaactctcactgggacatggaagatgcccatgttttatgc | |
| 621  Q Q L K C G V A L S I P G A P F G K G<br>1861 cagcagcttaaatgtggagttgccctttctatcccgggaggagcacctttgggaaagga | |
| 641  S E Q V W R H M F H C T G T E K H M G D<br>1921 agtgagcaggtctggaggcacatgtttcactgcactgggactgagaagcacatgggagat | |
| 661  C S V T A L G A S L C S S G Q V A S V I<br>1981 tgttccgtcactgctctgggcgcatcactctgttcttcagggcaagtggcctctgtaatc | |
| 681  C S G N Q S Q T L S P C N S S S S D P S<br>2041 tgctcagggaaccagagtcagacactatctccgtgcaattcatcatcctcggacccatca | |
| 701  S S I I S E E N G V A C I G S G Q L R L<br>2101 agctctattatttcagaagaaaatggtgttgcctgcataggggagtggtcaacttcgcctg | |
| 721  V D G G G R C A G R V E V Y H E G S W G<br>2161 gtcgatggaggtggtcgttgtgctgggagagtagaggtctatcatgagggctcctggggc | |
| 741  T I C D D S W D L N D A H V V C K Q L S<br>2221 accatctgtgatgacagctgggacctgaatgatgcccatgtggtgtgcaaacagctgagc | |
| 761  C G W A I N A T G S A H F G E G T G P I<br>2281 tgtggatgggccattaatgccactggttctgctcatttggggaaggaacagggcccatt | |
| 781  W L D E I N C N G K E S H I W Q C H S H<br>2341 tggctggatgagataaactgtaatggaaaagaatctcatatttggcaatgccactcacat | |
| 801  G W G R H N C R H K E D A G V I C S E F<br>2401 ggttgggggcggcacaattgcaggcataaggaggatgcaggagtcatctgctcagagttc | |
| 821  M S L R L I S E N S R E T C A G R L E V<br>2461 atgtctctgagactgatcagtgaaaacagcagagagacctgtgcagggcgcctggaagtt | |
| 841  F Y N G A W G S V G R N S M S P A T V G<br>2521 tttacaacggagcttggggcagcgttggcaggaatagcatgtctccagccacagtgggg | |
| 861  V V C R Q L G C A D R G D I S P A S S D<br>2581 gtggtatgcaggcagctgggctgtgcagacagaggggacatcagccctgcatcttcagac | |
| 881  K T V S R H M W V D N V Q C P K G P D T<br>2641 aagacagtgtccaggcacatgtgggtggacaatgttcagtgtcctaaaggacctgacaca | |
| 901  L W Q C P S S P W K K R L A S P S E E T<br>2701 ctatggcagtgcccatcatctccatggaagaagagactggccagcccctcagaggagaca | |
| 921  W I T C A N K I R L Q E G N T N C S G R<br>2761 tggatcacatgtgccaacaaaataagacttcaagaaggaaacactaattgttctggacgt | |

| SEQUENCE | SEQ ID NO |
|---|---|
| 941  V E I W Y G G S W G T V C D D S W D L E | |
| 2821 gtggagatctggtacggaggttcctggggcactgtgtgtgacgactcctgggaccttgaa | |
| 961  D A Q V V C R Q L G C G S A L E A G K E | |
| 2881 gatgctcaggtggtgtgccgacagctgggctgtggctcagcttttgaggcaggaaaagag | |
| 981  A A F G Q G T G P I W L N E V K C K G N | |
| 2941 gccgcatttggccaggggactgggcccatatggctcaatgaagtgaagtgcaaggggaat | |
| 1001 E T S L W D C P A R S W G H S D C G H K | |
| 3001 gaaacctccttgtgggattgtcctgccagatcctggggccacagtgactgtggacacaag | |
| 1021 E D A A V T C S E I A K S R E S L H A T | |
| 3061 gaggatgctgctgtgacgtgctcagaaattgcaaagagccgagaatccctacatgccaca | |
| 1041 G R S S F V A L A I F G V I L L A C L I | |
| 3121 ggtcgctcatcttttgttgcacttgcaatctttggggtcattctgttggcctgtctcatc | |
| 1061 A F L I W T Q K R R Q R Q R L S V F S G | |
| 3181 gcattcctcatttggactcagaagcgaagacagaggcagcggctctcagttttctcagga | |
| 1081 G E N S V H Q I Q Y R E M N S C L K A D | |
| 3241 ggagagaattctgtccatcaaattcaataccgggagatgaattcttgcctgaaagcagat | |
| 1101 E T D M L N P S G D H S E V Q | |
| 3301 gaaacggatatgctaaatccctcaggagaccactctgacctacaa | |
| 1    MDKLRMVLHE NSGSADFRRC SAHLSSFTFA VVAVLSACLV TSSLGGKDKE | SEQ ID |
| 51   LRLTGGENKC SGRVEVKVQE EWGTVCNNGW DMDVVSVVCR QLGCPTAIKA | NO: 14 |
| 101  TGWANFSAGS GRIWMDHVSC RGNESALWDC KHDGWGKHNC THQQDAGVTC | |
| 151  SDGSDLEMGL VNGGNRCLGR IEVKFQGRWG TVCDDNFNIN HASVVCKQLE | |
| 201  CGSAVSFSGS ANFGEGSGPI WFDDLVCNGN ESALWNCKHE GWGKHNCDHA | |
| 251  EDAGVICLNG ADLKLRVVDG VTECSGRLEV KFQGEWGTIC DDGWDSDDAA | |
| 301  VACKQLGCPT AVTAIGRVNA SEGTGHIWLD SVSCHGHESA LWQCRHHEWG | |
| 351  KHYCNHDEDA GVTCSDGSDL ELRLKGGGSH CAGTVEVEIQ KLVGKVCDRS | |
| 401  WGLKEADVVC RQLGCGSALK TSYQVYSKTK ATNTWLFVSS CNGNETSLWD | |
| 451  CKNWQWGGLS CDHYDEAKIT CSAHRKPRLV GGDIPCSGRV EVQHGDTWGT | |
| 501  VCDSDFSLEA ASVLCRELQC GTVVSLLGGA HFGEGSGQIW AEEFQCEGHE | |
| 551  SHLSLCPVAP RPDGTCSHSR DVGVVCSRYT QIRLVNGKTP CEGRVELNIL | |
| 601  GSWGSLCNSH WDMEDAHVLC QQLKCGVALS IPGGAPFGKG SEQVWRHMFH | |
| 651  CTGTEKHMGD CSVTALGASL CSSGQVASVI CSGNQSQTLS PCNSSSSDPS | |
| 701  SSIISEENGV ACIGSGQLRL VDGGGRCAGR VEVYHEGSWG TICDDSWDLN | |
| 751  DAHVVCKQLS CGWAINATGS AHFGEGTGPI WLDEINCNGK ESHIWQCHSH | |
| 801  GWGRHNCRHK EDAGVICSEF MSLRLISENS RETCAGRLEV FYNGAWGSVG | |
| 851  RNSMSPATVG VVCRQLGCAD RGDISPASSD KTVSRHMWVD NVQCPKGPDT | |
| 901  LWQCPSSPWK KRLASPSEET WITCANKIRL QEGNTNCSGR VEIWYGGSWG | |
| 951  TVCDDSWDLE DAQVVCRQLG CGSALEAGKE AAFGQGTGPI WLNEVKCKGN | |
| 1001 ETSLWDCPAR SWGHSDCGHK EDAAVTCSEI AKSRESLHAT GRSSFVALAI | |
| 1051 FGVILLACLI AFLIWTQKRR QRQRLSVFSG GENSVHQIQY REMNSCLKAD | |
| 1101 ETDMLNPSGD HSEVQ | |

Sus CD163 v2 in pCRsusCD163v2 was liberated from pCR2.1 vector after restriction enzymes Kpn I and Not I digestion and gel purification. Recipient vector pCMV-script was also cut with the same restriction enzyme pair and allowed for directional cloning of susCD163v2 into the pCMV-script. After ligation of susCD163 v2 with pCMV-script, the ligated mixture was used to transform STBL 2 *E. coli* cells (Invitrogen). One transformant was found to contain the CD163 gene by restriction enzyme digestion analysis and was designed pCMV-script susCD163v2 clone#3.

Example 5

Figure 4:
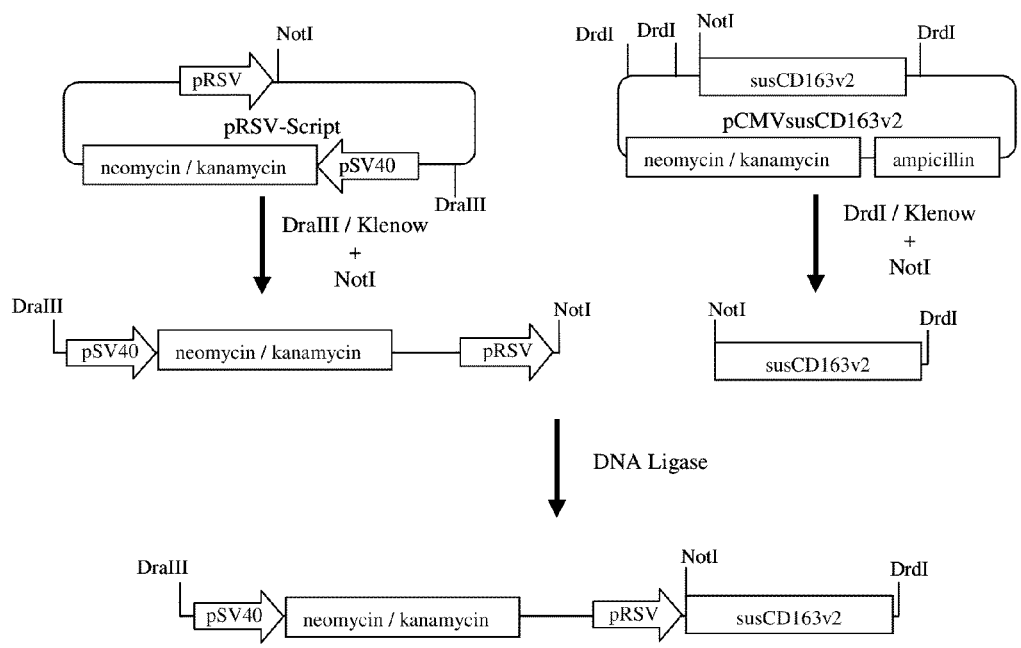
FIG. 4 Generation of DNA fragments and ligation to place CD163 directly behind the RSV promoter. Plasmids were digested with either DraIII or DrdI, followed by a blunting rea FIG. 8 Feline kidney cell lines stably expressing porcine CD163v1, showing PRRSV plaques. Cell lines NLFK-CMV-susCD163v1-G4F and NLFK-CMV-susCD163v1-G4L, both at passage 4, were infected with the P129 isolate of North American PRRSV and incubated for 6 days. Monolayers were fixed with 80% acetone and stained with monoclonal antibody SDOW17-FITC. Phase contrast microscopy (right) shows localized regions of viral CPE (plaques), while FA detection (left) shows co-localized viral nucleocapsid antigen.
Figure 5:
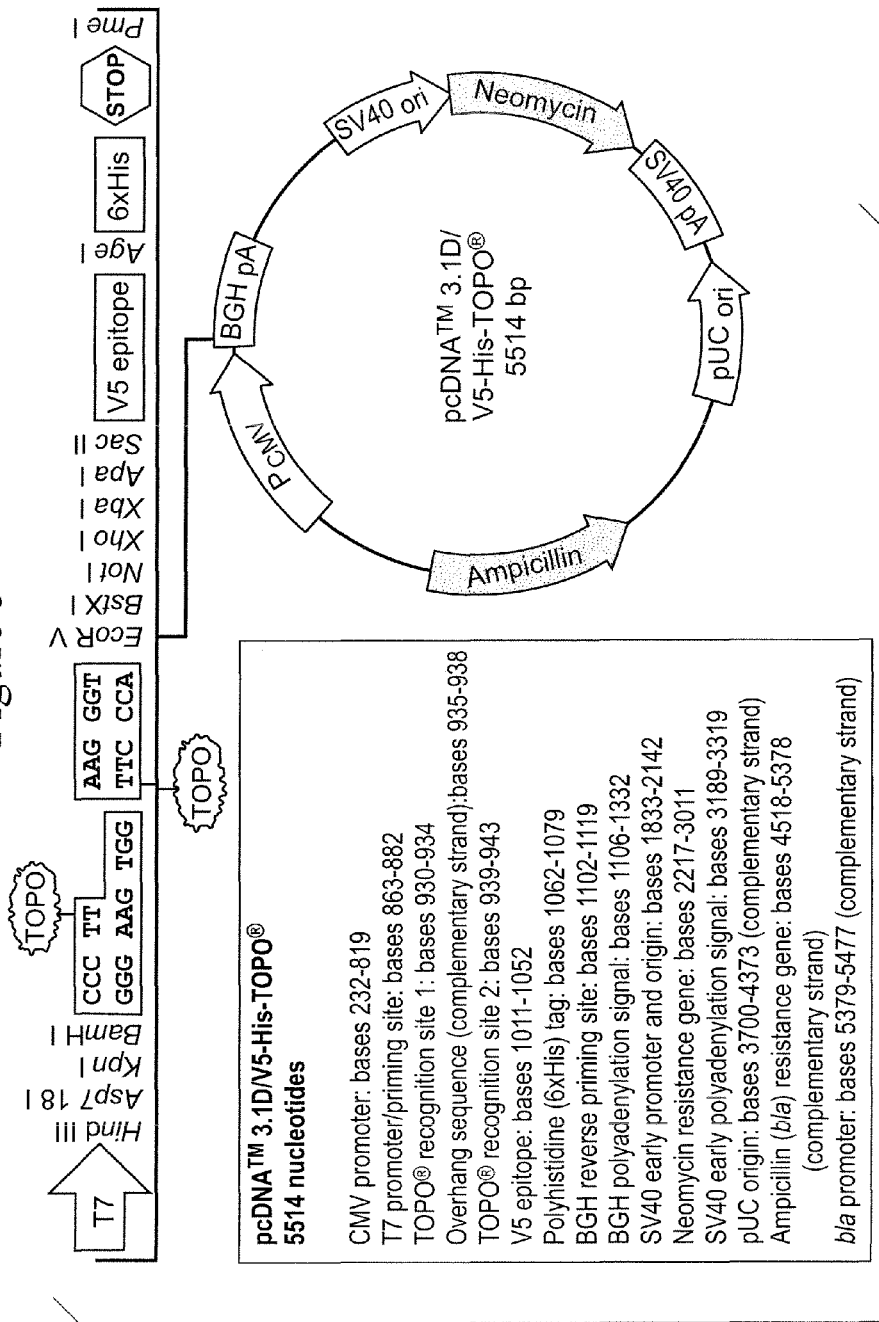

Preparation of a RSV Promoter Based Expression System by Direct Ligation and Transfection Method A non-cloning based procedure to generate microgram quantities of linear DNA suitable for use in generating stable cell lines expressing CD163 from an RSV promoter was developed (FIG. 4). The procedure involves the isolation and ligation of two pieces of DNA, one containing the neomycin gene and RSV promoter cassette derived from pRSV-script, and the other containing the susCD163v2 coding sequence from pCMVsusCD163v2. Vector plasmid pRSV-Script was linearized with DraIII upstream of the neomycin gene, and bunted with the Klenow fragment of *E. coli* DNA polymerase. This plasmid was then digested with NotI immediately downstream of the RSV promoter. The pCMVsusCD163v2 clone was digested in the vector sequence downstream of the CD163 insert with DrdI, and blunted with Klenow fragment of DNA polymerase. The CD163 coding sequence was liberated from the vector with a NotI located immediately upstream of the CD163 coding sequence. For each plasmid digestion the appropriate fragments were purified from agarose gels. A large-scale ligation reaction was performed as follows. Approximately 20 μg of each DNA fragment was incubated in a volume of 600 μl with 15 units of T4 DNA ligase. The reaction was incubated at room temperature for 20 minutes, at which time an aliquot was removed and the reaction frozen on dry ice. Agarose gel analysis of the aliquot revealed that a significant amount of non-ligated DNA remained, so another 15 units of ligase was added and incubated for another 10 minutes at room temperature. Following ligation, a linear piece of DNA containing all of the appropriate elements was purified by agarose gel electrophoresis. Ligation of the two DNA fragments via the cohesive Not I termini resulted in the placement of the 5' sequences of the CD163 gene downstream of the RSV promoter, allowing for directed expression of CD163 in mammalian cells. Once isolated, the purified DNA was used to transfect various mammalian cell lines.

Example 6

Cloning and Characterization of Human CD163 cDNA

Figure 6:
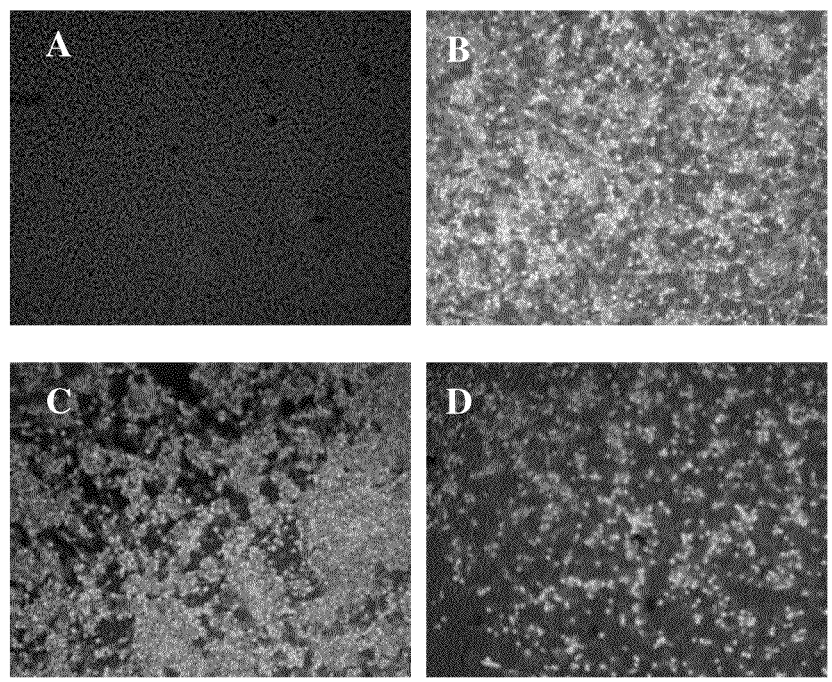

Based on a known human CD163 cDNA sequence (GenBank Accession No. BC051281), a forward primer Hu5'Not (SEQ ID NO: 15) (5'CACC GCGGCCGCGAAGTTATAAATCGCCACCATGAGCAA ACTCAGAAT GG-3') and a reverse primer Hu3'Kpn (SEQ ID NO: 16) (5'-TGCTCC GGTACCTAGTCCAGGTCTTCATCAAGGTATCTTA-3') were designed using the PrimerSelect program. Restriction sites for NotI and KpnI (underlined) were incorporated into the 5' and 3' primers, respectively, to facilitate cloning into expression vectors. The sequence CACC was added to the 5' end of the 5' primer to allow directional cloning into the pCDNA3.1DN5/V5/His/TOPO vector (Cat. No. K49001, Invitrogen, see FIG. 6). Human CD163 cDNAs were amplified from RNA extracted from the U937 cell line after stimulated with phorbol 12-myristate 13-acetate (100 ng/ml) for 3 days. Total cellular RNA was prepared using the RNeasy kit (Qiagen). RT-PCR reactions and sequencing methods were the same as described in Example 4. PCR products were separated on 0.8% SeaKem agarose gel and extracted from the gel using the GeneClean kit. PCR products were cloned directionally into the pCDNA3.1D/V5/His/TOPO vector following the manufacturer's instructions. Two clones with large inserts were sequenced. Sequencing and sequence analysis methods were described in Example 4. A clone with a correct insert was designed "pcDNA3.1D-humCD163v2" and we have designated the sequence of the insert SEQ ID NO: 17

The CD163 open reading frame in pCDNA3.1D-humCD163v2 is 1121 residues in length (designated SEQ ID NO: 18 which encodes SEQ ID NO:19 disclosed below), and is 100% identical to Genbank Z22968 (a human CD163 cDNA of the same length). Our human CD163v2 sequence is also 100% identical to Genbank BC051281 and Z22969 (splice variants of human CD163) except that 42 nonhomologous residues in the two Genbank sequences replace the seven carboxy-terminal residues of our sequence. This difference is due to the presence of an 83-nucleotide exon in BC051281 and Z22969, and the resulting frame shift at the 3' end of the exon. (Law, S. K., Micklem, K. J., Shaw, J. M., Zhang, X. P., Dong, Y., Willis, A. C. and Mason, D. Y. (1993) A new macrophage differentiation antigen which is a member of the scavenger receptor superfamily. European Journal of Immunology 23 (9), 2320-2325).

| SEQUENCE | | | | | | ID NO |
|---|---|---|---|---|---|---|
| atgagcaaac | tcagaatggt | gctacttgaa | gactctggat | ctgctgactt | cagaagacat | 60 | SEQ ID |
| tttgtcaacc | tgagtccctt | caccattact | gtggtcttac | ttctcagtgc | ctgttttgtc | 120 | ID: 17 |
| accagttctc | ttggaggaac | agacaaggag | ctgaggctag | tggatggtga | aaacaagtgt | 180 | |
| agcgggagag | tggaagtgaa | agtccaggag | gagtggggaa | cggtgtgtaa | taatggctgg | 240 | |
| agcatggaag | cggtctctgt | gatttgtaac | cagctgggat | gtccaactgc | tatcaaagcc | 300 | |
| cctggatggg | ctaattccag | tgcaggttct | ggacgcattt | ggatggatca | tgtttcttgt | 360 | |
| cgtgggaatg | agtcagctct | tgggattgc | aaacatgatg | gatggggaaa | gcatagtaac | 420 | |

| SEQUENCE | ID NO |
|---|---|
| tgtactcacc aacaagatgc tggagtgacc tgctcagatg gatccaattt ggaaatgagg | 480 |
| ctgacgcgtg gagggaatat gtgttctgga agaatagaga tcaaattcca aggacggtgg | 540 |
| ggaacagtgt gtgatgataa cttcaacata gatcatgcat ctgtcatttg tagacaactt | 600 |
| gaatgtggaa gtgctgtcag tttctctggt tcatctaatt ttggagaagg ctctggacca | 660 |
| atctggtttg atgatcttat atgcaacgga aatgagtcag ctctctggaa ctgcaaacat | 720 |
| caaggatggg gaaagcataa ctgtgaccat gctgaggatg ctggagtgat ttgctcaaag | 780 |
| ggagcagatc tgagcctgag actggtagat ggagtcactg aatgttcagg aagattagaa | 840 |
| gtgagattcc aagggaatg ggggacaata tgtgatgacg ctgggacag ttacgatgct | 900 |
| gctgtggcat gcaagcaact gggatgtcca actgccgtca cagccattgg tcgagttaac | 960 |
| gccagtaagg gatttggaca catctggctt gacagcgttt cttgccaggg acatgaacct | 1020 |
| gctgtctggc aatgtaaaca ccatgaatgg gaaaagcatt attgcaatca caatgaagat | 1080 |
| gctggcgtga catgttctga tggatcagat cggagctaa gacttagagg tggaggcagc | 1140 |
| cgctgtgctg gacagttga ggtggagatt cagagactgt tagggaaggt gtgtgacaga | 1200 |
| ggctggggac tgaaagaagc tgatgtggtt tgcaggcagc tgggatgtgg atctgcactc | 1260 |
| aaaacatctt atcaagtgta ctccaaaatc caggcaacaa acacatggct gtttctaagt | 1320 |
| agctgtaacg gaaatgaaac ttctctttgg gactgcaaga actggcaatg gggtggactt | 1380 |
| acctgtgatc actatgaaga agccaaaatt acctgctcag cccacaggga acccagactg | 1440 |
| gttggagggg acattccctg ttctggacgt gttgaagtga agcatggtga cacgtggggc | 1500 |
| tccatctgtg attcggactt ctctctggaa gctgccagcg ttctatgcag gaattacag | 1560 |
| tgtggcacag ttgtctctat cctgggggga gctcactttg gagagggaaa tggacagatc | 1620 |
| tgggctgaag aattccagtg tgagggacat gagtcccatc tttcactctg cccagtagca | 1680 |
| ccccgcccag aaggaacttg tagccacagc agggatgttg gagtagtctg ctcaagatac | 1740 |
| acagaaattc gcttggtgaa tggcaagacc ccgtgtgagg gcagagtgga gctcaaaacg | 1800 |
| cttggtgcct ggggatccct ctgtaactct cactgggaca tagaagatgc ccatgttctt | 1860 |
| tgccagcagc ttaaatgtgg agttgccctt tctaccccag gaggagcacg ttttggaaaa | 1920 |
| ggaaatggtc agatctggag gcatatgttt cactgcactg ggactgagca gcacatggga | 1980 |
| gattgtcctg taactgctct aggtgcttca ttatgtcctt cagagcaagt ggcctctgta | 2040 |
| atctgctcag gaaaccagtc ccaaacactg tcctcgtgca attcatcgtc tttgggccca | 2100 |
| acaaggccta ccattccaga agaaagtgct gtggcctgca tagagagtgg tcaacttcgc | 2160 |
| ctggtaaatg gaggaggtcg ctgtgctggg agagtagaga tctatcatga gggctcctgg | 2220 |
| ggcaccatct gtgatgacag ctgggacctg agtgatgccc acgtggtttg cagacagctg | 2280 |
| ggctgtgag aggccattaa tgccactggt tctgctcatt ttggggaagg aacagggccc | 2340 |
| atctggctgg atgagatgaa atgcaatgga aagaatcccg catttggca gtgccattca | 2400 |
| cacggctggg ggcagcaaaa ttgcaggcac aaggaggatg cggagttat ctgctcagaa | 2460 |
| ttcatgtctc tgagactgac cagtgaagcc agcagagagg cctgtgcagg gcgtctggaa | 2520 |
| gttttttaca atggagcttg gggcactgtt ggcaagagta gcatgtctga aaccactgtg | 2580 |
| ggtgtggtgt gcaggcagct gggctgtgca gacaaaggga aaatcaaccc tgcatcttta | 2640 |
| gacaaggcca tgtccattcc catgtgggtg gacaatgttc agtgtccaaa aggacctgac | 2700 |
| acgctgtggc agtgcccatc atctccatgg gagaagagac tggccagccc ctcggaggag | 2760 |

| SEQUENCE | | ID NO |
|---|---|---|
| acctggatca catgtgacaa caagataaga cttcaggaag gacccacttc ctgttctgga | 2820 | |
| cgtgtggaga tctggcatgg aggttcctgg gggacagtgt gtgatgactc ttgggacttg | 2880 | |
| gacgatgctc aggtggtgtg tcaacaactt ggctgtggtc cagcttttgaa agcattcaaa | 2940 | |
| gaagcagagt ttggtcaggg gactggaccg atatggctca atgaagtgaa gtgcaaaggg | 3000 | |
| aatgagtctt cctttgtggga ttgtcctgcc agacgctggg gccatagtga gtgtgggcac | 3060 | |
| aaggaagacg ctgcagtgaa ttgcacagat atttcagtgc agaaaacccc acaaaaagcc | 3120 | |
| acaacaggtc gctcatcccg tcagtcatcc tttattgcag tcgggatcct tggggttgtt | 3180 | |
| ctgttggcca ttttcgtcgc attattcttc ttgactaaaa agcgaagaca gagacagcgg | 3240 | |
| cttgcagttt cctcaagagg agagaactta gtccaccaaa ttcaataccg ggagatgaat | 3300 | |
| tcttgcctga atgcagatga tctggaccta atgaattcct caggaggcca ttctgagcca | 3360 | |
| cactgaaaag gaaaatggga atttataacc cagtgagttc agccttttaag ataccttgat | 3420 | |
| gaagacctgg acta | 3434 | |

```
  1  M  S  K  L  R  M  V  L  L  E  D  S  G  S  A  D  F  R  R  H        SEQ ID
  1  atgagcaaactcagaatggtgctacttgaagactctggatctgctgacttcagaagacat        NO: 18

21  F  V  N  L  S  P  F  T  I  T  V  V  L  L  L  S  A  C  F  V        and 19
 61  tttgtcaacctgagtcccttcaccattactgtggtcttacttctcagtgcctgttttgtc 41  T  S  S  L  G  G  T  D  K  E  L  R  L  V  D  G  E  N  K  C
121  accagttctcttggaggaacagacaaggagctgaggctagtggatggtgaaaacaagtgt 61  S  G  R  V  E  V  K  V  Q  E  E  W  G  T  V  C  N  N  G  W
181  agcgggagagtggaagtgaaagtccaggaggagtggggaacggtgtgtaataatggctgg 81  S  M  E  A  V  S  V  I  C  N  Q  L  G  C  P  T  A  I  K  A
241  agcatggaagcggtctctgtgatttgtaaccagctgggatgtccaactgctatcaaagcc 101  P  G  W  A  N  S  S  A  G  S  G  R  I  W  M  D  H  V  S  C
301  cctggatgggctaattccagtgcaggttctggacgcatttggatggatcatgtttcttgt 121  R  G  N  E  S  A  L  W  D  C  K  H  D  G  W  G  K  H  S  N
361  cgtgggaatgagtcagctctttgggattgcaaacatgatggatggggaaagcatagtaac 141  C  T  H  Q  Q  D  A  G  V  T  C  S  D  G  S  N  L  E  M  R
421  tgtactcaccaacaagatgctggagtgacctgctcagatggatccaatttggaaatgagg 161  L  T  R  G  G  N  M  C  S  G  R  I  E  I  K  F  Q  G  R  W
481  ctgacgcgtggagggaatatgtgttctggaagaatagagatcaaattccaaggacggtgg 181  G  T  V  C  D  D  N  F  N  I  D  H  A  S  V  I  C  R  Q  L
541  ggaacagtgtgtgatgataacttcaacatagatcatgcatctgtcatttgtagacaactt 201  E  C  G  S  A  V  S  F  S  G  S  S  N  F  G  E  G  S  G  P
601  gaatgtggaagtgctgtcagtttctctggttcatctaattttggagaaggctctggacca 221  I  W  F  D  D  L  I  C  N  G  N  E  S  A  L  W  N  C  K  H
661  atctggtttgatgatcttatatgcaacggaaatgagtcagctctctggaactgcaaacat 241  Q  G  W  K  H  N  C  H  D  H  A  E  D  A  G  V  I  C  S  K
721  caaggatggggaaagcataactgtgaccatgctgaggatgctggagtgatttgctcaaag 261  G  A  D  L  S  L  K  L  V  D  G  V  T  E  C  S  G  R  L  E
781  ggagcagatctgagcctgaagctggtagatggagtcactgaatgttcaggaagattagaa 281  V  R  F  Q  G  E  W  G  T  I  C  D  D  G  W  D  S  Y  D  A
841  gtgagattccaaggggaatgggggacaatatgtgatgacggctgggacagttacgatgct 301  A  V  A  C  K  Q  L  G  C  P  T  A  V  T  A  I  G  R  V  N
901  gctgtggcatgcaagcaactgggatgtccaactgccgtcacagccattggtcgagttaac 321  A  S  K  G  F  G  H  I  W  L  D  S  V  S  C  Q  G  H  E  P
961  gccagtaagggatttggacacatctggcttgacagcgtttcttgccagggacatgaacct 341  A  V  W  Q  C  K  H  H  E  W  G  K  H  Y  C  N  H  N  E  D
1021 gctgtctggcaatgtaaacaccatgaatggggaaagcattattgcaatcacaatgaagat
```

| SEQUENCE | | ID NO |
|---|---|---|
| 361<br>1081 | A G V T C S D G S D L E L R L R G G G S<br>gctggcgtgacatgttctgatggatcagatctggagctaagacttagaggtggaggcagc | |
| 381<br>1141 | R C A G T V E V E I Q R L L G K V C D R<br>cgctgtgctgggacagttgaggtggagattcagagactgttagggaaggtgtgtgacaga | |
| 401<br>1201 | G W G L K E A D V V C R Q L G C G S A L<br>ggctggggactgaaagaagctgatgtggtttgcaggcagctgggatgtggatctgcactc | |
| 421<br>1261 | K T S Y Q V Y S K I Q A T N T W L F L S<br>aaaacatcttatcaagtgtactccaaaatccaggcaacaaacacatggctgtttctaagt | |
| 441<br>1321 | S C N G N E T S L W D C K N W Q W G G L<br>agctgtaacggaaatgaaacttctctttgggactgcaagaactggcaatggggtggactt | |
| 461<br>1381 | T C D H Y E E A K I T C S A H R E P A L<br>acctgtgatcactatgaagaagccaaaattacctgctcagcccacagggaacccagactg | |
| 481<br>1441 | V G G D I P C S G R V E V K H G D T W G<br>gttggaggggacattccctgttctggacgtgttgaagtgaagcatggtgacacgtgggc | |
| 501<br>1501 | S I C D S D F S L E A A S V L C R E L Q<br>tccatctgtgattcggacttctctctggaagctgccagcgttctatgcagggaattacag | |
| 521<br>1561 | C G T V V S I L G G A H F G E G N G Q I<br>tgtggcacagttgtctctatcctggggggagctcactttggagagggaaatggacagatc | |
| 541<br>1621 | W A E E F Q C E G H E S H L S L C P V A<br>tgggctgaagaattccagtgtgagggacatgagtcccatctttcactctgcccagtagca | |
| 561<br>1681 | P R P E G T C S H S R D V G V V C S R Y<br>ccccgcccagaaggaacttgtagccacagcagggatgttggagtagtctgctcaagatac | |
| 581<br>1741 | T E I R L V N G K T P C E G R V E L K T<br>acagaaaattcgcttggtgaatggcaagaccccgtgtgagggcagagtggagctcaaaacg | |
| 601<br>1801 | L G A W G S L C N S H W D I E D A H V L<br>cttggtgcctgggatccctctgtaactctcactgggacatagaagatgcccatgttctt | |
| 621<br>1861 | C Q Q L K C G V A L S T P G G A R F G K<br>tgccagcagcttaaatgtggagttgcccttctaccccaggaggagcacgttttggaaaa | |
| 641<br>1921 | G N G Q I W R H M F H C T G T E Q H M G<br>ggaaatggtcagatctggaggcatatgtttcactgcactgggactgagcagcacatggga | |
| 661<br>1981 | D C P V T A L G A S L C P S E Q V A S V<br>gattgtcctgtaactgctctaggtgcttcattatgtccttcagagcaagtggcctctgta | |
| 681<br>2041 | I C S G N Q S Q T L S S C N S S S L G P<br>atctgctcaggaaaccagtcccaaacactgtcctcgtgcaattcatcgtctttgggccca | |
| 701<br>2101 | T R P T I P E E S A V A C I E S G Q L R<br>acaaggcctaccattccagaagaaagtgctgtggcctgcatagagagtggtcaacttcgc | |
| 721<br>2161 | L V N G G G R C A G R V E I Y H E G S W<br>ctggtaaatggaggaggtcgctgtgctgggagagtagagatctatcatgagggctcctgg | |
| 741<br>2221 | G T I C D D S W D L S D A H V V C R Q L<br>ggcaccatctgtgatgacagctgggacctgagtgatgcccacgtggtttgcagacagctg | |
| 761<br>2281 | G C G E A I N A T G S A H F G E G T G P<br>ggctgtggagaggccattaatgccactggttctgctcatttgggaaggaacagggccc | |
| 781<br>2341 | I W L D E M K C N G K E S R I W Q C H S<br>atctggctggatgagatgaaatgcaatggaaaagaatcccgcatttggcagtgccattca | |
| 801<br>2401 | H G W G Q Q N C R H K E D A G V I C S E<br>cacggctgggggcagcaaaattgcaggcacaaggaggatgcgggagttatctgctcagaa | |
| 821<br>2461 | F M S L R L T S E A S R E A C A G R L E<br>ttcatgtctctgagactgaccagtgaagccagcagagaggcctgtgcagggcgtctggaa | |
| 841<br>2521 | V F Y N G A W G T V G K S S M S E T T V<br>gttttttacaatggagcttggggcactgttggcaagagtagcatgtctgaaaccactgtg | |
| 861<br>2581 | G V V C R Q L G C A D K G K I N P A S L<br>ggtgtggtgtgcaggcagctgggctgtgcagacaaaggaaaatcaaccctgcatcttta | |

| | | | |
|---|---|---|---|
| SEQUENCE | | | ID NO |
| 881 | D K A M S I P M W V D N V Q C P K G P D | | |
| 2641 | gacaaggccatgtccattcccatgtgggtggacaatgttcagtgtccaaaaggacctgac | | |
| 901 | T L W Q C P S S P W E K R L A S P S E E | | |
| 2701 | acgctgtggcagtgcccatcatctccatgggagaagagactggccagccctcggaggag | | |
| 921 | T W I T C D N K I R L Q E G P T S C S G | | |
| 2761 | acctggatcacatgtgacaacaagataagacttcaggaaggacccacttcctgttctgga | | |
| 941 | R V E I W H G G S W G T V C D D S W D L | | |
| 2821 | cgtgtggagatctggcatggaggttcctgggggacagtgtgtgatgactcttgggacttg | | |
| 961 | D D A Q V V C Q Q L G C G P A L K A F K | | |
| 2881 | gacgatgctcaggtggtgtgtcaacaacttggctgtggtccagctttgaaagcattcaaa | | |
| 981 | E A E F G Q G T G P I W L N E V K C K G | | |
| 2941 | gaagcagagtttggtcaggggactggaccgatatggctcaatgaagtgaagtgcaaaggg | | |
| 1001 | N E S S L W D C P A R R W G H S E C G H | | |
| 3001 | aatgagtcttccttgtgggattgtcctgccagacgctggggccatagtgagtgtgggcac | | |
| 1021 | K E D A A V N C T D I S V Q K T P Q K A | | |
| 3061 | aaggaagacgctgcagtgaattgcacagatatttcagtgcagaaaaccccacaaaaagcc | | |
| 1041 | T T G R S S R Q S S F I A V G I L G V V | | |
| 3121 | acaacaggtcgctcatcccgtcagtcatcctttattgcagtcgggatccttggggttgtt | | |
| 1061 | L L A I F V A L F F L T K K A R Q R Q R | | |
| 3181 | ctgttggccattttcgtcgcattattcttcttgactaaaaaagcgaagacagagacagcgg | | |
| 1081 | L A V S S R G E N L V H Q I Q Y R E M N | | |
| 3241 | cttgcagtttcctcaagaggagagaacttagtccaccaaattcaataccgggagatgaat | | |
| 1101 | S C L N A D D L D L M N S S G G H S E P | | |
| 3301 | tcttgcctgaatgcagatgatctggacctaatgaattcctcaggaggccattctgagcca | | |
| 1121 | H | | |
| 3361 | cac | | |
| 1 | MSKLRMVLLE DSGSADFRRH FVNLSPFTIT VVLLLSACFV TSSLGGTDKE | | SEE ID |
| 51 | LRLVDGENKC SGRVEVKVQE EWGTVCNNGW SMEAVSVICN QLGCPTAIKA | | NO: 19 |
| 101 | PGWANSSAGS GRIWMDHVSC RGNESALWDC KHDGWGKHSN CTHQQDAGVT | | |
| 151 | CSDGSNLEMR LTRGGNMCSG RIEIKFQGRW GTVCDDNFNI DHASVICRQL | | |
| 201 | ECGSAVSFSG SSNFGEGSGP IWFDDLICNG NESALWNCKH QGWGKHNCDH | | |
| 251 | AEDAGVICSK GADLSLRLVD GVTECSGRLE VRFQGEWGTI CDDGWDSYDA | | |
| 301 | AVACKQLGCP TAVTAIGRVN ASKGFGHIWL DSVSCQGHEP AVWQCKHHEW | | |
| 351 | GKHYCNHNED AGVICSOGSD LELRLRGGGS RCAGTVEVEI QRLLGKVCDR | | |
| 401 | GWGLKEADVV CRQLGCGSAL KTSYQVYSKI QATNTWLFLS SCNGNETSLW | | |
| 451 | DCKNWQWGGL TCDRYEEAKI TCSAHREPRL VGGDIPCSGR VEVKHGDTWG | | |
| 501 | SICDSDFSLE AASVLCRELQ CGTVVSILGG AHFGEGNGQI WAEEFQCEGH | | |
| 551 | ESHLSLCPVA PRPEGTCSHS RDVGVVCSRY TEIRLVNGKT PCEGRVELKT | | |
| 601 | LGAWGSLCNS HWDIEDAHVL CQQLKCGVAL STPGGARFGK GNGQIWRHMF | | |
| 651 | HCTGTEQHMG DCPVTALGAS LCPSEQVASV ICSGNQSQTL SSCNSSSLGP | | |
| 701 | TRPTIPEESA VACIESGQLR LVNGGGRCAG RVEIYHEGSW GTICDDSWDL | | |
| 751 | SDAHVVCRQL GCGEAINATG SAHFGEGTGP IWLDEMKCNG KESRIWQCHS | | |
| 801 | HGWGQQNCRH KEDAGVICSE FMSLRLTSEA SREACAGRLE VFYNGAWGTV | | |
| 851 | GKSSMSETTV GVVCRQLGCA DKGKINPASL DKAMSIPMWV DNVQCPKGPD | | |
| 901 | TLWQCPSSPW EKRLASPSEE TWITCDNKIR LQEGPTSCSG RVEIWHGGSW | | |

| SEQUENCE | | | | | | ID NO |
|---|---|---|---|---|---|---|
| 951 | GTVCDDSWDL | DDAQVVCQQL | GCGPALKAFK | EAEFGQGTGP | IWLNEVKCKG | |
| 1001 | NESSLWDCPA | RRWGHSECGH | KIIOAVNCTD | ISVQKTPQKA | TTGRSSRQSS | |
| 1051 | FIAVGILGVV | LLAIFVALFF | LTKKRRQRQR | LAVSSRGENL | VHQIQYREMN | |
| 1101 | SCLNADDLDL | MNSSGGHSEP | H | | | |

Example 7

Cloning and Characterization of Murine CD163

Based on the murine CD163 sequence in GenBank (AF274883), a forward primer Mus-new5' (SEQ ID NO: 20) (5'-CACCGCGGCCGCCACACGGAGCCAT-CAAAATCATCAA-3') and a reverse primer Mus-new3' (SEQ ID NO:21) (5'-GGTACCGCGAACAAGCAAAC-CAATAGCAATATTGTTTAATTCCCTC-3') were designed using the PrimerSelect program. Restriction endonucleases sites for NotI and KpnI were included in 5' and 3' primers, respectively, to allow future cloning into other expression vectors. Mouse peritoneal macrophages were harvested from mice 2 days after injecting thioglycollate medium into the peritoneal cavity. Total cellular RNA was prepared from peritoneal macrophages using the RNeasy kit. RT-PCR reactions and RT-PCR parameters were the same as described in Example 4, except the annealing temperature was increased to 60° C. and extension temperature increased to 72° C. The PCR product was purified on a 0.8% SeaKem agarose gel and directionally cloned into pCDNA3.1D/V5/His/TOPO according to the manufacturer's instructions. Several clones with large inserts were identified for further analysis. A plasmid containing an insert (SEQ ID NO: 22) with a murine CD163 that encodes a protein of the same length as (1121 amino acids SEQ ID NO:24) and differs from Genbank AF274883 by only two amino acids (99.8% identity) was designated "pCDNA3.1D-murCD163v2".

Another plasmid, "pCDNA3.1D-murCD163v3 was generated which contained an insert (SEQ ID NO: 25) containing a murine CD163 coding sequence (SEQ ID NO: 26) which encodes a protein of 1159 amino acids in length (SEQ ID NO: 27). It differs from AF274883 by only 3 amino acids within the first 1107 residues (99.7% identity), but the sequences diverge completely beginning at residue 1108. This is due to an insertion of 82 nucleotides in the cDNA, and a concomitant shift in reading frame downstream of the insertion. As a result, murine CD163v3 contains 52 amino acids at its carboxy-terminus that are not homologous to the 14 carboxy-terminal residues of murine CD163v2. These two alternative versions of "full length" murine CD163 are most likely splice variant of the same gene, as has been described for human CD163 (Law, S. K., Micklem, K. J., Shaw, J. M., Zhang, X. P., Dong, Y., Willis, A. C. and Mason, D. Y. (1993) A new macrophage differentiation antigen which is a member of the scavenger receptor superfamily. European Journal of Immunology 23 (9), 2320-2325).

| SEQUENCE | | | | | | | ID NO |
|---|---|---|---|---|---|---|---|
| gctttggaat | gggtggacac | agaatggttc | ttcttggagg | tgctggatct | cctggttgta | 60 | SEQ ID |
| aaaggtttgt | ccatctaggt | ttctttgttg | tggctgtgag | ctcacttctc | agtgcctctg | 120 | NO: 22 |
| ctgtcactaa | cgctcctgga | gaaatgaaga | aggaactgag | actggcgggt | ggtgaaaaca | 180 | |
| actgtagtgg | gagagtggaa | cttaagatcc | atgacaagtg | gggcacagtg | tgcagtaacg | 240 | |
| gctggagcat | gaatgaagtg | tccgtggttt | gccagcagct | gggatgccca | acttctatta | 300 | |
| aagcccttgg | atgggctaac | tccagcgccg | gctctggata | tatctggatg | gacaaagttt | 360 | |
| cttgtacagg | gaatgagtca | gctctttggg | actgcaaaca | tgatgggtgg | ggaaagcata | 420 | |
| actgtaccca | tgaaaaagat | gctggagtga | cctgctcaga | tggatctaat | ttggagatga | 480 | |
| gactggtgaa | cagtgcgggc | caccgatgct | taggaagagt | agaaataaag | ttccagggaa | 540 | |
| agtgggggac | ggtgtgtgac | gacaacttca | gcaaagatca | cgcttctgtg | atttgtaaac | 600 | |
| agcttggatg | tggaagtgcc | attagtttct | ctggctcagc | taaattggga | gctggttctg | 660 | |
| gaccaatctg | gctcgatgac | ctggcatgca | atggaaatga | gtcagctctc | tgggactgca | 720 | |
| aacaccgggg | atggggcaag | cataactgtg | accatgctga | ggatgtcggt | gtgatttgct | 780 | |
| tagagggagc | agatctgagc | ctgagactag | tggatggagt | gtccagatgt | tcaggaagat | 840 | |
| tggaagtgag | attccaagga | gaatggggga | ccgtgtgtga | tgataactgg | gatctccggg | 900 | |
| atgcttctgt | ggtgtgcaag | caactgggat | gtccaactgc | catcagtgcc | attggtcgag | 960 | |
| ttaatgccag | tgagggatct | ggacagattt | ggcttgacaa | catttcatgc | gaaggacatg | 1020 | |

| SEQUENCE | ID NO |
|---|---|
| aggcaactct ttgggagtgt aaacaccaag agtggggaaa gcattactgt catcatagag | 1080 |
| aagacgctgg cgtgacatgt tctgatggag cagatctgga acttagactt gtaggtggag | 1140 |
| gcagtcgctg tgctggcatt gtggaggtgg agattcagaa gctgactggg aagatgtgta | 1200 |
| gccgaggctg gacactggca gatgcggatg tggtttgcag acagcttgga tgtggatctg | 1260 |
| cgcttcaaac ccaggctaag atctactcta aaactgggc aacaaatacg tggctctttc | 1320 |
| ctggatcttg taatggaaat gaaactactt tttggcaatg caaaaactgg cagtggggcg | 1380 |
| gcctttcctg tgataatttc gaagaagcca aagttacctg ctcaggccac agggaaccca | 1440 |
| gactggttgg aggagaaatc ccatgctctg gtcgtgtgga agtgaaacac ggagacgtgt | 1500 |
| ggggctccgt ctgtgatttt gacttgtctc tggaagctgc cagtgtggtg tgcagggaat | 1560 |
| tacaatgtgg aacagtcgtc tctatcctag ggggagcaca ttttggagaa ggaagtggac | 1620 |
| agatctgggt tgaagaattc cagtgtagtg gggatgagtc ccatctttca ctatgctcag | 1680 |
| tggcgccccc gctagacaga acttgtaccc acagcaggga tgtcagcgta gtctgctcac | 1740 |
| gatacataga tattcgtctg gcaggcggcg agtcctcctg tgagggaaga gtggagctca | 1800 |
| agacactcgg agcctggggt cccctctgca gttctcattg ggacatggaa gatgctcatg | 1860 |
| tcttatgtca gcagctgaag tgtgggggttg cccaatctat tccagaagga gcacattttg | 1920 |
| ggaaaggagc tggtcaggtc tggagtcaca tgttccactg cactggaact gaggaacata | 1980 |
| taggagattg cctcatgact gctctgggtg cgccgacgtg ttccgaagga caggtggcct | 2040 |
| ctgtcatctg ctcaggaaac caatcccaga cactattgcc atgtagttca ttgtctccag | 2100 |
| tccaaacaac aagctctaca attccaaagg agagtgaagt tccctgcata gcaagtggcc | 2160 |
| agcttcgctt ggtaggtgga ggtggtcgct gcgctggaag agtggaggtc taccacgagg | 2220 |
| gctcttgggg caccgtctgt gatgacaatt gggatatgac tgatgccaat gtggtgtgca | 2280 |
| agcagctgga ctgtggcgtg gcaattaacg ccactggctc tgcttacttc ggggaaggag | 2340 |
| caggagctat ctggctagac gaagtcatct gcactgggaa agagtctcat atttggcagt | 2400 |
| gccattcaca tggctgggga cgccataact gcaggcacaa agaagatgca ggtgttatct | 2460 |
| gctccgagtt catgtctctg aggctgacca acgaagccca caagaaaac tgcacaggtc | 2520 |
| gccttgaagt gttttacaat ggtacatggg gcagtattgg cagtagcaat atgtctccaa | 2580 |
| ccactgtggg ggtggtgtgc cgtcagctgg gctgtgcaga caacgggact gtgaaaccca | 2640 |
| taccttcaga caagacacca tccaggccca tgtgggtaga tcgtgtgcag tgtccaaaag | 2700 |
| gagttgacac tttgtggcag tgcccctcgt caccttggaa acagagacag gccagcccct | 2760 |
| cctcccagga gtcctggatc atctgtgaca acaaaataag actccaggaa gggcatacag | 2820 |
| actgttctgg acgtgtggag atctggcaca aaggttcctg gggaacagtg tgtgatgact | 2880 |
| cctgggatct taatgatgct aaggttgtat gtaagcagtt gggctgtggc caagctgtga | 2940 |
| aggcactaaa agaagcagca tttggtccag gaactgggcc catatggctc aatgaaatta | 3000 |
| agtgtagagg gaatgagtct tccctgtggg attgtcctgc caaccgtgg agtcacagcg | 3060 |
| actgtgggca caagaagat gcttccatcc agtgcctccc aaaaatgact tcagaatcac | 3120 |
| atcatggcac aggtcacccc accctcacgg cactcttggt ttgtggagcc attctattgg | 3180 |
| toctcctcat tgtcttcctc ctgtggactc tgaagcgacg acagattcag cgacttacag | 3240 |
| tttcctcaag aggagaggtc ttgatacatc aagttcagta ccaagagatg gattcaaagg | 3300 |
| cggatgatct ggacttgctg aaatcctcgg gggtcattca gaggcacact gagaaggaaa | 3360 |

| SEQUENCE | | ID NO |
|---|---|---|
| atgataattt ataatccact gaggttggag tttaagaagc cttgacagga cagccagcta | 3420 | |
| aatggaacaa gagcccaggc aacgcacgga tgaccacagc tgcatcttca tgcagtcctt | 3480 | |
| tgtttcctgg aactctgctg aacctgcaaa aaccatattt gtgaatgtga ccacttaata | 3540 | |
| gagatgggag actttt | 3556 | |

```
  1      M  G  G  H  R  M  V  L  L  G  G  A  G  S  P  G  C  K  R  F          SEQ ID
  1      atgggtggacacagaatggttcttcttggaggtgctggatctcctggttgtaaaaggttt          NO: 23

21      V  H  L  G  F  F  V  V  A  V  S  S  L  L  S  A  S  A  V  T          and 24
 61      gtccatctaggtttctttgttgtggctgtgagctcacttctcagtgcctctgctgtcact 41      N  A  P  G  E  M  K  K  E  L  R  L  A  G  G  E  N  N  C  S
121      aacgctcctggagaaatgaagaaggaactgagactggcgggtggtgaaaacaactgtagt 61      C  R  V  E  L  K  I  H  D  K  W  G  T  V  C  S  N  G  W  S
181      gggagagtggaacttaagatccatgacaagtggggcacagtgtgcagtaacggctggagc 81      M  N  E  V  S  V  V  C  Q  Q  L  G  C  P  T  S  I  K  A  L
241      atgaatgaagtgtccgtggtttgccagcagctgggatgcccaacttctattaaagccctt 101      G  W  A  N  S  S  A  G  S  G  Y  I  W  M  D  K  V  S  C  T
301      ggatgggctaactccagcgccggctctggatatatctggatggacaaagtttcttgtaca 121      G  N  E  S  A  L  W  D  C  K  H  D  G  W  G  K  H  N  C  T
361      gggaatgagtcagctcttttgggactgcaaacatgatgggtggggaaagcataactgtacc 141      H  E  K  D  A  G  V  T  C  S  D  G  S  N  L  E  M  R  L  V
421      catgaaaaagatgctggagtgacctgctcagatggatctaatttggagatgagactggtg 161      N  S  A  G  H  R  C  L  G  R  V  E  I  K  F  Q  G  K  W  G
481      aacagtgcgggccaccgatgcttaggaagagtagaaataaagttccagggaaagtggggg 181      T  V  C  D  D  N  F  S  K  D  H  A  S  V  I  C  K  Q  L  G
541      acggtgtgtgacgacaacttcagcaaagatcacgcttctgtgatttgtaaacagcttgga 201      C  G  S  A  I  S  F  S  G  S  A  K  L  G  A  G  S  G  P  I
601      tgtggaagtgccattagtttctctggctcagctaaattgggagctggttctggaccaatc 221      W  L  D  D  L  A  C  N  G  N  E  S  A  L  W  D  C  K  H  R
661      tggctcgatgacctggcatgcaatggaaatgagtcagctctctgggactgcaaacaccgg 241      G  W  G  K  H  N  C  D  H  A  E  D  V  G  V  I  C  L  E  G
721      ggatggggcaagcataactgtgaccatgctgaggatgtcggtgtgatttgcttagaggga 261      A  D  L  S  L  R  L  V  D  G  V  S  R  C  S  G  R  L  E  V
781      gcagatctgagcctgagactagtggatggagtgtccagatgttcaggaagattggaagtg 281      R  F  Q  G  E  W  G  T  V  C  D  D  N  W  D  L  R  D  A  S
841      agattccaaggagaatgggggaccgtgtgtgatgataactgggatctccgggatgcttct 301      V  V  C  K  Q  L  G  C  P  T  A  I  S  A  I  G  R  V  N  A
901      gtggtgtgcaagcaactgggatgtccaactgccatcagtgccattggtcgagttaatgcc 321      S  E  G  S  G  Q  I  W  L  D  N  I  S  C  E  G  H  E  A  T
961      agtgagggatctggacagatttggcttgacaacatttcatgcgaaggacatgaggcaact 341      L  W  E  C  K  H  Q  E  W  G  K  H  Y  C  H  H  R  E  D  A
1021     ctttggagtgtaaacaccaagagtggggaaagcattactgtcatcatagagaagacgct 361      G  V  T  C  S  D  G  A  D  L  E  L  R  L  V  G  G  S  R
1081     ggcgtgacatgttctgatggagcagatctggaacttagacttgtaggtggaggcagtcgc 381      C  A  G  I  V  E  V  E  I  Q  K  L  T  G  K  M  C  S  R  G
1141     tgtgctggcattgtggaggtggagattcagaagctgactgggaagatgtgtagccgaggc 401      W  T  L  A  D  A  D  V  V  C  R  Q  L  G  C  G  S  A  L  Q
1201     tggacactggcagatgcggatgtggtttgcagacagcttggatgtggatctgcgcttcaa 421      T  Q  A  K  I  Y  S  K  T  G  A  T  N  T  W  L  F  P  G  S
1261     acccaggctaagatctactctaaaactggggcaacaaatacgtggctcttttcctggatct 441      C  N  G  N  E  T  T  F  W  Q  C  K  N  W  Q  W  G  G  L  S
1321     tgtaatggaaatgaaactactttttggcaatgcaaaaactggcagtggggcggccttttcc
```

| SEQUENCE | | ID NO |
|---|---|---|
| 461<br>1381 | C D N F E E A K V T C S G H R E P R L V<br>tgtgataatttcgaagaagccaaagttacctgctcaggccacagggaacccagactggtt | |
| 481<br>1441 | G G E I P C S G R V E V K H G D V W G S<br>ggaggagaaatcccatgctctggtcgtgtggaagtgaaacacggagacgtgtggggctcc | |
| 501<br>1501 | V C D F D L S L E A A S V V C R E L Q C<br>gtctgtgattttgacttgtctctggaagctgccagtgtggtgtgcagggaattacaatgt | |
| 521<br>1561 | G T V V S I L G G A H F G E G S G Q I W<br>ggaacagtcgtctctatcctaggggagcacattttggagaaggaagtggacagatctgg | |
| 541<br>1621 | G E E F Q C S G D E S H L S L C S V A P<br>ggtgaagaattccagtgtagtggggatgagtcccatctttcactatgctcagtggcgccc | |
| 561<br>1681 | P L D R T C T H S R D V S V V C S R Y I<br>ccgctagacagaacttgtacccacagcagggatgtcagcgtagtctgctcacgatacata | |
| 581<br>1741 | D I R L A G G E S S C E G R V E L K T L<br>gatattcgtctggcaggcggcgagtcctcctgtgagggaagagtggagctcaagacactc | |
| 601<br>1801 | G A W G P L C S S H W D M E D A H V L C<br>ggagcctggggtcccctctgcagttctcattgggacatggaagatgctcatgtcttatgt | |
| 621<br>1861 | Q Q L K C G V A Q S I P E G A H F G K G<br>cagcagctgaagtgtggggttgcccaatctattccagaaggagcacattttgggaaagga | |
| 641<br>1921 | A G Q V W S H M F H C T G T E E H I G D<br>gctggtcaggtctggagtcacatgttccactgcactggaactgaggaacatataggagat | |
| 661<br>1981 | C L M T A L G A P T C S E G Q V A S V I<br>tgcctcatgactgctctgggtgcgccgacgtgttccgaaggacaggtggcctctgtcatc | |
| 681<br>2041 | C S G N Q S Q T L L P C S S L S P V Q T<br>tgctcaggaaaccaatcccagacactattgccatgtagttcattgtctccagtccaaaca | |
| 701<br>2101 | T S S T I P K E S E V P C I A S G Q L R<br>acaagctctacaattccaaaggagagtgaagttccctgcatagcaagtggccagcttcgc | |
| 721<br>2161 | L V G G G R C A G R V E V Y H E G S W<br>ttggtaggtggaggtggtcgctgcgctggaagagtggaggtctaccacgagggctcttgg | |
| 741<br>2221 | G T V C D D N W D M T D A N V V C K Q L<br>ggcaccgtctgtgatgacaattgggatatgactgatgccaatgtggtgtgcaagcagctg | |
| 761<br>2281 | D C G V A I N A T G S A Y F G E G A G A<br>gactgtggcgtggcaattaacgccactggctctgcttacttcggggaaggagcaggagct | |
| 781<br>2341 | I W L D E V I C T G K E S H I W Q C H S<br>atctggctagacgaagtcatctgcactgggaaagagtctcatatttggcagtgccattca | |
| 801<br>2401 | H G W G R H N C R H K E D A G V I C S E<br>catggctggggacgccataactgcaggcacaaagaagatgcaggtgttatctgctccgag | |
| 821<br>2461 | F M S L R L T N E A H K E N C T G R L E<br>ttcatgtctctgaggctgaccaacgaagcccacaaagaaaactgcacaggtcgccttgaa | |
| 841<br>2521 | V F Y N G T W G S I G S S N M S P T T V<br>gtgttttacaatggtacatggggcagtattggcagtagcaatatgtctccaaccactgtg | |
| 861<br>2581 | G V V C R Q L G C A D N G T V K P I P S<br>ggggtggtgtgccgtcagctgggctgtgcagacaacgggactgtgaaacccatacctca | |
| 881<br>2641 | D K T P S R P M W V D R V Q C P K G V D<br>gacaagacaccatccaggcccatgtgggtagatcgtgtgcagtgtccaaaaggagttgac | |
| 901<br>2701 | T L W Q C P S S P W K Q R Q A S P S S Q<br>actttgtggcagtgccccctcgtcaccttggaaacagagacaggccagcccctcctcccag | |
| 921<br>2761 | E S W I I C D N K I R L Q E G H T D C S<br>gagtcctggatcatctgtgacaacaaaataagactccaggaagggcatacagactgttct | |
| 941<br>2821 | G R V E I W H K G S W G T V C D D S W D<br>ggacgtgtggagatctggcacaaaggttcctggggaacagtgtgtgatgactcctgggat | |
| 961<br>2881 | L N D A K V V C K Q L G C G Q A V K A L<br>cttaatgatgctaaggttgtatgtaagcagttgggctgtggccaagctgtgaaggcacta | |

| SEQUENCE | | ID NO |
|---|---|---|
| 981<br>2941 | K E A A F G P G T G P I W L N E I K C R<br>aaagaagcagcatttggtccaggaactgggcccatatggctcaatgaaattaagtgtaga | |
| 1001<br>3001 | G N E S S L W D C P A K P W S H S D C G<br>gggaatgagtcttccctgtgggattgtcctgccaaaccgtggagtcacagcgactgtggg | |
| 1021<br>3061 | H K E D A S I Q C L P K M T S E S H H G<br>cacaaagaagatgcttccatccagtgcctcccaaaaatgacttcagaatcacatcatggc | |
| 1041<br>3121 | T G H P T L T A L L V C G A I L L V L L<br>acaggtcaccccaccctcacggcactcttggtttgtggagccattctattggtcctcctc | |
| 1061<br>3181 | I V F L L W T L K R R Q I Q R L T V S S<br>attgtcttcctcctgtggactctgaagcgacgacagattcagcgacttacagtttcctca | |
| 1081<br>3241 | R G E V L I H Q V Q Y Q E M D S K A D D<br>agaggagaggtcttgatacatcaagttcagtaccaagagatggattcaaaggcggatgat | |
| 1101<br>3301 | L D L L K S S G V I Q R H T E K E N D N<br>ctggacttgctgaaatcctcgggggtcattcagaggcacactgagaaggaaaatgataat | |
| 1121<br>3361 | L<br>tta | |
| 1<br>51<br>101<br>151<br>201<br>251<br>301<br>351<br>401<br>451<br>501<br>551<br>601<br>651<br>701<br>751<br>801<br>851<br>901<br>951<br>1001<br>1051<br>1101 | MGGHRMVLLG GAGSPGCKRF VHLGFFVVAV SSLLSASAVT NAPGEMKKEL<br>RLAGGENNCS GRVELKIHDK WGTVCSNGWS MNEVSVVCQQ LGCPTSIKAL<br>GWANSSAGSG YIWMDKVSCT GNESALWDCK HDGWGKHNCT HEKDAGVTCS<br>DGSNLEMRLV NSAGHRCLGR VEIKFQGKWG TVCDDNFSKD HASVICKQLG<br>CGSAISFSGS AKLGAGSGPI WLDDLACNGN ESALWDCKHR GWGKHNCDHA<br>EDVGVICLEG ADLSLRLVDG VSRCSGRLEV RFQGEWGTVC DDNWDLRDAS<br>VVCKQLGCPT AISAIGRVNA SEGSGQIWLD NISCEGHEAT LWECKHQEWG<br>KHYCHEREDA GVTCSDGADL ELRLVGGGSR CAGIVEVEIQ KLTGKMCSRG<br>WTLADADVVC RQLGCGSALQ TQAKIYSKTG ATNTWLFPGS CNGNETTFWQ<br>CKNWQWGGLS CDNEFEAKVT CSGHREPRLV GGEIPCSGRV EVKHGDVWGS<br>VCDFDLSLEA ASVVCRELQC GTVVSILGGA HFGEGSGQIW GEEFQCSGDE<br>SHLSLCSVAP PLDRTCTHSR DVSVVCSRYI DIRLAGGESS CEGRVELKTL<br>GAWGPLCSSH WDMEDAHVLC QQLKCGVAQS IPEGAHFGKG AGQVWSHMFH<br>CTGTEEHIGD CLMTALGAPT CSEGQVASVI CSGNQSQTLL PCSSLSPVQT<br>TSSTIPKESE VPCIASGQLR LVGGGGRCAG RVEVYHEGSW GTVCDDNWDM<br>TDANVVCKQL DCGVAINATG SAYFGEGAGA IWLDEVICTG KESHIWQCHS<br>HGWGRHNCRH KEDAGVICSE FMSLRLTNEA HKENCTGRLE VFYNGTWGSI<br>GSSNMSPTTV GVVCRQLGCA DNGTVKPIPS DKTPSRPMWV DRVQCPKGVD<br>TLWQCPSSPW KQRQASPSSQ ESWIICDNKI RLQEGHTDCS GRVEIWHKGS<br>WGTVCDDSWD LNDAKVVCKQ LGCGQAVKAL KEAAFGPGTG PIWLNEIKCR<br>GNESSLWDCP AKPWSHSDCG HKEDASIQCL PKMTSESHHG TGHPTLTALL<br>VCGAILLVLL IVFLLWTLKR RQIQRLTVSS RGEVLIHQVQ YQEMDSKADD<br>LDLLKSSGVI QRHTEKENDN L | SEQ ID<br>NO: 24 |
| gctttggaat gggtgacac agaatggttc tcttggagg tgctggatct cctggttgta | 60 | ID NO: 25 |
| aaaggtttgt ccatctaggt ttctttgttg tggctgtgag ctcacttctc agtgcctctg | 120 | |
| ctgtcactaa cgctcctgga gaaatgaaga aggaactgag actggcgggt ggtgaaaaca | 180 | |
| actgtagtgg gagagtggaa cttaagatcc atgacaagtg gggcacagtg tgcagtaacg | 240 | |

| SEQUENCE | | | | | ID NO |
|---|---|---|---|---|---|
| gctggagcat | gaatgaagtg | tccgtggttt | gccagcagct | gggatgccca acttctatta | 300 |
| aagcccttgg | atgggctaac | tccagcgccg | gctctggata | tatctggatg acaaagttt | 360 |
| cttgtacagg | gaatgagtca | gctctttggg | actgcaaaca | tgatgggtgg ggaaagcata | 420 |
| actgtaccca | tgaaaaagat | gctggagtga | cctgctcaga | tggatctaat ttggagatga | 480 |
| gactggtgaa | cagtgcgggc | caccgatgct | taggaagagt | agaaataaag ttccagggaa | 540 |
| agtgggggac | ggtgtgtgac | gacaacttca | gcaaagatca | cgcttctgtg atttgtaaac | 600 |
| agcttggatg | tggaagtgcc | attagtttct | ctggctcagc | taaattggga gctggttctg | 660 |
| gaccaatctg | gctcgatgac | ctggcatgca | atggaaatga | gtcagctctc tgggactgca | 720 |
| aacaccgggg | atggggcaag | cataactgtg | accatgctga | ggatgtcggt gtgatttgct | 780 |
| tagagggagc | agatctgagc | ctgagactag | tggatggagt | gtccagatgt tcaggaagat | 840 |
| tggaagtgag | attccaagga | gaatggggga | ccgtgtgtga | tgataactgg gatctccggg | 900 |
| atgcttctgt | ggtgtgcaag | caactgggat | gtccaactgc | catcagtgcc attggtcgag | 960 |
| ttaatgccag | tgagggatct | ggacagattt | ggcttgacaa | catttcatgc gaaggaaatg | 1020 |
| aggcaactct | ttgggagtgt | aaacaccaag | agtgggaaa | gcattactgt catcatagag | 1080 |
| aagacgctgg | cgtgacatgt | tctgatggag | cagatctgga | acttagactt gtaggtggag | 1140 |
| gcagtcgctg | tgctggcatt | gtggaggtgg | agattcagaa | gctgactggg aagatgtgta | 1200 |
| gccgaggctg | gacactggca | gatgcggatg | tggtttgcag | acagcttgga tgtggatctg | 1260 |
| cgcttcaaac | ccaggctaag | atctactcta | aaactggggc | aacaaatacg tggctctttc | 1320 |
| ctggatcttg | taatggaaat | gaaactactt | tttggcaatg | caaaaactgg cagtggggcg | 1380 |
| gcctttcctg | tgataatttc | gaagaagcca | agttacctg | ctcaggccac agggaaccca | 1440 |
| gactggttgg | aggagaaatc | ccatgctctg | gtcgtgtgga | aatgaaacac ggagacgtgt | 1500 |
| ggggctccgt | ctgtgatttt | gacttgtctc | tggaagctgc | cagtgtggtg tgcagggaat | 1560 |
| tacaatgtgg | aacagtcgtc | tctatcctag | ggggagcaca | ttttggagaa ggaagtggac | 1620 |
| agatctgggg | tgaagaattc | cagtgtagtg | gggatgagtc | ccatctttca ctatgctcag | 1680 |
| tggcgccccc | gctagacaga | acttgtaccc | acagcaggga | tgtcagcgta gtctgctcac | 1740 |
| gatacataga | tattcgtctg | gcaggcggcg | agtcctcctg | tgagggaaga gtggagctca | 1800 |
| agacactcgg | agcctggggt | cccctctgca | gttctcattg | ggacatggaa gatgctcatg | 1860 |
| tcttatgtca | gcagctgaag | tgtgggttg | cccaatctat | tccagaagga gcacattttg | 1920 |
| ggaaaggagc | tggtcaggtc | tggagtcaca | tgttccactg | cactggaact gaggaacata | 1980 |
| taggagattg | cctcatgact | gctctgggtg | cgccgacgtg | ttccgaagga caggtggcct | 2040 |
| ctgtcatctg | ctcaggaaac | caatcccaga | cactattgcc | atgtagttca ttgtctccag | 2100 |
| tccaaacaac | aagctctaca | attccaaagg | agagtgaagt | tccctgcata gcaagtggcc | 2160 |
| agcttcgctt | ggtaggtgga | ggtggtcgct | gcgctggaag | agtggaggtc taccacgagg | 2220 |
| gctcttgggg | caccgtctgt | gatgacaatt | gggatatgac | tgatgccaat gtggtgtgca | 2280 |
| agcagctgga | ctgtggcgtg | gcaattaacg | ccactggctc | tgcttacttc ggggaaggag | 2340 |
| caggagctat | ctggctagac | gaagtcatct | gcactgggaa | agagtctcat atttggcagt | 2400 |
| gccattcaca | tggctgggga | cgccataact | gcaggcacaa | agaagatgca ggtgttatct | 2460 |
| gctccgagtt | catgtctctg | aggctgacca | acgaagccca | caaagaaaac tgcacaggtc | 2520 |
| gccttgaagt | gttttacaat | ggtacatggg | gcagtattgg | cagtagcaat atgtctccaa | 2580 |

-continued

| SEQUENCE | | ID NO |
|---|---|---|
| ccactgtggg ggtggtgtgc cgtcagctgg gctgtgcaga caacgggact gtgaaaccca | 2640 | |
| taccttcaga caagacacca tccaggccca tgtgggtaga tcgtgtgcag tgtccaaaag | 2700 | |
| gagttgacac tttgtggcag tgcccctcgt caccttggaa acagagacag gccagcccct | 2760 | |
| cctcccagga gtcctggatc atctgtgaca acaaaataag actccaggaa gggcatacag | 2820 | |
| actgttctgg acgtgtggag atctggcaca aaggttcctg gggaacagtg tgtgatgact | 2880 | |
| cctgggatct taatgatgct aaggttgtat gtaagcagtt gggctgtggc caagctgtga | 2940 | |
| aggcactaaa agaagcagca tttggtccag gaactgggcc catatggctc aatgaaatta | 3000 | |
| agtgtagagg gaatgagtct tccctgtggg attgtcctgc caaccgtgg agtcacagcg | 3060 | |
| actgtgggca caagaagat gcttccatcc agtgcctccc caaaatgact tcagaatcac | 3120 | |
| atcatggcac aggtcacccc accctcacgg cactcttggt ttgtggagcc attctattgg | 3180 | |
| tcctcctcat tgtcttcctc ctgtggactc tgaagcgacg acagattcag cgacttacag | 3240 | |
| tttcctcaag aggagaggtc ttgatacatc aagttcagta ccaagagatg gattcaaagg | 3300 | |
| cggatgatct ggacttgctg aaatcctcgg aaaattccaa caattcatat gatttttaatg | 3360 | |
| atgatggact gacatctttg tctaaatatc ttcctatttc tggaattaaa aagggggtcat | 3420 | |
| tcagaggcac actgagaagg aaaatgataa tttataatcc actgaggttg gagtttaaga | 3480 | |
| agccttgaca ggacagccag ctaaatggaa caagagccca ggcaacgcac ggatgaccac | 3540 | |
| agctgcatct tcatgcagtc cttgtgtttcc tggaactctg ctgaacctgc aaaaaccata | 3600 | |
| tttgtgaatg tgaccactta atagagatgg gagactttt | 3639 | |

| 1<br>1 | M G G H R M V L L G G A G S P G C K R F<br>atgggtggacacagaatggttcttcttggaggtgctggatctcctggttgtaaaaggttt | ID NO: 26<br>and 27 |
|---|---|---|
| 21<br>61 | V H L G F F V V A V S S L L S A S A V T<br>gtccatctaggtttctttgttgtggctgtgagctcacttctcagtgcctctgctgtcact | |
| 41<br>121 | N A P G E M K K E L R L A G G E N N C S<br>aacgctcctggagaaatgaagaaggaactgagactggcgggtggtgaaaacaactgtagt | |
| 61<br>181 | G R V E L K I H D K W G T V C S N G W S<br>gggagagtggaacttaagatccatgacaagtggggcacagtgtgcagtaacggctggagc | |
| 81<br>241 | M N E V S V V C Q Q L G C P T S I K A L<br>atgaatgaagtgtccgtggtttgccagcagctgggatgcccaacttctattaaagccctt | |
| 101<br>301 | G W A N S S A G S G Y I W M D K V S C T<br>ggatgggctaactccagcgccggctctggatatatctggatggacaaagtttcttgtaca | |
| 121<br>361 | G N E S A L W D C K H D G W G K H N C T<br>gggaatgagtcagctctttgggactgcaaacatgatgggtgggaaagcataactgtacc | |
| 141<br>421 | H E K D A G V T C S D G S N L E M R L V<br>catgaaaaagatgctggagtgacctgctcagatggatctaattgtgagatgagactggtg | |
| 161<br>481 | N S A G H R C L G R V E I K F Q G K W G<br>aacagtgcgggccaccgatgcttaggaagagtagaaataaagttccagggaaagtggggg | |
| 181<br>541 | T V C D D N F S K D H A S V I C K Q L G<br>acggtgtgtgacgacaacttcagcaaagatcacgcttctgtgatttgtaaacagcttgga | |
| 201<br>601 | C G S A I S F S G S A K L G A G S G P I<br>tgtggaagtgccattagttttctctggctcagctaaattgggagctggttctggaccaatc | |
| 221<br>661 | W L D D L A C N G N E S A L W D C K H R<br>tggctcgatgacctggcatgcaatggaaatgagtcagctctctgggactgcaaacaccgg | |
| 241<br>721 | G W G K H N C D H A E D V G V I C L E G<br>ggatggggcaagcataactgtgaccatgctgaggatgtcggtgtgatttgcttagaggga | |
| 261<br>781 | A D L S L R L V D G V S R C S G R L E V<br>gcagatctgagcctgagactagtggatggagtgtccagatgttcaggaagattggaagtg | |

-continued

| SEQUENCE | | ID NO |
|---|---|---|
| 281 | R F Q G E W G T V C D D N W D L R D A S | |
| 841 | agattccaaggagaatgggggaccgtgtgtgatgataactgggatctccgggatgcttct | |
| 301 | V V C K Q L G C P T A I S A I G R V N A | |
| 901 | gtggtgtgcaagcaactgggatgtccaactgccatcagtgccattggtcgagttaatgcc | |
| 321 | S E G S G Q I W L D N I S C E G H E A T | |
| 961 | agtgagggatctggacagatttggcttgacaacatttcatgcgaaggacatgaggcaact | |
| 341 | L W E C K H Q E W G K H Y C H H R E D A | |
| 1021 | cttttggagtgtaaacaccaagagtggggaaagcattactgtcatcatagaagacgct | |
| 361 | G V T C S D G A D L E L R L V G G G S R | |
| 1081 | ggcgtgacatgttctgatggagcagatctggaacttagacttgtaggtggaggcagtcgc | |
| 381 | C A G I V E V E I Q K L T G K M C S R G | |
| 1141 | tgtgctggcattgtggaggtggagattcagaagctgactgggaagatgtgtagccgaggc | |
| 401 | W T L A D A D V V C R Q L G C G S A L Q | |
| 1201 | tggacactggcagatgcggatgtggtttgcagacagcttggatgtggatctgcgcttcaa | |
| 421 | T Q A K I Y S K T G A T N T W L F P G S | |
| 1261 | acccaggctaagatctactctaaaactggggcaacaaatacgtggctctttcctggatct | |
| 441 | C N G N E T T F W Q C K N W Q W G G L S | |
| 1321 | tgtaatggaaatgaaactactttttggcaatgcaaaaactggcagtggggcggcctttcc | |
| 461 | C D N F E E A K V T C S G H R E P R L V | |
| 1381 | tgtgataatttcgaagaagccaaagttacctgctcaggccacagggaacccagactggtt | |
| 481 | G G E I P C S G R V E M K H G D V W G S | |
| 1441 | ggaggagaaatcccatgctctggtcgtgtggaaatgaaacacggagacgtgtggggctcc | |
| 501 | V C D F D L S L E A A S V V C R E L Q C | |
| 1501 | gtctgtgattttgacttgtctctggaagctgccagtgtggtgtgcagggaattacaatgt | |
| 521 | G T V V S I L G G A H F G E G S G Q I W | |
| 1561 | ggaacagtcgtctctatcctaggggagcacattttggagaaggaagtggacagatctgg | |
| 541 | G E E F Q C S G D E S H L S L C S V A P | |
| 1621 | ggtgaagaattccagtgtagtggggatgagtcccatctttcactatgctcagtggcgccc | |
| 561 | P L D R T C T H S R D V S V V C S R Y I | |
| 1681 | ccgctagacagaacttgtacccacagcagggatgtcagcgtagtctgctcacgatacata | |
| 581 | D I R L A G G E S S C E G R V E L K T L | |
| 1741 | gatattcgtctggcaggcggcgagtcctcctgtgagggaagagtggagctcaagacactc | |
| 601 | G A W G P L C S S H W D M E D A H V L C | |
| 1801 | ggagcctggggtcccctctgcagttctcattgggacatggaagatgctcatgtcttatgt | |
| 621 | Q Q L K C G V A Q S I P E G A H F G K G | |
| 1861 | cagcagctgaagtgtggggttgcccaatctattccagaaggagcacattttgggaaagga | |
| 641 | A G Q V W S H M F H C T G T E E H I G D | |
| 1921 | gctggtcaggtctggagtcacatgttccactgcactggaactgaggaacatataggagat | |
| 661 | C L M T A L G A P T C S E G Q V A S V I | |
| 1981 | tgcctcatgactgctctgggtgcgccgacgtgttccgaaggacaggtggcctctgtcatc | |
| 681 | C S G N Q S Q T L L P C S S L S P V Q T | |
| 2041 | tgctcaggaaaccaatcccagacactattgccatgtagttcattgtctccagtccaaaca | |
| 701 | T S S T I P K E S E V P C I A S G Q L R | |
| 2101 | acaagctctacaattccaaggagagtgaagttccctgcatagcaagtggccagcttcgc | |
| 721 | L V G G G R C A G R V E V Y H E G S W | |
| 2161 | ttggtaggtggaggtggtcgctgcgctggaagagtggaggtctaccacgagggctcttgg | |
| 741 | G T V C D D N W D M T D A N V V C K Q L | |
| 2221 | ggcaccgtctgtgatgacaattgggatatgactgatgccaatgtggtgtgcaagcagctg | |
| 761 | D C G V A I N A T G S A Y F G E G A G A | |
| 2281 | gactgtggcgtggcaattaacgccactggctctgcttacttcggggaaggagcaggagct | |
| 781 | I W L D E V I C T G K E S H I W Q C H S | |
| 2341 | atctggctagacgaagtcatctgcactgggaaagagtctcatatttggcagtgccattca | |

| SEQUENCE | | ID NO |
|---|---|---|
| 801 | H G W G R H N C R H K E D A G V I C S E | |
| 2401 | catggctggggacgccataactgcaggcacaaagaagatgcaggtgttatctgctccgag | |
| 821 | F M S L R L T N E A H K E N C T G R L E | |
| 2461 | ttcatgtctctgaggctgaccaacgaagcccacaaagaaaactgcacaggtcgccttgaa | |
| 841 | V F Y N G T W G S I G S S N M S P T T V | |
| 2521 | gtgttttacaatggtacatgggcagtattggcagtagcaatatgtctccaaccactgtg | |
| 861 | G V V C R Q L G C A D N G T V K P I P S | |
| 2581 | ggggtggtgtgccgtcagctgggctgtgcagacaacgggactgtgaaacccataccttca | |
| 881 | D K T P S R P M W V D R V Q C P K G V D | |
| 2641 | gacaagacaccatccaggcccatgtgggtagatcgtgtgcagtgtccaaaaggagttgac | |
| 901 | T L W Q C P S S P W K Q R Q A S P 9 S Q | |
| 2701 | actttgtggcagtgcccctcgtcacctttggaaacagagacaggccagcccctcctcccag | |
| 921 | E S W I I C D N K I R L Q E G H T D C S | |
| 2761 | gagtcctggatcatctgtgacaacaaaataagactccaggaagggcatacagactgttct | |
| 941 | G R V E I W H K G S W G T V C D D S W D | |
| 2821 | ggacgtgtggagatctggcacaaaggttcctggggaacagtgtgtgatgactcctgggat | |
| 961 | L N D A K V V C K Q L G C G Q A V K A L | |
| 2881 | cttaatgatgctaaggttgtatgtaagcagttgggctgtggccaagctgtgaaggcacta | |
| 981 | K E A A F G P G T G P I W L N E I K C R | |
| 2941 | aaagaagcagcatttggtccaggaactgggcccatatggctcaatgaaattaagtgtaga | |
| 1001 | G N E S S L W D C P A K P W S H S D C G | |
| 3001 | gggaatgagtcttccctgtgggattgtcctgccaaaccgtggagtcacagcgactgtggg | |
| 1021 | H K E D A S I Q C L P K M T S E S H H G | |
| 3061 | cacaaagaagatgcttccatccagtgcctccccaaaatgacttcagaatcacatcatggc | |
| 1041 | T G H P T L T A L L V C G A I L L V L L | |
| 3121 | acaggtcaccccaccctcacggcactcttggtttgtggagccattctattggtcctcctc | |
| 1061 | I V F L L W T L K R R Q I Q R L T V S S | |
| 3181 | attgtcttcctcctgtggactctgaagcgacgacagattcagcgacttacagtttcctca | |
| 1081 | R G E V L I H Q V Q Y Q E M D S K A D D | |
| 3241 | agaggagaggtcttgatacatcaagttcagtaccaagagatggattcaaaggcggatgat | |
| 1101 | L D L L K S S E N S N N S Y D F N D D G | |
| 3301 | ctggacttgctgaaatcctcggaaaattccaacaattcatatgattttaatgatgatgga | |
| 1121 | L T S L S K Y L P I S G I K K G S F R G | |
| 3361 | ctgacatctttgtctaaatatcttcctatttctggaattaaaaagggtcattcagaggc | |
| 1141 | T L R R K M I I Y N P L R L E F K K P | |
| 3421 | acactgagaaggaaaatgataatttataatccactgaggttggagtttaagaagcct | |
| 1 | MGGHRMVLLG GAGSPGCKRF VHLGFFVVAV SSLLSASAVT NAPGEMKKEL | ID NO: 27 |
| 51 | RLAGGENNCS GRVELKIHDK WGTVCSNGWS MNEVSVVCQQ LGCPTSIKAL | |
| 101 | GWANSSAGSG YIWMDKVSCT GNESALWDCK HDGWGKHNCT HEKDAGVTCS | |
| 151 | DGSNLEMRLV NSAGHRCLGR VEIKFQGKWG TVCDDNFSKD HASVICKQLG | |
| 201 | CGSAISFSGS AKLGAGSGPI WLDDLACNGN ESALWDCKHR GWGKHNCDHA | |
| 251 | EDVGVICLEG ADLSLRLVDG VSRCSGRLEV RFQGEWGTVC DDNWDLRDAS | |
| 301 | VVCKQLGCPT AISAIGRVNA SEGSGQIWLD NISCEGHEAT LWECKHQEWG | |
| 351 | KHYCHHREDA GVTCSDGADL ELRLVGGGSR CAGIVEVEIQ KLTGKMCSRG | |
| 401 | WTLADADVVC RQLGCGSALQ TQAKIYSKTG ATNTWLFPGS CNGNETTFWQ | |
| 451 | CKNWQWGGLS CDNFEEAKVT CSGHREPRLV GGEIPCSGRV EMKHGDVWGS | |
| 501 | VCDFDLSLEA ASVVCRELQC GTVVSILGGA HFGEGSGQIW GEEFQCSGDE | |
| 551 | SHLSLCSVAP PLDRTCTHSR DVSVVCSRYI DIRLAGGESS CEGRVELKTL | |

-continued

| SEQUENCE | | | | | | ID NO |
|---|---|---|---|---|---|---|
| 601 | GAWGPLCSSH | WDMEDAHVLC | QQLKCGVAQS | IPEGAREGKG | AGQVWSHMFH | |
| 651 | CTGTEEHIGD | CLMTALGAPT | CSEGQVASVI | CSGNQSQTLL | PCSSLSPVQT | |
| 701 | TSSTIPKESE | VPCIASGQLR | LVGGGGRCAG | RVEVYHEGSW | GTVCDDNWDM | |
| 751 | TDANVVCKQL | DCGVAINATG | SAYFGEGAGA | IWLDEVICTG | KESHIWQCHS | |
| 801 | HGWGRHNCRH | KEDAGVICSE | FMSLRLTNEA | HKENCTGRLE | VFYNGTWGSI | |
| 851 | GSSNMSPTTV | GVVCRQLGCA | DNGTVKPIPS | DKTPSRPMWV | DRVQCPKGVD | |
| 901 | TLWQCPSSPW | KQRQASPSSQ | ESWIICDNKI | RLQEGHTDCS | GRVEIWHKGS | |
| 951 | WGTVCDDSWD | LNDAKVVCKQ | LGCGQAVKAL | KEAAFGPGTG | PIWLNEIKCR | |
| 1001 | GNESSLWDCP | AKPWSHSDCG | HKEDASIQCL | PKMTSESHHG | TGHPTLTALL | |
| 1051 | VCGAILLVLL | IVFLLWTLKR | RQIQRLTVSS | RGEVLIHQVQ | YQEMDSKADD | |
| 1101 | LDLLKSSENS | NNSYDFNDDG | LTSLSKYLPI | SGIKKGSFRG | TLRRKMIIYN | |
| 1151 | PLRLEFKKP | | | | | |

Example 8

Cloning and Characterization of MARC-145 CD163

A forward primer 5' simianCD163 (SEQ ID NO: 28) (5'-CACCGGAATGAGCAAACTCAGAATGG-3' based on human CD163) and a reverse primer HuCD163-3'Kpn (SEQ ID NO:29) (5'-TGCTCCGGTACCTAGTCCAGGTCT-TCATCAAGGTATCTTA-3') were used to amplify CD163 cDNA from MARC-145 African Green Monkey kidney cells. Total cellular RNA was prepared from MARC-145 cells using the RNeasy kit. RT-PCR parameters were the same as described in Example 4. RT-PCR products were cloned directionally into the pCDNA3.1D/V5/His/TOPO vector according to the manufacturer's instruction. Several clones containing large inserts were analyzed. Clone #25 was designated "pCDNA3.1D-MARC-CD163v2". This novel CD163 cDNA from MARC-145 cells is 1116 amino acids in length. When compared to the sequences in GenBank database, the MARC-145 CD163 amino acid sequence is 96.3% identical to human CD163 (Genbank Z22968), 84.7% identical to pig CD163 (Genbank AJ311716), and 73.9% identical to mouse CD163 (Genbank AF274883).

| SEQUENCE | | | | | | | ID NO |
|---|---|---|---|---|---|---|---|
| atgagcaaac | tcagaatggt | gctacttgaa | gactctggat | ctgctgacgt | cagaagacat | 60 | SEQ ID |
| tttgtcaact | tgagtccctt | cactattgct | gtggtcttac | ttctccgtgc | ctgttttgtc | 120 | NO: 30 |
| accagttctc | ttggaggaac | aaccaaggag | ctgaggctag | tggatggtga | aaacaagtgt | 180 | |
| agtgggagag | tggaagtgaa | aatccaggag | gagtggggaa | cggtgtgtaa | taatggctgg | 240 | |
| agcatggaag | cagtctctgt | gatttgtaac | cagctgggat | gtccaactgc | tatcaaagcc | 300 | |
| actgatggg | ctaattccag | tgcaggttct | ggacgcattt | ggatggatca | tgtttcttgt | 360 | |
| cgtgggaatg | agtcagctct | ttgggactgc | aaacatgatg | gatggggaaa | gcatagtaac | 420 | |
| tgtactcacc | aacaagatgc | tggagtgact | tgctcagatg | gatccgattt | ggaaatgagg | 480 | |
| ctgacgaatg | gagggaatat | gtgttctgga | agaatagaga | tcaaattcca | aggacagtgg | 540 | |
| ggaacagtgt | gtgatgataa | cttcaacatc | aatcatgcat | ctgtggtttg | taaacaactt | 600 | |
| gaatgtggaa | gtgctgtcag | tttctctggt | tcagctaatt | ttggagaagg | ctctggacca | 660 | |
| atctggtttg | atgatcttat | atgcaacgga | aatgagtcag | ctctctggaa | ctgcaaacat | 720 | |
| caaggatggg | gaaagcataa | ctgtgatcat | gctgaggatg | ctggagtgat | ttgctcaaag | 780 | |
| ggagcagatc | tgagcctgag | actggtagat | ggagtcactg | aatgttcagg | aagattagaa | 840 | |
| gtgagattcc | aaggagaatg | ggggacaata | tgtgatgacg | gctgggacag | tcatgatgct | 900 | |
| gctgtggcat | gcaagcaact | gggatgtcca | actgctatca | ccgccattgg | tcgagttaac | 960 | |
| gccagtgagg | gatttggaca | catctggctt | gacagtgttt | cttgccaggg | acatgaacct | 1020 | |
| gcggtctggc | aatgtaaaca | ccatgaatgg | ggaaagcatt | attgcaatca | caatgaagat | 1080 | |
| gctggcgtaa | catgttctga | tggatcagat | ctggagctaa | gacttagagg | tggaggcagc | 1140 | |
| cgctgtgctg | ggacagttga | ggtggagatt | cagagactgt | tagggaaggt | gtgtgacaga | 1200 | |
| ggctggggac | tgaaagaagc | tgatgtggtt | tgcaggcagc | tgggatgtgg | atctgcactc | 1260 | |
| aaaacatcct | atcaagtata | ctccaaaatc | caggcaacaa | acatgtggct | gtttctaagt | 1320 | |
| agctgtaacg | gaaatgaaac | ttctctttgg | gactgcaaga | actggcaatg | gggtggactt | 1380 | |
| acctgtgatc | actatgaaga | agccaaaatt | acctgctcag | cccacaggga | acccagactg | 1440 | |
| gttggaggag | acattccctg | ttctggacgc | gttgaagtga | agcatggtga | cacatggggc | 1500 | |
| tccgtctgtg | attcggattt | ctctctggaa | gctgccagcg | ttctatgcag | ggaattacag | 1560 | |
| tgtgcacag | tcgtctctat | cctggggga | gctcactttg | gagagggaaa | tggacagatc | 1620 | |
| tgggctgaag | aattccagtg | tgagggacat | gagtcccatc | tttcactctg | cccagtagca | 1680 | |
| ccccgcccag | aaggaacttg | tagccacagc | agggatgttg | gagtagtctg | ctcaagatac | 1740 | |
| acagaaattc | gcttggtgaa | tggcaagacc | ccatgtgagg | gcagagtgga | gctcaaaacg | 1800 | |
| cttaatgcct | ggggatccct | ctgcaactct | cactgggaca | tagaagatgc | ccacgttctt | 1860 | |
| tgccaacaac | ttaaatgtgg | agttgccctt | tctaccccag | gaggagcaca | ttttggaaaa | 1920 | |

| SEQUENCE | ID NO |
|---|---|
| ggaaatggtc aggtctggag gcatatgttt cactgcactg ggactgagca gcacatggga 1980 | |
| gattgtcctg taactgctct gggtgcttca ctatgtcctt cagggcaagt ggcctctgta 2040 | |
| atttgctcag gaaaccagtc ccaaacactg tcctcgtgca attcatcatc tctgggccca 2100 | |
| acaaggccta ccattccaga agaaagtgct gtggcctgca tagagagtgg tcaacttcgc 2160 | |
| ttggtaaatg gaggaggtcg ctgtgctggg agagtagaga tttatcatga gggctcctgg 2220 | |
| ggcaccatct gtgatgacag ctgggacctg agcgatgccc acgtggtgtg cagacagctg 2280 | |
| ggctggtgga aggccattaa tgccactggt tctgctcatt ttggagaagg aacagggccc 2340 | |
| atctggctgg atgagatgaa atgcaatgga aaagaatccc gcatttggca gtgccattca 2400 | |
| catggctggg gcagcaaaa ctgcaggcac aaggaggatg caggagttat ctgctcagag 2460 | |
| ttcatgtctc tgagactgac cagtgaagcc agcagagagg cctgtgcagg gcgtctagaa 2520 | |
| gtttttttaca acggagcttg ggcagtgtt ggcaggagta acatgtctga aaccactgtg 2580 | |
| ggtgtggtgt gcaggcagct gggctgtgca gacaaaggga aaatcaaccc tgcatcttta 2640 | |
| gacaaggcca tgtccattcc catgggggtg gacaatgttc agtgtccaaa aggacctgac 2700 | |
| acgctgtggc agtgcccatc atctccatgg gagaagagac tggccaggcc ctcggaggag 2760 | |
| acctgatca catgtgacaa caagatgaga ctacaagaag gacccacttc ctgttctgga 2820 | |
| cgtgtggaga tctggcacgg aggttcctgg gggacagtgt gtgatgactc ctgggacttg 2880 | |
| aacgatgctc aggtggtgtg tcaacaactt ggctgtggtc cagcttttgaa agcattcaaa 2940 | |
| gaagcagagt ttggtcaggg gactggaccc atatggctca atgaagtgaa gtgcaaaggg 3000 | |
| aatgagtctt ccttgtggga ttgtcctgcc agacgctggg gccacagtga gtgtggacac 3060 | |
| aaggaagacg ctgcagtgaa ttgcacagat atttcaacga acaaaacccc acaaaaagcc 3120 | |
| acaacaggtc agtcatccct tattgcagtc ggaatccttg gagttgttct cttggtcatt 3180 | |
| ttcgtcgcat tattcttgac tcaaaagcga agacagagac agcggcttac agtttcctca 3240 | |
| agaggagaga acttagtcca ccaaattcaa taccgggaga tgaattcttg cctgaatgca 3300 | |
| gatgatctgg acctaatgaa ttcctcagga ggccattctg aggcacactg aaaaggaaaa 3360 | |
| tgggaattta aacccagtg agccttgaag ataccttgat gaagacctgg acta 3414 | |

```
  1 M  S  K  L  R  M  V  L  L  E  D  S  G  S  A  D  V  R  R  H        SEQ ID NO:
  1 atgagcaaactcagaatggtgctacttgaagactctggatctgctgacgtcagaagacat       31 and 32

21 F  V  N  L  S  P  F  T  I  A  V  V  L  L  L  R  A  C  F  V
 61 tttgtcaacttgagtccctcactattgctgtggtcttacttctccgtgcctgttttgtc 41 T  S  S  L  G  G  T  T  K  E  L  R  L  V  D  G  E  N  K  C
121 accagttctcttggaggaacaaccaaggagctgaggctagtggatggtgaaaacaagtgt 61 S  G  R  V  E  V  K  I  Q  E  E  W  G  T  V  C  N  N  G  W
181 agtgggagagtggaagtgaaaatccaggaggagtggggaacggtgtgtaataatggctgg 81 S  M  E  A  V  S  V  I  C  N  Q  L  G  C  P  T  A  I  K  A
241 agcatggaagcagtctctgtgatttgtaaccagctgggatgtccaactgctatcaaagcc 101 T  G  W  A  N  S  S  A  G  S  G  R  I  W  M  D  H  V  S  C
301 actggatgggctaattccagtgcaggttctggacgcatttggatggatcatgtttcttgt 121 R  G  N  E  S  A  L  W  D  C  K  H  D  G  W  G  K  H  S  N
361 cgtgggaatgagtcagctctttgggactgcaaacatgatggatggggaaagcatagtaac 141 C  T  H  Q  Q  D  A  G  V  T  C  S  D  G  S  D  L  E  M  R
421 tgtactcaccaacaagatgctggagtgacttgctcagatggatccgatttggaaatgagg 161 L  T  N  G  G  N  M  C  S  G  R  I  E  I  K  F  Q  G  Q  W
481 ctgacgaatggagggaatatgtgttctggaagaatagagatcaaattccaaggacagtgg 181 G  T  V  C  D  D  N  F  N  I  N  H  A  S  V  V  C  K  Q  L
541 ggaacagtgtgtgatgataacttcaacatcaatcatgcatctgtggtttgtaaacaactt 201 E  C  G  S  A  V  S  F  S  G  S  A  N  F  G  E  G  S  G  P
601 gaatgtggaagtgctgtcagtttctctggttcagctaattttggagaaggctctggacca 221 I  W  F  D  D  L  I  C  N  G  N  E  S  A  L  W  N  C  K  H
661 atctggtttgatgatcttatatgcaacggaaatgagtcagctctctggaactgcaaacat 241 Q  G  W  G  K  H  N  C  D  H  A  E  D  A  G  V  I  C  S  K
721 caaggatggggaaagcataactgtgatcatgctgaggatgctggagtgatttgctcaaag 261 G  A  D  L  S  L  R  L  V  D  G  V  T  E  C  S  G  R  L  E
781 ggagcagatctgagcctgagactggtagatggagtcactgaatgttcaggaagattagaa 281 V  R  F  Q  G  E  W  G  T  I  C  D  D  G  W  D  S  H  D  A
841 gtgagattccaaggagaatgggggacaatatgtgatgacggctgggacagtcatgatgct 301 A  V  A  C  K  Q  L  G  C  P  T  A  I  T  A  I  G  R  V  N
901 gctgtggcatgcaagcaactgggatgtccaactgctatcaccgccattggtcgagttaac 321 A  S  E  G  F  G  H  I  W  L  D  S  V  S  C  Q  G  H  E  P
961 gccagtgagggatttggacacatctggcttgacagtgttccttgccagggacatgaacct
```

| SEQUENCE | ID NO |
|---|---|

```
341 A   V   W   Q   C   K   H   H   E   W   G   K   H   Y   G   N   H   N   E   D
1021 gcggtctggcaatgtaaacaccatgaatggggaaagcattattgcaatcacaatgaagat 361 A   G   V   T   C   S   D   G   S   D   L   E   L   R   L   R   G   G   G   S
1081 gctggcgtaacatgttctgatggatcagatctggagctaagacttagaggtggaggcagc 381 R   C   A   G   T   V   E   V   E   I   Q   R   L   L   G   K   V   C   D   R
1141 cgctgtgctgggacagttgaggtggagattcagagactgttagggaaggtgtgtgacaga 401 G   W   G   L   K   E   A   D   V   V   C   R   Q   L   G   C   G   S   A   L
1201 ggctggggactgaaagaagctgatgtggtttgcaggcagctgggatgtggatctgcactc 421 K   T   S   Y   Q   V   Y   S   K   I   Q   A   T   N   M   W   L   F   L   S
1261 aaaacatcctatcaagtatactccaaaatccaggcaacaaacatgtggctgtttctaagt 441 S   C   N   G   N   E   T   S   L   W   D   C   K   N   W   Q   W   G   G   L
1321 agctgtaacggaaatgaaacttctctttgggactgcaagaactggcaatggggtggactt 461 T   C   D   H   Y   E   E   A   K   I   T   C   S   A   H   R   E   P   R   L
1381 acctgtgatcactatgaagaagccaaaattacctgctcagcccacagggaacccagactg 481 V   G   G   D   I   P   C   S   G   R   V   E   V   K   H   G   D   T   W   G
1441 gttggaggagacattccctgttctggacgcgttgaagtgaagcatggtgacacatggggc 501 S   V   C   D   S   D   F   S   L   E   A   A   S   V   L   C   R   E   L   Q
1501 tccgtctgtgattcggatttctctctggaagctgccagcgttctatgcagggaattacag 521 C   G   T   V   V   S   I   L   G   G   A   H   F   G   E   G   N   G   Q   I
1561 tgtggcacagtcgtctctatcctggggggagctcactttggagagggaaatggacagatc 541 W   A   E   E   F   Q   C   E   G   H   E   S   H   L   S   L   C   P   V   A
1621 tgggctgaagaattccagtgtgagggacatgagtcccatcttcactctgcccagtagca 561 P   R   P   E   G   T   C   S   H   S   R   D   V   G   V   V   C   S   R   Y
1681 ccccgcccagaaggaacttgtagccacagcagggatgttggagtagtctgctcaagatac 581 T   E   I   R   L   V   N   G   K   T   P   C   E   G   R   V   E   L   K   T
1741 acagaaattcgcttggtgaatggcaagaccccatgtgagggcagagtggagctcaaaacg 601 L   N   A   W   G   S   L   C   N   S   H   W   D   I   E   D   A   H   V   L
1801 cttaatgcctggggatccctctgcaactctcactgggacatagaagatgcccacgttctt 621 C   Q   Q   L   K   C   G   V   A   L   S   T   P   G   G   A   H   F   G   K
1861 tgccaacaacttaaatgtggagttgccctttctaccccaggaggagcacattttggaaaa 641 G   N   G   Q   V   W   R   H   M   F   H   C   T   G   T   E   Q   H   M   G
1921 ggaaatggtcaggtctggaggcatatgtttcactgcactgggactgagcagcacatggga 661 D   C   P   V   T   A   L   G   A   S   L   C   P   S   G   Q   V   A   S   V
1981 gattgtcctgtaactgctctgggtgcttcactatgtccttcagggcaagtggcctctgta 681 I   C   S   G   N   Q   S   Q   T   L   S   S   C   N   S   S   S   L   G   P
2041 atttgctcaggaaaccagtcccaaacactgtcctcgtgcaattcatcatctctgggccca 701 T   R   P   T   I   P   E   E   S   A   V   A   C   I   E   S   G   Q   L   R
2101 acaaggcctaccattccagaagaaagtgctgtggcctgcatagagagtggtcaacttcgc 721 L   V   N   G   G   G   R   C   A   G   R   V   E   I   Y   H   E   G   S   W
2161 ttggtaaatggaggaggtcgctgtgctgggagagtagagatttatcatgagggctcctgg 741 G   T   I   C   D   D   S   W   D   L   S   D   A   H   V   V   C   R   Q   L
2221 ggcaccatctgtgatgacagctgggacctgagcgatgcccacgtggtgtgcagacagctg 761 G   C   G   E   A   I   N   A   T   G   S   A   H   F   G   E   G   T   G   P
2281 ggctgtggagaggccattaatgccactggttctgctcattttggagaaggaacagggccc 781 I   W   L   D   E   M   K   C   N   G   K   E   S   R   I   W   Q   C   H   S
2341 atctggctggatgagatgaaatgcaatggaaaagaatcccgcatttggcagtgccattca 801 H   G   W   G   Q   Q   N   C   R   H   K   E   D   A   G   V   I   C   S   E
2401 catggctgggggcagcaaaactgcaggcacaaggaggatgcaggagttatctgctcagag 821 F   M   S   L   R   L   T   S   E   A   S   R   E   A   C   A   G   R   L   E
2461 ttcatgtctctgagactgaccagtgaagccagcagagaggcctgtgcagggcgtctagaa 841 V   F   Y   N   G   A   W   G   S   V   G   R   S   N   M   S   E   T   T   V
2521 gtttttacaacggagcttggggcagtgttggcaggagtaacatgtctgaaaccactgtg
```

-continued

```
SEQUENCE                                                            ID NO

861 G   V   V   C   R   Q   L   G   C   A   D   K   G   K   I   N   P   A   S   L
2581 ggtgtggtgtgcaggcagctgggctgtgcagacaaagggaaaatcaaccctgcatcttta 881 D   K   A   M   S   I   P   M   W   V   D   N   V   Q   C   P   K   G   P   D
2641 gacaaggccatgtccattcccatgtgggtggacaatgttcagtgtccaaaaggacctgac 901 T   L   W   Q   C   P   S   S   P   W   E   K   R   L   A   R   P   S   E   E
2701 acgctgtggcagtgcccatcatctccatgggagaagagactggccaggccctcggaggag 921 T   W   I   T   C   D   N   K   M   R   L   Q   E   G   P   T   S   C   S   G
2761 acctggatcacatgtgacaacaagatgagactacaagaaggacccacttcctgttctgga 941 R   V   E   I   W   H   G   G   S   W   G   T   V   C   D   D   S   W   D   L
2821 cgtgtggagatctggcacggaggttcctggggacagtgtgtgatgactcctgggacttg 961 N   D   A   Q   V   V   C   Q   Q   L   G   C   G   P   A   L   K   A   F   K
2881 aacgatgctcaggtggtgtgtcaacaacttggctgtggtccagcttttgaaagcattcaaa 981 E   A   E   F   G   Q   G   T   G   P   I   W   L   N   E   V   K   C   K   G
2941 gaagcagagtttggtcaggggactggacccatatggctcaatgaagtgaagtgcaaaggg 1001 N   E   S   S   L   W   D   C   P   A   R   R   W   G   H   S   E   C   G   H
3001 aatgagtcttccttgtgggattgtcctgccagacgctggggccacagtgagtgtggacac 1021 K   E   D   A   A   V   N   C   T   D   I   S   T   N   K   T   P   Q   K   A
3061 aaggaagacgctgcagtgaattgcacagatatttcaacgaacaaaacccacaaaaagcc 1041 T   T   G   Q   S   S   L   I   A   V   G   I   L   G   V   V   L   L   V   I
3121 acaacaggtcagtcatcccttattgcagtcggaatccttggagttgttctcttggtcatt 1061 F   V   A   L   F   L   T   Q   K   R   R   Q   R   Q   R   L   T   V   S   S
3181 ttcgtcgcattattcttgactcaaaagcgaagacagagacagcggcttacagtttcctca 1081 R   G   E   N   L   V   H   Q   I   Q   Y   R   E   M   N   S   C   L   N   A
3241 agaggagagaacttagtccaccaaattcaataccgggagatgaattcttgcctgaatgca 1101 D   D   L   D   L   M   N   S   S   G   G   H   S   E   A   H
3301 gatgatctggacctaatgaattcctcaggaggccattctgaggcacac 1 MSKLRMVLLE DSGSADVRRH FVNLSPFTIA VVLLLRACFV TSSLGGTTKE         SEQ ID
  51 LRLVDGENKC SGRVEVKIQE EWGTVCNNGW SMEAVSVICN QLGCPTAIKA         NO: 32
 101 TGWANSSAGS GRIWNDHVSC RGNESALWDC KHDGWGKHSN CTHQQDAGVT
 151 CSDGSDLEMR LTNGGNMCSG RIEIKFQGQW CTVCDDNFNI NHASVVCKQL
 201 ECGSAVSFSG SANFGEGSGP IWFDDLICNG NESALWNCKH QGWGKHNCDH
 251 AEDAGVICSK GADLSLRLVD GVTECSGRLE VRFQGEWGTI CDDGWDSHDA
 301 AVACKQLGCP TAITAIGRVN ASEGFGHIWL DSVSCQGHEP AVWQCKHHEW
 351 GKHYCNHNED AGVTCSDGSD LELRLRGGGS RCAGTVEVEI QRLLCKVCDR
 401 GWGLKEADVV CRQLGCGSAL KTSYQVYSKI QATNMWLFLS SCNGNETSLW
 451 DCKNWQWGGL TCDHYEEAKI TCSAHREPRL VGGDIPCSGR VEVKHGDTWG
 501 SVCDSDFSLE AASVLCRELQ CGTVVSILGG AHFGEGNGQI WAEEFQCECH
 551 ESHLSLCPVA PRPECTCSHS RDVGVVCSRY TEIRLVNGKT PCEGRVELKT
 601 LNAWGSLCNS HWDIEDAHVL CQQLKCGVAL STPGGAHFGK GNGQVWRHMF
 651 HCTGTEQHMG DCPVTALGAS LCPSGQVASV ICSGNQSQTL SSCNSSSLGP
 701 TRPTIPEESA VACIESGQLR LVNGGGRCAG RVEIYHEGSW GTICDDSWDL
 751 SDAHVVCRQL GCGEAINATG SAHFGEGTGP IWLDEMKCNG KESRIWQCHS
 801 HGWGQQNCRH KEDAGVICSE FMSLRLTSEA SREACAGRLE VFYNGAWGSV
 851 GRSNMSETTV GVVCRQLGCA DKGKINPASL DKAMSIPMWV DNVQCPKGPD
 901 TLWQCPSSPW EKRLARPSEE TWITCDNKMR LQEGPTSCSG RVEIWHGGSW
 951 GTVCDDSWDL NDAQVVCQQL GCGPALKAFK EAEFGQGTGP IWLNEVKCKG
1001 NESSLWDCPA RRWGHSECGH KEDAAVNCTD ISTNKTPQKA TTGQSSLIAV
1051 GILGVVLLVI FVALFLTQKR RQRQRLTVSS RGENLVHQIQ YREMNSCLNA
1101 DDLDLMNSSG GHSEAH
```

Example 9

Cloning and Characterization of Simian CD163 from Vero Cells

Figure 17:
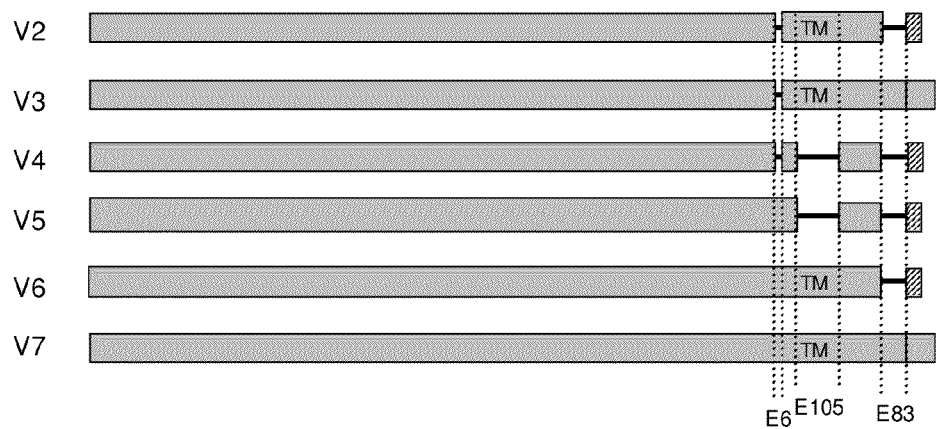
FIG. 17. Graphical depiction of six alternative splicing variants of CD163 mRNA recovered from Vero cells. The six variants differ in the presence or absence of three exons, designated E6, E105, and E83. Exons E6 and E105 have lengths that are multiples of three, and therefore do not result in a change in reading frame when absent. In contrast, the absence of E83 results in a shifted reading frame and an alternative amino acid sequence at the carboxy terminus of the protein (indicated by a hatched pattern in the figure). The hydrophobic transmembrane (TM) region is encoded within E105.
Figure 18:
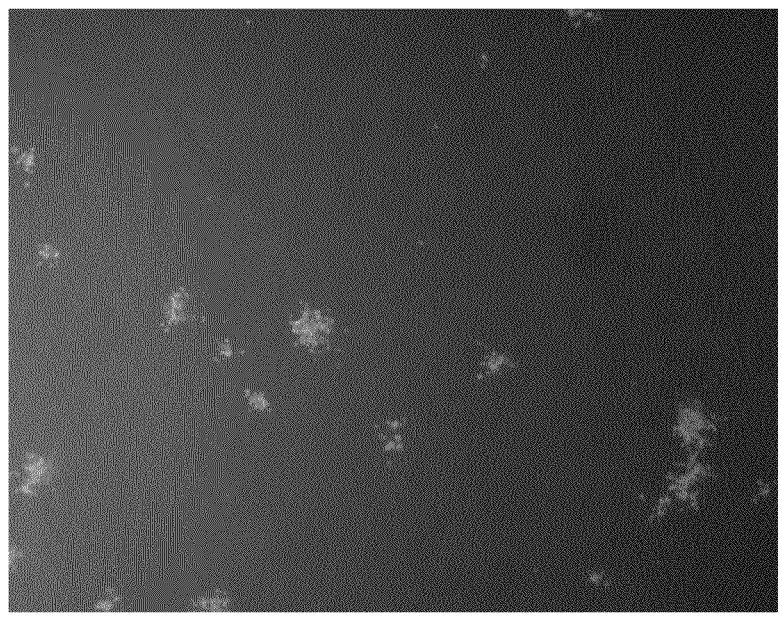
FIG. 18. PK-RSVScript-susCD163v2 #9 cells infected with PRRSV isolate P129. Undiluted supernatant from PRRSV isolate P201 infected PAMs was used to infect PK-RSVScript-susCD163v2 #9 cells. After two days of incubation the cells were fixed and stained with monoclonal antibody SDOW17 as described in Example 11.
Figure 19:
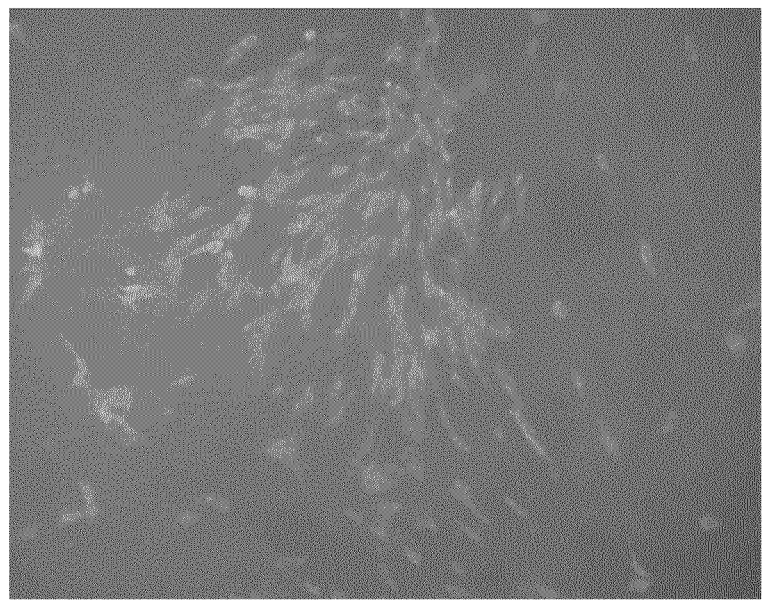
FIG. 19. FK-RSVScript-susCD163v2 #51 cells infected with PRRSV isolate P129. Undiluted supernatant from PRRSV isolate P201 infected PAMs was used to infect FK-RSVScript-susCD163v2 #51 cells. Two days post infection the cells were acetone fixed and stained with monoclonal antibody SDOW17 as described in Example 11.
Figure 20A:
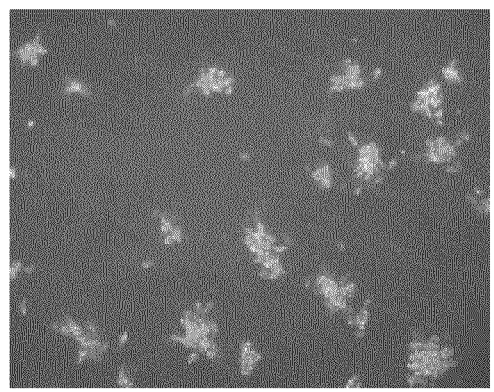
FIG. 20. Infection of PK-RSVScript-susCD163v2 clone #9 cells with PRRSV isolate P201. Panel A shows a monolayer of cells infected with PRRSV P201 at passage 1, twenty-four hours post infection. Panel B shows a monolayer of cells 2 days post infection with cell free supernatant PRRSV P201 at passage 10.
Figure 20B:
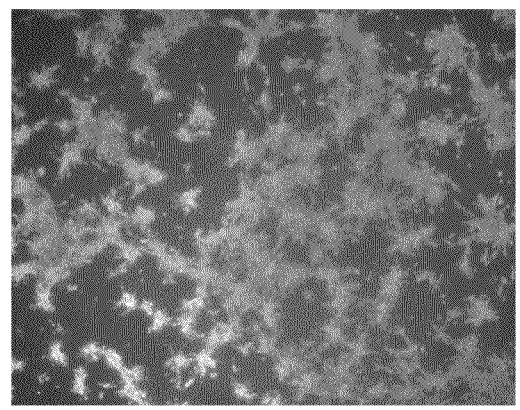

A forward primer 5' simianCD163 (SEQ ID NO: 28) (5'-CACCGGAATGAGCAAACTCAGAATGG-3' based on human CD163) and a reverse primer HuCD163-3'Kpn (SEQ ID NO:29) (5'-TGCTCCGGTACCTAGTCCAGGTCT-TCATCAAGGTATCTTA-3') were used to amplify CD163 cDNA from Vero cells. Total cellular RNA was prepared from Vero cells using the RNeasy kit. RT-PCR parameters were the same as described in Example 4. RT-PCR products were cloned directionally into the pCDNA3.1D/V5/His/TOPO vector according to the manufacturer's instruction. Eight clones containing large inserts were sequenced, and six discreet splicing patterns were found. These patterns are depicted graphically in FIG. 17.

The six splicing variants differ in the presence or absence of three exons, designated E6, E105, and E83. Omissions of E6 or E105 do not change the reading frame, whereas omission of E83 does. Patterns similar to v2 and/or v3 were also seen in porcine, murine, human, and MARC-145 monkey cells. Patterns v4 and v5 lack the 105-nucleotide exon that encodes the hydrophobic transmembrane region. These cDNAs were unable to render BHK cells permissive to PRRSV infection in a transient transfection assay, probably because the CD163 is secreted rather than remaining membrane bound. Although CD163 molecules lacking a transmembrane region appear to be non-functional as cellular permissivity factors, it is possible that they may have utility either in direct virus neutralization (similar to neutralizing antibodies), or as an immunogen for the induction of anti-CD163 antibodies which would block viral infection in the host animal.

The longest splice variant, v7, contains all three of the exons E6, E105, and E83. This novel CD163 cDNA from Vero cells encodes a polypeptide that is 1153 amino acids in length. When compared to the sequences in Genbank database, the Vero CD163v7 amino acid sequence is 95.4% identical to human CD163 (Genbank Z22968), 83.7% identical to pig CD163 (Genbank AJ311716), and 72.1% identical to mouse CD163 (Genbank AF274883). The nucleotide and amino acid sequences of the six splice variants found in Vero cells are provided below (SEQ ID NOS:33-44).

| SEQUENCE | ID NO |
|---|---|
| 1   M  S  K  L  R  M  V  L  L  E  D  S  G  S  A  D  V  R  R  H<br>1   ATGAGCAAACTCAGAATGGTGCTACTTGAAGACTCTGGATCTGCTGACGTCAGAAGACAT | SEQ ID NO:<br>33 and 34 |
| 21  F  V  N  L  S  P  F  T  I  A  V  V  L  L  L  R  A  C  F  V<br>61  TTTGTCAACTTGAGTCCCTTCACTATTGCTGTGGTCTTACTTCTCCGTGCCTGTTTTGTC | |
| 41  T  S  S  L  G  G  T  T  K  E  L  R  L  V  D  G  E  N  K  C<br>121 ACCAGTTCTCTTGGAGGAACAACCAAGGAGCTGAGGCTAGTGGATGGTGAAAACAAGTGT | |
| 61  S  G  R  V  E  V  K  I  Q  E  E  W  G  T  V  C  N  N  G  W<br>181 AGTGGGAGAGTGGAAGTGAAAATCCAGGAGGAGTGGGGAACGGTGTGTAATAATGGCTGG | |
| 81  S  M  E  A  V  S  V  I  C  N  Q  L  G  C  P  T  A  I  K  A<br>241 AGCATGGAAGCAGTCTCTGTGATTTGTAACCAGCTGGGATGTCCAACTGCTATCAAAGCC | |
| 101 T  G  W  A  N  S  S  A  G  S  G  R  I  W  M  D  H  V  S  C<br>301 ACTGGATGGGCTAATTCCAGTGCAGGTTCTGGACGCATTTGGATGGATCATGTTTCTTGT | |
| 121 R  G  N  E  S  A  L  W  D  C  K  H  D  G  W  G  K  H  S  N<br>361 CGTGGGAATGAGTCAGCTCTTTGGGACTGCAAACATGATGGATGGGGAAAGCATAGTAAC | |
| 141 C  T  H  Q  Q  D  A  G  V  T  C  S  D  G  S  D  L  E  M  R<br>421 TGTACTCACCAACAAGATGCTGGAGTAACTTGCTCAGATGGATCCGATTTGGAAATGAGG | |
| 161 L  T  N  G  G  N  M  C  S  G  R  I  E  I  K  F  Q  G  Q  W<br>481 CTGACGAATGGAGGGAATATGTGTTCTGGAAGAATAGAGATCAAATTCCAAGGACAGTGG | |
| 181 G  T  V  C  D  D  N  F  N  I  N  H  A  S  V  V  C  K  Q  L<br>541 GGAACAGTGTGTGATGATAACTTCAACATCAATCATGCATCTGTGGTTTGTAAACAACTT | |
| 201 E  C  G  S  A  V  S  F  S  G  S  A  N  F  G  E  G  S  G  P<br>601 GAATGTGGAAGTGCTGTCAGTTTCTCTGGTTCAGCTAATTTTGGAGAAGGCTCTGGACCA | |
| 221 I  W  F  D  D  L  I  C  N  G  N  E  S  A  L  W  N  C  K  H<br>661 ATCTGGTTTGATGATCTTATATGCAACGGAAATGAGTCAGCTCTCTGGAACTGCAAACAT | |
| 241 Q  G  W  G  K  H  N  C  D  H  A  E  D  A  G  V  I  C  S  K<br>721 CAAGGATGGGGAAAGCATAACTGTGATCATGCTGAGGATGCTGGAGTGATTTGCTCAAAG | |
| 261 G  A  D  L  S  L  R  L  V  D  G  V  T  E  C  S  G  R  L  E<br>781 GGAGCAGATCTGAGCCTGAGACTGGTAGATGGAGTCATGAATGTTCAGGAAGATTAGAA | |
| 281 V  R  F  Q  G  E  W  G  T  I  C  D  D  G  W  D  S  H  D  A<br>841 GTGAGATTCCAAGGAGAATGGGGGACAATATGTGATGACGGCTGGGACAGTCATGATGCT | |
| 301 A  V  A  C  K  Q  L  G  C  P  T  A  I  T  A  I  G  R  V  N<br>901 GCTGTGGCATGCAAGCAACTGGGATGTCCAACTGCTATCACCGCCATTGGTCGAGTTAAC | |
| 321 A  S  E  G  F  G  H  I  W  L  D  S  V  S  C  Q  G  H  E  P<br>961 GCCAGTGAGGGATTTGGACACATCTGGCTTGACAGTGTTTCTTGCCAGGGACATGAACCT | |
| 341 A  V  W  Q  C  K  H  H  E  W  G  K  H  Y  C  N  H  N  E  D<br>1021 GCGGTCTGGCAATGTAAACACCATGAATGGGGAAAGCATTATTGCAATCACAATGAAGAT | |
| 361 A  G  V  T  C  S  D  G  S  G  L  E  L  R  L  R  G  G  G  S<br>1081 GCTGGCGTAACATGTTCTGATGGATCAGGTCTGGAGCTAAGACTTAGAGGTGGAGGCAGC | |
| 381 R  C  A  G  T  V  E  V  E  I  Q  R  L  L  G  K  V  C  D  R<br>1141 CGCTGTGCTGGGACAGTTGAGGTGGAGATTCAGAGACTGTTAGGGAAGGTGTGTGACAGA | |
| 401 G  W  G  L  K  E  A  D  V  V  C  R  Q  L  G  C  G  S  A  L<br>1201 GGCTGGGGACTGAAAGAAGCTGATGTGGTTTGCAGGCAGCTGGGATGTGGATCTGCACTC | |

```
-continued
SEQUENCE                                                                    ID NO 421  K  T  S  Y  Q  V  Y  S  K  I  Q  A  T  N  M  W  L  F  L  S
1261  AAAACATCCTATCAAGTATACTCCAAAATCCAGGCAACAAACATGTGGCTGTTTCTAAGT 441  S  C  N  G  N  E  T  S  L  W  D  C  K  N  W  Q  W  G  G  L
1321  AGCTGTAACGGAAATGAAACTTCTCTTTGGGACTGCAAGAACTGGCAATGGGGTGGACTT 461  T  C  D  H  Y  E  E  A  K  I  T  C  S  A  H  R  E  P  R  L
1381  ACCTGTGATCACTATGAAGAAGCCAAAATTACCTGCTCAGCCCACAGGGAACCCAGACTG 481  V  G  G  D  I  P  C  S  G  R  V  E  V  K  H  G  D  T  W  G
1441  GTTGGAGGAGACATTCCCTGTTCTGGACGCGTTGAAGTGAAGCATGGTGACACATGGGGC 501  S  V  C  D  S  D  F  S  L  E  A  A  S  V  L  C  R  E  L  Q
1501  TCCGTCTGTGATTCGGATTTCTCTCTGGAAGCTGCCAGCGTTCTATGCAGGGAATTACAG 521  C  G  T  V  V  S  I  L  G  G  A  H  F  G  E  G  N  G  Q  I
1561  TGTGGCACAGTCGTCTCTATCCTGGGGGGAGCTCACTTTGGAGAGGGAAATGGACAGATC 541  W  T  E  E  F  Q  C  E  G  H  E  S  H  L  S  L  C  P  V  A
1621  TGGACTGAAGAATTCCAGTGTGAGGGACATGAGTCCCATCTTTCACTCTGCCCAGTAGCA 561  P  R  P  E  G  T  C  S  H  S  R  D  V  G  V  V  C  S  R  Y
1681  CCCCGCCCAGAAGGAACTTGTAGCCACAGCAGGGATGTTGGAGTAGTCTGCTCAAGATAC 581  T  E  I  R  L  V  N  G  K  T  P  C  E  G  R  V  E  L  K  T
1741  ACAGAAATTCGCTTGGTGAATGGCAAGACCCCATGTGAGGGCAGAGTGGAGCTCAAAACG 601  L  N  A  W  G  S  L  C  N  S  H  W  D  I  E  D  A  H  V  L
1801  CTTAATGCCTGGGGATCCCTCTGCAACTCTCACTGGGACATAGAAGATGCCCACGTTCTT 621  C  Q  Q  L  K  C  G  V  A  L  S  T  P  G  G  A  H  F  G  K
1861  TGCCAACAACTTAAATGTGGAGTTGCCCTTTCTACCCCAGGAGGAGCACATTTTGGAAAA 641  G  N  G  Q  V  W  R  H  M  F  H  C  T  G  T  E  Q  H  M  G
1921  GGAAATGGTCAGGTCTGGAGGCATATGTTTCACTGCACTGGGACTGAGCAGCACATGGGA 661  D  C  P  V  T  A  L  G  A  S  L  C  P  S  G  Q  V  A  S  V
1981  GATTGTCCTGTAACTGCTCTGGGTGCTTCACTATGTCCTTCAGGGCAAGTGGCCTCTGTA 681  I  C  S  G  N  Q  S  Q  T  L  S  S  R  N  S  S  S  L  G  P
2041  ATTTGCTCAGGAAACCAGTCCCAAACACTGTCCTCGCGCAATTCATCATCTCTGGGCCCA 701  T  R  P  T  I  P  E  E  S  A  V  A  C  I  E  S  G  Q  L  R
2101  ACAAGGCCTACCATTCCAGAAGAAAGTGCTGTGGCCTGCATAGAGAGTGGTCAACTTCGC 721  L  V  N  G  G  G  R  C  A  G  R  V  E  I  Y  H  E  G  S  W
2161  TTGGTAAATGGAGGAGGTCGCTGTGCTGGGAGAGTAGAGATTTATCATGAGGGCTCCTGG 741  G  T  I  C  D  D  S  W  D  L  S  D  A  H  V  V  C  R  Q  L
2221  GGCACCATCTGTGATGACAGCTGGGACCTGAGCGATGCCCACGTGGTGTGCAGACAGCTG 761  G  C  G  E  A  I  N  A  T  G  S  A  H  F  G  E  G  T  G  P
2281  GGCTGTGGAGAGGCCATTAATGCCACTGGTTCTGCTCATTTTGGAGAAGGAACAGGGCCC 781  I  W  L  D  E  M  K  C  N  G  K  E  S  R  I  W  Q  C  H  S
2341  ATCTGGCTGGATGAGATGAAATGCAATGGAAAAGAATCCCGCATTTGGCAGTGCCATTCA 801  H  G  W  G  Q  Q  N  C  R  H  K  E  D  A  G  V  I  C  S  E
2401  CATGGCTGGGGGCAGCAAAACTGCAGGCACAAGGAGGATGCAGGAGTTATCTGCTCAGAG 821  F  M  S  L  R  L  T  S  E  A  S  R  E  A  C  A  G  R  L  E
2461  TTCATGTCTCTGAGACTGACCAGTGAAGCCAGGAGAGAGGCCTGTGCAGGGCGTCTAGAA 841  V  F  Y  N  G  A  W  G  S  V  G  R  S  N  M  S  E  T  T  V
2521  GTTTTTTACAACGGAGCTTGGGGCAGTGTTGGCAGGAGTAACATGTCTGAAACCACTGTG 861  G  V  V  C  R  Q  L  G  C  A  D  K  G  K  I  N  S  A  S  L
2581  GGTGTAGTGTGCAGGCAGCTGGGCTGTGCAGACAAAGGGAAAATCAACTCTGCATCTTTA 881  D  K  A  M  S  I  P  M  W  V  D  N  V  Q  C  P  K  G  P  D
2641  GACAAGGCCATGTCCATTCCCATGTGGGTGGACAATGTTCAGTGTCCAAAAGGACCTGAC 901  T  L  W  Q  C  P  S  S  P  W  E  K  R  L  A  R  P  S  E  E
2701  ACGCTGTGGCAGTGCCCATCATCTCCATGGGAGAAGAGACTGGCCAGGCCCTCGGAGGAG 921  T  W  I  T  C  D  N  K  M  R  L  Q  E  G  P  T  S  C  S  G
2761  ACCTGGATCACATGTGACAACAAGATGAGACTACAAGAAGGACCCACTTCCTGTTCTGGA
```

| SEQUENCE | ID NO |
|---|---|
| 941 R V E I W H G G S W G T V C D D S W D L<br>2821 CGTGTGGAGATCTGGCACGGAGGTTCCTGGGGACAGTGTGTGATGACTCCTGGGACTTG | |
| 961 N D A Q V V C Q Q L G C G P A L K A F K<br>2881 AACGATGCTCAGGTGGTGTGTCAACAACTTGGCTGTGGTCCAGCTTTGAAAGCATTCAAA | |
| 981 E A E F G Q G T G P I W L N E V K C E G<br>2941 GAAGCAGAGTTTGGTCAGGGGACTGGACCCATATGGCTCAATGAAGTGAAGTGCGAAGGG | |
| 1001 N E S S L W D C P A R R W G H S E C G H<br>3001 AATGAGTCTTCCTTGTGGGATTGTCCTGCCAGACGCTGGGGCCACAGTGAGTGTGGACAC | |
| 1021 K E D A A V N C T D I S T R K T P Q K A<br>3061 AAGGAAGACGCTGCAGTGAATTGCACAGATATTTCAACGCGCAAAACCCCACAAAAGCC | |
| 1041 T T G Q S S L I A V G I L I V V L L A I<br>3121 ACAACAGGTCAGTCATCCCTTATTGCAGTCGGAATCCTTGGAGTTGTTCTCTTGGCCATT | |
| 1061 F V A L F L T Q K R R Q R Q R L T V S S<br>3181 TTCGTCGCATTATTCTTGACTCAAAAGCGAAGACAGAGACAGCGGCTTACAGTTTCCTCA | |
| 1081 R G E N L V H Q I Q Y R E M N S C L N A<br>3241 AGAGGAGAGAACTTAGTCCACCAAATTCAATACCGGGAGATGAATTCTTGCCTGAATGCA | |
| 1101 D D L D L M N S S G G H S E A H<br>3301 GATGATCTGGACCTAATGAATTCCTCAGGAGGCCATTCTGAGGCACAC | |
| 1 MSKLRMVLLE DSGSADVRRH FVNLSPFTIA VVLLLRACFV TSSLGGTTKE LRLVDGENKC<br>61 SGRVEVKIQE EWGTVCNNGW SMEAVSVICN QLGCPTAIKA TGWANSSAGS GRIWMDHVSC<br>121 RGNESALWDC KHDGWKHSN CTHQQDAGVT CSDGSDLEMR LTNGGNMCSG RIEIKFQGQW<br>181 GTVCDDNFNI NHASVVCKQL ECGSAVSFSG SANFGEGSGP IWFDDLICNG NESALWNCKH<br>241 QGWGKHNCDH AEDAGVICSK GADLSLRLVD GVTECSGRLE VRFQGEWGTI CDDGWDSHDA<br>301 AVACKQLGCP TAITAIGRVN ASEGFGHIWL DSVSCQGHEP AVWQCKHHEW GKHYCNHNED<br>361 AGVTCSDGSG LELRLRGGGS RCAGTVEVEI QRLLGKVCDR GWGLKEADVV CRQLGCGSAL<br>421 KTSYQVYSKI QATNMWLFLS SCNGNETSLW DCKNWQWGGL TCDHYEEAKI TCSAHREPRL<br>481 VGGDIPCSGR VEVKHGDTWG SVCDSDFSLE AASVLCRELQ CGTVVSILGG AHFGEGNGQI<br>541 WTEEFQCEGH ESHLSLCPVA PRPEGTCSHS RDVGVVCSRY TEIRLVNGKT PCEGRVELKT<br>601 LNAWGSLCNS HWDIEDAHVL CQQLKCGVAL STPGGAHFGK GNGQVWRHMF HCTGTEQHMG<br>661 DCPVTALGAS LCPSGQVASV ICSGNQSQTL SSRNSSSLGP TRPTIPEESA VACIESGQLR<br>721 LVNGGGRCAG RVEIYHEGSW GTICDDSWDL SDAHVVCRQL GCGEAINATG SAHFGEGTGP<br>781 IWLDEMKCNG KESRIWQCHS HGWGQQNCRH KEDAGVICSE FMSLRLTSEA SREACAGRLE<br>841 VFYNGAWGSV GRSNMSETTV GVVCRQLGCA DKGKINSASL DKAMSIPMWV DNVQCPKGPD<br>901 TLWQCPSSPW EKRLARPSEE TWITCDNKMR LQEGPTSCSG RVEIWHGGSW GTVCDDSWDL<br>961 NDAQVVCQQL GCGPALKAFK EAEFGQGTGP IWLNEVKCEG NESSLWDCPA RRWGHSECGH<br>1021 KEDAAVNCTD ISTRKTPQKA TTGQSSLIAV GILGVVLLAI FVALFLTQKR RQRQRLTVSS<br>1081 RGENLVHQIQ YREMNSCLNA DDLDLMNSSG GHSEAH | SEQ ID NO: 34 |
| 1 M S K L R M V L L E D S G S A D V R R H<br>1 ATGAGCAAACTCAGAATGGTGCTACTTGAAGACTCTGGATCTGCTGACGTCAGAAGACAT | SEQ ID NO: 35 and 36 |
| 21 F V N L S P F T I A V V L L L R A C F V<br>61 TTTGTCAACTTGAGTCCCTTCACTATTGCTGTGGTCTTACTTCTCCGTGCCTGTTTTGTC | |
| 41 T S S L G G T T K E L R L V D G E N K C<br>121 ACCAGTTCTCTTGGAGGAACAACCAAGGAGCTGAGGCTAGTGGATGGTGAAAACAAGTGT | |
| 61 S G R V E V K I Q E E W G T V C N N G W<br>181 AGTGGGAGAGTGGAAGTGAAAATCCAGGAGGAGTGGGGAACGGTGTGTAATAATGGCTGG | |
| 81 S M E A V S V I C N Q L G C P T A I K A<br>241 AGCATGGAAGCAGTCTCTGTGATTTGTAACCAGCTGGGATGTCCAACTGCTATCAAAGCC | |
| 101 T G W A N S S A G S G R I W M D H V S C<br>301 ACTGGATGGGCTAATTCCAGTCAGGTTCTGGACGCATTTGGATGGATCATGTTTCTTGT | |
| 121 R G N E S A L W D C K H D G W G K H S N<br>361 CGTGGGAATGAGTCAGCTCTTTGGGACTGCAAACATGATGGATGGGAAAGCATAGTAAC | |
| 141 C T H Q Q D A G V T C S D G S D L E M R<br>421 TGTACTCACCAACAAGATGCTGGAGTAACTTGCTCAGATGGATCCGATTTGGAAATGAGG | |
| 161 L T N G G N M C S G R I E I K F Q G Q W<br>481 CTGACGAATGGAGGGAATATGTGTTCTGGAAGAATAGAGATCAAATTCCAAGGACAGTGG | |
| 181 G T V C D D N F N I N H A S V V C K Q L<br>541 GGAACAGTGTGTGATGATAACTTCAACATCAATCATGCATCTGTGGTTTGTAAACAACTT | |

```
    201 E   C   G   S   A   V   S   F   S   G   S   A   N   F   G   E   G   S   G   P
    601 GAATGTGGAAGTGCTGTCAGTTTCTCTGGTTCAGCTAATTTTGGAGAAGGCTCTGGACCA

221 I   W   F   D   D   L   I   C   N   G   N   E   S   A   L   W   N   C   K   H
    661 ATCTGGTTTGATGATCTTATATGCAACGGAAATGAGTCAGCTCTCTGGAACTGCAAACAT

241 Q   G   W   G   K   H   N   C   D   H   A   E   D   A   G   V   I   C   S   K
    721 CAAGGATGGGGAAAGCATAACTGTGATCATGCTGAGGATGCTGGAGTGATTTGCTCAAAG

261 G   A   D   L   S   R   L   V   D   G   V   T   E   C   S   G   R   L   E
    781 GGAGCAGATCTGAGCCTGAGACTGGTAGATGGAGTCACTGAATGTTCAGGAAGATTAGAA

281 V   R   F   Q   G   E   W   G   T   I   C   D   D   G   W   D   S   H   D   A
    841 GTGAGATTCCAAGGAGAATGGGGACAATATGTGATGACGGCTGGGACAGTCATGATGCT

301 A   V   A   C   K   Q   L   G   C   P   T   A   I   T   A   I   G   R   V   N
    901 GCTGTGGCATGCAAGCAACTGGGATGTCCAACTGCTATCACCGCCATTGGTCGAGTTAAC

321 A   S   E   G   F   G   H   I   W   L   D   S   V   S   C   Q   G   H   E   P
    961 GCCAGTGAGGGATTTGGACACATCTGGCTTGACAGTGTTTCTTGCCAGGGACATGAACCT

341 A   V   W   Q   C   K   H   H   E   W   G   K   H   Y   C   N   H   N   E   D
   1021 GCGGTCTGGCAATGTAAACACCATGAATGGGGAAAGCATTATTGCAATCACAATGAAGAT

361 A   G   V   T   C   S   D   G   S   D   L   E   L   R   L   R   G   G   G   S
   1081 GCTGGCGTAACATGTTCTGATGGATCAGATCTGGAGCTAAGACTTAGAGGTGGAGGCAGC

381 R   C   A   G   T   V   E   V   E   I   Q   R   L   L   G   K   V   C   D   R
   1141 CGCTGTGCTGGgACAGTTGAGGTgGAGATTCAGAGACTGTTAGGGAAGGTGTGTGACAGA

401 G   W   G   L   K   E   A   D   V   V   C   R   Q   L   G   C   G   S   A   L
   1201 GGCTGGGGACTGAAAGAAGCTGATGTGGTTTGCAGGCAGCTGGGATGTGGATCTGCACTC

421 K   T   S   Y   Q   V   Y   S   K   I   Q   A   T   N   M   W   L   F   L   S
   1261 AAAACATCCTATCAAGTATACTCCAAAATCCAGGCAACAAACATGTGGCTGTTTCTAAGT

441 S   C   N   G   N   E   T   S   L   W   D   C   K   N   W   Q   W   G   G   L
   1321 AGCTGTAACGGAAATGAAACTTCTCTTTGGGACTGCAAGAACTGGCAATGGGTGGACTT

461 T   C   D   H   Y   E   E   A   K   I   T   C   S   A   H   R   E   P   R   L
   1381 ACCTGTGATCACTATGAAGAAGCCAAAATTACCTGCTCAGCCCACAGGGAACCCAGACTG

481 V   G   G   D   I   P   C   S   G   R   V   E   V   K   H   G   D   T   W   G
   1441 GTTGGAGGAGACATTCCCTGTTCTGGACGCGTTGAAGTGAAGCATGGTGACACATGGGGC

501 S   V   C   D   S   D   F   S   L   E   A   A   S   V   L   C   R   E   L   Q
   1501 TCCGTCTGTGATTCGGATTTCTCTCTGGAAGCTGCCAGCGTTCTATGCAGGGAATTACAG

521 C   G   T   V   V   S   I   L   G   G   A   H   F   G   E   G   N   G   Q   I
   1561 TGTGGCACAGTCGTCTCTATCCTGGGGGAGGCTCACTTTGGAGAGGGAAATGGACAGATC

541 W   T   E   E   F   Q   C   E   G   H   E   S   H   L   S   L   C   P   V   A
   1621 TGGACTGAAGAATTCCAGTGTGAGGGACATGAGTCCCATCTTTCACTCTGCCCAGTAGCA

561 P   R   P   E   G   T   C   S   H   S   R   D   V   G   V   V   C   S   R   Y
   1681 CCCCGCCCAGAAGGAACTTGTAGCCACAGCAGGGATGTTGGAGTAGTCTGCTCAAGATAC

581 T   E   I   R   L   V   N   G   K   T   P   C   E   G   R   V   E   L   K   T
   1741 ACAGAAATTCGCTTGGTGAATGGCAAGACCCCATGTGAGGGCAGAGTGGAGCTCAAAACG

601 L   N   A   W   G   S   L   C   N   S   H   W   D   I   E   D   A   H   V   L
   1801 CTTAATGCCTGGGGATCCCTCTGCAACTCTCACTGGGACATAGAAGATGCCCACGTTCTT

621 C   Q   Q   L   K   C   G   V   A   L   S   T   P   G   G   A   H   F   G   K
   1861 TGCCAACAACTTAAATGTGGAGTTGCCCTTTCTACCCCAGGAGGAGCACATTTTGGAAAA

641 G   N   G   Q   V   W   R   H   M   F   H   C   T   G   T   E   Q   H   M   G
   1921 GGAAATGGTCAGGTCTGGAGGCATATGTTTCACTGCACTGGGACTGAGCAGCACATGGGA

661 D   C   P   V   T   A   L   G   A   S   L   C   P   S   G   Q   V   A   S   V
   1981 GATTGTCCTGTAACTGCTCTGGGTGCTTCACTATGTCCTTCAGGGCAAGTGGCCTCTGTA

681 I   C   S   G   N   Q   S   Q   T   L   S   S   C   N   S   S   S   L   G   P
   2041 ATTTGCTCAGGAAACCAGTCCCAAACACTGTCCTCGTGCAATTCATCATCTCTGGGCCCA

701 T   R   P   T   I   P   E   E   S   A   V   A   C   I   E   S   G   Q   L   R
   2101 ACAAGGCCTACCATTCCAGAAGAAAGTGCTGTGGCCTGCATAGAGAGTGGTCAACTTCGC
```

```
SEQUENCE                                                                    ID NO

721 L  V  N  G  G  G  R  C  A  G  R  V  E  I  Y  H  E  G  S  W
2161 TTGGTAAATGGAGGAGGTCGCTGTGCTGGGAGAGTAGAGATTTATCATGAGGGCTCCTGG

741 G  T  I  C  D  D  S  W  D  L  S  D  A  H  V  V  C  R  Q  L
2221 GGCACCATCTGTGATGACAGCTGGGACCTGAGCGATGCCCACGTGGTGTGCAGACAGCTG

761 G  C  G  E  A  I  N  A  T  G  S  A  H  F  G  E  G  T  G  P
2281 GGCTGTGGAGAGGCCATTAATGCCACTGGTTCTGCTCATTTTGGAGAAGGAACAGGGCCC

781 I  W  L  D  E  M  K  C  N  G  K  E  S  R  I  W  Q  C  H  S
2341 ATCTGGCTGGATGAGATGAAATGCAATGGAAAAGAATCCCGCATTTGGCAGTGCCATTCA

801 H  G  W  G  Q  Q  N  C  R  H  K  E  D  A  G  V  I  C  S  E
2401 CATGGCTGGGGGCAGCAAAACTGCAGGCACAAGGAGGATGCAGGAGTTATCTGCTCAGAG

821 F  M  S  L  R  L  T  S  E  A  S  R  E  A  C  A  G  R  L  E
2461 TTCATGTCTCTGAGACTGACCAGTGAAGCCAGCAGAGAGGCCTGTGCAGGGCGTCTAGAA

841 V  F  Y  N  G  A  W  G  S  V  G  R  S  N  M  S  E  T  T  V
2521 GTTTTTTACAACGGAGCTTGGGGCAGTGTTGGCAGGAGTAACATGTCTGAAACCACTGTG

861 G  V  V  C  R  Q  L  G  C  A  D  K  G  K  I  N  S  A  S  L
2581 GGTGTAGTGTGCAGGCAGCTGGGCTGTGCAGACAAAGGGAAAATCAACTCTGCATCTTTA

881 D  K  A  M  S  I  P  M  W  V  D  N  V  Q  C  P  K  G  P  D
2641 GACAAGGCCATGTCCATTCCCATGTGGGTGGACAATGTTCAGTGTCCAAAAGGACCTGAC

901 T  L  W  Q  C  P  S  S  P  W  E  K  R  L  A  R  P  S  E  E
2701 ACGCTGTGGCAGTGCCCATCATCTCCATGGGAAGAGACTGGCCAGGCCCTCGGAGGAG

921 T  W  I  T  C  D  N  K  M  R  L  Q  E  G  P  T  S  C  S  G
2761 ACCTGGATCACATGTGACAACAAGATGAGACTACAAGAAGGACCCACTTCCTGTTCTGGA

941 R  V  E  I  W  H  G  G  S  W  G  T  V  C  D  D  S  W  D  L
2821 CGTGTGGAGATCTGGCACGGAGGTTCCTGGGGGACAGTGTGTGATGACTCCTGGGACTTG

961 N  D  A  Q  V  V  C  Q  Q  L  G  C  G  P  A  L  K  A  F  K
2881 AACGATGCTCAGGTGGTGTGTCAACAACTTGGCTGTGGTCCAGCTTTGAAAGCATTCAAA

981 E  A  E  F  G  Q  G  T  G  P  I  W  L  N  E  V  K  C  K  G
2941 GAAGCAGAGTTTGGTCAGGGGACTGGACCCATATGGCTCAATGAAGTGAAGTGCAAAGGG

1001 N  E  S  S  L  W  D  C  P  A  R  R  W  G  H  S  E  C  G  H
3001 AATGAGTCTTCCTTGTGGGATTGTCCTGCCAGACGCTGGGGCCACAGTGAGTGTGGACAC

1021 K  E  D  A  A  V  N  C  T  D  I  S  T  R  K  T  P  Q  K  A
3061 AAGGAAGACGCTGCAGTGAATTGCACAGATATTTCAACGCGCAAAACCCCACAAAAAGCC

1041 T  T  G  Q  S  S  L  I  A  V  G  I  L  G  V  V  L  L  A  I
3121 ACAACAGGTCAGTCATCCCTTATTGCAGTCGGAATCCTTGGAGTTGTTCTCTTGGCCATT

1061 F  V  A  L  F  L  T  Q  K  R  R  Q  R  Q  R  L  T  V  S  S
3181 TTCGTCGCATTATTCTTGACTCAAAAGCGAAGACAGAGACAGCGGCTTACAGTTTCCTCA

1081 R  G  E  N  L  V  H  Q  I  Q  Y  R  E  M  N  S  C  L  N  A
3241 AGAGGAGAGAACTTAGTCCACCAAATTCAATACCGGGAGATGAATTCTTGCCTGAATGCA

1101 D  D  L  D  L  M  N  S  S  E  N  S  N  E  S  A  D  F  N  A
3301 GATGATCTGGACCTAATGAATTCCTCAGAAAATTCCAATGAGTCAGCTGATTTCAATGCT

1121 A  E  L  I  S  V  S  K  F  L  P  I  S  G  M  E  K  E  A  I
3361 GCTGAACTAATTTCTGTGTCTAAATTTCTTCCTATTTCTGGAATGGAAAAGGAGGCCATT

1141 L  R  H  T  E  K  E  N  G  N  L
3421 CTGAGGCACACTGAAAAGGAAAATGGGAATTTA

1 MSKLRMVLLE DSGSADVRRH FVNLSPFTIA VVLLLRACFV TSSLGGTTKE LRLVDGENKC    SEQ ID
  61 SGRVEVKIQE EWGTVCNNGW SMEAVSVICN QLGCPTAIKA TGWANSSAGS GRIWMDHVSC    NO: 36
 121 RGNESALWDC KHDGWGKHSN CTHQQDAGVT CSDGSDLEMR LTNGGNMCSG RIEIKFQGQW
 181 GTVCDDNFNI NHASVVCKQL ECGSAVSFSG SANFGEGSGP IWFDDLICNG NESALWNCKH
 241 QGWGKHNCDH AEDAGVICSK GADLSLRLVD GVTECSGRLE VRFQGEWGTI CDDGWDSHDA
 301 AVACKQLGCP TAITAIGRVN ASEGFGHIWL DSVSCQGHEP AVWQCKHHEW GKHYCNHNED
 361 AGVTCSDGSD LELRLRGGGS RCAGTVEVEI QRLLGKVCDR GWGLKEADVV CRQLGCGSAL
 421 KTSYQVYSKI QATNMWLFLS SCNGNETSLW DCKNWQWGGL TCDHYEEAKI TCSAHREPRL
 481 VGGDIPCSGR VEVKHGDTWG SVCDSDFSLE AASVLCRELQ CGTVVSILGG AHFGEGNGQI
 541 WTEEFQCEGH ESHLSLCPVA PRPEGTCSHS RDVGVVCSRY TEIRLVNGKT PCEGRVELKT
 601 LNAWGSLCNS HWDIEDAHVL CQQLKCGVAL STPGGAHFGK GNGQVWRHMF HCTGTEQHMG
 661 DCPVTALGAS LCPSGQVASV ICSGNQSQTL SSCNSSSLGP TRPTIPEESA VACIESGQLR
```

```
SEQUENCE                                                                    ID NO

721  LVNGGGRCAG RVEIYHEGSW GTICDDSWDL SDAHVVCRQL GCGEAINATG SAHFGEGTGP
 781  IWLDEMKCNG KESRIWQCHS HGWGQQNCRH KEDAGVICSE FMSLRLTSEA SREACAGRLE
 841  VFYNGAWGSV GRSNMSETTV GVVCRQLGCA DKGKINSASL DKAMSIPMWV DNVQCPKGPD
 901  TLWQCPSSPW EKRLARPSEE TWITCDNKMR LQEGPTSCSG RVEIWHGGSW GTVCDDSWDL
 961  NDAQVVCQQL GCGPALKAFK EAEFGQGTGP IWLNEVKCKG NESSLWDCPA RRWGHSECGH
1021  KEDAAVNCTD ISTRKTPQKA TTGQSSLIAV GILGVVLLAI FVALFLTQKR RQRQRLTVSS
1081  RGENLVHQIQ YREMNSCLNA DDLDLMNSSE NSNESADFNA AELISVSKFL PISGMEKEAI
1141  LRHTEKENGN L

1  M  S  K  L  R  M  V  L  L  E  D  S  G  S  A  D  V  R  R  H            SEQ ID NO:
   1  ATGAGCAAACTCAGAATGGTGCTACTTGAAGACTCTGGATCTGCTGACGTCAGAAGACAT           37 and 38

21  F  V  N  L  S  P  F  T  I  A  V  V  L  L  L  R  A  C  F  V
  61  TTTGTCAACTTGAGTCCCTTCACTATTGCTGTGGTCTTACTTCTCCGTGCCTGTTTTGTC

41  T  S  S  L  G  G  T  T  K  E  L  R  L  V  D  G  E  N  K  C
 121  ACCAGTTCTCTTGGAGGAACAACCAAGGAGCTGAGGCTAGTGGATGGTGAAAACAAGTGT

61  S  G  R  V  E  V  K  I  Q  E  E  W  G  T  V  C  N  N  G  W
 181  AGTGGGAGAGTGGAAGTGAAAATCCAGGAGGAGTGGGGAACGGTGTGTAATAATGGCTGG

81  S  M  E  A  V  S  V  I  C  N  Q  L  G  C  P  T  A  I  K  A
 241  AGCATGGAAGCAGTCTCTGTGATTTGTAACCAGCTGGGATGTCCAACTGCTATCAAAGCC

101  T  G  W  A  N  S  S  A  G  S  G  R  I  W  M  D  H  V  S  C
 301  ACTGGATGGGCTAATTCCAGTGCAGGTTCTGGACGCATTTGGATGGATCATGTTTCTTGT

121  R  G  N  E  S  A  L  W  D  C  K  H  D  G  W  G  K  H  S  N
 361  CGTGGGAATGAGTCAGCTCTTTGGGACTGCAAACATGATGGATGGGAAAGCATAGTAAC

141  C  T  H  Q  Q  D  A  G  V  T  C  S  D  G  S  D  L  E  M  R
 421  TGTACTCACCAACAAGATGCTGGAGTAACTTGCTCAGATGGATCCGATTTGGAAATGAGG

161  L  T  N  G  G  N  M  C  S  G  R  I  E  I  K  F  Q  G  Q  W
 481  CTGACGAATGGAGGGAATATGTGTTCTGGAAGAATAGAGATCAAATTCCAAGGACAGTGG

181  G  T  V  C  D  D  N  F  N  I  N  H  A  S  V  V  C  K  Q  L
 541  GGAACAGTGTGTGATGATAACTTCAACATCAATCATGCATCTGTGGTTTGTAAACAACTT

201  E  C  G  S  A  V  S  F  S  G  S  A  N  F  G  E  G  S  G  P
 601  GAATGTGGAAGTGCTGTCAGTTTCTCTGGTTCAGCTAATTTTGGAGAAGGCTCTGGACCA

221  I  W  F  D  D  L  I  C  H  G  N  E  S  A  L  W  N  C  K  H
 661  ATCTGGTTTGATGATCTTATATGCAACGGAAATGAGTCAGCTCTCTGGAACTGCAAACAT

241  Q  G  W  G  K  H  N  C  D  H  A  E  D  A  G  V  I  C  S  K
 721  CAAGGATGGGGAAAGCATAACTGTGATCATGCTGAGGATGCTGGAGTGATTTGCTCAAAG

261  G  A  D  L  S  L  R  L  V  D  G  V  T  E  C  S  G  R  L  E
 781  GGAGCAGATCTGAGCCTGAGACTGGTAGATGGAGTCACTGAATGTTCAGGAAGATTAGAA

281  V  R  F  Q  G  E  W  G  T  I  C  D  D  G  W  D  S  H  D  A
 841  GTGAGATTCCAAGGAGAATGGGGGACAATATGTGATGACGGCTGGGACAGTCATGATGCT

301  A  V  A  C  K  Q  L  G  C  P  T  A  I  T  A  I  G  R  V  N
 901  GCTGTGGCATGCAAGCAACTGGGATGTCCAACTGCTATCACCGCCATTGGTCGAGTTAAC

321  A  S  E  G  F  G  H  I  W  L  D  S  V  S  C  Q  G  H  E  P
 961  GCCAGTGAGGGATTTGGACACATCTGGCTTGACAGTGTTTCTTGCCAGGGACATGAACCT

341  A  V  W  Q  C  K  H  H  E  W  G  K  H  Y  C  N  H  N  E  D
1021  GCGGTCTGGCAATGTAAACACCATGAATGGGGAAAGCATTATTGCAATCACAATGAAGAT

361  A  G  V  T  C  S  D  G  S  D  L  E  L  R  L  A  G  G  G  S
1081  GCTGGCGTAACATGTTCTGATGGATCAGATCTGGAGCTAAGACTTAGAGGTGGAGGCAGC

381  R  C  A  G  T  V  E  V  E  I  Q  R  L  L  G  K  V  C  D  R
1141  CGCTGTGCTGGGACAGTTGAGGTGGAGATTCAGAGACTGTTAGGGAAGGTGTGTGACAGA

401  G  W  G  L  K  E  A  D  V  V  C  R  Q  L  G  C  G  S  A  L
1201  GGCTGGGGACTGAAAGAAGCTGATGTGGTTTGCAGGCAGCTGGGATGTGGATCTGCACTC

421  K  T  S  Y  Q  V  Y  S  K  I  Q  A  T  N  M  W  L  F  L  S
1261  AAAACATCCTATCAAGTATACTCCAAAATCCAGGCAACAAACATGTGGCTGTTTCTAAGT

441  S  C  N  G  N  E  T  S  L  W  D  C  K  N  W  Q  W  G  G  L
1321  AGCTGTAACGGAAATGAAACTTCTCTTTGGGACTGCAAGAACTGGCAATGGGGTGGACTT
```

```
SEQUENCE                                                                    ID NO

461  T  C  D  H  Y  E  E  A  K  I  T  C  S  A  H  R  E  P  R  L
1381  ACCTGTGATCACTATGAAGAAGCCAAAATTACCTGCTCAGCCCACAGGGAACCCAGACTG

481  V  G  G  D  I  P  C  S  G  R  V  E  V  K  H  G  D  T  W  G
1441  GTTGGAGGAGACATTCCCTGTTCTGGACGCGTTGAAGTGAAGCATGGTGACACATGGGGC

501  S  V  C  D  S  D  F  S  L  E  A  A  S  V  L  C  R  E  L  Q
1501  TCCGTCTGTGATTCGGATTTCTCTCTGGAAGCTGCCAGCGTTCTATGCAGGGAATTACAG

521  C  G  T  V  V  S  I  L  G  G  A  H  F  G  E  G  N  G  Q  I
1561  TGTGGCACAGTCGTCTCTATCCTGGGGGGAGCTCACTTTGGAGAGGGAAATGGACAGATC

541  W  T  E  E  F  Q  C  E  G  H  E  S  H  L  S  L  C  P  V  A
1621  TGGACTGAAGAATTCCAGTGTGAGGGACATGAGTCCCATCTTTCACTCTGCCCAGTAGCA

561  P  R  P  E  G  T  C  S  H  S  R  D  V  G  V  V  C  S  R  Y
1681  CCCCGCCCAGAAGGAACTTGTAGCCACAGCAGGGATGTTGGAGTAGTCTGCTCAAGATAC

581  T  E  I  R  L  V  N  G  K  T  P  C  E  G  R  V  E  L  K  T
1741  ACAGAAATTCGCTTGGTGAATGGCAAGACCCCATGTGAGGGCAGAGTGGAGCTCAAAACG

601  L  N  A  W  G  S  L  C  N  S  H  W  D  I  E  D  A  H  V  L
1801  CTTAATGCCTGGGGATCCCTCTGCAACTCTCACTGGGACATAGAAGATGCCCACGTTCTT

621  C  Q  Q  L  K  C  G  V  A  L  S  T  P  G  G  A  H  F  G  K
1861  TGCCAACAACTTAAATGTGGAGTTGCCCTTTCTACCCCAGGAGGAGCACATTTTGGAAAA

641  G  N  G  Q  V  W  R  H  M  F  H  C  T  G  T  E  Q  H  M  G
1921  GGAAATGGTCAGGTCTGGAGGCATATGTTTCACTGCACTGGGACTGAGCAGCACATGGGA

661  D  C  P  V  T  A  L  G  A  S  L  C  P  S  G  Q  V  A  S  V
1981  GATTGTCCTGTAACTGCTCTGGGTGCTTCACTATGTCCTTCAGGGCAAGTGGCCTCTGTA

681  I  C  S  G  N  Q  S  Q  T  L  S  S  C  N  S  S  L  G  P
2041  ATTTGCTCAGGAAACCAGTCCCAAACACTGTCCTCGTGCAATTCATCATCTCTGGGCCCA

701  T  R  P  T  I  P  E  E  S  A  V  A  C  I  E  S  G  Q  L  R
2101  ACAAGGCCTACCATTCCAGAAGAAAGTGCTGTGGCCTGCATAGAGAGTGGTCAACTTCGC

721  L  V  N  G  G  G  R  C  A  G  R  V  E  I  Y  H  E  G  S  W
2161  TTGGTAAATGGAGGAGGTCGCTGTGCTGGGAGAGTAGAGATTTATCATGAGGGCTCCTGG

741  G  T  I  C  D  D  S  W  D  L  S  D  A  H  V  V  C  R  Q  L
2221  GGCACCATCTGTGATGACAGCTGGGACCTGAGCGATGCCCACGTGGTGTGCAGACAGCTG

761  G  C  G  E  A  I  N  A  T  G  S  A  H  F  G  E  G  T  G  P
2281  GGCTGTGGAGAGGCCATTAATGCCACTGGTTCTGCTCATTTTGGAGAAGGAACAGGGCCC

781  I  W  L  D  E  M  K  C  N  G  K  E  S  R  I  W  Q  C  H  S
2341  ATCTGGCTGGATGAGATGAAATGCAATGGAAAAGAATCCCGCATTTGGCAGTGCCATTCA

801  H  G  W  G  Q  Q  N  C  R  H  K  E  D  A  G  V  I  C  S  E
2401  CATGGCTGGGGGCAGCAAAACTGCAGGCACAAGGAGGATGCAGGAGTTATCTGCTCAGAG

821  F  M  S  L  R  L  T  S  E  A  S  R  E  A  C  A  G  R  L  E
2461  TTCATGTCTCTGAGACTGACCAGTGAAGCCAGCAGAGAGGCCTGTGCAGGGCGTCTAGAA

841  V  F  Y  N  G  A  W  G  S  V  G  R  S  N  M  S  E  T  T  V
2521  GTTTTTTACAACGGAGCTTGGGGCAGTGTTGGCAGGAGTAACATGTCTGAAACCACTGTG

861  G  V  V  C  R  Q  L  G  C  A  D  K  G  K  I  N  S  A  S  L
2581  GGTGTAGTGTGCAGGCAGCTGGGCTGTGCAGACAAAGGGAAAATCAACTCTGCATCTTTA

881  D  K  A  M  S  I  P  M  W  V  D  N  V  Q  C  P  K  G  P  D
2641  GACAAGGCCATGTCCATTCCCATGTGGGTGGACAATGTTCAGTGTCCAAAAGGACCTGAC

901  T  L  W  Q  C  P  S  S  P  W  E  K  R  L  A  R  P  S  E  E
2701  ACGCTGTGGCAGTGCCCATCATCTCCATGGGAGAAGAGACTGGCCAGGCCCTCGGAGGAG

921  T  W  I  T  C  D  N  K  M  R  L  Q  E  G  P  T  S  C  S  G
2761  ACCTGGATCACATGTGACAACAAGATGAGACTACAAGAAGGACCCACTTCCTGTTCTGGA

941  R  V  E  I  W  H  G  G  S  W  G  T  V  C  D  D  S  W  D  L
2821  CGTGTGGAGATCTGGCACGGAGGTTCCTGGGGACAGTGTGTGATGACTCCTGGGACTTG

961  N  D  A  Q  V  V  C  Q  Q  L  G  C  G  P  A  L  K  A  F  K
2881  AACGATGCTCAGGTGGTGTGTCAACAACTTGGCTGTGGTCCAGCTTTGAAAGCATTCAAA
```

| SEQUENCE | ID NO |
|---|---|
| 981  E  A  E  F  G  Q  G  T  G  P  I  W  L  N  E  V  K  C  K  G<br>2941 GAAGCAGAGTTTGGTCAGGGGACTGGACCCATATGGCTCAATGAAGTGAAGTGCAAAGGG | |
| 1001  N  E  S  S  L  W  D  C  P  A  R  R  W  G  H  S  E  C  G  H<br>3001 AATGAGTCTTCCTTGTGGGATTGTCCTGCCAGACGCTGGGGCCACAGTGAGTGTGGACAC | |
| 1021  K  E  D  A  A  V  N  C  T  D  I  S  T  R  K  T  P  Q  K  A<br>3061 AAGGAAGACGCTGCGGTGAATTGCACAGATATTTCAACGCGCAAAACCCCACAAAAAGCC | |
| 1041  T  T  V  S  S  R  G  E  N  L  V  H  Q  I  Q  Y  R  E  M  N<br>3121 ACAACGGTTTCCTCAAGAGGAGAGAACTTAGTCCACCAAATTCAATACCGGGAGATGAAT | |
| 1061  S  C  L  N  A  D  D  L  N  L  M  N  S  S  G  G  H  S  E  A<br>3181 TCTTGCCTGAATGCAGATGATCTGAACCTAATGAATTCCTCAGGAGGCCATTCTGAGGCA | |
| 1081  H  *  K  G  K  W  E  F  I  T  Q<br>3241 CACTGAAAAGGAAAATGGGAATTTATAACCCAG | |
| 1 MSKLRMVLLE DSGSADVRRH FVNLSPFTIA VVLLLRACFV TSSLGGTTKE LRLVDGENKC<br>61 SGRVEVKIQE EWGTVCNNGW SMEAVSVICN QLGCPTAIKA TGWANSSAGS GRIWMDHVSC<br>121 RGNESALWDC KHDGWGKHSN CTHQQDAGVT CSDGSDLEMR LTNGGNMCSG RIEIKFQGQW<br>181 GTVCDDNFNI NHASVVCKQL ECGSAVSFSG SANFGEGSGP IWFDDLICNG NESALWNCKH<br>241 QGWGKENCDH AEDAGVICSK GADLSLRLVD GVTECSGRLE VRFQGEWGTI CDDGWDSHDA<br>301 AVACKQLGCP TAITAIGRVN ASEGFGHIWL DSVSCQGHEP AVWQCKHHEW GKHYCNHNED<br>361 AGVTCSDGSD LELRLRGGGS RCAGTVEVEI QRLLGKVCDR GWGLKEADVV CRQLGCGSAL<br>421 KTSYQVYSKI QATNMWLFLS SCNGNETSLW DCKNWQWGGL TCDHYEEAKI TCSAHREPRL<br>481 VGGDIPCSGR VEVKHGDTWG SVCDSDFSLE AASVLCRELQ CGTVVSILGG AHFGEGNGQI<br>541 WTEEFQCEGH ESHLSLCPVA PRPEGTCSHS RDVGVVCSRY TEIRLVNGKT PCEGRVELKT<br>601 LNAWGSLCNS HWDIEDAHVL CQQLKCGVAL STPGGAHFGK GNGQVWRHMF HCTGTEQHMG<br>661 DCPVTALGAS LCPSGQVASV ICSGNQSQTL SSCNSSSLGP TRPTIPEESA VACIESGQLR<br>721 LVNGGGRCAG RVEIYHEGSW GTICDDSWDL SDAHVVCRQL GCGEAINATG SAHFGEGTGP<br>781 IWLDEMKCNG KESRIWQCHS HGWGQQNCRH KEDAGVICSE FMSLRLTSEA SREACAGRLE<br>841 VFYNGAWGSV GRSNMSETTV GVVCRQLGCA DKGKINSASL DKAMSIPMWV DNVQCPKGPD<br>901 TLWQCPSSPW EKRLARPSEE TWITCDNKMR LQEGPTSCSG RVEIWHGGSW GTVCDDSWDL<br>961 NDAQVVCQQL GCGPALKAFK EAEFGQGTGP IWLNEVKCKG NESSLWDCPA RRWGHSECGH<br>1021 KEDAVNCTD ISTRKTPQKA TTVSSRGENL VHQIQYREMN SCLNADDLNL MNSSGGHSEA<br>1081 H | SEQ ID NO: 38 |
| 1  M  S  K  L  R  M  V  L  L  E  D  S  G  S  A  D  V  R  R  H<br>1 ATGAGCAAACTCaGAATGGTGCTACTTGAAGACTCTGGATCTGCTGACGTCAGAAGACAT | SEQ ID NO: 39 and 40 |
| 21  F  V  N  L  S  P  F  T  I  A  V  V  L  L  L  R  A  C  F  V<br>61 TTTGTCAACTTGAGTCCCTTCACTATTGCTGTGGTCTTACTTCTCCGTGCCTGTTTTGTC | |
| 41  T  S  S  L  G  G  T  T  K  E  L  R  L  V  D  G  E  N  K  C<br>121 ACCAGTTCTCTTGGAGGAACAACCAAGGAGCTGAGGCTAGTGGATGGTGAAAACAAGTGT | |
| 61  S  G  R  V  E  V  K  I  Q  E  E  W  G  T  V  C  N  N  G  W<br>181 AGTGGGAGAGTGGAAGTGAAAATCCAGGAGGAGTGGGGAACGGTGTGTAATAATGGCTGG | |
| 81  S  M  E  A  V  S  V  I  C  N  Q  L  G  C  R  T  A  I  K  A<br>241 AGCATGGAAGCAGTCTCTGTGATTTGTAACCAGCTGGGATGTCCAACTGCTATCAAAGCC | |
| 101  T  G  W  A  N  S  S  A  G  S  G  R  I  W  M  D  M  V  S  C<br>301 ACTGGATGGGCTAATTCCAGTGCAGGTTCTGGACGCATTTGGATGGATCATGTTTCTTGT | |
| 121  R  G  N  E  S  A  L  W  D  C  K  H  D  G  W  G  K  H  S  N<br>361 CGTGGGAATGAGTCAGCTCTTTGGGACTGCAAACATGATGGATGCGAAAGCATAGTAAC | |
| 141  C  T  H  Q  Q  D  A  G  V  T  C  S  D  G  S  D  L  E  M  R<br>421 TGTACTCACCAACAAGATGCTGGAGTGACTTGCTCAGATGGATCCGATTTGGAAATGAGG | |
| 161  L  T  N  G  G  N  M  C  S  G  R  I  E  I  K  E  Q  G  Q  W<br>481 CTGACGAATGGAGGGAATATGTGTTCTGGAAGAATAGAGATCAAATTCCAAGGACAGTGG | |
| 181  G  T  V  C  D  D  N  F  N  V  N  H  A  S  V  V  C  K  Q  L<br>541 GGAACAGTGTGTGATGATAACTTCAACGTCAATCATGCATCTGTGGTTTGTAAACAACTT | |
| 201  E  C  G  S  A  V  S  E  S  G  S  A  N  F  G  E  G  S  G  P<br>601 GAATGTGGAAGTGCTGTCAGTTTCTCTGGTTCAGCTAATTTTGGAGAAGGCTCTGGACCA | |
| 221  I  W  F  D  D  L  I  C  N  G  N  E  S  A  L  W  N  C  K  H<br>661 ATCTGGTTTGATGATCTTATATGCAACGGAAATGAGTCAGCTCTCTGGAACTGCAAACAT | |
| 241  Q  G  W  G  K  H  N  C  D  H  A  E  D  A  G  V  I  C  S  K<br>721 CAAGGATGGGGAAAGCATAACTGTGATCATGCTGAGGATGCTGGAGTGATTTGCTCAAAG | |

```
                                     -continued
SEQUENCE                                                              ID NO 261 G  A  D  L  S  L  R  L  V  D  G  V  T  E  C  S  G  R  L  E
 781 GGAGCAGATCTGAGCCTGAGACTGGTAGATGGAGTCACTGAATGTTCAGGAAGATTAGAA 281 V  R  F  Q  G  E  W  G  T  I  C  D  D  G  W  D  S  H  D  A
 841 GTGAGATTCCAAGGAGAATGGGGGACAATATGTGATGACGGCTGGGACACTCATGATGCT 301 A  V  A  C  K  Q  L  G  C  P  T  A  I  T  A  I  G  R  V  N
 901 GCTGTGGCATGCAAGCAACTGGGATGTCCAACTGCTATCACCGCCATTGGTCGAGTTAAC 321 A  S  E  G  F  G  H  I  W  L  D  S  V  S  C  Q  G  H  E  P
 961 GCCAGTGAGGGATTTGGACACATCTGGCTTGACAGTGTTTCTTGCCAGGCACATGAACCT 341 A  V  W  Q  C  K  H  H  E  W  G  K  H  Y  C  N  H  N  E  D
1021 GCGGTCTGGCAATGTAAACACCATGAATGGGGAAAGCATTATTGCAATCACAATGAAGaT 361 A  G  V  T  C  S  D  G  S  D  L  E  L  R  L  A  G  G  G  S
1081 GCTGGCGTAACATGTTCTGATGGATCAGATCTGGAGCTAAGACTTAGAGGTGGAGGCAGC 381 R  C  A  G  T  V  E  V  E  I  Q  R  L  L  G  K  V  C  D  R
1141 CGCTGTGCTGGGACAGTTGAGGTGGAGATtCAGAGACTGTTAGGGAAGGTGTGTGACAGA 401 G  W  G  L  K  E  A  D  V  V  C  R  Q  L  G  C  G  S  A  L
1201 GGCTGGGGACTGAAAGAAGCTGATGTGGTTTGCAGGCAGCTGGATGTGGATCTGCACTC 421 K  T  S  Y  Q  V  Y  S  K  I  Q  A  T  N  M  W  L  F  L  S
1261 AAAACATCCTATCAAGTATACTCCAAAATCCAGGCAACAAACATGTGGCTGTTTCTAAGT 441 S  C  N  G  N  E  T  S  L  W  D  C  K  N  W  Q  W  G  G  L
1321 AGCTGTAACGGAAATGAAACTTCTCTTTGGGACTGCAAGAACTGGCAATGGGGTGGACTT 461 T  C  D  H  Y  E  E  A  K  I  T  C  S  A  H  R  E  P  R  L
1381 ACCTGTGATCACTATGAAGAAGCCAAAATTACCTGCTCAGCCCACAGGGAACCCAGACTG 481 V  G  G  D  I  P  C  S  G  R  V  E  V  K  H  G  D  T  W  G
1441 GTTGGAGGAGACATTCCCTGTTCTGGACGCGTTGAAGTGAAGCATGGTGACACATGGGGC 501 S  V  C  D  S  D  F  S  L  E  A  A  S  V  L  C  R  E  L  Q
1501 TCCGTCTGTGATTCGGATTTCTCTCTGGAAGCTGCCAGCGTTCTATGCAGGGAATTACAG 521 C  G  T  V  V  S  I  L  G  G  A  H  F  G  E  G  N  G  Q  I
1561 TGTGGCACAGTCGTCTCTATCCTGGGGGAGCTCACTTTGGAGAGGGAAATGGACAGATC 541 W  A  E  E  F  Q  C  E  G  H  E  S  H  L  S  L  C  P  V  A
1621 TGGGCTGAAGAATTCCAGTGTGAGGGACATGAGTCCCATCTTTCACTCTGCCCAGTAGCA 561 P  R  P  E  G  T  C  S  H  S  R  D  V  G  V  V  C  S  R  Y
1681 CCCCGCCCAGAAGGAACTTGTAGCCACAGCAGGGATGTTGGAGTAGTCTGCTCAAGATAC 581 T  E  I  R  L  V  N  G  K  T  P  C  E  G  R  V  E  L  K  T
1741 ACAGAAATTCGCTTGGTGAATGGCAAGACCCCATGTGAGGGCAGAGTGGAGCTCAAAACG 601 L  N  A  W  G  S  L  C  N  S  H  W  D  I  E  D  A  H  V  L
1801 CTTAATGCCTGGGGATCCCTCTGCAACTCTCACTGGGACATAGAAGATGCCCACGTTCTT 621 C  Q  Q  L  K  C  G  V  A  L  S  T  P  G  G  A  H  F  G  K
1861 TGCCAACAACTTAAATGTGGAGTTGCCCTTTCTACCCCAGGAGGAGCACATTTGGAAAA 641 G  N  G  Q  V  W  R  H  M  F  H  C  T  G  T  E  Q  H  M  G
1921 GGAAATGGTCAGGTCTGGAGGCATATGTTTCACTGCACTGGGACTGAGCAGCACATGGGA 661 D  C  P  V  T  A  L  G  A  S  L  C  P  S  G  Q  V  A  S  V
1981 GATTGTCCTGTAACTGCTCTGGGTGCTTCACTATGTCCTTCAGGGCAAGTGGCCTCTGTA 681 I  C  S  G  N  Q  S  Q  T  L  S  S  C  N  S  S  L  G  P
2041 ATTTGCTCAGGAAACCAGTCCCAAACACTGTCCTCGTGCAATTCATCATCTCTGGGCCCA 701 T  R  P  T  I  P  E  E  S  A  V  A  C  I  E  S  G  Q  L  R
2101 ACAAGGCCTACCATTCCAGAAGAAAGTGCTGTGGCCTGCATAGAGAGTGGTCAACTTCGC 721 L  V  N  G  G  R  C  A  G  R  V  E  I  Y  H  E  G  S  W
2161 TTGGTAAATGGAGGAGGTCGCTGTGCTGGGAGAGTAGAGATTTATCATGAGGGCTCCTGG 741 G  T  I  C  D  D  S  W  D  L  S  D  A  H  V  V  C  R  Q  L
2221 GGCACCATCTGTGATGACAGCTGGGACCTGAGCGATGCCCACGTGGTGTGCAGACAGCTG 761 G  C  G  E  A  I  N  A  T  G  S  A  H  F  G  E  G  T  G  P
2281 GGCTGTGGAGAGGCCATTAATGCCACTGGTTCTGCTCATTTTGGAGAAGGAACAGGGCCC
```

```
 781 I  W  L  D  E  M  K  C  N  G  K  E  S  R  I  W  Q  C  H  S
2341 ATCTGGCTGGATGAGATGAAATGCAATGGAAAAGAATCCCGTATTTGGCAGTGCCATTCA

801 H  G  W  G  Q  Q  N  C  R  H  K  E  D  A  G  V  I  C  S  E
2401 CATGGCTGGGGGCAGCAAAACTGCAGGCACAAGGAGGATGCAGGAGTTATCTGCTCAGAG

821 F  M  S  L  R  L  T  S  E  A  S  R  E  A  C  A  G  R  L  E
2461 TTCATGTCTCTGAGACTGACCAGTGAAGCCAGCAGAGAGGCCTGTGCAGGGCGTCTAGAA

841 V  F  Y  N  G  A  W  G  S  V  G  R  S  N  M  S  E  T  T  V
2521 GTTTTTTACAACGGAGCTTGGGGCAGTGTTGGCAGGAGTAACATGTCTGAAACCACTGTG

861 G  V  V  C  R  Q  L  G  C  A  D  K  G  K  I  N  S  A  S  L
2581 GGTGTGGTGTGCAGGCAGCTGGGCTGTGCAGACAAAGGGAAAATCAACTCTGCATCTTTA

881 D  K  A  M  S  I  P  M  W  V  D  N  V  Q  C  P  K  G  P  D
2641 GACAAGGCCATGTCCATTCCCATGTGGGTGGACAATGTTCAGTGTCCAAAAGGACCTGAC

901 T  L  W  Q  C  P  S  S  P  W  E  K  R  L  A  R  P  S  E  E
2701 ACGCTGTGGCAGTGCCCATCATCTCCATGGGAGAAGAGACTGGCCAGGCCCTCGGAGGAG

921 T  W  I  T  C  D  N  K  M  R  L  Q  E  G  P  T  S  C  S  G
2761 ACCTGGATCACATGTGACAACAAGATGAGACTACAAGAAGGACCCACTTCCTGTTCTGGA

941 R  V  E  I  W  H  G  G  S  W  G  T  V  C  D  D  S  W  D  L
2821 CGTGTGGAGATCTGGCACGGAGGTTCCTGGGGACAGTGTGTGATGACTCCTGGGACTTG

961 N  D  A  Q  V  V  C  Q  Q  L  G  C  G  P  A  L  K  A  F  K
2881 AACGATGCTCAGGTGGTGTGTCAACAACTTGGCTGTGGTCCAGCTTTGAAAGCATTCAAA

981 E  A  E  F  G  Q  G  T  G  P  I  W  L  N  E  V  K  C  K  G
2941 GAAGCAGAGTTTGGTCAGGGGACTGGACCCATATGGCTCAATGAAGTGAAGTGCAAAGGG

1001 N  E  S  S  L  W  D  C  P  A  R  R  W  G  H  S  E  C  G  H
3001 AATGAGTCTTCCTTGTGGGATTGTCCTGCCAGACGCTGGGGCCACAGTGAGTGTGGACAC

1021 K  E  D  A  A  V  N  C  T  A  Q  K  I  S  T  H  K  T  P  Q
3061 AAGGAAGACGCTGCAGTGAATTGCACAGCACAAAAAATTTCAACGCACAAAACCCCACAA

1041 K  A  T  T  V  S  S  R  G  E  N  L  V  H  Q  I  Q  Y  R  E
3121 AAAGCCACAACAGTTTCCTCAAGAGGAGAGAACTTAGTCCACCAAATTCAATACCGGGAG

1061 M  N  S  C  L  N  A  D  D  L  D  L  M  N  S  S  G  G  H  S
3181 ATGAATTCTTGCCTGAATGCAGATGATCTGGACCTAATGAATTCCTCAGGAGGCCATTCT

1081 E  A  H  *  K  G  K  W  E  F  I  T  Q
3241 GAGGCACACTGAAAAGGAAAATGGAATTTATAACCCAG
```

```
   1 MSKLRMVLLE DSGSADVRRH FVNLSPFTIA VVLLLRACFV TSSLGGTTKE LRLVDGENKC   SEQ ID
  61 SGRVEVKIQE EWGTVCNNGW SMEAVSVICN QLGCPTAIKA TGWANSSAGS GRIWMDHVSC   NO: 40
 121 RGNESALWDC KHDGWGKHSN CTHQQDAGVT CSDGSDLEMR LTNGGNMCSG RIEIKFQGQW
 181 GTVCDDNFNV NHASVVCKQL ECGSAVSFSG SANFGEGSGP IWFDDLICNG NESALWNCKH
 241 QGWGKENCDH AEDAGVICSK GADLSLRLVD GVTECSGRLE VRFQGEWGTI CDDGWDSHDA
 301 AVACKQLGCP TAITAIGRVN ASEGFGHIWL DSVSCQGHEP AVWQCKHHEW GKHYCNHNED
 361 AGVTCSDGSD LELRLRGGGS RCAGTVEVEI QRLLGKVCDR GWGLKEADVV CRQLGCGSAL
 421 KTSYQVYSKI QATNMWLFLS SCNGNETSLW DCKNWQWGGL TCDHYEEAKI TCSAHREPRL
 481 VGGDIPCSGR VEVKHGDTWG SVCDSDFSLE AASVLCRELQ CGTVVSILGG AHFGEGNGQI
 541 WAEEFQCEGH ESHLSLCPVA PRPEGTCSHS RDVGVVCSRY TEIRLVNGKT PCEGRVELKT
 601 LNAWGSLCNS HWDIEDAHVL CQQLKCGVAL STPGGAHFGK GNGQVWRHMF HCTGTEQHMG
 661 DCPVTALGAS LCPSGQVASV ICSGNQSQTL SSCNSSSLGP TRPTIPEESA VACIESGQLR
 721 LVNGGGRCAG RVEIYHEGSW GTICDDSWDL SDAHVVCRQL GCGEAINATG SAHFGEGTGP
 781 IWLDEMKCNG KESRIWQCHS HGWGQQNCRH KEDAGVICSE FMSLRLTSEA SREACAGRLE
 841 VFYNGAWGSV GRSNMSETTV GVVCRQLGCA DKGKINSASL DKAMSIPMWV DNVQCPKGPD
 901 TLWQCPSSPW EKRLARPSEE TWITCDNKMR LQEGPTSCSG RVEIWHGGSW GTVCDDSWDL
 961 NDAQVVCQQL GCGPALKAFK EAEFGQGTGP IWLNEVKCKG NESSLWDCPA RRWGHSECGH
1021 KEDAAVNCTA QKISTHKTPQ KATTVSSRGE NLVHQIQYRE MNSCLNADDL DLMNSSGGHS
1081 EAH
```

```
   1 M  S  K  L  R  M  V  L  L  E  D  S  G  S  A  D  V  R  R  H    SEQ ID NO:
   1 ATGAGCAAACTCAGAATGGTGCTACTTGAAGACTCTGGATCTGCTGACGTCAGAAGACAT    41 and 42

21 F  V  N  L  S  P  F  T  I  A  V  V  L  L  L  R  A  C  F  V
  61 TTTGTCAACTTGAGTCCCTTCATTATTGCTGTGGTCTTACTTCTCCGTGCCTGTTTTGTC

41 T  S  S  L  G  G  T  T  K  E  L  R  L  V  D  G  E  N  K  C
 121 ACCAGTTCTCTTGGAGGAACAACCAAGGAGCTGAGGCTAGTGGATGGTGAAAACAAGTGT
```

```
    61 S   G   R   V   E   V   K   I   Q   E   E   W   G   T   V   C   N   N   G   W
   181 AGTGGGAGAGTGGAAGTGAAAATCCAGGAGGAGTGGGGAACGGTGTGTAATAATGGCTGG

81 S   M   E   A   V   S   V   I   C   N   Q   L   G   C   P   T   A   I   K   A
   241 AGCATGGAAGCAGTCTCTGTGATTTGTAACCAGCTGGGATGTCCAACTGCTATCAAAGCC

101 T   G   W   A   N   S   S   A   G   S   G   R   I   W   M   D   H   V   S   C
   301 ACTGGATGGGCTAATTCCAGTGCAGGTTCTGGACGCATTTGGATGGATCATGTTTCTTGT

121 R   G   N   E   S   A   L   W   D   C   K   H   D   G   W   G   K   H   S   N
   361 CGTGGGAATGAGTCAGCTCTTTGGGACTGCAAACATGATGGATGGGGAAAGCATAGTAAC

141 C   T   H   Q   Q   D   A   G   V   T   C   S   D   G   S   D   L   E   M   R
   421 TGTACTCACCAACAAGATGCTGGAGTGACTTGCTCAGATGGATCCGATTTGGAAATGAGG

161 L   T   N   G   G   N   M   C   S   G   R   I   E   I   K   F   Q   G   Q   W
   481 CTGACGAATGGAGGGAATATGTGTTCTGGAAGAATAGAGATCAAATTCCAAGGACAGTGG

181 G   T   V   C   D   D   N   F   N   I   N   H   A   S   V   V   C   K   Q   L
   541 GGAACAGTGTGTGATGATAACTTCAACATCAATCATGCATCTGTGGTTTGTAAACAACTT

201 E   C   G   S   A   V   S   F   S   G   S   A   N   F   G   E   G   S   G   P
   601 GAATGTGGAAGTGCTGTCAGTTTCTCTGGTTCAGCTAATTTTGGAGAAGGCTCTGGACCA

221 I   W   F   D   D   L   I   C   N   G   N   E   S   A   L   W   N   C   K   H
   661 ATCTGGTTTGATGATCTTATATGCAACGGAAATGAGTCAGCTCTCTGGAACTGCAAACAT

241 Q   G   W   G   K   H   N   C   D   H   A   E   D   A   G   V   I   C   S   K
   721 CAAGGATGGGGAAAGCATAACTGTGATCATGCTGAGGATGCTGGAGTGATTTGCTCAAAG

261 G   A   D   L   S   R   L   V   D   G   V   T   E   C   S   G   R   L   E
   781 GGAGCAGATCTGAGCCTGAGACTGGTAGATGGAGTCACTGAATGTTCAGGAAGATTAGAA

281 V   R   F   Q   G   E   W   G   T   I   C   D   D   G   W   D   S   H   D   A
   841 GTGAGATTCCAAGGAGAATGGGGACAATATGTGATGACGGCTGGGACAGTCATGATGCT

301 A   V   A   C   K   Q   L   G   C   P   T   A   I   T   A   I   G   R   V   N
   901 GCTGTGGCATGCAAGCAACTGGGATGTCCAACTGCTATCACCGCCATTGGTCGAGTTAAC

321 A   S   E   G   F   G   H   I   W   L   D   S   V   S   C   Q   G   H   E   P
   961 GCCAGTGAGGGATTTGGACACATCTGGCTTGACAGTGTTTCTTGCCAGGGACATGAACCT

341 A   V   W   Q   C   K   H   H   E   W   G   K   H   Y   C   N   H   N   E   D
  1021 GCGGTCTGGCAATGTAAACACCATGAATGGGGAAAGCATTATTGCAATCACAATGAAGAT

361 A   G   V   T   C   S   D   G   S   D   L   E   L   R   L   R   G   G   G   S
  1081 GCTGGCGTAACATGTTCTGATGGATCAGATCTGGAGCTAAGACTTAGAGGTGGAGGCAGC

381 R   C   A   G   T   V   E   V   E   I   Q   R   L   L   G   K   V   C   D   R
  1141 CGCTGTGCTGGGACAGTTGAGGTGGAGATTCAGAGACTGTTAGGGAAGGTGTGtGACAGA

401 G   W   G   L   K   E   A   D   V   V   C   R   Q   L   G   C   G   S   A   L
  1201 GGCTGGGGACTGAAAGAAGCTGATGTGGTTTGCAGGCAGCTGGGATGTGGATCTGCACTC

421 K   T   S   Y   Q   V   Y   S   K   I   Q   A   T   N   M   W   L   F   L   S
  1261 AAAACATCCTATCAAGTATACTCCAAAATCCAGGCAACAAACATGTGGCTGTTTCTAAGT

441 S   C   N   G   N   E   T   S   L   W   D   C   K   N   W   Q   W   G   G   L
  1321 AGCTGTAACGGAAATGAAACTTCTCTTTGGGACTGCAAGAACTGGCAATGGGGTGGACTT

461 T   C   D   H   Y   E   E   A   K   I   T   C   S   A   H   R   E   P   R   L
  1381 ACCTGTGATCACTATGAAGAAGCCAAAATTACCTGCTCAGCCCACAGGGAACCCAGACTG

481 V   G   G   D   I   P   C   S   G   R   V   E   V   K   H   G   D   T   W   G
  1441 GTTGGAGGAGACATTCCCTGTTCTGGACGCGTTGAAGTGAAGCATGGTGACACATGGGGC

501 S   V   C   D   S   D   F   S   L   E   A   A   S   V   L   C   R   E   L   Q
  1501 TCCGTCTGTGATTCGGATTTCTCTCTGGAAGCTGCCAGCGTTCTATGCAGGGAATTACAG

521 C   G   T   V   V   S   I   L   G   G   A   H   F   G   E   G   N   G   Q   I
  1561 TGTGGCACAGTCGTCTCTATCCTGGGGGGAGCTCACTTTGGAGAGGGAAATGGACAGATC

541 W   A   E   E   F   Q   C   E   G   H   E   S   H   L   S   L   C   P   V   A
  1621 TGGGCTGAAGAATTCCAGTGTGAGGGACATGAGTCCCATCTTTCACTCTGCCCAGTAGCA

561 P   R   P   E   G   T   C   S   H   S   R   D   V   G   V   V   C   S   R   Y
  1681 CCCCGCCCAGAAGGAACTTGTAGCCACAGCAGGGATGTTGGAGTAGTCTGCTCAAGATAC
```

-continued

| SEQUENCE | ID NO |
|---|---|

```
 581  T  E  I  R  L  V  N  G  K  T  P  C  E  G  R  V  E  L  K  T
1741  ACAGAAATTCGCTTGGTGAATGGCAAGACCCCATGTGAGGGCAGAGTGGAGCTCAAAACG

601  L  N  A  W  G  S  L  C  N  S  H  W  D  I  E  D  A  H  V  L
1801  CTTAATGCCTGGGGATCCCTCTGCAACTCTCACTGGGACATAGAAGATGCCCACGTTCTT

621  C  Q  Q  L  K  C  G  V  A  L  S  T  P  G  G  A  H  F  G  K
1861  TGCCAACAACTTAAATGTGGAGTTGCCCTTTCTACCCCAGGAGGAGCACATTTTGGAAAA

641  G  N  G  Q  V  W  R  H  M  F  H  C  T  G  T  E  Q  H  M  G
1921  GGAAATGGTCAGGTCTGGAGGCATATGTTTCACTGCACTGGGACTGAGCAGCACATGGGA

661  D  C  P  V  T  A  L  G  A  S  L  C  P  S  G  Q  V  A  S  V
1981  GATTGTCCTGTAACTGCTCTGGGTGCTTCACTATGTCCTTCAGGGCAAGTGGCCTCTGTA

681  I  C  S  G  N  Q  S  Q  T  L  S  S  C  N  S  S  S  L  G  P
2041  ATTTGCTCAGGAAACCAGTCCCAAACACTGTCCTCGTGCAATTCATCATCTCTGGGCCCA

701  T  R  P  T  I  P  E  E  S  A  V  A  C  I  E  S  G  Q  L  R
2101  ACAAGGCCTACCATTCCAGAAGAAAGTGCTGTGGCCTGCATAGAGAGTGGTCAACTTCGC

721  L  V  N  G  G  G  R  C  A  G  R  V  E  I  Y  H  E  G  S  W
2161  TTGGTAAATGGAGGAGGTCGCTGTGCTGGGAGAGTAGAGATTTATCATGAGGGCTCCTGG

741  G  T  I  C  D  D  S  W  D  L  S  D  A  H  V  V  C  R  Q  L
2221  GGCACCATCTGTGATGACAGCTGGGACCTGAGCGATGCCCACGTGGTGTGCAGACAGCTG

761  G  C  G  E  A  I  N  A  T  G  S  A  H  F  G  E  G  T  G  P
2281  GGCTGTGGAGAGGCCATTAATGCCACTGGTTCTGCTCATTTTGGAGAAGGAACAGGGCCC

781  I  W  L  D  E  M  K  C  N  G  K  E  S  R  I  W  Q  C  H  S
2341  ATCTGGCTGGATGAGATGAAATGCAATGGAAAAGAATCCCGTATTTGGCAGTGCCATTCA

801  H  G  W  G  Q  Q  N  C  R  H  K  E  D  A  G  V  I  C  S  E
2401  CATGGCTGGGGGCAGCAAAACTGCAGGCACAAGGAGGATGCAGGAGTTATCTGCTCAGAG

821  F  M  S  L  R  L  T  S  E  A  S  R  E  A  C  A  G  R  L  E
2461  TTCATGTCTCTGAGACTGACCAGTGAAGCCAGCAGAGAGGCCTGTGCAGGGCGTCTAGAA

841  V  F  Y  N  G  A  W  G  S  V  G  R  S  N  M  S  E  T  T  V
2521  GTTTTTTACAACGGAGCTTGGGGCAGTGTTGGCAGGAGTAACATGTCTGAAACCACTGTG

861  G  V  V  C  R  Q  L  G  C  A  D  K  G  K  I  N  S  A  S  L
2581  GGTGTGGTGTGCAGGCAGCTGGGCTGTGCAGACAAAGGGAAAATCAACTCTGCATCTTTA

881  D  K  A  M  S  I  P  M  W  V  D  N  V  Q  C  P  K  G  P  D
2641  GACAAGGCCATGTCCATTCCCATGTGGGTGGACAATGTTCAGTGTCCAAAAGGACCTGAC

901  T  L  W  Q  C  P  S  S  P  W  E  K  R  L  A  R  P  S  E  E
2701  ACGCTGTGGCAGTGCCCATCATCTCCATGGGAGAAGAGACTGGCCAGGCCCTCGGAGGAG

921  T  W  I  T  C  D  N  K  M  R  L  Q  E  G  P  T  S  C  S  G
2761  ACCTGGATCACATGTGACAACAAGATGAGACTACAAGAAGGACCCACTTCCTGTTCTGGA

941  R  V  E  I  W  H  G  G  S  W  G  T  V  C  D  D  S  W  D  L
2821  CGTGTGGAGATCTGGCACGGAGGTTCCTGGGGACAGTGTGTGATGACTCCTGGGACTTG

961  N  D  A  Q  V  V  C  Q  Q  L  G  C  G  P  A  L  K  A  F  K
2881  AACGATGCTCAGGTGGTGTGTCAACAACTTGGCTGTGGTCCAGCTTTGAAAGCATTCAAA

981  E  A  E  F  G  Q  G  T  G  P  I  W  L  N  E  V  K  C  K  G
2941  GAAGCAGAGTTTGGTCAGGGGACTGGACCCATATGGCTCAATGAAGTGAAGTGCAAAGGG

1001  N  E  S  S  L  W  D  C  P  A  R  R  W  G  H  S  E  C  G  H
3001  AATGAGTCTTCCTTGTGGGATTGTCCTGCCAGACGCTGGGGCCACAGTGAGTGTGGACAC

1021  K  E  D  A  A  V  N  C  T  A  Q  K  I  S  T  H  K  T  P  Q
3061  AAGGAAGACGCTGCAGTGAATTGCACAGCACAAAAAATTTCAACGCACAAAACCCCACAA

1041  K  A  T  T  G  R  S  F  L  I  A  F  G  I  L  G  V  V  L  L
3121  AAAGCCACAACAGGTCGGTCATTCCTTATTGCATTCGGAATCCTTGGAGTTGTTCTCTTG

1061  A  I  F  V  A  L  F  L  T  Q  K  R  R  Q  R  Q  R  L  T  V
3181  GCCATTTTCGTCGCATTATTCTTGACTCAAAAGCGAAGACAGAGACAGCGGCTTACAGTT

1081  S  S  R  G  E  N  L  V  H  Q  I  Q  Y  R  E  M  N  S  C  L
3241  TCCTCAAGAGGAGAGAACTTAGTCCACCAAATTCAATACCGGGAGATGAATTCTTGCCTG
```

| SEQUENCE | ID NO |
|---|---|
| 1101 N A D D L D L M N S S G G H S E A H<br>3301 AATGCAGATGATCTGGACCTAATGAATTCCTCAGGAGGCCATTCTGAGGCACAC | |
| 1 MSKLRMVLLE DSGSADVRRH FVNLSPFTIA VVLLLRACFV TSSLGGTTKE LRLVDGENKC<br>61 SGRVEVKIQE EWGTVCNNGW SMEAVSVICN QLGCPTAIKA TGWANSSAGS GRIWMDHVSC<br>121 RGNESALWDC KHDGWGKHSN CTHQQDAGVT CSDGSDLEMR LTNGGNMCSG RIEIKFQGQW<br>181 GTVCDDNFNI NHASVVCKQL ECGSAVSFSG SANFGEGSGP IWFDDLICNG NESALWNCKH<br>241 QGWGKHNCDH AEDAGVICSK GADLSLRLVD GVTECSGRLE VRFQGEWGTI CDDGWDSHDA<br>301 AVACKQLGCP TAITAIGRVN ASEGFGHIWL DSVSCQGHEP AVWQCKHHEW GKHYCNHNED<br>361 AGVTCSDGSD LELRLRGGGS RCAGTVEVEI QRLLGKVCDR GWGLKEADVV CRQLGCGSAL<br>421 KTSYQVYSKI QATNMWLFLS SCNGNETSLW DCKNWQWGGL TCDHYEEAKI TCSAHREPRL<br>481 VGGDIPCSGR VEVKHGDTWG SVCDSDFSLE AASVLCRELQ CGTVVSILGG AHFGEGNGQI<br>541 WAEEFQCEGH ESHLSLCPVA PRPEGTCSHS RDVGVVCSRY TEIRLVNGKT PCEGRVELKT<br>601 LNAWGSLCNS HWDIEDAHVL CQQLKCGVAL STPGGAHFGK GNGQVWRHMF HCTGTEQHMG<br>661 DCPVTALGAS LCPSGQVASV ICSGNQSQTL SSCNSSSLGP TRPTIPEESA VACIESGQLR<br>721 LVNGGGRCAG RVEIYHEGSW GTICDDSWDL SDAHVVCRQL GCGEAINATG SAHFGEGTGP<br>781 IWLDEMKCNG KESRIWQCHS HGWGOQNCRH KEDAGVICSE FMSLRLTSEA SREACAGRLE<br>841 VFYNGAWGSV GRSNMSETTV GVVCRQLGCA DKGKINSASL DKAMSIPMWV DNVQCPKGPD<br>901 TLWQCPSSPW EKRLARPSEE TWITCDNKMR LQEGPTSCSG RVEIWHGGSW GTVCDDSWDL<br>961 NDAQVVCQQL GCGPALKAFK EAEFGQGTGP IWLNEVKCKG NESSLWDCPA RRWGHSECGH<br>1021 KEDAAVNCTA QKISTHKTPQ KATTGRSFLI AFGILGVVLL AIFVALFLTQ KRRQRQRLTV<br>1081 SSRGENLVHQ IQYREMNSCL NADDDLDLMNS SGGHSEAH | SEQ ID<br>NO: 42 |
| 1 M S K L R M V L L E D S G S A D V R R H<br>1 ATGAGCAAACTCAGAATGGTGCTACTTGAAGACTCTGGATCTGCTGACGTCAGAAGACAT | SEQ ID NO:<br>43 and 44 |
| 21 F V N L S P F T I A V V L L L R A C F V<br>61 TTTGTCAACTTGAGTCCCTTCACTATTGCTGTGGTCTTACTTCTCCGTGCCTGTTTTGTC | |
| 41 T S S L G G T T K E L R L V D G E N K C<br>121 ACCAGTTCTCTTGGAGGAACAACCAAGGAGCTGAGGCTAGTGGATGGTGAAAACAAGTGT | |
| 61 S G R V E V K I Q E E W G T V C N N G W<br>181 AGTGGGAGAGTGGAAGTGAAAATCCAGGAGGAGTGGGGAACGGTGTGTAATAATGGCTGG | |
| 81 S M E A V S V I C N Q L G C P T A I K A<br>241 AGCATGGAAGCAGTCTCTGTGATTTGTAACCAGCTGGGATGTCCAACTGCTATCAAAGCC | |
| 101 T G W A N S S A G S G R I W M D H V S C<br>301 ACTGGATGGGCTAATTCCAGTGCAGGTTCTGGACGCATTTGGATGGATCATGTTTCTTGT | |
| 121 R G N E S A L W D C K H D G W G K H S N<br>361 CGTGGGAATGAGTCAGCTCTTTGGGACTGCAAACATGATGGATGGGGAAAGCATAGTAAC | |
| 141 C T H Q Q D A G V T C S D G S D L E M R<br>421 TGTACTCACCAACAAGATGCTGGAGTGACTTGCTCAGATGGATCCGATTTGGAAATGAGG | |
| 161 L T N G G N M C S G R I E I K F Q G Q W<br>481 CTGACGAATGGAGGGAATATGTGTTCTGGAAGAATAGAGATCAAATTCCAAGGACAGTGG | |
| 181 G T V C D D N F N I N H A S V V C K Q L<br>541 GGAACAGTGTGTGATGATAACTTCAACATCAATCATGCATCTGTGGTTTGTAAACAACTT | |
| 201 E C G S A V S F S G S A N F G E G S G P<br>601 GAATGTGGAAGTGCTGTCAGTTTCTCTGGTTCAGCTAATTTTGGAGAAGGCTCTGGACCA | |
| 221 I W F D D L I C N G N E S A L W N C K H<br>661 ATCTGGTTTGATGATCTTATATGCAACGGAAATGAGTCAGCTCTCTGGAACTGCAAACAT | |
| 241 Q G W G K H N C D H A E D A G V I C S K<br>721 CAAGGATGGGGAAAGCATAACTGTGATCATGCTGAGGATGCTGGAGTGATTTGCTCAAAG | |
| 261 G A D L S L R L V D G V T E C S G R L E<br>781 GGAGCAGATCTGAGCCTGAGACTGGTAGATGGAGTCACTGAATGTTCAGGAAGATTAGAA | |
| 281 V R F Q G E W G T I C D D G W D S H D A<br>841 GTGAGATTCCAAGGAGAATGGGGGACAATATGTGATGACGGCTGGGACAGTCATGATGCT | |
| 301 A V A C K Q L G C P T A I T A I G R V N<br>901 GCTGTGGCATGCAAGCAACTGGGATGTCCAACTGCTATCACCGCCATTGGTCGAGTTAAC | |
| 321 A S E G F G H I W L D S V S C Q G H E P<br>961 GCCAGTGAGGGATTTGGACACATCTGGCTTGACAGTGTTTCTTGCCAGGGACATGAACCT | |
| 341 A V W Q C K H H E W G K H Y C N H N E D<br>1021 GCCGTCTGGCAATGTAAACACCATGAATGGGGAAAGCATTATTGCAATCACAATGAAGAT | |

```
                                      -continued
SEQUENCE                                                                    ID NO 361 A  G  V  T  C  S  D  G  S  D  L  E  L  R  L  R  G  G  G  S
1081 GCTGGCGTAACATGTTCTGATGGATCAGATCTGGAGCTAAGACTTAGAGGTGGAGGCAGC 381 R  C  A  G  T  V  E  V  E  I  Q  R  L  L  G  K  V  C  D  R
1141 CGCTGTGCTGGGACAGTTGAGGTGGAGATTCAGAGACTGTTAGGGAAGGTGTGTGACAGA 401 G  W  G  L  K  E  A  D  V  V  C  R  Q  L  G  C  G  S  A  L
1201 GGCTGGGGACTGAAAGAAGCTGATGTGGTTTGCAGGCAGCTGGGATGTGGATCTGCACTC 421 K  T  S  Y  Q  V  Y  S  K  I  Q  A  T  N  M  W  L  F  L  S
1261 AAAACATCCTATCAAGTATACTCCAAAATCCAGGCAACAAACATGTGGCTGTTTCTAAGT 441 S  C  N  G  N  E  T  S  L  W  D  C  K  N  W  Q  W  G  G  L
1321 AGCTGTAACGGAAATGAAACTTCTCTTTGGGACTGCAAGAACTGGCAATGGGGTGGACTT 461 T  C  D  H  Y  E  E  A  K  I  T  C  S  A  H  R  E  P  R  L
1381 ACCTGTGATCACTATGAAGAAGCCAAAATTACCTGCTCAGCCCACAGGGAACCCAGACTG 481 V  G  G  D  I  P  C  S  G  R  V  E  V  K  H  G  D  T  W  G
1441 GTTGGAGGAGACATTCCCTGTTCTGGACGCGTTGAAGTGAAGCATGGTGACACATGGGGC 501 S  V  C  D  S  D  F  S  L  E  A  A  S  V  L  C  R  E  L  Q
1501 TCCGTCTGTGATTCGGATTTCTCTCTGGAAGCTGCCAGCGTTCTATGCAGGGAATTACAG 521 C  G  T  V  V  S  I  L  G  G  A  H  F  G  E  G  N  G  Q  I
1561 TGTGGCACAGTCGTCTCTATCCTGGGGGGAGCTCACTTTGGAGAGGGAAATGGACAGATC 541 W  A  E  E  F  Q  C  E  G  H  E  S  H  L  S  L  C  P  V  A
1621 TGGGCTGAAGAATTCCAGTGTGAGGGACATGAGTCCCATCTTTCACTCTGCCCAGTAGCA 561 P  R  P  E  G  T  C  S  H  S  R  D  V  G  V  V  C  S  R  Y
1681 CCCCGCCCAGAAGGAACTTGTAGCCACAGCAGGGATGTTGGAGTAGTCTGCTCAAGATAC 581 T  E  I  R  L  V  N  G  K  T  P  C  E  G  R  V  E  L  K  T
1741 ACAGAAATTCGCTTGGTGAATGGCAAGACCCCATGTGAGGGCAGAGTGGAGCTCAAAACG 601 L  N  A  W  G  S  L  C  N  S  H  W  D  I  E  D  A  H  V  L
1801 CTTAATGCCTGGGGATCCCTCTGCAACTCTCACTGGGACATAGAAGATGCCCACGTTCTT 621 C  Q  Q  L  K  C  G  V  A  L  S  T  P  G  G  A  H  F  G  K
1861 TGCCAACAACTTAAATGTGGAGTTGCCCTTTCTACCCCAGGAGGAGCACATTTTGGAAAA 641 G  N  G  Q  V  W  R  H  M  F  H  C  T  G  T  E  Q  H  M  G
1921 GGAAATGGTCAGGTCTGGAGGCATATGTTTCACTGCACTGGGACTGAGCAGCACATGGGA 661 D  C  P  V  T  A  L  G  A  S  L  C  P  S  G  Q  V  A  S  V
1981 GATTGTCCTGTAACTGCTCTGGGTGCTTCACTATGTCCTTCAGGGCAAGTGGCCTCTGTA 681 I  C  S  G  N  Q  S  Q  T  L  S  S  C  N  S  S  L  G  P
2041 ATTTGCTCAGGAAACCAGTCCCAAACACTGTCCTCGTGCAATTCATCATCTCTGGGCCCA 701 T  R  P  T  I  P  E  E  S  A  V  A  C  I  E  S  G  Q  L  R
2101 ACAAGGCCTACCATTCCAGAAGAAAGTGCTGTGCCCTGCATAGAGAGTGGTCAACTTCGC 721 L  V  N  G  G  G  R  C  A  G  R  V  E  I  Y  H  R  G  S  W
2161 TTGGTAAATGGAGGAGGTCGCTGTGCTGGGAGAGTAGAGATTTATCATGAGGGCTCCTGG 741 G  T  I  C  D  D  S  W  D  L  S  D  A  H  V  V  C  R  Q  L
2221 GGCACCATCTGTGATGACAGCTGGGACCTGAGCGATGCCCACGTGGTGTGCAGACAGCTG 761 G  C  G  R  A  I  N  A  T  G  S  A  H  F  G  E  G  T  G  P
2281 GGCTGTGGAGAGGCCATTAATGCCACTGGTTCTGCTCATTTTGGAGAAGGAACAGCGCCC 781 I  W  L  D  E  M  K  C  N  G  K  E  S  R  I  W  Q  C  H  S
2341 ATCTGGCTGGATGAGATGAAATGCAATGGAAAAGAATCCCGTATTTGGCAGTGCCATTCA 801 H  G  W  G  Q  Q  N  C  R  H  K  E  D  A  G  V  I  C  S  E
2401 CATGGCTGGGGGCAGCAAAACTGCAGGCACAAGGAGGATGCAGGAGTTATCTGCTCAGAG 821 F  M  S  L  R  L  T  S  E  A  S  R  E  A  C  A  G  R  L  E
2461 TTCATGTCTCTGAGACTGACCAGTGAAGCCAGGAGAGAGGCCTGTGCAGGGCGTCTAGAA 841 V  F  Y  N  G  A  W  G  S  V  G  A  S  N  M  S  E  T  T  V
2521 GTTTTTTACAACGGAGCTTGGGGCAGTGTTGGCAGGAGTAACATGTCTGAAACCACTGTG 861 G  V  V  C  R  Q  L  G  C  A  D  K  G  K  I  N  S  A  S  L
2581 GGTGTGGTGTGCAGGCAGCTGGGCTGTGCAGACAAAGGGAAAATCAACTCTGCATCTTTA
```

```
SEQUENCE                                                                    ID NO

881 D   K   A   M   S   I   P   M   W   V   D   N   V   Q   C   P   K   G   P   D
2641 GACAAGGCCATGTCCATTCCCATGTGGGTGGACAATGTTCAGTGTCCAAAAGGACCTGAC

901 T   L   W   Q   C   P   S   S   P   W   E   K   R   L   A   R   P   S   E   E
2701 ACGCTGTGGCAGTGCCCATCATCTCCATGGGAGAAGAGACTGGCCAGGCCCTCGGAGGAG

921 T   W   I   T   C   D   N   K   M   R   L   Q   E   G   P   T   S   C   S   G
2761 ACCTGGATCACATGTGACAACAAGATGAGACTACAAGAAGGACCCACTTCCTGTTCTGGA

941 R   V   E   I   W   H   G   G   S   W   G   T   V   C   D   D   S   W   D   L
2821 CGTGTGGAGATCTGGCACGGAGGTTCCTGGGGGACAGTGTGTGATGACTCCTGGGACTTG

961 N   D   A   Q   V   V   C   Q   Q   L   G   C   G   P   A   L   K   A   F   K
2881 AACGATGCTCAGGTGGTGTGTCAACAACTTGGCTGTGGTCCAGCTTTGAAAGCATTCAAA

981 E   A   E   F   G   Q   G   T   G   P   I   W   L   N   E   V   K   C   K   G
2941 GAAGCAGAGTTTGGTCAGGGGACTGGACCCATATGGCTCAATGAAGTGAAGTGCAAAGGG

1001 N   E   S   S   L   W   D   C   P   A   R   R   W   G   H   S   E   C   G   H
3001 AATGAGTCTTCCTTGTGGGATTGTCCTGCCAGACGCTGGGGCCACAGTGAGTGTGGACAC

1021 K   E   D   A   A   V   N   C   T   A   Q   K   I   S   T   H   K   T   P   Q
3061 AAGGAAGACGCTGCAGTGAATTGCACAGCACAAAAAATTTCAACGCACAAAACCCCACAA

1041 K   A   T   T   G   Q   S   F   L   I   A   F   G   I   L   G   V   V   L   L
3121 AAAGCCACAACAGGTCAGTCATTCCTTATTGCATTCGGAATCCTTGGAGTTGTTCTCTTG

1061 A   I   F   V   A   L   F   L   T   Q   K   R   R   Q   R   Q   R   L   T   V
3181 GCCATTTTCGTCGCATTATTCTTGACTCAAAAGCGAAGACAGAGACAGCGGCTTACAGTT

1081 S   S   R   G   E   N   L   V   H   Q   I   Q   Y   R   E   M   N   S   C   L
3241 TCCTCAAGAGGAGAGAACTTAGTCCACCAAATTCAATACCGGGAGATGAATTCTTGCCTG

1101 N   A   D   D   L   D   L   M   N   S   S   E   N   S   N   E   S   A   D   F
3301 AATGCAGATGATCTGGACCTAATGAATTCCTCAGAAAATTCCAATGAGTCAGCTGATTTC

1121 N   A   A   E   L   I   S   V   S   K   F   L   P   I   S   G   M   E   K   E
3361 AATGCTGCTGAACTAATTTCTGTGTCTAAATTTCTTCCTATTTCTGGAATGGAAAAGGAG

1141 A   I   L   R   H   T   E   K   E   N   G   N   L
3421 GCCATTCTGAGGCACACTGAAAAGGAAAATGGGAATTTA

1 MSKLRMVLLE  DSGSADVRRH  FVNLSPFTIA  VVLLLRACFV  TSSLGGTTKE  LRLVDGENKC    SEQ ID
  61 SGRVEVKIQE  EWGTVCNNGW  SMEAVSVICN  QLGCPTAIKA  TGWANSSAGS  GRIWMDHVSC    NO: 44
 121 RGNESALWDC  KEDGWGKESN  CTHQQDAGVT  CSDGSDLEMR  LTNGGNMCSG  RIEIKFQGQW
 181 GTVCDDNFNI  NHASVVCKQL  ECGSAVSFSG  SANFGEGSGP  IWFDDLICNG  NESALWNCKH
 241 QGWGKHNCDH  AEDAGVICSK  GADLSLRLVD  GVTECSGRLE  VRFQGEWGTI  CDDGWDSHDA
 301 AVACKQLGCP  TAITAIGRVN  ASEGFGHIWL  DSVSCQGHEP  AVWQCKHHEW  GKHYCNHNED
 361 AGVTCSDGSD  LELRLRGGGS  RCAGTVEVEI  QRLLGKVCDR  GWGLKEADVV  CRQLGCGSAL
 421 KTSYQVYSKI  QATNMWLFLS  SCNGNETSLW  DCKNWQWGGL  TCDHYEEAKI  TCSAHREPRL
 481 VGGDIPCSGR  VEVYHGDTWG  SVCDSDFSLE  AASVLCRELQ  CGTVVSILGG  AHFGEGNGQI
 541 WAEEFQCEGH  ESHLSLCPVA  PRPEGTCSHS  RDVGVVCSRY  TEIRLVNGKT  PCEGRVELKT
 601 LNAWGSLCNS  HWDIEDAHVL  CQQLKCGVAL  STPGGAHFGK  GNGQVWRHMF  HCTGTEQHMG
 661 DCPVTALGAS  LCPSGQVASV  ICSGNQSQTL  SSCNSSSLGP  TRPTIPEESA  VACIESGQLR
 721 LVNGGGRCAG  RVEIYHEGSW  GTICDDSWDL  SDAHVVCRQL  GCGEAINATG  SAHFGEGTGP
 781 IWLDEMKCNG  KESRIWQCHS  HGWGQQNCRH  KEDAGVICSE  FMSLRLTSEA  SREACAGRLE
 841 VFYNGAWGSV  GRSNMSETTV  GVVCRQLGCA  DKGKINSASL  DKAMSIPMWV  DNVQCPKGPD
 901 TLWQCPSSPW  EKRLARPSEE  TWITCDNKMR  LQEGPTSCSG  RVEIWHGGSW  GTVCDDSWDL
 961 NDAQVVCQQL  GCGPALKAFK  EAEFGQGTGP  IWLNEVKCKG  NESSLWDCPA  RRWGHSECGH
1021 KEDAAVNCTA  QKISTHKTPQ  KATTGQSFLI  AFGILGVVLL  AIFVALFLTQ  KRRQRQRLTV
1081 SSRGENLVHQ  IQYREMNSCL  NADDLDLMNS  SENSNESADF  NAAELISVSK  FLPISGMEKE
1141 AILRHTEKEN  GNL
```

Example 10

Cloning and Characterization of Canine CD163 from DH82 Cells

A forward primer 5' simianCD163 (SEQ ID NO: 28) (5'-CACCGGAATGAGCAAACTCAGAATGG-3' based on human CD163) and a reverse primer HuCD163-3'Kpn (SEQ ID NO: 29) (5'-GCTCCGGTACCTAGTCCAGGTCTTCA TCAAGGTATCTTA-3') were used to amplify CD163 cDNA from DH82 cells. Total cellular RNA was prepared from DH82 cells using the RNeasy kit. RT-PCR parameters were the same as described in Example 4. RT-PCR products were cloned directionally into the pCDNA3.1D/V5/His/TOPO vector according to the manufacturer's instruction. Several clones containing large inserts were analyzed. Several clones with large inserts were analyzed, and these fell into either the v2 or v3 splicing patterns seen in other species. The v2 variant is missing an 81-nucleotide exon (E81) relative to the v3 variant, which results in a reading frame shift and alternative carboxy terminal amino acid sequences. The canine CD163v2 cDNA from DH82 cells encodes a peptide of 1115 amino acids. When compared to the sequences in Genbank database, it is 83.9% identical to human CD163 (Genbank Z22968), 85.1% identical to pig CD163 (Genbank AJ311716), and 74.3% identical to mouse CD163 (Genbank AF274883). The nucleotide and amino acid sequences of the two splice variants found in DH82 cells are provided below (SEQ ID NOS: 45-48).

| SEQUENCE | ID NO |
|---|---|
| 1 M S K L R M V P H G N S G S A D F R R C<br>1 ATGAGCAAACTCAGAATGGTCCCACATGGAAACTCTGGATCTGCTGACTTTAGAAGATGT | SEQ ID NO: 45 and 46 |
| 21 F A L L C P S A V A V V S I L S T C L M<br>61 TTTGCCCTCTTGTGTCCCTCTGCTGTGGCTGTGGTCTCCATTCTCAGTACCTGTTTGATG | |
| 41 T N S L G R A D K E M R L T D G E D N C<br>121 ACCAATTCTCTTGGGAGAGCAGATAAAGAGATGAGGCTAACGGATGGTGAAGACAATTGC | |
| 61 S G R V E V K V Q E E W G T V C N N G W<br>181 TCCGGGAGAGTGGAAGTGAAAGTCCAGGAGGAGTGGGGAACGGTGTGTAATAATGGCTGG | |
| 81 G M D E V S V I C R Q L G C P T A I K A<br>241 GGCATGGATGAAGTCTCTGTGATTTGCAGGCAGCTGGGATGTCCCACTGCTATCAAAGCC | |
| 101 A G W A N S R A G S G R I W M D H V S C<br>301 GCTGGATGGGCCAATTCCAGGGCAGGCTCTGGACGAATCTGGATGGATCATGTTTCTTGT | |
| 121 R G N E S A L W D C K H D G W G K H N C<br>361 CGAGGGAATGAATCTGCTCTCTGGGACTGCAAACATGATGGATGGGAAAGCACAACTGC | |
| 141 S H Q Q D A G V T C S D G S S L E M R L<br>421 AGTCATCAACAGGATGCTGGAGTAACCTGTTCAGATGGATCCAGTTTGGAGATGAGGTTG | |
| 161 M N G G N Q C S G R I E V K F Q G Q W G<br>481 ATGAACGGCGGAAACCAGTGTTCTGGCAGAATAGAAGTCAAGTTCCAGGGACAGTGGGGA | |
| 181 T V C D D N F N I D H A S V V C K Q L E<br>541 ACAGTGTGTGATGACAACTTCAACATAGATCATGCTTCTGTGGTTTGTAAACAGCTCGAA | |
| 201 C G S A V S F S G S A N F G E G S G P I<br>601 TGTGGAAGTGCTGTCAGTTTCTCTGGTTCAGCTAATTTTGGAGAAGGTTCTGGGCCAATC | |
| 221 W F D D L V C S G N E S A L W N C K H E<br>661 TGGTTTGATGATCTTGTGTGCAGTGGAAATGAGTCAGCTCTCTGGAACTGCAAGCATGAA | |
| 241 G W G K H N C D H A E D V G V I C L D G<br>721 GGATGGGGAAAGCATAACTGTGATCACGCTGAGGATGTTGGAGTGATTTGCTTGGATGGA | |
| 261 A D L S L R L V D G V T E C S G R L E V<br>781 GCAGATCTGAGCCTGAGACTGGTAGATGGAGTCACTGAATGTTCAGGAAGATTAGAAGTA | |
| 281 K F Q G E W G T V C D D G W D S N D A A<br>841 AAATTCCAAGGGGAATGGGGACAGTGTGTGATGATGGCTGGGATAGTAATGATGCTGCT | |
| 301 V V C K Q L G C P T A V T A I G R V N A<br>901 GTGGTATGTAAACAACTGGGATGCCCAACTGCTGTCACCGCCATTGGTCGAGTTAACGCC | |
| 321 S E G S G H I W L D N L S C Q G D E S A<br>961 AGTGAGGGAAGTGGACACATTTGGCTTGACAATCTTTCCTGCCAAGGAGACGAATCTGCT | |
| 341 L W Q C R H H E W G K H Y C N H N E D A<br>1021 CTCTGGCAGTGTAGACACCATGAATGGGGAAAGCATTATTGCAATCATAATGAAGATGCT | |
| 361 G V T C S D G S D L E L R L V G G G S R<br>1081 GGTGTGACATGTTCTGATGGATCAGACCTGGAGCTGAGACTTGTCGGTGGAGGCAGCCGC | |
| 381 C A G T V E V E I Q K L L G K V C D R G<br>1141 TGTGCTGGGACAGTGGAGGTTGAAATTCAGAAACTGCTAGGGAAAGTATGTGATAGAGGC | |
| 401 W G L K E A D V V C K Q L G C G S A L K<br>1201 TGGGGACTGAAAGAAGCCGATGTGGTTTGCAAGCAGTTGGGATGTGGATCTGCTCTCAAA | |
| 421 T S Y Q R Y S K V K A T N T W L F L S R<br>1261 ACGTCCTATCAGCGTTATTCCAAAGTTAAGGCAACAAACACATGGCTGTTTTTAAGCCGC | |

```
                              -continued
SEQUENCE                                                          ID NO 441  C  S  G  N  E  T  S  L  W  D  C  K  N  W  Q  W  G  G  L  S
1321  TGTAGTGGCAATGAAACTTCCCTTTGGGACTGCAAGAACTGGCAGTGGGGTGGACTGAGC 461  C  D  H  Y  E  E  A  K  V  T  C  S  A  H  R  E  P  R  L  V
1381  TGTGATCACTATGAAGAAGCTAAAGTTACCTGCTCAGCCCACAGGGAACCCAGACTAGTT 481  G  G  D  I  P  C  S  G  R  V  E  V  K  H  G  D  T  W  G  T
1441  GGAGGAGATATTCCCTGCTCTGGTCGTGTTGAAGTGAAACATGGTGACACATGGGGCACC 501  V  C  D  S  D  F  S  L  E  A  A  S  V  L  C  R  E  L  Q  C
1501  GTCTGTGATTCCGACTTCTCTTTGGAAGCTGCCAGTGTGCTGTGCAGAGAGTTACAGTGT 521  G  T  V  I  S  I  L  G  G  A  H  F  G  E  G  N  G  Q  I  W
1561  GGCACAGTCATCTCCATCCTAGGGGGAGCTCACTTTGGAGAAGGAAATGGACAGATCTGG 541  A  E  E  F  Q  C  E  G  Q  E  S  H  L  S  L  C  S  V  A  S
1621  GCTGAAGAATTCCAGTGTGAGGGGCAGGAGTCCCATCTTTCACTCTGTTCAGTAGCCTCT 561  R  P  D  G  T  C  S  H  S  R  D  V  G  V  V  C  S  R  Y  T
1681  CGCCCAGATGGGACCTGTAGCCACAGCAGGGATGTTGGAGTCGTCTGCTCAAGATACACG 581  E  I  R  L  V  N  G  Q  S  P  C  E  G  R  V  E  L  K  I  L
1741  GAAATCCGCTTGGTGAATGGCCAGTCCCCGTGTGAAGGAAGAGTGGAGCTCAAGATACTT 601  G  N  W  G  S  L  C  N  S  H  W  D  I  E  D  A  H  V  F  C
1801  GGGAACTGGGGATCCCTCTGCAACTCTCACTGGGACATAGAAGATGCCCATGTTTTCTGT 621  Q  Q  L  K  C  G  V  A  L  S  I  P  G  G  A  H  F  G  K  G
1861  CAGCAGCTCAAATGTGGAGTTGCCCTTTCTATTCCGGGAGGAGCACATTTTGGGAAAGGA 641  S  G  Q  I  W  R  H  M  F  H  C  T  G  T  E  Q  H  M  G  D
1921  AGTGGTCAGATCTGGAGGCACATGTTTCACTGCACTGGGACTGAGCAGCACATGGGAGAT 661  C  P  V  T  A  L  G  A  T  L  C  S  A  G  Q  V  A  S  V  I
1981  TGCCCTGTAACTGCTCTGGGCGCGACGCTGTGTTCTGCTGGGCAAGTGGCCTCTGTAATC 681  C  S  G  N  Q  S  Q  T  L  S  P  C  N  S  T  S  L  D  P  T
2041  TGCTCAGGAAATCAGAGCCAGACGCTATCCCCATGCAATTCAACATCTCTGGACCCAACA 701  R  S  T  T  S  E  E  S  A  V  A  C  I  A  S  G  Q  L  R  L
2101  AGATCTACCACTTCGGAAGAAAGTGCTGTTGCTTGTATTGCGAGTGGGCAACTTCGCCTG 721  V  N  G  G  R  C  A  G  R  I  E  V  Y  H  E  G  S  W  G
2161  GTAAATGGAGGCGGTCGCTGTGCTGGGAGAATAGAGGTCTACCATGAGGGCTCCTGGGGC 741  T  I  C  D  D  S  W  D  L  S  D  A  H  V  V  C  R  Q  L  G
2221  ACCATCTGTGATGACAGCTGGGACCTGAGTGATGCCCATGTGGTGTGCAGACAGCTGGGC 761  C  G  V  A  I  N  A  T  G  S  A  H  F  G  E  G  T  G  P  I
2281  TGTGGAGTGGCCATTAATGCCACTGGCTCTGCTCATTTTGGGGAAGGAACAGGGCCCATC 781  W  L  D  E  V  N  C  N  G  K  E  S  H  I  W  Q  C  R  S  H
2341  TGGCTGGACGAGGTGAACTGTAATGGAAAGGAATCTCATATCTGGCAATGCCGCTCACAC 801  G  W  G  Q  H  N  C  R  H  K  E  D  A  G  V  I  C  S  E  F
2401  GGCTGGGGGCAACACAACTGCAGACATAAGGAGGATGCAGGAGTTATCTGCTCAGAGTTC 821  M  S  L  R  L  I  D  E  T  S  R  D  I  C  A  G  R  L  E  V
2461  ATGTCTCTCAGACTGATTGATGAAACCAGCAGAGACATCTGTGCAGGGCGTCTTGAAGTT 841  F  Y  N  G  A  W  G  S  V  G  K  S  N  M  S  A  T  T  V  E
2521  TTTTACAATGGAGCTTGGGGCAGCGTTGGCAAGAGTAATATGTCTGCAACCACTGTGGAG 861  V  V  C  R  Q  L  G  C  A  D  K  G  S  I  N  P  A  S  S  D
2581  GTGGTATGCAGGCAACTGGGTTGTGCAGACAAGGGGAGCATCAACCCTGCATCTTCAGAC 881  K  P  M  S  R  H  M  W  V  D  N  V  Q  C  P  K  G  P  D  T
2641  AAGCCCATGTCCAGGCACATGTGGGTGGACAATGTCCAGTGTCCAAAAGGACCTGACACC 901  L  W  Q  C  P  S  S  P  W  K  Q  R  V  A  S  S  S  E  E  T
2701  TTATGGCAGTGCCCATCTTCTCCATGGAAACAGAGAGTGGCCAGTTCTTCAGAGGAGACC 921  W  I  T  C  A  N  K  I  R  L  Q  E  G  T  S  N  C  S  G  R
2761  TGGATCACATGTGCCAACAAGATAAGACTTCAAGAAGGAACCTCTAATTGTTCTGGACGT 941  V  E  L  W  H  G  G  S  W  G  T  V  C  D  S  S  H  D  L  E
2821  GTGGAGCTCTGGCACGGAGGTTCCTGGGGGACAGTGTGCGATGACTCCTGGGACCTTGAA
```

-continued

| SEQUENCE | | ID NO |
|---|---|---|
| 961 D A Q V V C R Q L G C G P A L E A L K E<br>2881 GATGCACAAGTGGTGTGTCGACAGCTGGGCTGTGGCCCAGCATTAGAAGCACTAAAAGAG | | |
| 981 A A F G Q G T G P I W L N D V K C K G N<br>2941 GCAGCATTTGGTCAGGGGACTGGGCCTATATGGCTCAATGACGTGAAGTGCAAAGGGAAT | | |
| 1001 E S S L W D C P A R P W G H S D C G H K<br>3001 GAGTCTTCCTTGTGGGATTGTCCTGCTAGACCCTGGGGGCACAGTGACTGTGGCCACAAG | | |
| 1021 E D A A V R C S E I A M A Q R S S N P R<br>3061 GAAGATGCTGCTGTGAGGTGCTCAGAAATTGCAATGGCCCAAAGATCATCAAATCCTAGA | | |
| 1041 G H S S L V A L G I F G V I L L A F L I<br>3121 GGTCACTCATCCCTTGTTGCATTGGGGATCTTTGGTGTCATTCTTCTGGCCTTTCTCATC | | |
| 1061 A L L L W T Q R R R Q Q Q R L T V S L R<br>3181 GCTCTCCTCTTGTGGACTCAAAGGCGAAGACAGCAACAGCGGCTTACAGTTTCCTTGAGA | | |
| 1081 G E N S V H Q I Q Y R E M N S S L K A D<br>3241 GGAGAGAATTCTGTCCACCAAATTCAATACCGGGAAATGAATTCTTCCCTGAAAGCAGAT | | |
| 1101 D L D V L T S S E D H F E V H<br>3301 GATCTGGACGTGCTGACTTCCTCAGAAGACCATTTTGACGTACAC | | |

```
   1 MSKLRMVPHG NSGSADFRRC FALLCPSAVA VVSILSTCLM TNSLGRADKE MRLTDGEDNC   SEQ ID
  61 SGRVEVKVQE ENGTVCNNGW GMDEVSVICR QLGCPTAIKA AGWANSRAGS GRIWMDHVSC   NO: 46
 121 RGNESALWDC KHDGWGKHNC SHQQDAGVTC SDGSSLEMRL MNGGNQCSGR IEVKFQGQWG
 181 TVCDDNFNID HASVVCKQLE CGSAVSFSGS ANFGEGSGPI WFDDLVCSGN ESALWNCKHE
 241 GWGKHNCDHA EDVGVICLDG ADLSLRLVDG VTECSGRLEV KFQGEWGTVC DDGWDSNDAA
 301 VVCKQLGCPT AVTAIGRVNA SEGSGHIWLD NLSCQGDESA LWQCRHHEWG KHYCNHNEDA
 361 GVTCSDGSDL ELRLVGGGSR CAGTVEVEIQ KLLGKVCDRG WGLKEADVVC KQLGCGSALK
 421 TSYQRYSKVK ATNTWLFLSR CSGNETSLWD CKNWQWGGLS CDHYEEAKVT CSAHREPRLV
 481 GGDIPCSGRV EVKHGDTWGT VCDSDFSLEA ASVLCRELQC GTVISILGGA HFGEGNGQIW
 541 AEEFQCEGQE SHLSLCSVAS RPDGTCSHSR DVGVVCSRYT EIRLVNGQSP CEGRVELKIL
 601 GNWGSLCNSH WDIEDAHVFC QQLKCGVALS IPGGAHFGKG SGQIWRHMPH CTGTEQHMGD
 661 CPVTALGATL CSAGQVASVI CSGNQSQTLS PCNSTSLDPT RSTTSEESAV ACIASGQLRL
 721 VNGGGRCAGR IEVYHEGSWG TICDDSWDLS DAHVVCRQLG CGVAINATGS AHFGEGTGPI
 781 WLDEVNCNGK ESHIWQCRSH GWGQHNCRHK EDAGVICSEF MSLRLIDETS RDICAGRLEV
 841 FYNGAWGSVG KSNMSATTVE VVCRQLGCAD KGSINPASSD KPMSRHMWVD NVQCPKGPDT
 901 LWQCPSSPWK QRVASSSEET WITCANKIRL QEGTSNCSGR VELWHGGSWG TVCDDSWDLE
 961 DAQVVCRQLG CGPALEALKE AAFGQGTGPI WLNDVKCKGN ESSLWDCPAR PWGHSDCGHK
1021 EDAAVRCSEI AMAQRSSNPR GHSSLVALGI FGVILLAFLI ALLLWTQRRR QQQRLTVSLR
1081 GENSVHQIQY REMNSSLKAD DLDVLTSSED HFEVH
```

| 1 M S K L R M V P H G N S G S A D F R R C<br>1 ATGAGCAAACTCAGAATGGTCCCACATGGAAACTCTGGATCTGCTGACTTTAGAAGATGT | | SEQ ID<br>NO: 47 |
|---|---|---|
| 21 F A L L C P S A V A V V S I L S T C L M<br>61 TTTGCCCTCTTGTGTCCCTCTGCTGTGGCTGTGGTCTCCATTCTCAGTACCTGTTTGATG | | |
| 41 T N S L G R A D K E M R L T D G E D N C<br>121 ACCAATTCTCTTGGGAGAGCAGATAAAGAGATGAGGCTAACGGATGGTGAAGACAATTGC | | |
| 61 S G R V E V K V Q E E W G T V C N N G W<br>181 TCCGGGAGAGTGGAAGTGAAAGTCCAGGAGGAGTGGGGAACGGTGTGTAATAATGGCTGG | | |
| 81 G M D E V S V I C R Q L G C P T A I K A<br>241 GGCATGGATGAAGTCTCTGTGATTTGCAGGCAGCTGGGATGTCCCACTGCTATCAAAGCC | | |
| 101 A G W A N S R A G S G R I W M D H V S C<br>301 GCTGGATGGGCCAATTCCAGGGCAGGCTCTGGACGAATCTGGATGGATCATGTTTCTTGT | | |
| 121 R G N E S A L W D C K H D G W G K H N C<br>361 CGAGGGAATGAATCTGCTCTCTGGGACTGCAAACATGATGGATGGGGAAAGCACAACTGC | | |
| 141 S H Q Q D A G V T C S D G S S L E M R L<br>421 AGTCATCAACAGGATGCTGGAGTAACCTGTTCAGATGGATCCAGTTTGGAGATGAGGTTG | | |
| 161 M N G G N Q C S G R I E V K F Q G Q W G<br>481 ATGAACGGCGGAAACCAGTGTTCTGGCAGAATAGAAGTCAAGTTCCAGGGACAGTGGGGA | | |
| 181 T V C D D N F N I D H A S V V C K Q L E<br>541 ACAGTGTGTGATGACAACTTCAACATAGATCATGCTTCTGTGGTTTGTAAACAGCTCGAA | | |
| 201 C G S A V S F S G S A N F G E G S G P I<br>601 TGTGGAAGTGCTGTCAGTTTCTCTGGTTCAGCTAATTTTGGAGAAGGTTCTGGGCCAATC | | |

```
            221 W  F  D  D  L  V  C  S  G  N  E  S  A  L  W  N  C  K  H  E
            661 TGGTTTGATGATCTTGTGTGCAGTGGAAATGAGTCAGCTCTCTGGAACTGCAAGCATGAA

241 G  W  G  K  H  N  C  D  H  A  E  D  V  G  V  I  C  L  D  G
            721 GGATGGGAAAGCATAACTGTGATCACGCTGAGGATGTTGGAGTGATTTGCTTGGATGGA

261 A  D  L  S  R  L  V  D  G  V  T  E  C  S  G  R  L  E  V
            781 GCAGATCTGAGCCTGAGACTGGTAGATGGAGTCACTGAATGTTCAGGAAGATTAGAAGTA

281 K  F  Q  G  E  W  G  T  V  C  D  D  G  W  D  S  N  D  A  A
            841 AAATTCCAAGGGGAATGGGGACAGTGTGTGATGATGGCTGGGATAGTAATGATGCTGCT

301 V  V  C  K  Q  L  G  C  P  T  A  V  T  A  I  G  R  V  N  A
            901 GTGGTATGTAAACAACTGGGATGCCCAACTGCTGTCACCGCCATTGGTCGAGTTAACGCC

321 S  E  G  S  G  H  I  W  L  D  N  L  S  C  Q  G  D  E  S  A
            961 AGTGAGGGAAGTGGACACATTTGGCTTGACAATCTTTCCTGCCAAGGAGACGAATCTGCT

341 L  W  Q  C  R  H  H  E  W  G  K  H  Y  C  N  H  N  E  D  A
           1021 CTCTGGCAGTGTAGACACCATGAATGGGGAAAGCATTATTGCAATCATAATGAAGATGCT

361 G  V  T  C  S  D  G  S  D  L  E  L  R  L  V  G  G  G  S  R
           1081 GGTGTGACATGTTCTGATGGATCAGACCTGGAGCTGAGACTTGTCGGTGGAGGCAGCCGC

381 C  A  G  T  V  E  V  E  I  Q  K  L  L  G  K  V  C  D  R  G
           1141 TGTGCTGGGACAGTGGAGGTTGAAATTCAGAAACTGCTAGGGAAAGTATGTGATAGAGGC

401 W  G  L  K  E  A  D  V  V  C  K  Q  L  G  C  G  S  A  L  K
           1201 TGGGGACTGAAAGAAGCCGATGTGGTTTGCAAGCAGTTGGGATGTGGATCTGCTCTCAAA

421 T  S  Y  Q  R  Y  S  K  V  K  A  T  N  T  W  L  F  L  S  R
           1261 ACGTCCTATCAGCGTTATTCCAAAGTTAAGGCAACAAACACATGGCTGTTTTTAAGCCGC

441 C  S  G  N  E  T  S  L  W  D  C  K  N  W  Q  W  G  G  L  S
           1321 TGTAGTGGCAATGAAACTTCCCTTTGGGACTGCAAGAACTGGCAGTGGGGTGGACTGAGC

461 C  D  H  Y  E  E  A  K  V  T  C  S  A  H  R  E  P  R  L  V
           1381 TGTGATCACTATGAAGAAGCTAAAGTTACCTGCTCAGCCCACAGGGAACCCAGACTAGTT

481 G  G  D  I  P  C  S  G  R  V  E  V  K  H  G  D  T  W  G  T
           1441 GGAGGAGATATTCCCTGCTCTGGTCGTGTTGAAGTGAAACATGGTGACACATGGGGCACC

501 V  C  D  S  D  F  S  L  E  A  A  S  V  L  C  R  E  L  Q  C
           1501 GTCTGTGATTCCGACTTCTCTTTGGAAGCTGCCAGTGTGCTGTGCAGAGAGTTACAGTGT

521 G  T  V  I  S  I  L  G  G  A  H  F  G  E  G  N  G  Q  I  W
           1561 GGCACAGTCATCTCCATCCTAGGGGGAGCTCACTTTGGAGAAGGAAATGGACAGATCTGG

541 A  E  E  F  Q  C  E  G  Q  E  S  H  L  S  L  C  S  V  A  S
           1621 GCTGAAGAATTCCAGTGTGAGGGGCAGGAGTCCCATCTTTCACTCTGTTCAGTAGCCTCT

561 R  P  D  G  T  C  S  H  S  R  D  V  G  V  V  C  S  R  Y  T
           1681 CGCCCAGATGGGACCTGTAGCCACAGCAGGGATGTTGGAGTCGTCTGCTCAAGATACACG

581 E  I  R  L  V  N  G  Q  S  P  C  E  G  R  V  E  L  K  I  L
           1741 GAAATCCGCTTGGTGAATGGCCAGTCCCCGTGTGAAGGAAGAGTGGAGCTCAAGATACTT

601 G  N  W  G  S  L  C  N  S  H  W  D  I  E  D  A  H  V  F  C
           1801 GGGAACTGGGGATCCCTCTGCAACTCTCACTGGGACATAGAAGATGCCCATGTTTTCTGT

621 Q  Q  L  K  C  G  V  A  L  S  I  P  G  G  A  H  F  G  K  G
           1861 CAGCAGCTCAAATGTGGAGTTGCCCTTTCTATTCCGGGAGGAGCACATTTTGGGAAAGGA

641 S  G  Q  I  W  R  H  M  F  H  C  T  G  T  E  Q  H  M  G  D
           1921 AGTGGTCAGATCTGGAGGCACATGTTTCACTGCACTGGGACTGAGCAGCACATGGGAGAT

661 C  P  V  T  A  L  G  A  T  L  C  S  A  G  Q  V  A  S  V  I
           1981 TGCCCTGTAACTGCTCTGGGCGCGACGCTGTGTTCTGCTGGGCAAGTGGCCTCTGTAATC

681 C  S  G  N  Q  S  Q  T  L  S  P  C  N  S  T  S  L  D  P  T
           2041 TGCTCAGGAAATCAGAGCCAGACGTATCCCCATGCAATTCAACATCTCTGGACCCAACA

701 R  S  T  T  S  E  E  S  A  V  A  C  I  A  S  G  Q  L  R  L
           2101 AGATCTACCACTTCGGAAGAAAGTGCTGTTGCTTGTATTGCGAGTGGCAACTTCGCCTG

721 V  N  G  G  G  R  C  A  G  R  I  E  V  Y  H  E  G  S  W  G
           2161 GTAAATGGAGGCGGTCGCTGTGCTGGGAGAATAGAGGTCTACCATGAGGGCTCCTGGGGC
```

```
SEQUENCE                                                                           ID NO

741 T   I   C   D   D   S   W   D   L   S   D   A   H   V   V   C   R   Q   L   G
2221 ACCATCTGTGATGACAGCTGGGACCTGAGTGATGCCCATGTGGTGTGCAGACAGCTGGGC

761 C   G   V   A   I   N   A   T   G   S   A   H   F   G   E   G   T   G   P   I
2281 TGTGGAGTGGCCATTAATGCCACTGGCTCTGCTCATTTTGGGGAAGGAACAGGGCCCATC

781 W   L   D   E   V   N   C   N   G   K   E   S   H   I   W   Q   C   R   S   H
2341 TGGCTGGACGAGGTGAACTGTAATGGAAAGGAATCTCATATCTGGCAATGCCGCTCACAC

801 G   W   G   Q   H   N   C   R   H   K   E   D   A   G   V   I   C   S   E   F
2401 GGCTGGGGGCAACACAACTGCAGACATAAGGAGGATGCAGGAGTTATCTGCTCAGAGTTC

821 M   S   L   R   L   I   D   E   T   S   R   D   I   C   A   G   R   L   E   V
2461 ATGTCTCTCAGACTGATTGATGAAACCAGCAGAGACATCTGTGCAGGGCGTCTTGAAGTT

841 F   Y   N   G   A   W   G   S   V   G   K   S   N   M   S   A   T   T   V   E
2521 TTTTACAATGGAGCTTGGGGCAGCGTTGGCAAGAGTAATATGTCTGCAACCACTGTGGAG

861 V   V   C   R   Q   L   G   C   A   D   K   G   S   I   N   P   A   S   S   D
2581 GTGGTATGCAGGCAACTGGGTTGTGCAGACAAGGGGAGCATCAACCCTGCATCTTCAGAC

881 K   P   M   S   R   H   M   W   V   D   N   V   Q   C   P   K   G   P   D   T
2641 AAGCCCATGTCCAGGCACATGTGGGTGGACAATGTCCAGTGTCCAAAAGGACCTGACACC

901 L   W   Q   C   P   S   S   P   W   K   Q   R   V   A   S   S   S   E   E   T
2701 TTATGGCAGTGCCCATCTTCTCCATGGAAACAGAGAGTGGCCAGTTCTTCAGAGGAGACC

921 W   I   T   C   A   N   K   I   R   L   Q   E   G   T   S   N   C   S   G   R
2761 TGGATCACATGTGCCAACAAGATAAGACTTCAAGAAGGAACCTCTAATTGTTCTGGACGT

941 V   E   L   W   H   G   G   S   W   G   T   V   C   D   D   S   W   D   L   E
2821 GTGGAGCTCTGGCACGGAGGTTCCTGGGGACAGTGTGCGATGACTCCTGGGACCTTGAA

961 D   A   Q   V   V   C   R   Q   L   G   C   G   P   A   L   E   A   L   K   E
2881 GATGCACAAGTGGTGTGTCGACAGCTGGGCTGTGGCCCAGCATTAGAAGCACTAAAAGAG

981 A   A   F   G   Q   G   T   G   P   I   W   L   N   D   V   K   C   K   G   N
2941 GCAGCATTTGGTCAGGGGACTGGGCCTATATGGCTCAATGACGTGAAGTGCAAAGGGAAT

1001 E   S   S   L   W   D   C   P   A   R   P   W   G   H   S   D   C   G   H   K
3001 GAGTCTTCCTTGTGGGATTGTCCTGCTAGACCCTGGGGGCACAGTGACTGTGGCCACAAG

1021 E   D   A   A   V   R   C   S   E   I   A   M   A   Q   R   S   S   N   P   R
3061 GAAGATGCTGCTGTGAGGTGCTCAGAAATTGCAATGGCCCAAAGATCATCAAATCCTAGA

1041 G   H   S   S   L   V   A   L   G   I   F   G   V   I   L   L   A   F   L   I
3121 GGTCACTCATCCCTTGTTGCATTGGGGATCTTTGGTGTCATTCTTCTGGCCTTTCTCATC

1061 A   L   L   L   W   T   Q   R   R   R   Q   Q   Q   R   L   T   V   S   L   R
3181 GCTCTCCTCTTGTGGACTCAAAGGCGAAGACAGCAACAGCGGCTTACAGTTTCCTTGAGA

1081 G   E   N   S   V   H   Q   I   Q   Y   R   E   M   N   S   S   L   K   A   D
3241 GGAGAGAATTCTGTCCACCAAATTCAATACCGGGAAATGAATTCTTCCCTGAAAGCAGAT

1101 D   L   D   V   L   T   S   S   E   Y   P   N   E   S   D   D   E   N   D   A
3301 GATCTGGACGTGCTGACTTCCTCAGAATATCCCAATGAGTCAGATGATTTTAATGATGCT

1121 G   L   I   S   V   K   S   L   P   I   S   G
3361 GGGCTAATTTCTGTGTCTAAATCTCTTCCTATTTCTGGA

1 MSKLRMVPHG NSGSADFRRC FALLCPSAVA VVSILSTCLM TNSLGRADKE MRLTDGEDNC    SEQ ID
  61 SGRVEVKVQE EWGTVCNNGW GMDEVSVICR QLGCPTAIKA AGWANSRAGS GRIWMDHVSC    NO: 48
 121 RGNESALWDC KHDGWGKHNC SHQQDAGVTC SDGSSLEMRL MNGGNQCSGR IEVKFQGQWG
 181 TVCDDNFNID HASVVCKQLE CGSAVSFSGS ANFGEGSGPI WFDDLVCSGN ESALWNCKHE
 241 GWGKHNCDHA EDVGICLDG  ADLSLRLVDG VTECSGRLEV KFQGEWGTVC DDGWDSNDAA
 301 VVCKQLGCPT AVTAIGRVNA SEGSGHIWLD NLSCQGDESA LWQCRHHEWG KHYCNHNEDA
 361 GVTCSDGSDL ELRLVGGGSR CAGTVEVEIQ KLLGKVCDRG WGLKEADVVC KQLGCGSALK
 421 TSYQRYSKVK ATNTWLFLSR CSGNETSLWD CKNWQWGGLS CDHYEEAKVT CSAHREPRLV
 481 GGDIPCSGRV EVKHGDTWGT VCDSDFSLEA ASVLCRELQC GTVISILGGA HFGEGNGQIW
 541 AEEFQCEGQE SHLSLCSVAS RPDGTCSHSR DVGVVCSRYT EIRLVNGQSP CEGRVELKIL
 601 GNWGSLCNSH WDIEDAHVFC QQLKCGVALS IPGGAHFGKG SGQIWRHMPH CTGTEQHMGD
 661 CPVTALGATL CSAGQVASVI CSGNQSQTLS PCNSTSLDPT RSTTSEESAV ACIASGQLRL
 721 VNGGGRCAGR IEVYHEGSWG TICDDSWDLS DAHVVCRQLG CGVAINATGS AHFGEGTGPI
 781 WLDEVNCNGK ESHIWQCRSH GWGQHNCRHK EDAGVICSEF MSLRLIDETS RDICAGRLEV
 841 FYNGAWGSVG KSNMSATTVE VVCRQLGCAD KGSINPASSD KPMSRHMWVD NVQCPKGPDT
 901 LWQCPSSPWK QRVASSSEET WITCANKIRL QEGTSNCSGR VELWHGGSWG TVCDDSWDLE
 961 DAQVVCRQLG CGPALEALKE AAFGQGTGPI WLNDVKCKGN ESSLWDCPAR PWGHSDCGHK
```

-continued

| SEQUENCE | ID NO |
|---|---|
| 1021 EDAAVRCSEI AMAQRSSNPR GHSSLVALGI FGVILLAFLI ALLLWTQRRR QQQRLTVSLR | |
| 1081 GENSVHQIQY REMNSSLKAD DLDVLTSSEY PNESDDFNDA GLISVSKSLP ISG | |

Example 11

Various Cell Lines are Rendered Permissive to North American PRRSV Infection Following Transient Transfection with pCMV-susCD163v1

Porcine Kidney (PK032495), Norden Labs Swine Testicular (NLST-1), Norden Labs Dog Kidney (NLDK-1) were obtained from Pfizer Inc. and were grown at 37° C. and 5% $CO_2$ in growth media consisting of Dulbecco's Modified Eagle Medium (DMEM, Invitrogen catalog number 11965) supplemented with 5% fetal bovine serum (FBS), 1 mM sodium pyruvate, 2 mM L-glutamine and antibiotics. Cell lines Baby Hamster Kidney (BHK21), Norden Labs Feline Kidney (NLFK-1), and Rabbit Lung (RL) were obtained from Pfizer Inc. and were grown at 37° C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Vero cells were obtained from Pfizer Inc. and were grown at 37° C. and 5% $CO_2$ in growth media consisting of Minimum Essential Medium Alpha (MEM, Pfizer Inc. formulation) supplemented with 10% fetal bovine serum (FBS), 2 mM L-glutamine and Gentamicin at 20 micrograms per mL. Cell culture wells (35 mm) containing approximately $1 \times 10^6$ cells were transfected with 2 micrograms per well of plasmid pCMV-susCD163v1, in DMEM without FBS or antibiotics, using Lipofectamine 2000 (Invitrogen catalog number 11668-027) according to the manufacturer's instructions. Cell line RL was transfected with 1.0 micrograms per well of plasmid pCMV-susCD163v1. A member of the PAM cell cDNA library without an insert, designated pPAMB (essentially and empty pSport plasmid vector), was used as a negative control plasmid. At 24 hours post transfection wells were aspirated and washed twice with DMEM/5% FBS followed by infection with North American PRRSV isolate P129. Virus was allowed to adsorb in 0.5 ml growth media for a minimum of two hours, after which additional media was added to a final volume of 2.0 ml and incubated overnight. The virus was then removed, wells washed twice with growth media, and fresh growth media added (2.0 ml per well). A time zero sample of culture fluid was immediately taken in order to determine the background level of infectious virus from the inoculum. At a minimum of 48 hours post infection cultures were screened for permissivity by removing culture fluids in order to assay viable virus, and permissive cells in the monolayer were detected by fluorescent antibody assay (FA). The FA was completed by fixing the monolayer with 80% acetone and stained with FITC-conjugated monoclonal antibody SDOW17 (Rural Technologies Inc), which is specific for the PRRSV nucleocapsid protein. Viable virus was titrated by inoculating dilutions of culture fluids onto MARC-145 cells. Table 5 shows the results of virus infection by FA and the presence of progeny virus for each cell line tested.

Failure to detect progeny virus from some cell lines may be the result of low virus titer in the cell culture fluids, below the assay's limit of detection. Permissivity of Vero cells to PRRSV infection was augmented by the expression of susCD163v1. Compared to the time zero measurement of background virus, there was nearly a two-log increase in virus titers in Vero cells transfected with pCMV-susCD163v1, whereas there was less than a one-log in titer increase in cells transfected with negative control plasmid pPAMB. All cell lines except NLDK-1 were positive by FA for permissivity to North American PRRSV isolate P129 infection after transfection with pCMV-susCD163v1.

TABLE 5

Screening of various cell lines for permissivity to NA PRRSV isolate P129 following transient transfection with pCMV-susCD163v1 or pPAMB

| Transfected cell line | Fluorescent Antibody assay | | Progeny virus produced | |
|---|---|---|---|---|
| | pCMV-susCD163v1 | pPAMB | pCMV-susCD163v1 | pPAMB |
| BHK21 | +++ | − | +++ | − |
| PK032495 | + | − | + | − |
| NKFK-1 | + | − | + | − |
| NLST-1 | + | − | − | − |
| NLDK-1 | − | − | NT | NT |
| RL | + | − | − | − |
| Vero | ++ | + | ++ | + |

+++ = Highly positive
++ = Moderately positive
+ = Slightly positive
− = Not detectible
NT = Not tested Example 12

BHK21 Cells are Rendered Permissive to European PRRSV Infection Following Transient Transfection with pCMV-susCD163v1

Cell line Baby Hamster Kidney (BHK21) was obtained from Pfizer Inc. and grown at 37° C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Cell culture wells (35 mm) containing approximately $1 \times 10^6$ cells were transfected with 2 micrograms per well of plasmid pCMV-susCD163v1, in DMEM without FBS or antibiotics, using Lipofectamine 2000 (Invitrogen catalog number 11668-027) according to the manufacturer's instructions. At 24 hours post transfection wells were aspirated and washed twice with DMEM/5% FBS followed by infection with European PRRSV isolate 96V198. Virus was allowed to adsorb for a minimum of 2 hours. The virus was then removed, wells washed twice with growth media, and fresh growth media added (2.0 ml per well). A time zero sample of culture fluid was immediately taken in order to determine the background level of infectious virus from the inoculum. At a minimum of 48 hours post infection cultures were screened for permissivity by removing culture fluids in order to assay viable virus, and permissive cells in the monolayer were detected by fluorescent antibody assay (FA). The FA was completed by fixing the monolayer with 80% acetone and stained with FITC-conjugated monoclonal antibody SDOW17 (Rural Technologies Inc), which is specific for the PRRSV nucleocapsid protein. Viable virus was titrated by inoculating dilutions of culture fluids onto MARC-145 cells. As a result of the transient transfection of BKH21 with pCMV-susCD163v1, cells were rendered permissive to European PRRSV isolate 96V198 infection and yielded progeny virus.

Example 13

CD163 Genes from Multiple Animal Species Render BHK21 Cells Permissive to PRRS Virus Infection BHK21 cells grown in DMEM (Invitrogen catalog number 11965) supplemented with 10% fetal bovine serum, 1 mM sodium pyruvate, and antibiotics, were used in transient transfection experiments. Before transfection cells were washed once with OptiMEM (Invitrogen) without serum or other additives. Lipofectamine 2000 (Invitrogen) was used in all transfection experiments according to the protocol provided by the manufacturer. The transfection mixture consisted of 10 microliters of Lipofectamine 2000 and 2-3 micrograms of DNA per 35 mm well. After overnight incubation, transfection medium was removed and cells were infected with PRRSV isolate P129. Infection was allowed to progress for 24-48 hours, when cells were fixed with 80% acetone and stained with monoclonal antibody SDOW17 conjugated with FITC (Rural Technology Inc., Brookings, S. Dak.). Staining of the nucleocapsid protein was visualized under a fluorescence microscope. Table 6. Transient transfection of BHK21 cells with various CD163 genes renders them permissive to PRRS virus infection

TABLE 6

| Plasmid backbone | CD163 gene | PRRSV infection (FA) |
| --- | --- | --- |
| pCMV-Script | Swine CD163v1 | +++ |
| pRSV-Script | Swine CD163v1 | +++ |
| pcDNA3.1D | Swine CD163v2 | ++ |
| pcDNA3.1D | Human CD163v2 | ++ |
| pcDNA3.1D | Mouse CD163v3 | + |
| pcDNA3.1D | African green monkey (MARC-145 cell) CD163v2 | +++ |
| pcDNA3.1D | Vero cells CD163v7 | +++ |
| pcDNA3.1D | DH82 cell CD163v2 | +++ |

+++ = Highly positive
++ = Moderately positive
+ = Slightly positive

Example 14

Generation of PRRSV-Permissive BHK21 Stable Cell Lines Using pCMV-susCD163v1

BHK-21 cells were grown in Dulbecco's Modified Eagle Media (DMEM) supplemented with 10% fetal bovine serum, 1 mM sodium pyruvate, and antibiotics. For transfection, cells were seeded at approximately 90% confluency in 6 well plates and incubated over night at 37° C. in 5% $CO_2$. Cells were transfected with pCMV-susCD163v1 DNA using Lipofectamine 2000 (Invitrogen) according to the manufacturer's instructions. One day after transfection the cells were trypsinized and re-seeded in 96 well plates in a dilution series. To select for stable transfectants, the media was supplemented with 1 mg/ml Geneticin (G418 sulfate, Invitrogen catalog number 10131-027) from this point forward. Medium was changed every 3-5 days. Plates were cultured until those wells with colonies derived from single cells reached confluency, at which point the plates were trypsinized and seeded into duplicate 96 well plates. One of the duplicate 96 well plates was infected with PRRSV isolate P129 and clones permissive to infection were identified by staining with FITC conjugated monoclonal antibody SDOW17. Positive clones were then expanded from the second duplicate plate. To ensure homogeneity the positive cultures were single-cell cloned by limiting dilution. At each cloning the subclones that displayed robust growth and high PRRSV permissivity were chosen for expansion. Three clones designated BHK/CMV/v1 #3, BHK/CMV/v1 #5, and BHK/CMV/v1 #12 (FIG. 6) were selected. These cell lines have maintained the permissive phenotype through 20 passages.

Example 15

Generation of PRRSV-Permissive BHK21 Stable Cell Lines Using pRSV-susCD163v1

Figure 7:
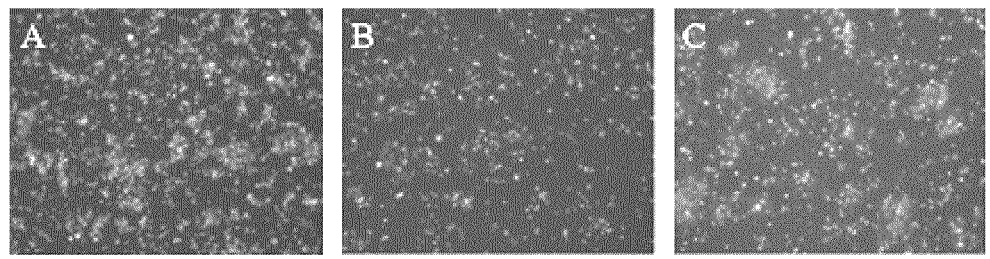

BHK-21 cells were cultured as described in Example 14. BHK-21 cells were transfected with pRSVsusCD163v1 using Lipofectamine 2000 as described in Example 14. Cloning of transfected cells and screening for permissive clones was performed essentially as described in Example 14. From the original cloning 3 single cell clones were identified as permissive and were subsequently recloned two more times to ensure homogeneity and to attempt to isolate subclones of higher permissivity (see FIG. 7). The resulting cell lines were named BHK/RSV/v1, #2, #3, and #4. All of these clones have maintained the permissive phenotype through the highest passage tested (passage 11 for clone #2, passage 7 for clone #3, and passage 5 for clone #4).

Example 16

Generation of PRRSV-Permissive Feline Kidney Stable Cell Lines Using pCMV-susCD163v1

Parental Norden Labs Feline Kidney (NLFK) cells were grown at 37 degrees C. and 5% $CO_2$ in Dulbecco's Modified Eagle Medium (Invitrogen catalog number 11965-092) supplemented with 10% fetal bovine serum, 1 mM sodium pyruvate, and antibiotics. Several 35 mm wells containing approximately $2 \times 10^6$ cells each were transfected with 4 micrograms per well of pCMV-susCD163v1, in OptiMEM, using Lipofectamine 2000 (Invitrogen catalog number 11668-027) according to the manufacturer's instructions. After overnight incubation, cells were removed from the substrate using Accutase (Innovative Cell Technologies, catalog number AT104) diluted in medium, and seeded into three 96-well plates at three densities (approximately $2 \times 10^2$, $2 \times 10^3$, and $2 \times 10^4$ cells per well). The cells were allowed to settle overnight at 37 degrees C. before beginning selection of stable transformants. The next morning medium was replaced with 100 microliters/well fresh medium containing 500 micrograms/ml Geneticin (G418 sulfate, Invitrogen catalog number 10131-027) to select for cells expressing the neomycin resistance gene. Medium was changed every 2 or 3 days to maintain Geneticin potency. After 19 days of selection, the 96-well plate with the lowest initial cell density (approximately 200 cells/well) yielded 70 empty wells and 26 wells with one or more colonies of G418-resistant cells (calculated number of resistant cells/well is 0.3, using the Poisson distribution). These 26 wells were split into duplicate wells and allowed to settle overnight. One set of wells was infected with PRRSV isolate P129, incubated for 24 hours, then fixed with 80% acetone and stained with FITC-conjugated monoclonal antibody SDOW17 (Rural Technologies Inc), which is specific for PRRSV nucleocapsid. Of the 26 clones, 8 contained some cells that were infected by PRRSV. One of these, designated "NLFK-CMV-susCD163v1-G4", was clearly more permissive than the others with nearly 100% of the cells staining positive for viral antigen.

Figure 8:
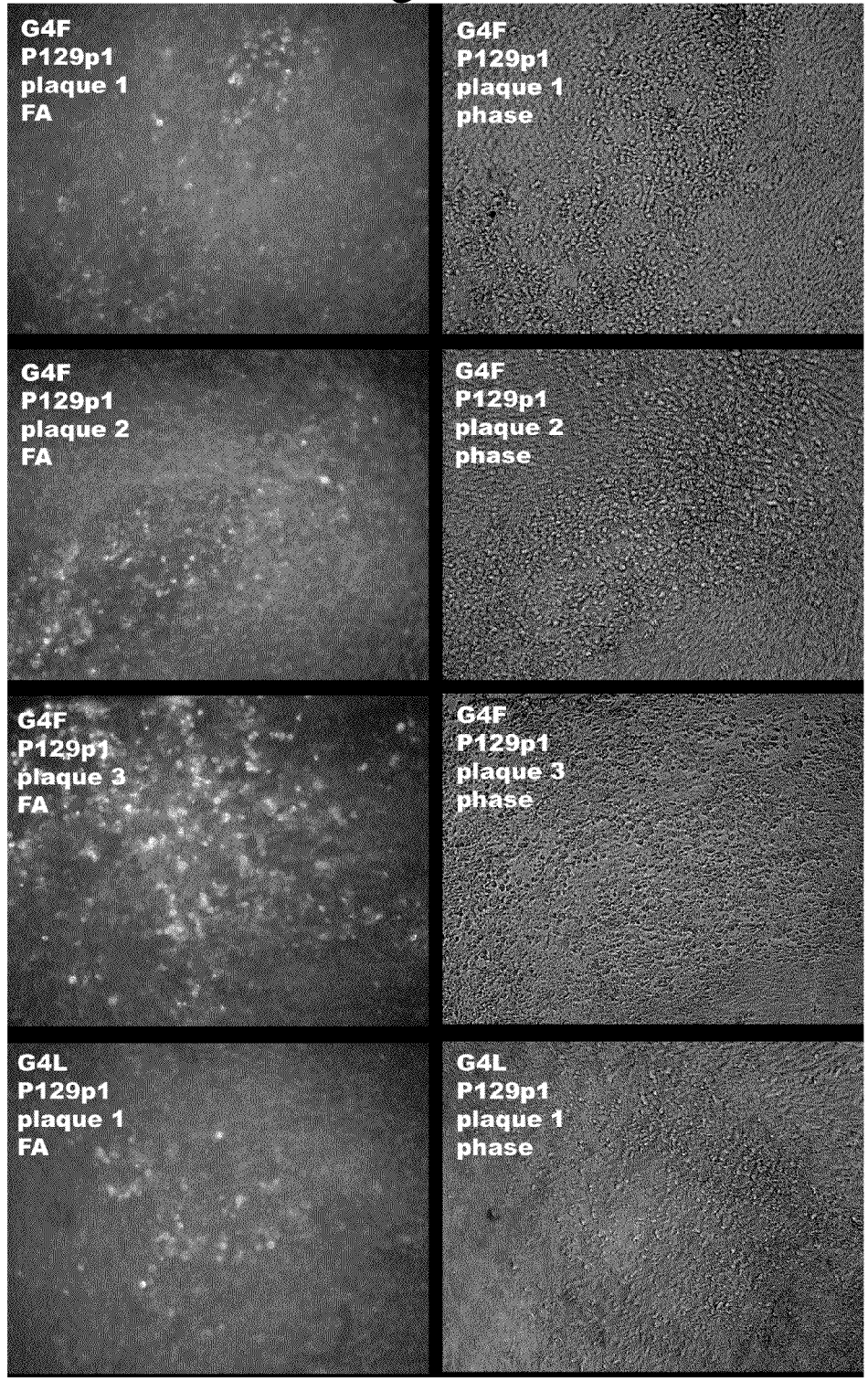

By cell passage number 5, there was some evidence of phenotypic heterogeneity in the NLFK-CMV-susCD163v1-G4 cell line. Therefore, the cells were single-cell cloned by limiting dilution in G418-containing medium, starting with frozen stocks of NLFK-CMV-susCD163v1-G4 passage 4. Twelve such clones ("A"-"L") were expanded for study. Of these, clones NLFK-CMV-susCD163v1-G4F and NLFK-CMV-susCD163v1-G4L were notable for their ability to form discrete plaques (localized areas of CPE) when infected with PRRSV isolate P129 (see FIG. 8).

Example 17

Generation of PRRSV-Permissive Feline Kidney Stable Cell Lines Using pRSV-susCD163v1

Figure 9:
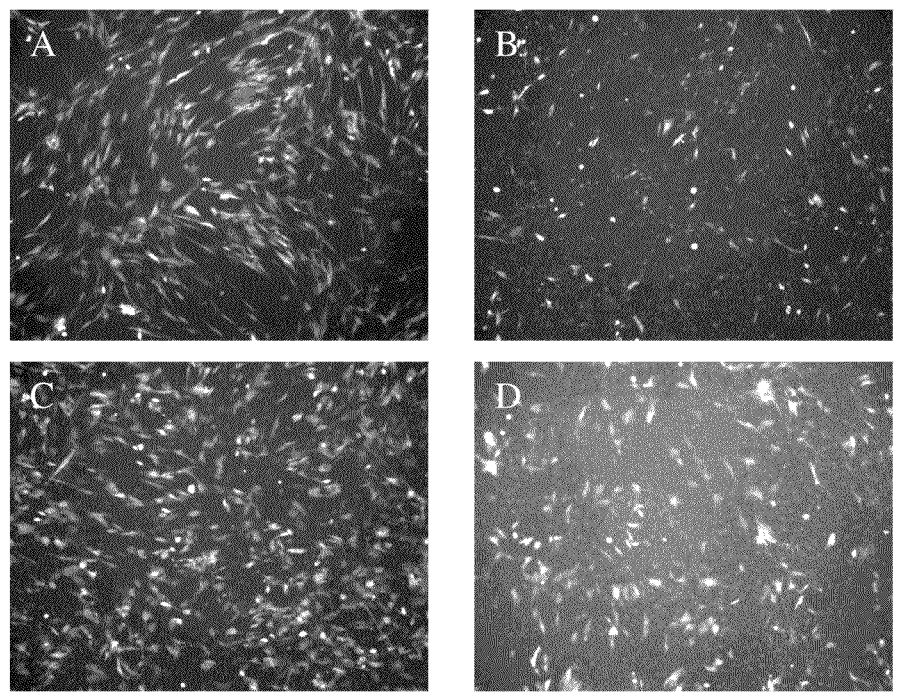
FIG. 9 Four FK/RSV/v1 cell lines, #1, #2, #3, and #4 were infected with PRRSV isolate P129 and stained with monoclonal antibody SDOW17-FITC. Panel A shows FK/RSVv1 #1 cell clone. Panel B shows FK/RSV/v1 clone #2. Panel C shows FK/RSV/v1 clone #3. Panel D shows FK/RSV/v1 #4.

Norden Labs Feline Kidney (NLFK) cells were grown at 37° C. and 5% $CO_2$ in Minimal Essential Medium Alpha Medium (Invitrogen catalog number 12571-071) supplemented with 10% fetal bovine serum and antibiotics. NLFK cells were seeded in 6 well plates at approximately 90% confluency and allowed to attach overnight. The cells were then transfected with plasmid pRSV-susCD163v1 using Lipofectamine 2000 (Invitrogen) following the manufacturer's instructions. After 24 hours the cells were cloned as described in Example 14. Screening for PRRSV permissive cell clones was performed as described in Example 14. Four clones were selected from the screening and were single cell cloned by limiting dilution two more times. Four clones named FK/RSV/v1 #1, FK/RSV/v1 #2, FK/RSV/v1 #3, and FK/RSV/v1 #4 were selected. These cell lines have maintained the PRRSV permissive phenotype through at least 8 passages (see FIG. 9).

Example 18

Generation of PRRSV-Permissive Porcine Kidney Stable Cell Lines Using pCMV-susCD163v1

Figure 10:
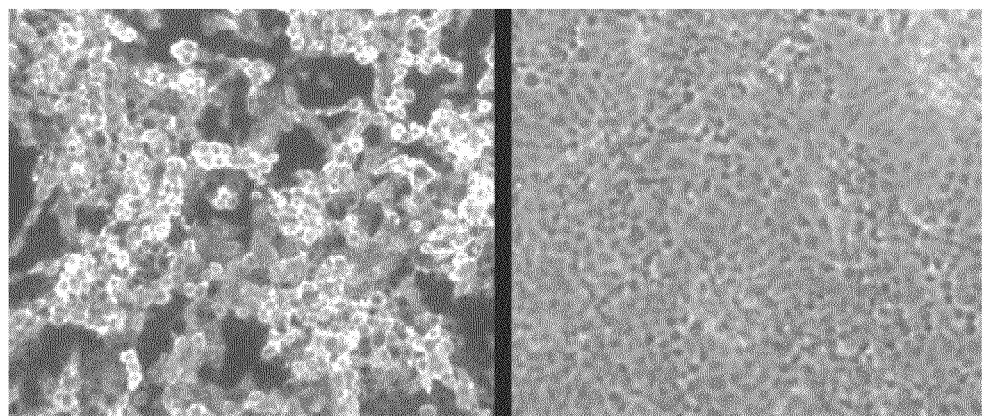
FIG. 10 PK-CMV-susCD163v1-A10 cells at passage 19, infected with PRRSV isolate P129. Left: The monolayer was fixed with 80% acetone and stained with FITC-conjugated monoclonal antibody SDOW17 (Rural Technologies Inc), which is specific for PRRSV nucleocapsid. Right: The same well under bright field illumination, showing cell distribution.

Parental Porcine Kidney (PK032495) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 5% fetal bovine serum (FBS), 1 mM sodium pyruvate, 2 mM L-glutamine and antibiotics. Tissue culture wells (35 mm) containing approximately $1 \times 10^6$ cells each were transfected with 2 micrograms per well of plasmid pCMV-susCD163v1, in DMEM without FBS or antibiotics, using Lipofectamine 2000 (Invitrogen catalog number 11668-027) according to the manufacturer's instructions. After overnight incubation, cells were washed with PBS and removed from the substrate using Accutase (Innovative Cells Technologies, catalog number AT104) and diluted in growth medium containing Geneticin (G418 sulfate, Invitrogen catalog number 10131-027) at 1.0 milligram per ml and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and allowed to incubate until 100% confluency was achieved. One set of wells was screened for PRRSV-permissivity by infecting with PRRSV isolate P129 for a minimum of 48 hours. Eleven clones were found to be permissive for PRRSV. One of these, designated "PK-CMV-susCD163v1-A10", clearly retained the permissive phenotype after numerous passages (see FIG. 10).

Example 19

Generation of PRRSV-Permissive BHK21 Stable Cell Lines Using pCMVScript-susCD163v2

Figure 11:
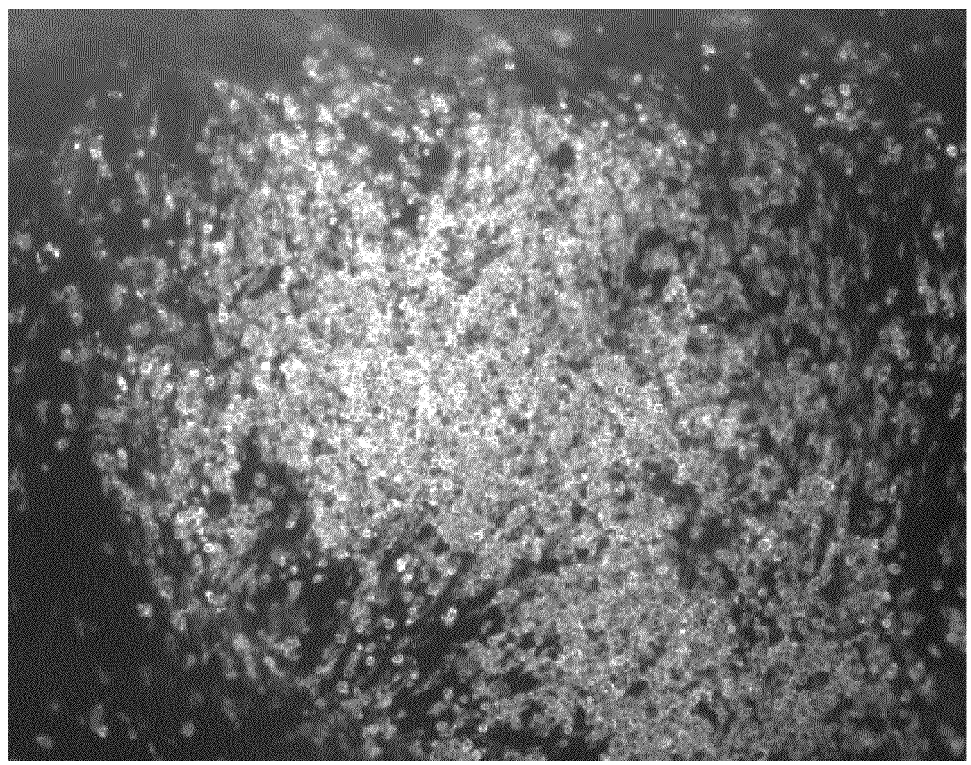
FIG. 11 BHK-CMVScript-susCD163v2-A9 at passage 17 infected with PRRSV isolate P129. The monolayer was fixed with 80% acetone and stained with FITC-conjugated monoclonal antibody SDOW17 (Rural Technologies Inc), which is specific for PRRSV nucleocapsid.

Parental Baby Hamster Kidney (BHK21) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Tissue culture wells (35 mm) containing approximately $1 \times 10^6$ cells each were transfected with 2 micrograms per well of pCMVScript-susCD163v2, in DMEM without FBS or antibiotics, using Lipofectamine 2000 (Invitrogen catalog number 11668-027) according to the manufacturer's instructions. After overnight incubation, cells were washed with PBS and removed from the substrate using Accutase (Innovative Cells Technologies, catalog number AT104) and diluted in growth medium containing Geneticin (G418 sulfate, Invitrogen catalog number 10131-027) at 1.0 milligram per ml and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for permissivity by infecting with PRRSV isolate P129 and incubating for a minimum of 48 hours. Three clones were found to be PRRSV-permissive, and one of these, designated "BHK-CMVScript-susCD163v2-A9", was chosen for further study (see FIG. 11).

Example 20

Generation of PRRSV-Permissive BHK-21 Stable Cell Lines Using pRSV-susCD163v2

Figure 12:
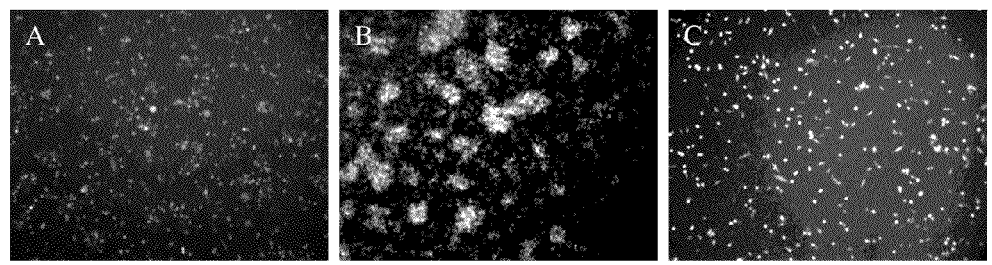
FIG. 12 Three representative examples of the BHK/RSV/v2 cell lines. The cells were infected with PRRSV isolate P129 and subsequently stained with SDOW17-FITC. Panel A shows cell line BHK/RSV/v2 #1, panel B shows cell line BHK/RSV/v2 #34, and panel C shows cell line BHK/RSV/v2 #47.

BHK-21 cells were cultured as described in Example 14. BHK-21 cells were transfected with the ligated pRSV-susCD163v2 DNA construct described in Example 5 using Lipofectamine 2000 (Invitrogen) following manufacture's instructions. Subsequent cloning and selection of PRRSV permissive cell lines was performed as described in Example 14. Of 336 single cell clones screened, 129 were positive. Several of these cell clones have been passed up to 7 times and they have maintained the PRRSV permissive phenotype (see FIG. 12). These cell lines have been named BHK/RSV/v2, followed by a numerical clone number.

Example 21

Generation of PRRSV-Permissive Porcine Kidney Stable Cell Lines Using pCMVScript-susCD163v2

Parental Porcine Kidney (PK032495) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 5% fetal bovine serum (FBS), 1 mM sodium pyruvate, 2 mM L-glutamine and antibiotics. Tissue culture wells (35 mm) containing approximately 1×10⁶ cells each were transfected with 2 micrograms per well of pCMVScript-susCD163v2 in DMEM without FBS or antibiotics, using Lipofectamine 2000 (Invitrogen catalog number 11668-027) according to the manufacturer's instructions. After overnight incubation, cells were washed with PBS and removed from the substrate using Accutase (Innovative Cells Technologies, catalog number AT104) and diluted in growth medium containing Geneticin (G418 sulfate, Invitrogen catalog number 10131-027) at 1.0 milligram per ml and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for permissivity by infecting with PRRSV isolate P129 and incubating for a minimum 48 hours. One clone designated "PK-CMVScript-susCD163v2-D1" showed the PRRSV-permissive phenotype.

Example 22

Generation of PRRSV-Permissive BHK21 Stable Cell Lines Using pcDNA3.1D-humCD163v2

Parental Baby Hamster Kidney (BHK21) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Tissue culture wells (35 mm) containing approximately 1×10⁶ cells each were transfected with 2 micrograms per well of pcDNA3.1D-humCD163v2, in DMEM without FBS or antibiotics, using Lipofectamine 2000 (Invitrogen catalog number 11668-027) according to the manufacturer's instructions. After overnight incubation, cells were washed with PBS and removed from the substrate using Accutase (Innovative Cells Technologies, catalog number AT104) and diluted in growth medium containing Geneticin (G418 sulfate, Invitrogen catalog number 10131-027) at 1.0 milligram per ml and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for permissivity by infecting with PRRSV isolate P129, incubated for a minimum 48 hours. Seven candidate clones were found to be PRRSV-permissive. There was some evidence of phenotypic heterogeneity in each of the seven candidate clones, likely because they were not clonal. Therefore, the candidate clones were single-cell cloned by limiting dilution in G418 containing medium. One single cell clone with clear PRRS-permissivity was obtained and designated BHK-cDNA3.1D-humCD163v2-H9.

Example 23

Generation of PRRSV-Permissive Feline Kidney Stable Cell Lines Using pcDNA3.1D-humCD163v2

Figure 13:
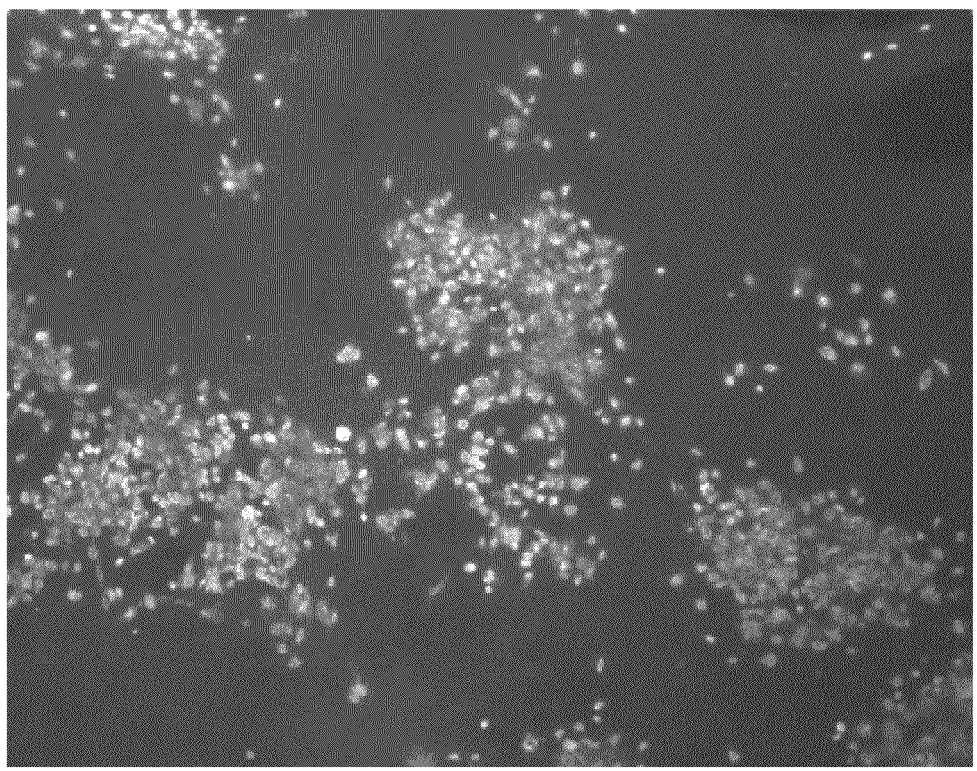
FIG. 13 FK-cDNA3.1D-humCD163v2-A6 at passage 15 infected with PRRSV isolate P129. The monolayer was then fixed with 80% acetone and stained with FITC-conjugated monoclonal antibody SDOW17 (Rural Technologies Inc), which is specific for PRRSV nucleocapsid.

Parental Norden Labs Feline Kidney (NLFK) cells were grown at 37 degrees C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Tissue culture wells (35 mm) containing approximately 1×10⁶ cells each were transfected with 2 micrograms per well of pcDNA3.1D-humCD163v2 in DMEM without FBS or antibiotics, using Lipofectamine 2000 (Invitrogen catalog number 11668-027) according to the manufacturer's instructions. After overnight incubation, cells were washed with PBS, removed from the substrate using Accutase (Innovative Cells Technologies, catalog number AT104), diluted in growth medium containing Geneticin (G418 sulfate, Invitrogen catalog number 10131-027) at 500 micrograms per ml, and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for PRRSV-permissivity by infecting with PRRSV isolate P129 for a minimum 48 hours. Five clones were found to be permissive. One of these, designated "FK-cDNA3.1D-humCD163v2-A6", clearly displayed the permissive phenotype (see FIG. 13).

Figure 21A:
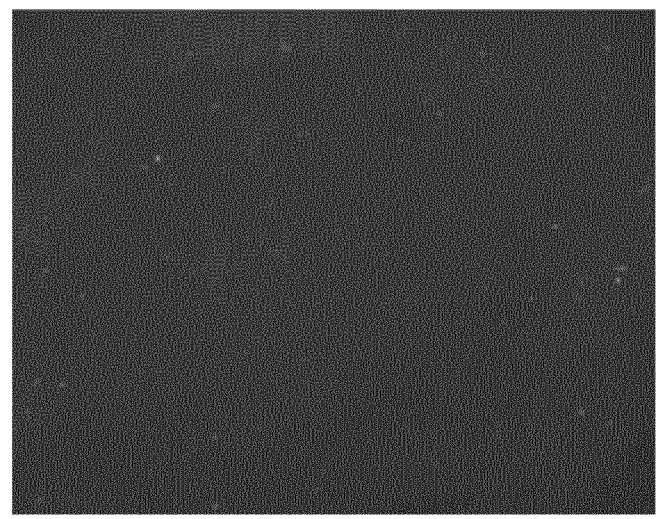
FIG. 21. NLFK parent cells and one subclone of FK-cDNA3.1D-humCD163v2-A6 were examined for the CD163 expression. Cells were fixed in 80% acetone and reacted with Goat anti-human CD163 (R&D System at 1:200) for one hour following by washing with PBS. For visualization, donkey anti-Goat IgG conjugated with FITC (Biodesign Inc at 1:100) were used. No specific fluorescence was detected in the NLFK parent cells as shown in FIG. 21A. The majority of the FK.A6.A2 subclone showed good fluorescent staining indicating the presence of CD163 (FIG. 21B).
Figure 21B:
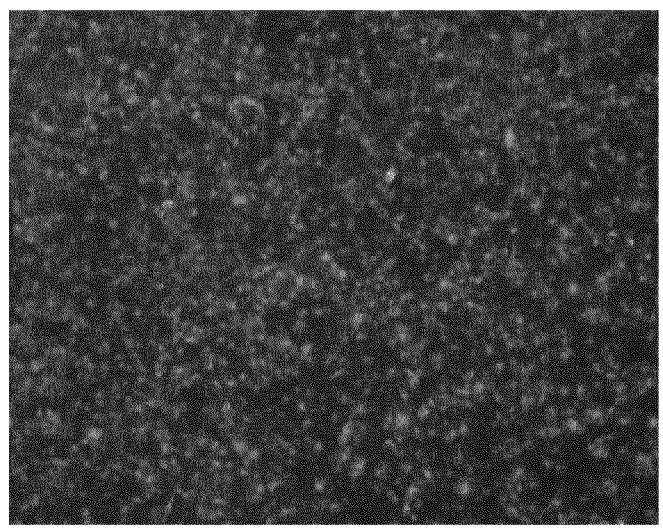

NLFK parent cells and one subclone of FK-cDNA3.1D-humCD163v2-A6 were examined for the CD163 expression. Cells were fixed in 80% acetone and reacted with Goat anti-human CD163 (R&D System at 1:200) for one hour following by washing with PBS. For visualization, donkey anti-Goat IgG conjugated with FITC (Biodesign Inc at 1:100) were used. No specific fluorescence was detected in the NLFK parent cells as shown in FIG. 21A. The majority of the FK.A6.A2 subclone showed good fluorescent staining indicating the presence of CD163 (FIG. 21B).

Example 24

Generation of PRRSV-Permissive Porcine Kidney Stable Cell Lines Using pcDNA3.1D-humCD163v2

Parental Porcine Kidney (PK032495) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 5% fetal bovine serum (FBS), 1 mM sodium pyruvate, 2 mM L-glutamine and antibiotics. Tissue culture wells (35 mm) containing approximately 1×10⁶ cells each were transfected with 2 micrograms per well of pcDNA3.1D-humCD163v2, in DMEM without FBS or antibiotics, using Lipofectamine 2000 (Invitrogen catalog number 11668-027) according to the manufacturer's instructions. After overnight incubation, cells were washed with PBS, removed from the substrate using Accutase (Innovative Cells Technologies, catalog number AT104), diluted in growth medium containing Geneticin (G418 sulfate, Invitrogen catalog number 10131-027) at 1.0 milligram per ml, and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for PRRSV-permissivity by infecting with PRRSV isolate P129 for a minimum 48 hours. Two clones were found to be permissive. One of these, designated "PK-cDNA3.1D-humCD163v2-B11" clearly showed the PRRSV-permissive phenotype.

Example 25

Generation of PRRSV-Permissive Feline Kidney Stable Cell Line Using Ligated pRSV-Script MARC CD163v2

A non-cloning based procedure to generate microgram quantities of linear DNA suitable for use in generating stable cell lines expressing CD163 from an RSV promoter was developed (FIG. 4). A similar process was adapted to place simian CD163v2 from MARC-145 cells behind the RSV promoter. The procedure involves the isolation and ligation of two pieces of DNA, one containing the neomycin gene and RSV promoter cassette derived from pRSV-script, and the other containing the MARC CD163v2 coding sequence from pCDNA3.1D MARC CD163v2. Vector plasmid pRSV-Script was linearized with Hind III and Kpn I. Plasmid was first digested with Kpn I and was bunted with the Klenow fragment of E. coli DNA polymerase. This plasmid was then digested with Hind III immediately downstream of the RSV promoter. The pCDNA3.1D MARC CD163v2 clone was digested in the vector sequence downstream of the CD163 insert with EcoRV, and Hind III upstream of CD163. The CD163 coding sequence was liberated from the vector. For each plasmid digestion the appropriate fragments were purified from agarose gels. A large-scale ligation reaction was performed as follows. Approximately 20 µg of each DNA fragment was incubated in a volume of 600 µL with 15 units of T4 DNA ligase. The reaction was incubated at room temperature for 1 hour. Following ligation, a linear piece of DNA containing all of the appropriate elements was purified by agarose gel electrophoresis. Restriction enzyme digestion analysis was performed to confirm the authenticity of each ligated fragment. Ligation of the two DNA fragments via the cohesive Hind III termini resulted in the placement of the 5' sequences of the MARC CD163 gene downstream of the RSV promoter, allowing for directed expression of CD163 in mammalian cells. Once isolated, the purified DNA was used to transfect selected mammalian cell lines.

Norden Labs Feline Kidney (NLFK) cells were grown at 37° C. and 5% $CO_2$ in DMEM supplemented with 5% fetal bovine serum and antibiotics. NLFK cells were seeded in 6 well plates at approximately 90% confluency and allowed to attach overnight. The cells were then transfected with ligated plasmid pRSV-MARC CD163v2 using Lipofectamine 2000 following the manufacturer's instructions. After 24 hours the cells were cloned as described in Example 12. Screening for PRRSV permissive cell clones was performed as described in Example 12. One clone was positive for PRRSV infection and designated NLFK-MARC CD163 D4. This D4 clone has maintained the PRRSV permissive phenotype through 9 passages.

Example 26

Figure 14:
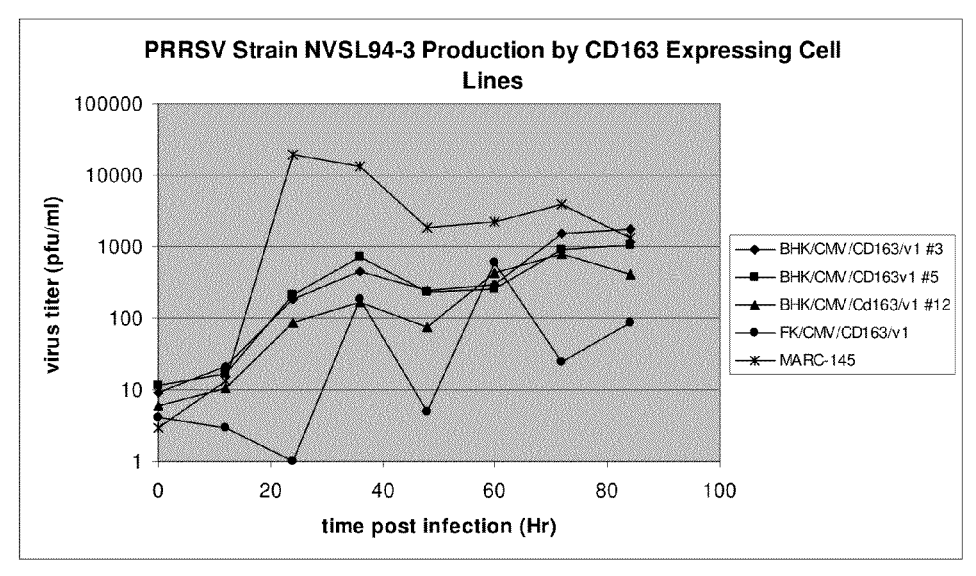

Growth Kinetics of PRRSV Isolate NVSL 94-3 in Recombinant BHK-21 and NLFK Cells Stably Expressing susCD163v1 from the CMV Promoter The amounts of progeny virus produced by PRRSV-infected BHK-21 or NLFK cells stably engineered to express susCD163v1 were quantitated. Four cell lines expressing susCD163v1, BHK/CMV/susv1 #3, BHK/CMV/susv1 #5, BHK/CMV/susv1 #12, and FK/CMV/susv1 G4 were seeded at sub confluency in 6 well plates and, after overnight incubation, were infected with the NVSL 94-3 isolate of PRRSV. MARC-145 cells were included in the experiment for comparison. The cells were infected with virus at an m.o.i. of approximately 0.1. Virus was adsorbed for 60-90 minutes and was removed. Cells were washed three times with PBS to remove residual virus. One-milliliter aliquots were harvested from the cultures at 12-hour intervals starting immediately after infection and continued through 96 hrs. Fresh culture media was added to the cells at various time points to maintain a culture volume sufficient to prevent the cell monolayer from drying out. Culture supernatants were stored at −80° until all samples were collected. The amount of PRRSV present in the culture supernatants was determined by plaque assay on MARC-145 cells. FIG. 14 shows that all CD163 expressing recombinant cell lines tested were able to produce progeny PRRSV.

Example 27

Blocking PRRSV Infection with Anti-CD163 Antibody

Transiently Transfected Cells

Figure 15:
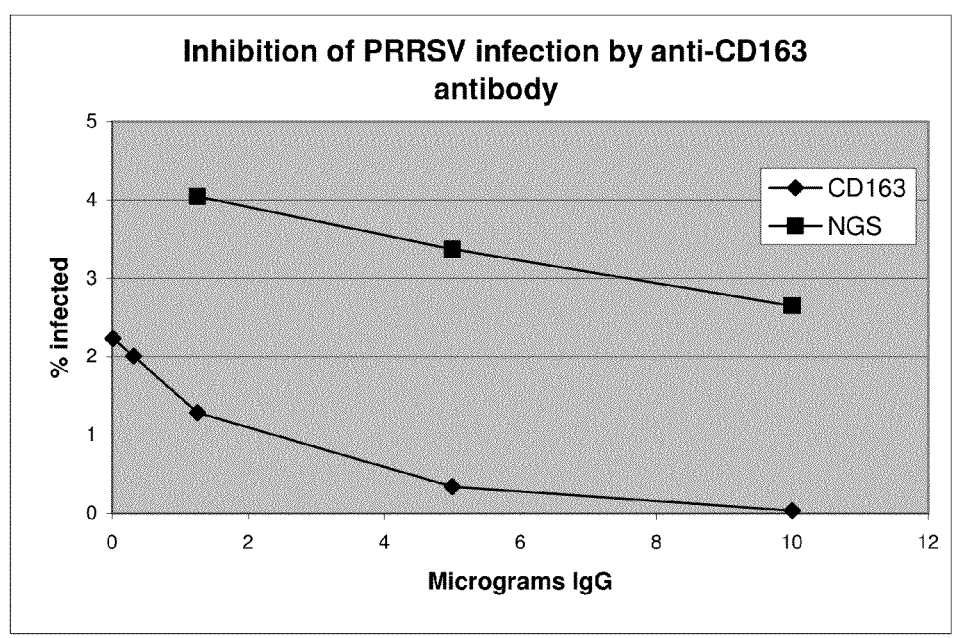
FIG. 15 Flow cytometry analysis of PRRSV infection in the presence of CD163 specific antibody. BHK-21 cells expressing MARC-145 CD163 from transient transfection were incubated with either CD163 specific antibody or normal goat IgG (NGS) and infected with a GFP-expressing PRRSV. Each data point represents the results of triplicate wells.

BHK-21 cells, seeded in 24 well plates, were transiently transfected with the plasmid pCDNA3.1D-MARC-CD163v2 described in example 8, using Lipofectamine 2000 as described in example 14. After overnight incubation to allow expression of CD163, a titration of goat polyclonal antibody specific for human CD163 (R&D Systems, cat #AF1607) in PBS was added to the cells in a volume of 100 µl. As a control, equivalent amounts of normal goat IgG (R&D Systems, cat #AB-108-C) were used. Following a one-hour incubation at 37° C., the monolayers were infected with approximately $1 \times 10^7$ pfu of a recombinant P129 strain of PRRSV that expresses GFP. The cell monolayers, with anti-CD163 antibody and PRRSV, were incubated at 37° C. for one hour at which time the virus inoculum/antibody mixture was aspirated, the cell monolayer washed once with PBS, and 1 ml of growth medium added to the wells. The cells were incubated for 24 hours at 37° C. to allow PRRSV directed GFP expression. For analysis, the cells were trypsinized, resuspended in 500 µl of PBS and analyzed by flow cytometry to innumerate the PRRSV infected cells via GFP expression. For flow cytometry, uninfected BI-IK-21 cells were used to set the baseline for fluorescence detection, and approximately 100,000 cells were analyzed from each subsequent sample. The results of this analysis, shown in FIG. 15, show that the CD163 specific antibody was able to significantly reduce the number of infected cells when compared to cells incubated with normal goat IgG.

Example 28

Blocking PRRSV Infection by Anti CD163 Antibody

Stably Transfected Cells

The NLFK cells that stably express human CD163 (FK-cDNA3.1D-humCD163v2-A6), described in Example 23, were seeded into 24 wells plates. After allowing the cells to attach overnight, a titration of goat polyclonal antibody specific for human CD163 (R&D Systems, cat #AF1607) in PBS was added to the cells in a volume of 100 µl. As a control, equivalent amounts of normal goat IgG (R&D Systems, cat

AB-108-C) were used. Following a one-hour incubation at 37° C., the monolayers were infected with approximately 1×10⁷ pfu of a recombinant P129 strain of PRRSV that expresses GFP. The cell monolayers, with anti-CD163 antibody and PRRSV, were incubated at 37° C. for one hour at which time the virus inoculum/antibody mixture was aspirated, the cell monolayer washed once with PBS, and 1 ml of growth medium added to the wells. The cells were incubated for 24 hours at 37° C. to allow PRRSV directed GFP expression. For analysis, the cells were trypsinized, resuspended in 500 µl of PBS, and analyzed by flow cytometry to innumerate the PRRSV infected cells via GFP expression. Appro -continued FA results of screening of various CD163 cell lines for permissivity to European and North American PRRSV isolates

| CD163 Cell Line | PRRSV Isolate[a] | | | | | |
|---|---|---|---|---|---|---|
| | EU98V226 | P129 | P201 | 1151 | 94-3 | IND5 |
| Porcine Kidney (parental) | − | − | − | − | − | − |
| Feline Kidney (parental) | − | − | − | − | − | − |

[a]All PRRSV isolates are North American except EU98V226 is a European isolate.

Example 33

Phorbol 12-myristate 13-acetate (PMA) Induction of CD163 Renders Human U937 Cells Permissive to PRRSV Infection Human U937 cells obtained from ATCC (CRL-1593.2) were propagated in RPMI medium containing serum and additives according to ATCC specifications. These cells are known to express CD163 when activated by PMA treatment (Gronlund et al., 2000). U937 cells were seeded in duplicate in wells of a 6-well plate. One set of wells was treated with 100 ng/ml of PMA and the other set was left untreated. Three days after PMA stimulation, one well from each set was infected with the P129 isolate of PRRSV. The other well from each set was fixed and stained for expression of CD163 in an indirect immunofluorescent antibody assay using goat-anti human CD163 (R&D System) and donkey anti-goat IgG conjugated with FITC (BioDesign International).

Untreated U937 cells continued propagation to high density 3 days after initial planting. PMA-treated U937 cells stopped propagating, became enlarged, and attached to the surface of the culture wells. A small fraction of untreated U937 were positive for CD163 staining, whereas almost all PMA-treated U937 were positive for CD163 staining. In untreated U937 no PRRSV infected cells were observed. However, hundreds of PMA treated U937 cells became infected by PRRSV. This demonstrates that non-permissive cells can be rendered permissive for PRRSV infection following chemical induction of CD163 expression.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations that are described herein as critical to the invention should be viewed as such; variations of the invention lacking limitations that have not been described herein as critical are intended as aspects of the invention.

It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference to the extent they are not inconsistent to the disclosure herein.

The invention claimed is:

1. A method of facilitating production of Porcine Reproductive and Respiratory Syndrome Virus (PRRSV) from a culture of vertebrate cells, comprising the steps of:
   (a) providing a recombinant vertebrate cell transfected with an exogenous polynucleotide that encodes a polypeptide having a transmembrane domain and at least 90% sequence identity to SEQ ID NO:24 or SEQ ID NO:27, so that expression of CD163 polypeptide in said cell is increased;
   (b) contacting a culture of said cell with PRRSV virus under conditions which permit infection of the cells and growth of the virus; and
   (c) recovering virus from said culture.

2. The method of claim 1, wherein the cell was previously PRRSV permissive and is rendered more PRRSV permissive.

3. The method of claim 2, wherein the cell did not previously express a CD163 polypeptide and is induced to express CD163.

4. The method of claim 3, wherein the cell is selected from the group consisting of baby hamster kidney cells (BHK21), porcine kidney cells, feline kidney cells, avian cells, and swine testicular cells.

5. The method of Claim 1, wherein the PRRSV is of the European genotype.

6. The method of claim 1, wherein the PRRSV is of the North American genotype.

7. The method of claim 1, wherein the polynucleotide encodes a polypeptide having a transmembrane domain and at least 95% sequence identity to SEQ ID NO:24 or SEQ ID NO:27.

8. The method of claim 1, wherein the polynucleotide encodes a apolypeptide having a transmembrane domain and at least 99% sequence identity to SEQ ID NO:24 or SEQ ID NO:27.

9. The method of claim 1, further comprising the step of producing a vaccine from the recovered virus.

\* \* \* \* \*

SEQUENCE LISTING

```
<160> NUMBER OF SEQ ID NOS: 48

<210> SEQ ID NO 1
<211> LENGTH: 2607
<212> TYPE: DNA
<213> ORGANISM: Sus scrofa

<400> SEQUENCE: 1
atggacaaac tcagaatggt gctacatgaa aactctggat ctgcagacct gaaactgaga       60
gtggtagatg gagtcactga atgttcagga agattggaag tgaaattcca aggagaatgg      120
ggaacaatct gtgatgatgg ctgggatagt gatgatgccg ctgtggcatg taagcaactg      180
ggatgtccaa ctgctgtcac tgccattggt cgagttaacg ccagtgaggg aactggacac      240
atttggcttg acagtgtttc ttgccatgga cacgagtctg ctctctggca gtgtagacac      300
catgaatggg gaaagcatta ttgcaatcat aatgaagatg ctggtgtgac atgttctgat      360
ggatcagatc tggaactgag acttaaaggt ggaggcagcc actgtgctgg gacagtggag      420
gtggaaattc agaaactggt aggaaaagtg tgtgataaga gctggggact gaaagaagct      480
gatgtggttt gcaggcagct gggatgtgga tctgcactca aaacatcata tcaagtttat      540
tccaaaacca aggcaacaaa cacatggctg tttgtaagca gctgtaatgg aaatgaaact      600
tctctttggg actgcaagaa ttggcagtgg ggtggactta gttgtgatca ctatgacgaa      660
gccaaaatta cctgctcagc ccacaggaaa cccaggctgg ttggagggga cattccctgc      720
tctggtcgtg ttgaagtaca acatggagac acgtgggca ccgtctgtga ttctgacttc      780
```

```
tctctggagg cggccagcgt gctgtgcagg gaactacagt gcggcactgt ggtttccctc    840 ctgggggag ctcactttgg agaaggaagt ggacagatct gggctgaaga attccagtgt      900
gaggggcacg agtcccacct ttcactctgc ccagtagcac cccgccctga cgggacatgt     960
agccacagca gggacgtcgg cgtagtctgc tcaagataca cacaaatccg cttggtgaat    1020
ggcaagaccc catgtgaagg aagagtggag ctcaacattc ttgggtcctg ggggtccctc    1080
tgcaactctc actgggacat ggaagatgcc catgttttat gccagcagct aaatgtgga    1140 gttgcccttt ctatcccggg aggagcacct tttgggaaag gaagtgagca ggtctggagg    1200
cacatgtttc actgcactgg gactgagaag cacatgggag attgttccgt cactgctctg    1260
ggcgcatcac tctgttcttc agggcaagtg gcctctgtaa tctgctcagg gaaccagagt    1320
cagacactat ccccgtgcaa ttcatcatcc tcggacccat caagctctat tatttcagaa    1380
gaaaatggtg ttgcctgcat agggagtggt caacttcgcc tggtcgatgg aggtggtcgt    1440
tgtgctggga gagtagaggt ctatcatgag ggctcctggg gcaccatctg tgatgacagc    1500
tgggacctga atgatgccca tgtggtgtgc aaacagctga gctgtggatg gccattaat    1560 gccactggtt ctgctcattt tggggaagga cagggccca tttggctgga tgagataaac    1620
tgtaatggaa aagaatctca tatttggcaa tgccactcac atggttgggg gcggcacaat    1680
tgcaggcata aggaggatgc aggagtcatc tgctcggagt tcatgtctct cagactgatc    1740
agtgaaaaca gcagagagac ctgtgcaggg cgcctggaag ttttttacaa cggagcttgg    1800
ggcagcgttg gcaagaatag catgtctcca gccacagtgg gggtggtatg caggcagctg    1860
ggctgtgcag acagagggga catcagccct gcatcttcag acaagacagt gtccaggcac    1920
atgtgggtgg acaatgttca gtgtcctaaa ggacctgaca ccctatggca gtgcccatca    1980
tctccatgga agaagagact ggccagcccc tcagaggaga catggatcac atgtgccaac    2040
aaaataagac ttcaagaagg aaacactaat tgttctggac gtgtggagat ctggtacgga    2100
ggttcctggg gcactgtgtg tgacgactcc tgggaccttg aagatgctca ggtggtgtgc    2160
cgacagctgg gctgtggctc agctttggag gcaggaaaag aggccgcatt tggccagggg    2220
actgggccca tatggctcaa tgaagtgaag tgcaagggga tgaaacctc cttgtgggat    2280 tgtcctgcca gatcctgggg ccacagtgac tgtggacaca aggaggatgc tgctgtgacg    2340
tgttcagaaa ttgcaaagag ccgagaatcc ctacatgcca caggtcgctc atcttttgtt    2400
gcacttgcaa tctttggggt cattctgttg gcctgtctca tcgcattcct catttggact    2460
cagaagcgaa gacagaggca gcggctctca gtttttctcag gaggagagaa ttctgtccat    2520
caaattcaat accgggagat gaattcttgc ctgaaagcag atgaaacgga tatgctaaat    2580
ccctcaggag accactctga agtacaa                                        2607
```

<210> SEQ ID NO 2
<211> LENGTH: 869
<212> TYPE: PRT
<213> ORGANISM: Sus scrofa

<400> SEQUENCE: 2

```
Met Asp Lys Leu Arg Met Val Leu His Glu Asn Ser Gly Ser Ala Asp
1               5                   10                  15

Leu Lys Leu Arg Val Val Asp Gly Val Thr Glu Cys Ser Gly Arg Leu
            20                  25                  30

Glu Val Lys Phe Gln Gly Glu Trp Gly Thr Ile Cys Asp Asp Gly Trp
        35                  40                  45

Asp Ser Asp Asp Ala Ala Val Ala Cys Lys Gln Leu Gly Cys Pro Thr
```

```
                50                  55                  60
Ala Val Thr Ala Ile Gly Arg Val Asn Ala Ser Glu Gly Thr Gly His
65                  70                  75                  80

Ile Trp Leu Asp Ser Val Ser Cys His Gly His Glu Ser Ala Leu Trp
                    85                  90                  95

Gln Cys Arg His His Glu Trp Gly Lys His Tyr Cys Asn His Asn Glu
                    100                 105                 110

Asp Ala Gly Val Thr Cys Ser Asp Gly Asp Leu Glu Leu Arg Leu
                115                 120                 125

Lys Gly Gly Gly Ser His Cys Ala Gly Thr Val Glu Val Ile Gln
130                 135                 140

Lys Leu Val Gly Lys Val Cys Asp Arg Ser Trp Gly Leu Lys Glu Ala
145                 150                 155                 160

Asp Val Val Cys Arg Gln Leu Gly Cys Gly Ser Ala Leu Lys Thr Ser
                    165                 170                 175

Tyr Gln Val Tyr Ser Lys Thr Lys Ala Thr Asn Thr Trp Leu Phe Val
                180                 185                 190

Ser Ser Cys Asn Gly Asn Glu Thr Ser Leu Trp Asp Cys Lys Asn Trp
                195                 200                 205

Gln Trp Gly Gly Leu Ser Cys Asp His Tyr Asp Glu Ala Lys Ile Thr
                210                 215                 220

Cys Ser Ala His Arg Lys Pro Arg Leu Val Gly Gly Asp Ile Pro Cys
225                 230                 235                 240

Ser Gly Arg Val Glu Val Gln His Gly Asp Thr Trp Gly Thr Val Cys
                    245                 250                 255

Asp Ser Asp Phe Ser Leu Glu Ala Ala Ser Val Leu Cys Arg Glu Leu
                260                 265                 270

Gln Cys Gly Thr Val Val Ser Leu Leu Gly Gly Ala His Phe Gly Glu
                275                 280                 285

Gly Ser Gly Gln Ile Trp Ala Glu Glu Phe Gln Cys Glu Gly His Glu
                290                 295                 300

Ser His Leu Ser Leu Cys Pro Val Ala Pro Arg Pro Asp Gly Thr Cys
305                 310                 315                 320

Ser His Ser Arg Asp Val Gly Val Val Cys Ser Arg Tyr Thr Gln Ile
                    325                 330                 335

Arg Leu Val Asn Gly Lys Thr Pro Cys Glu Gly Arg Val Glu Leu Asn
                340                 345                 350

Ile Leu Gly Ser Trp Gly Ser Leu Cys Asn Ser His Trp Asp Met Glu
                355                 360                 365

Asp Ala His Val Leu Cys Gln Gln Leu Lys Cys Gly Val Ala Leu Ser
370                 375                 380

Ile Pro Gly Gly Ala Pro Phe Gly Lys Gly Ser Glu Gln Val Trp Arg
385                 390                 395                 400

His Met Phe His Cys Thr Gly Thr Glu Lys His Met Gly Asp Cys Ser
                    405                 410                 415

Val Thr Ala Leu Gly Ala Ser Leu Cys Ser Ser Gly Gln Val Ala Ser
                420                 425                 430

Val Ile Cys Ser Gly Asn Gln Ser Gln Thr Leu Ser Pro Cys Asn Ser
                435                 440                 445

Ser Ser Ser Asp Pro Ser Ser Ser Ile Ile Ser Glu Glu Asn Gly Val
                450                 455                 460

Ala Cys Ile Gly Ser Gly Gln Leu Arg Leu Val Asp Gly Gly Gly Arg
465                 470                 475                 480
```

```
Cys Ala Gly Arg Val Glu Val Tyr His Glu Gly Ser Trp Gly Thr Ile
                485                 490                 495

Cys Asp Asp Ser Trp Asp Leu Asn Asp Ala His Val Val Cys Lys Gln
            500                 505                 510

Leu Ser Cys Gly Trp Ala Ile Asn Ala Thr Gly Ser Ala His Phe Gly
        515                 520                 525

Glu Gly Thr Gly Pro Ile Trp Leu Asp Glu Ile Asn Cys Asn Gly Lys
    530                 535                 540

Glu Ser His Ile Trp Gln Cys His Ser His Gly Trp Gly Arg His Asn
545                 550                 555                 560

Cys Arg His Lys Glu Asp Ala Gly Val Ile Cys Ser Glu Phe Met Ser
                565                 570                 575

Leu Arg Leu Ile Ser Glu Asn Ser Arg Glu Thr Cys Ala Gly Arg Leu
            580                 585                 590

Glu Val Phe Tyr Asn Gly Ala Trp Gly Ser Val Gly Lys Asn Ser Met
        595                 600                 605

Ser Pro Ala Thr Val Gly Val Val Cys Arg Gln Leu Gly Cys Ala Asp
    610                 615                 620

Arg Gly Asp Ile Ser Pro Ala Ser Ser Asp Lys Thr Val Ser Arg His
625                 630                 635                 640

Met Trp Val Asp Asn Val Gln Cys Pro Lys Gly Pro Asp Thr Leu Trp
                645                 650                 655

Gln Cys Pro Ser Ser Pro Trp Lys Lys Arg Leu Ala Ser Pro Ser Glu
            660                 665                 670

Glu Thr Trp Ile Thr Cys Ala Asn Lys Ile Arg Leu Gln Glu Gly Asn
        675                 680                 685

Thr Asn Cys Ser Gly Arg Val Glu Ile Trp Tyr Gly Gly Ser Trp Gly
    690                 695                 700

Thr Val Cys Asp Asp Ser Trp Asp Leu Glu Asp Ala Gln Val Val Cys
705                 710                 715                 720

Arg Gln Leu Gly Cys Gly Ser Ala Leu Glu Ala Gly Lys Glu Ala Ala
                725                 730                 735

Phe Gly Gln Gly Thr Gly Pro Ile Trp Leu Asn Glu Val Lys Cys Lys
            740                 745                 750

Gly Asn Glu Thr Ser Leu Trp Asp Cys Pro Ala Arg Ser Trp Gly His
        755                 760                 765

Ser Asp Cys Gly His Lys Glu Asp Ala Ala Val Thr Cys Ser Glu Ile
    770                 775                 780

Ala Lys Ser Arg Glu Ser Leu His Ala Thr Gly Arg Ser Ser Phe Val
785                 790                 795                 800

Ala Leu Ala Ile Phe Gly Val Ile Leu Leu Ala Cys Leu Ile Ala Phe
                805                 810                 815

Leu Ile Trp Thr Gln Lys Arg Arg Gln Arg Gln Arg Leu Ser Val Phe
            820                 825                 830

Ser Gly Gly Glu Asn Ser Val His Gln Ile Gln Tyr Arg Glu Met Asn
        835                 840                 845

Ser Cys Leu Lys Ala Asp Glu Thr Asp Met Leu Asn Pro Ser Gly Asp
    850                 855                 860

His Ser Glu Val Gln
865

<210> SEQ ID NO 3
<211> LENGTH: 3400
<212> TYPE: DNA
<213> ORGANISM: Sus scrofa
```

```
<400> SEQUENCE: 3
atggtgctac ttgaagactc tggatctgca gactttagaa gatgttctgc ccatttaagt    60
tccttcactt ttgctgtagt cgctgttctc agtgcctgct tggtcactag ttctcttgga   120
ggaaaagaca aggagctgag gctaacgggt ggtgaaaaca agtgctctgg aagagtggag   180
gtgaaagtgc aggaggagtg gggaactgtg tgtaataatg ctgggacat ggatgtggtc    240 tctgttgttt gtaggcagct gggatgtcca actgctatca aagccactgg atgggctaat   300
tttagtgcag gttctggacg catttggatg gatcatgttt cttgtcgagg aatgagtca    360 gctctctggg actgcaaaca tgatggatgg ggaaagcata actgtactca ccaacaggat   420
gctggagtaa cctgctcaga tggatctgat ttagagatga ggctggtgaa tggaggaaac   480
cggtgcttag gaagaataga agtcaaattt caagagcggt ggggaacagt gtgtgatgat   540
aacttcaaca taaatcatgc ttctgtggtt tgtaaacaac ttgaatgtgg aagtgctgtc   600
agtttctctg gttcagctaa ttttggagaa ggttctggac caatctggtt tgatgatctt   660
gtatgcaatg gaaatgagtc agctctctgg aactgcaaac atgaaggatg gggaaagcac   720
aattgcgatc atgctgagga tgctggagtg atttgcttaa atggagcaga cctgaaactg   780
agagtggtag atggactcac tgaatgttca ggaagattgg aagtgaaatt ccaaggagaa   840
tggggaacaa tctgtgatga tggctggat agtgatgatg ccgctgtggc atgtaagcaa   900
ctgggatgtc caactgctgt cactgccatt ggtcgagtta acgccagtga gggaactgga   960
cacatttggc ttgacagtgt tcttgccat ggacacgagt ctgctctctg gcagtgtaga   1020
caccatgaat ggggaaagca ttattgcaat cataatgaag atgctggtgt gacatgttct  1080
gatggatcag atctggaact gagacttaaa ggtggaggca gccactgtgc tgggacagtg  1140
gaggtggaaa ttcagaaact ggtaggaaaa gtgtgtgata aagctgggg actgaaagaa  1200 gctgatgtgg tttgcaggca gctgggatgt ggatctgcac tcaaaacatc atatcaagtt  1260
tattccaaaa ccaaggcaac aaacacatgg ctgtttgtaa gcagctgtaa tggaaatgaa  1320
acttctcttt gggactgcaa gaattggcag tggggtggac ttagttgtga tcactatgac  1380
gaagccaaaa ttacctgctc agcccacagg aaacccaggc tggttggagg ggacattccc  1440
tgctctggtc gtgttgaagt acaacatgga gacacgtggg gcaccgtctg tgattctgac  1500
ttctctctgg aggcggccag cgtgctgtgc agggaactac agtgcggcac tgtggtttcc  1560
ctcctggggg gagctcactt tggagaagga agtggacaga tctgggctga agaattccag  1620 tgtgagggc acgagtccca cctttcactc tgcccagtag caccccgccc tgacgggaca  1680
tgtagccaca gcagggacgt cggcgtagtc tgctcaagat acacacaaat ccgcttggtg  1740
aatggcaaga ccccatgtga aggaagagtg gagctcaaca ttcttgggtc ctgggggtcc  1800
ctctgcaact ctcactggga catgaagat gcccatgttt tatgccagca gcttaaatgt  1860
ggagttgccc tttctatccc gggaggagca ccttttggga aaggaagtga gcaggtctgg  1920
aggcacatgt ttcactgcac tgggactgag aagcacatgg gagattgttc cgtcactgct  1980
ctgggcgcat cactctgttc ttcagggcaa gtggcctctg taatctgctc agggaaccag  2040
agtcagacac tatccccgtg caattcatca tcctcggacc catcaagctc tattatttca  2100
gaagaaagtg gtgttgcctg catagggagt ggtcaacttc gcctggtcga tggaggtggt  2160
cgttgtgctg ggagagtaga ggtctatcct ggggcatcct ggggcaccat ctgtgatgac  2220
agctgggacc tgaatgatgc ccatgtgtg tgcaaacagc tgagctgtgg atgggccatt  2280
aatgccactg gttctgctca ttttggggaa ggaacagggc ccatttggct ggatgagata  2340
```

```
aactgtaatg gaaaagaatc tcatatttgg caatgccact cacatggttg ggggcggcac    2400
aattgcaggc ataaggagga tgcaggagtc atctgctcag agttcatgtc tctgagactg    2460
atcagtgaaa acagcagaga gacctgtgca gggcgcctgg aagttttta caacggagct     2520 tggggcagcg ttggcaggaa tagcatgtct ccagccacag tggggtggt atgcaggcag     2580 ctgggctgtg cagacagagg ggacatcagc cctgcatctt cagacaagac agtgtccagg    2640
cacatgtggg tggacaatgt tcagtgtcct aaaggacctg acacactatg gcagtgcccc    2700
tcatctccat ggaagaagag actggccagc ccctcagagg agacatggat cacatgtgcc    2760
aacaaaataa gacttcaaga aggaaacact aattgttctg gacgtgtgga gatctggtac    2820
ggaggttcct ggggcactgt gtgtgacgac tcctgggacc ttgaagatgc tcaggtggtg    2880
tgccgacagc tgggctgtgg ctcagctttg gaggcaggaa aagagcccgc atttggccag    2940
gggactgggc ccatatggct caatgaagtg aagtgcaagg ggaatgaacc ctccttgtgg    3000
gattgtcctg ccagatcctg ggggccacagt gactgtggac acaaggagga tgctgctgtg   3060
acgtgctcag aaattgcaaa gagccgagaa tccctacatg ccacaggtcg ctcatctttt    3120
gttgcacttg caatctttgg ggtcattctg ttggcctgtc tcatcgcatt cctcatttgg    3180
actcagaagc gaagacagag gcagcggctc tcagttttct caggaggaga gaattctgtc    3240
catcaaattc aataccggga gatgaattct tgcctgaaag cagatgaaac ggatatgcta    3300
aatccctcag gagaccactc tgaagtacaa tgaaaaggaa aatgggaatt ataacctggt    3360
gagttcagcc tttaagatac cttgatgaag acctggacta                          3400
```

<210> SEQ ID NO 4
<211> LENGTH: 1110
<212> TYPE: PRT
<213> ORGANISM: Sus scrofa

<400> SEQUENCE: 4

```
Met Val Leu Leu Glu Asp Ser Gly Ser Ala Asp Phe Arg Arg Cys Ser
1               5                   10                  15

Ala His Leu Ser Ser Phe Thr Phe Ala Val Val Ala Val Leu Ser Ala
            20                  25                  30

Cys Leu Val Thr Ser Ser Leu Gly Gly Lys Asp Lys Glu Leu Arg Leu
        35                  40                  45

Thr Gly Gly Glu Asn Lys Cys Ser Gly Arg Val Glu Val Lys Val Gln
    50                  55                  60

Glu Glu Trp Gly Thr Val Cys Asn Asn Gly Trp Asp Met Asp Val Val
65                  70                  75                  80

Ser Val Val Cys Arg Gln Leu Gly Cys Pro Thr Ala Ile Lys Ala Thr
                85                  90                  95

Gly Trp Ala Asn Phe Ser Ala Gly Ser Gly Arg Ile Trp Met Asp His
            100                 105                 110

Val Ser Cys Arg Gly Asn Glu Ser Ala Leu Trp Asp Cys Lys His Asp
        115                 120                 125

Gly Trp Gly Lys His Asn Cys Thr His Gln Gln Asp Ala Gly Val Thr
    130                 135                 140

Cys Ser Asp Gly Ser Asp Leu Glu Met Arg Leu Val Asn Gly Gly Asn
145                 150                 155                 160

Arg Cys Leu Gly Arg Ile Glu Val Lys Phe Gln Glu Arg Trp Gly Thr
                165                 170                 175

Val Cys Asp Asp Asn Phe Asn Ile Asn His Ala Ser Val Val Cys Lys
            180                 185                 190
```

-continued

```
Gln Leu Glu Cys Gly Ser Ala Val Ser Phe Ser Gly Ser Ala Asn Phe
        195                 200                 205

Gly Glu Gly Ser Gly Pro Ile Trp Phe Asp Asp Leu Val Cys Asn Gly
        210                 215                 220

Asn Glu Ser Ala Leu Trp Asn Cys Lys His Glu Gly Trp Gly Lys His
225                 230                 235                 240

Asn Cys Asp His Ala Glu Asp Ala Gly Val Ile Cys Leu Asn Gly Ala
                245                 250                 255

Asp Leu Lys Leu Arg Val Val Asp Gly Leu Thr Glu Cys Ser Gly Arg
            260                 265                 270

Leu Glu Val Lys Phe Gln Gly Glu Trp Gly Thr Ile Cys Asp Asp Gly
        275                 280                 285

Trp Asp Ser Asp Asp Ala Ala Val Ala Cys Lys Gln Leu Gly Cys Pro
    290                 295                 300

Thr Ala Val Thr Ala Ile Gly Arg Val Asn Ala Ser Glu Gly Thr Gly
305                 310                 315                 320

His Ile Trp Leu Asp Ser Val Ser Cys His Gly His Glu Ser Ala Leu
                325                 330                 335

Trp Gln Cys Arg His His Glu Trp Gly Lys His Tyr Cys Asn His Asn
            340                 345                 350

Glu Asp Ala Gly Val Thr Cys Ser Asp Gly Ser Asp Leu Glu Leu Arg
        355                 360                 365

Leu Lys Gly Gly Gly Ser His Cys Ala Gly Thr Val Glu Val Glu Ile
    370                 375                 380

Gln Lys Leu Val Gly Lys Val Cys Asp Arg Ser Trp Gly Leu Lys Glu
385                 390                 395                 400

Ala Asp Val Val Cys Arg Gln Leu Gly Cys Gly Ser Ala Leu Lys Thr
                405                 410                 415

Ser Tyr Gln Val Tyr Ser Lys Thr Lys Ala Thr Asn Thr Trp Leu Phe
            420                 425                 430

Val Ser Ser Cys Asn Gly Asn Glu Thr Ser Leu Trp Asp Cys Lys Asn
        435                 440                 445

Trp Gln Trp Gly Gly Leu Ser Cys Asp His Tyr Asp Glu Ala Lys Ile
    450                 455                 460

Thr Cys Ser Ala His Arg Lys Pro Arg Leu Val Gly Gly Asp Ile Pro
465                 470                 475                 480

Cys Ser Gly Arg Val Glu Val Gln His Gly Asp Thr Trp Gly Thr Val
                485                 490                 495

Cys Asp Ser Asp Phe Ser Leu Glu Ala Ala Ser Val Leu Cys Arg Glu
            500                 505                 510

Leu Gln Cys Gly Thr Val Val Ser Leu Leu Gly Gly Ala His Phe Gly
        515                 520                 525

Glu Gly Ser Gly Gln Ile Trp Ala Glu Glu Phe Gln Cys Glu Gly His
    530                 535                 540

Glu Ser His Leu Ser Leu Cys Pro Val Ala Pro Arg Pro Asp Gly Thr
545                 550                 555                 560

Cys Ser His Ser Arg Asp Val Gly Val Val Cys Ser Arg Tyr Thr Gln
                565                 570                 575

Ile Arg Leu Val Asn Gly Lys Thr Pro Cys Glu Gly Arg Val Glu Leu
            580                 585                 590

Asn Ile Leu Gly Ser Trp Gly Ser Leu Cys Asn Ser His Trp Asp Met
        595                 600                 605

Glu Asp Ala His Val Leu Cys Gln Gln Leu Lys Cys Gly Val Ala Leu
```

```
                610                 615                 620
Ser Ile Pro Gly Gly Ala Pro Phe Gly Lys Gly Ser Glu Gln Val Trp
625                 630                 635                 640

Arg His Met Phe His Cys Thr Gly Thr Glu Lys His Met Gly Asp Cys
                645                 650                 655

Ser Val Thr Ala Leu Gly Ala Ser Leu Cys Ser Ser Gly Gln Val Ala
                660                 665                 670

Ser Val Ile Cys Ser Gly Asn Gln Ser Gln Thr Leu Ser Pro Cys Asn
                675                 680                 685

Ser Ser Ser Ser Asp Pro Ser Ser Ser Ile Ile Ser Glu Glu Ser Gly
690                 695                 700

Val Ala Cys Ile Gly Ser Gly Gln Leu Arg Leu Val Asp Gly Gly
705                 710                 715                 720

Arg Cys Ala Gly Arg Val Glu Val Tyr Pro Gly Ala Ser Trp Gly Thr
                725                 730                 735

Ile Cys Asp Asp Ser Trp Asp Leu Asn Asp Ala His Val Val Cys Lys
                740                 745                 750

Gln Leu Ser Cys Gly Trp Ala Ile Asn Ala Thr Gly Ser Ala His Phe
                755                 760                 765

Gly Glu Gly Thr Gly Pro Ile Trp Leu Asp Glu Ile Asn Cys Asn Gly
                770                 775                 780

Lys Glu Ser His Ile Trp Gln Cys His Ser Gly Trp Gly Arg His
785                 790                 795                 800

Asn Cys Arg His Lys Glu Asp Ala Gly Val Ile Cys Ser Glu Phe Met
                805                 810                 815

Ser Leu Arg Leu Ile Ser Glu Asn Ser Arg Glu Thr Cys Ala Gly Arg
                820                 825                 830

Leu Glu Val Phe Tyr Asn Gly Ala Trp Gly Ser Val Gly Arg Asn Ser
                835                 840                 845

Met Ser Pro Ala Thr Val Gly Val Val Cys Arg Gln Leu Gly Cys Ala
850                 855                 860

Asp Arg Gly Asp Ile Ser Pro Ala Ser Ser Asp Lys Thr Val Ser Arg
865                 870                 875                 880

His Met Trp Val Asp Asn Val Gln Cys Pro Lys Gly Pro Asp Thr Leu
                885                 890                 895

Trp Gln Cys Pro Ser Ser Pro Trp Lys Arg Leu Ala Ser Pro Ser
                900                 905                 910

Glu Glu Thr Trp Ile Thr Cys Ala Asn Lys Ile Arg Leu Gln Glu Gly
                915                 920                 925

Asn Thr Asn Cys Ser Gly Arg Val Glu Ile Trp Tyr Gly Gly Ser Trp
930                 935                 940

Gly Thr Val Cys Asp Asp Ser Trp Asp Leu Glu Asp Ala Gln Val Val
945                 950                 955                 960

Cys Arg Gln Leu Gly Cys Gly Ser Ala Leu Glu Ala Gly Lys Glu Pro
                965                 970                 975

Ala Phe Gly Gln Gly Thr Gly Pro Ile Trp Leu Asn Glu Val Lys Cys
                980                 985                 990

Lys Gly Asn Glu Pro Ser Leu Trp Asp Cys Pro Ala Arg Ser Trp Gly
                995                 1000                1005

His Ser Asp Cys Gly His Lys Glu Asp Ala Ala Val Thr Cys Ser
                1010                1015                1020

Glu Ile Ala Lys Ser Arg Glu Ser Leu His Ala Thr Gly Arg Ser
                1025                1030                1035
```

```
Ser Phe Val Ala Leu Ala Ile Phe Gly Val Ile Leu Leu Ala Cys
    1040                1045                1050

Leu Ile Ala Phe Leu Ile Trp Thr Gln Lys Arg Arg Gln Arg Gln
    1055                1060                1065

Arg Leu Ser Val Phe Ser Gly Gly Glu Asn Ser Val His Gln Ile
    1070                1075                1080

Gln Tyr Arg Glu Met Asn Ser Cys Leu Lys Ala Asp Glu Thr Asp
    1085                1090                1095

Met Leu Asn Pro Ser Gly Asp His Ser Glu Val Gln
    1100                1105                1110

<210> SEQ ID NO 5
<211> LENGTH: 2930
<212> TYPE: DNA
<213> ORGANISM: Sus scrofa

<400> SEQUENCE: 5
gtaataatac aagaagattt aaatgggcat aaaaccttgg aatggacaaa ctcagaatgg      60
tgctacatga aaactctgga tctgcagacc tgaaactgag agtggtagat ggagtcactg     120
aatgttcagg aagattggaa gtgaaattcc aaggagaatg gggaacaatc tgtgatgatg     180
gctgggatag tgatgatgcc gctgtggcat gtaagcaact gggatgtcca actgctgtca     240
ctgccattgg tcgagttaac gccagtgagg gaactggaca catttggctt gacagtgttt     300
cttgccatgg acacgagtct gctctctggc agtgtagaca ccatgaatgg ggaaagcatt     360
attgcaatca taatgaagat gctggtgtga catgttctga tggatcagat ctggaactga     420
gacttaaagg tggaggcagc cactgtgctg ggacagtgga ggtggaaatt cagaaactgg     480
taggaaaagt gtgtgataga agctggggac tgaaagaagc tgatgtggtt tgcaggcagc     540
tgggatgtgg atctgcactc aaaacatcat atcaagttta ttccaaaacc aaggcaacaa     600
acacatggct gtttgtaagc agctgtaatg gaaatgaaac ttctctttgg gactgcaaga     660
attggcagtg gggtggactt agttgtgatc actatgacga agccaaaatt acctgctcag     720
cccacaggaa acccaggctg gttggagggg acattccctg ctctggtcgt gttgaagtac     780
aacatggaga cacgtggggc accgtctgtg attctgactt ctctctggag gcggccagcg     840
tgctgtgcag ggaactacag tgcggcactg tggtttccct cctggggggga gctcactttg     900 gagaaggaag tggacagatc tgggctgaag aattccagtg tgaggggcac gagtcccacc     960
tttcactctg cccagtagca ccccgccctg acgggacatg tagccacagc agggacgtcg    1020
gcgtagtctg ctcaagatac acacaaatcc gcttggtgaa tggcaagacc ccatgtgaag    1080
gaagagtgga gctcaacatt cttgggtcct gggggtccct ctgcaactct cactgggaca    1140
tggaagatgc ccatgtttta tgccagcagc ttaaatgtgg agttgccctt tctatcccgg    1200
gaggagcacc ttttgggaaa ggaagtgagc aggtctggag gcacatgttt cactgcactg    1260
ggactgagaa gcacatggga gattgttccg tcactgctct gggcgcatca ctctgttctt    1320
cagggcaagt ggcctctgta atctgctcag ggaaccagag tcagacacta tccccgtgca    1380
attcatcatc ctcggaccca tcaagctcta ttatttcaga agaaaatggt gttgcctgca    1440
tagggagtgg tcaacttcgc ctggtcgatg gaggtggtcg ttgtgctggg agagtagagg    1500
tctatcatga gggctcctgg ggcaccatct gtgatgacag ctgggaccta aatgatgccc    1560
atgtggtgtg caaacagctg agctgtggat gggccattaa tgccactggt tctgctcatt    1620 ttgggggaagg aacagggccc atttggctgg atgagataaa ctgtaatgga aaagaatctc    1680
atatttggca atgccactca catggttggg ggcggcacaa ttgcaggcat aaggaggatg    1740
```

-continued

```
caggagtcat ctgctcggag ttcatgtctc tcagactgat cagtgaaaac agcagagaga    1800
cctgtgcagg gcgcctggaa gttttttaca acggagcttg gggcagcgtt ggcaagaata    1860
gcatgtctcc agccacagtg ggggtggtat gcaggcagct gggctgtgca gacagagggg    1920
acatcagccc tgcatcttca gacaagacag tgtccaggca catgtgggtg acaatgttc     1980 agtgtcctaa aggacctgac accctatggc agtgcccatc atctccatgg aagaagagac    2040
tggccagccc ctcagaggag acatggatca catgtgccaa caaaataaga cttcaagaag    2100
gaaacactaa ttgttctgga cgtgtggaga tctggtacgg aggttcctgg ggcactgtgt    2160
gtgacgactc ctgggacctt gaagatgctc aggtggtgtg ccgacagctg ggctgtggct    2220
cagctttgga ggcaggaaaa gaggccgcat ttggccaggg gactgggccc atatggctca    2280
atgaagtgaa gtgcaagggg aatgaaacct ccttgtggga ttgtcctgcc agatcctggg    2340
gccacagtga ctgtggacac aaggaggatg ctgctgtgac gtgttcagaa attgcaaaga    2400
gccgagaatc cctacatgcc acaggtcgct catcttttgt tgcacttgca atctttgggg    2460
tcattctgtt ggcctgtctc atcgcattcc tcatttggac tcagaagcga agacagaggc    2520
agcggctctc agttttctca ggaggagaga attctgtcca tcaaattcaa taccgggaga    2580
tgaattcttg cctgaaagca gatgaaacgg atatgctaaa tccctcagga gaccactctg    2640
aagtacaatg aaaaggaaaa tgggaattat aacctggtgg gttcagcctt taagatacct    2700
tgatgaagac ctggactatt gaatgagcaa gaatctgcct cttacactga agattacaat    2760
acagtcctct gtctcctggt attccaaaga ctgctgttga atttctaaaa aatagattgg    2820
tgaatgtgac tactcaaagt tgtatgtaag actttcaagg gcattaaata aaaaagaata    2880
ttgctgaaaa aaaaaaaaaa aaaaaaaaaa aaaaaaaaaa aaaaaaaaa                2930
```

```
<210> SEQ ID NO 6
<211> LENGTH: 32
<212> TYPE: DNA
<213> ORGANISM: Artificial
<220> FEATURE:
<223> OTHER INFORMATION: PCR primer

<400> SEQUENCE: 6
cggaattccg cggatgtaat aatacaagaa ga                                    32

<210> SEQ ID NO 7
<211> LENGTH: 36
<212> TYPE: DNA
<213> ORGANISM: Artificial
<220> FEATURE:
<223> OTHER INFORMATION: PCR Primer

<400> SEQUENCE: 7
ccgctcgagt agtccaggtc ttcatcaagg tatctt                                36

<210> SEQ ID NO 8
<211> LENGTH: 38
<212> TYPE: DNA
<213> ORGANISM: Artificial
<220> FEATURE:
<223> OTHER INFORMATION: PCR Primer

<400> SEQUENCE: 8
acactcgaca tgtcgatgta cgggccagat atacgcgt                              38

<210> SEQ ID NO 9
<211> LENGTH: 38
```

```
<212> TYPE: DNA
<213> ORGANISM: Artificial
<220> FEATURE:
<223> OTHER INFORMATION: PCR Primer

<400> SEQUENCE: 9
ttccttacag agctcgaggt gcacaccaat gtggtgaa                                   38

<210> SEQ ID NO 10
<211> LENGTH: 46
<212> TYPE: DNA
<213> ORGANISM: Artificial
<220> FEATURE:
<223> OTHER INFORMATION: PCR Primer

<400> SEQUENCE: 10
cggtccggag cggccgcgat gtaataatac aagaagattt aaatgg                          46

<210> SEQ ID NO 11
<211> LENGTH: 38
<212> TYPE: DNA
<213> ORGANISM: Artificial
<220> FEATURE:
<223> OTHER INFORMATION: PCR Primer

<400> SEQUENCE: 11
cggttggtac ccagcaatat tcttttttat ttaatgcc                                   38

<210> SEQ ID NO 12
<211> LENGTH: 3623
<212> TYPE: DNA
<213> ORGANISM: Sus scrofa

<400> SEQUENCE: 12
gtaataatac aagaagattt aaatggcata aaaccttgga atggacaaac tcagaatggt           60
gctacatgaa aactctggat ctgcagactt tagaagatgt tctgcccatt taagttcctt          120
cacttttgct gtagtcgctg ttctcagtgc ctgcttggtc actagttctc ttggaggaaa          180
agacaaggag ctgaggctaa cgggtggtga aaacaagtgc tctggaagag tggaggtgaa          240
agtgcaggag gagtggggaa ctgtgtgtaa taatggctgg acatggatg tggtctctgt           300 tgtttgtagg cagctgggat gtccaactgc tatcaaagcc actggatggg ctaattttag          360
tgcaggttct ggacgcattt ggatggatca tgtttcttgt cgagggaatg agtcagctct          420
ctgggactgc aaacatgatg gatggggaaa gcataactgt actcaccaac aggatgctgg          480
agtaacctgc tcagatggat ctgatttaga gatggggctg gtgaatggag gaaaccggtg          540
cttaggaaga atagaagtca aatttcaagg acggtgggga acagtgtgtg atgataactt          600
caacataaat catgcttctg tggtttgtaa acaacttgaa tgtggaagtg ctgtcagttt          660
ctctggttca gctaattttg gagaaggttc tggaccaatc tggttgatg atcttgtatg           720 caatggaaat gagtcagctc tctggaactg caaacatgaa ggatgggaa agcacaattg           780 cgatcatgct gaggatgctg gagtgatttg cttaaatgga gcagacctga aactgagagt          840
ggtagatgga gtcactgaat gttcaggaag attggaagtg aaattccaag agaatgggg           900 aacaatctgt gatgatggct gggatagtga tgatgccgct gtggcatgta agcaactggg          960
atgtccaact gctgtcactg ccattggtcg agttaacgcc agtgagggaa ctggacacat         1020
ttggcttgac agtgtttctt gccatggaca cgagtctgct ctctggcagt gtagacacca        1080
tgaatgggga aagcattatt gcaatcatga tgaagatgct ggtgtgacat gttctgatgg        1140
atcagatctg gaactgagac ttaaaggtgg aggcagccac tgtgctggga cagtggaggt        1200
```

```
ggaaattcag aaactggtag gaaaagtgtg tgatagaagc tggggactga aagaagctga    1260
tgtggtttgc aggcagctgg gatgtggatc tgcactcaaa acatcatatc aagtttattc    1320
caaaaccaag gcaacaaaca catggctgtt tgtaagcagc tgtaatggaa atgaaacttc    1380
tctttgggac tgcaagaatt ggcagtgggg tggacttagt tgtgatcact atgacgaagc    1440
caaaattacc tgctcagccc acaggaaacc caggctggtt ggaggggaca ttccctgctc    1500
tggtcgtgtt gaagtacaac atggagacac gtggggcacc gtctgtgatt ctgacttctc    1560
tctggaggcg gccagcgtgc tgtgcaggga actacagtgc ggcactgtgg tttccctcct    1620 gggggagct cactttggag aaggaagtgg acagatctgg gctgaagaat tccagtgtga      1680
ggggcacgag tcccaccttt cactctgccc agtagcaccc cgccctgacg ggacatgtag    1740
ccacagcagg gacgtcggcg tagtctgctc aagatacaca caaatccgct tggtgaatgg    1800
caagacccca tgtgaaggaa gagtggagct caacattctt gggtcctggg ggtccctctg    1860
caactctcac tgggacatgg aagatgccca tgttttatgc cagcagctta aatgtggagt    1920
tgccctttct atcccgggag gagcaccttt gggaaagga agtgagcagg tctggaggca     1980
catgtttcac tgcactggga ctgagaagca catgggagat tgttccgtca ctgctctggg    2040
cgcatcactc tgttcttcag gcaagtggc ctctgtaatc tgctcaggga accagagtca     2100
gacactatct ccgtgcaatt catcatcctc ggacccatca agctctatta tttcagaaga    2160
aaatggtgtt gcctgcatag ggagtggtca acttcgcctg gtcgatggag tggtcgttg     2220 tgctgggaga gtagaggtct atcatgaggg ctcctgggc accatctgtg atgacagctg     2280
ggacctgaat gatgcccatg tggtgtgcaa acagctgagc tgtggatggg ccattaatgc    2340
cactggttct gctcattttg gggaaggaac agggcccatt tggctggatg agataaactg    2400
taatggaaaa gaatctcata tttggcaatg ccactcacat ggttgggggc ggcacaattg    2460
caggcataag gaggatgcag gagtcatctg ctcagagttc atgtctctga gactgatcag    2520
tgaaaacagc agagagacct gtgcagggcg cctggaagtt ttttacaacg gagcttgggg    2580
cagcgttggc aggaatagca tgtctccagc cacagtgggg gtggtatgca ggcagctggg    2640
ctgtgcagac agagggaca tcagccctgc atcttcagac aagacagtgt ccaggcacat     2700
gtgggtggaa aatgttcagt gtcctaaagg acctgacaca ctatggcagt gcccatcatc    2760
tccatggaag aagagactgg ccagcccctc agaggagaca tggatcacat gtgccaacaa    2820
aataagactt caagaaggaa acactaattg ttctggacgt gtggagatct ggtacggagg    2880
ttcctggggc actgtgtgtg acgactcctg ggaccttgaa gatgctcagg tggtgtgccg    2940
acagctgggc tgtggctcag ctttggaggc aggaaaagag gccgcatttg gcaggggac    3000 tgggcccata tggctcaatg aagtgaagtg caagggggaat gaaacctcct tgtgggattg    3060
tcctgccaga tcctggggcc acagtgactg tggacacaag gaggatgctg ctgtgacgtg    3120
ctcagaaatt gcaaagagcc gagaatccct acatgccaca ggtcgctcat cttttgttgc    3180
acttgcaatc tttggggtca ttctgttggc ctgtctcatc gcattcctca tttggactca    3240
gaagcgaaga cagaggcagc ggctctcagt tttctcagga ggagagaatt ctgtccatca    3300
aattcaatac cggagatga attcttgcct gaaagcagat gaaacggata tgctaaatcc    3360
ctcaggagac cactctgaag tacaatgaaa aggaaatgg gaattataac ctggtgagtt      3420 cagccttta gataccttga tgaagacctg gactattgaa tgagcaagaa tctgcctctt      3480
acactgaaga ttacaataca gtcctctgtc tcctggtatt ccaaagactg ctgctgaatt    3540
tctaaagaat agattggtga atgtgactac tcaaagttgt atgtaagact ttcaagggca    3600
```

```
ttaaataaaa aagaatattg ctg                                      3623

<210> SEQ ID NO 13
<211> LENGTH: 3345
<212> TYPE: DNA
<213> ORGANISM: Sus scrofa

<400> SEQUENCE: 13
atggacaaac tcagaatggt gctacatgaa aactctggat ctgcagactt tagaagatgt    60
tctgcccatt taagttcctt cacttttgct gtagtcgctg ttctcagtgc ctgcttggtc   120
actagttctc ttggaggaaa agacaaggag ctgaggctaa cgggtggtga aaacaagtgc   180
tctggaagag tggaggtgaa agtgcaggag gagtggggaa ctgtgtgtaa taatggctgg   240
gacatggatg tggtctctgt tgtttgtagg cagctgggat gtccaactgc tatcaaagcc   300
actggatggg ctaattttag tgcaggttct ggacgcattt ggatggatca tgtttcttgt   360
cgagggaatg agtcagctct ctgggactgc aaacatgatg gatggggaaa gcataactgt   420
actcaccaac aggatgctgg agtaacctgc tcagatggat ctgatttaga gatggggctg   480
gtgaatggag gaaaccggtg cttaggaaga atagaagtca aatttcaagg acggtgggga   540
acagtgtgtg atgataactt caacataaat catgcttctg tggtttgtaa acaacttgaa   600
tgtggaagtg ctgtcagttt ctctggttca gctaattttg gagaaggttc tggaccaatc   660
tggtttgatg atcttgtatg caatggaaat gagtcagctc tctggaactg caaacatgaa   720
ggatggggaa agcacaattg cgatcatgct gaggatgctg gagtgatttg cttaaatgga   780
gcagacctga aactgagagt ggtagatgga gtcactgaat gttcaggaag attggaagtg   840
aaattccaag gagaatgggg aacaatctgt gatgatggct gggatagtga tgatgccgct   900
gtggcatgta gcaactggg atgtccaact gctgtcactg ccattggtcg agttaacgcc   960
agtgagggaa ctggacacat ttggcttgac agtgtttctt gccatggaca cgagtctgct  1020
ctctggcagt gtagacacca tgaatgggga agcattatt gcaatcatga tgaagatgct  1080
ggtgtgacat gttctgatgg atcagatctg gaactgagac ttaaaggtgg aggcagccac  1140
tgtgctggga cagtggaggt ggaaattcag aaactggtag aaaagtgtg tgatagaagc  1200
tggggactga agaagctga tgtggtttgc aggcagctgg gatgtggatc tgcactcaaa  1260
acatcatatc aagtttattc aaaaccaag gcaacaaaca catggctgtt tgtaagcagc  1320
tgtaatggaa atgaaacttc tctttgggac tgcaagaatt ggcagtgggg tggacttagt  1380
tgtgatcact atgacgaagc caaaattacc tgctcagccc acaggaaacc caggctggtt  1440
ggagggggaca ttccctgctc tggtcgtgtt gaagtacaac atggagacac gtggggcacc  1500
gtctgtgatt ctgacttctc tctggaggcg gccagcgtgc tgtgcaggga actacagtgc  1560
ggcactgtgg tttccctcct gggggagct cactttggag aaggaagtgg acagatctgg  1620
gctgaagaat tccagtgtga ggggcacgag tcccaccttt cactctgccc agtagcaccc  1680
cgccctgacg ggacatgtag ccacagcagg gacgtcggcg tagtctgctc aagatacaca  1740
caaatccgct tggtgaatgg caagacccca tgtgaaggaa gagtggagct caacattctt  1800
gggtcctggg ggtccctctg caactctcac tgggacatgg aagatgccca tgttttatgc  1860
cagcagctta atgtggagt tgccctttct atcccgggga gcaccttt tgggaaagga  1920
agtgagcagg tctggaggca catgtttcac tgcactggga ctgagaagca catgggagat  1980
tgttccgtca ctgctctggg cgcatcactc tgttcttcag gcaagtggc ctctgtaatc  2040
tgctcaggga accagagtca gacactatct ccgtgcaatt catcatcctc ggacccatca  2100
```

```
agctctatta tttcagaaga aaatggtgtt gcctgcatag ggagtggtca acttcgcctg    2160
gtcgatggag gtggtcgttg tgctgggaga gtagaggtct atcatgaggg ctcctggggc    2220
accatctgtg atgacagctg ggacctgaat gatgcccatg tggtgtgcaa acagctgagc    2280
tgtggatggg ccattaatgc cactggttct gctcattttg gggaaggaac agggcccatt    2340
tggctggatg agataaactg taatggaaaa gaatctcata tttggcaatg ccactcacat    2400 ggttggggc ggcacaattg caggcataag gaggatgcag gagtcatctg ctcagagttc    2460
atgtctctga gactgatcag tgaaaacagc agagagacct gtgcagggcg cctggaagtt    2520
ttttacaacg gagcttgggg cagcgttggc aggaatagca tgtctccagc cacagtgggg    2580
gtggtatgca ggcagctggg ctgtgcagac agagggggaca tcagccctgc atcttcagac    2640
aagacagtgt ccaggcacat gtgggtggac aatgttcagt gtcctaaagg acctgacaca    2700
ctatggcagt gcccatcatc tccatggaag aagagactgg ccagcccctc agaggagaca    2760
tggatcacat gtgccaacaa aataagactt caagaaggaa acactaattg ttctggacgt    2820
gtggagatct ggtacggagg ttcctggggc actgtgtgtg acgactcctg ggaccttgaa    2880
gatgctcagg tggtgtgccg acagctgggc tgtggctcag cttttggaggc aggaaaagag    2940 gccgcatttg ccaggggac tgggcccata tggctcaatg aagtgaagtg caaggggaat    3000
gaaacctcct tgtgggattg tcctgccaga tcctggggcc acagtgactg tggacacaag    3060
gaggatgctg ctgtgacgtg ctcagaaatt gcaaagagcc gagaatccct acatgccaca    3120
ggtcgctcat cttttgttgc acttgcaatc tttggggtca ttctgttggc ctgtctcatc    3180
gcattcctca tttggactca gaagcgaaga cagaggcagc ggctctcagt tttctcagga    3240
ggagagaatt ctgtccatca aattcaatac cggagatgaa attcttgcct gaaagcagat    3300
gaaacggata tgctaaatcc ctcaggagac cactctgaag tacaa                    3345
```

<210> SEQ ID NO 14
<211> LENGTH: 1115
<212> TYPE: PRT
<213> ORGANISM: Sus scrofa

<400> SEQUENCE: 14

```
Met Asp Lys Leu Arg Met Val Leu His Glu Asn Ser Gly Ser Ala Asp
1               5                   10                  15

Phe Arg Arg Cys Ser Ala His Leu Ser Ser Phe Thr Phe Ala Val Val
            20                  25                  30

Ala Val Leu Ser Ala Cys Leu Val Thr Ser Ser Leu Gly Gly Lys Asp
        35                  40                  45

Lys Glu Leu Arg Leu Thr Gly Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Asp Met Asp Val Val Ser Val Val Cys Arg Gln Leu Gly Cys Pro Thr
                85                  90                  95

Ala Ile Lys Ala Thr Gly Trp Ala Asn Phe Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Asn Cys Thr His Gln Gln
    130                 135                 140

Asp Ala Gly Val Thr Cys Ser Asp Gly Ser Asp Leu Glu Met Gly Leu
145                 150                 155                 160
```

-continued

Val Asn Gly Gly Asn Arg Cys Leu Gly Arg Ile Glu Val Lys Phe Gln
            165                 170                 175

Gly Arg Trp Gly Thr Val Cys Asp Asp Asn Phe Asn Ile Asn His Ala
            180                 185                 190

Ser Val Val Cys Lys Gln Leu Glu Cys Gly Ser Ala Val Ser Phe Ser
            195                 200                 205

Gly Ser Ala Asn Phe Gly Glu Gly Ser Gly Pro Ile Trp Phe Asp Asp
    210                 215                 220

Leu Val Cys Asn Gly Asn Glu Ser Ala Leu Trp Asn Cys Lys His Glu
225                 230                 235                 240

Gly Trp Gly Lys His Asn Cys Asp His Ala Glu Asp Ala Gly Val Ile
            245                 250                 255

Cys Leu Asn Gly Ala Asp Leu Lys Leu Arg Val Val Asp Gly Val Thr
            260                 265                 270

Glu Cys Ser Gly Arg Leu Glu Val Lys Phe Gln Gly Glu Trp Gly Thr
        275                 280                 285

Ile Cys Asp Asp Gly Trp Asp Ser Asp Ala Ala Val Ala Cys Lys
        290                 295                 300

Gln Leu Gly Cys Pro Thr Ala Val Thr Ala Ile Gly Arg Val Asn Ala
305                 310                 315                 320

Ser Glu Gly Thr Gly His Ile Trp Leu Asp Ser Val Ser Cys His Gly
            325                 330                 335

His Glu Ser Ala Leu Trp Gln Cys Arg His His Glu Trp Gly Lys His
            340                 345                 350

Tyr Cys Asn His Asp Glu Asp Ala Gly Val Thr Cys Ser Asp Gly Ser
        355                 360                 365

Asp Leu Glu Leu Arg Leu Lys Gly Gly Ser His Cys Ala Gly Thr
    370                 375                 380

Val Glu Val Glu Ile Gln Lys Leu Val Gly Lys Val Cys Asp Arg Ser
385                 390                 395                 400

Trp Gly Leu Lys Glu Ala Asp Val Val Cys Arg Gln Leu Gly Cys Gly
            405                 410                 415

Ser Ala Leu Lys Thr Ser Tyr Gln Val Tyr Ser Lys Thr Lys Ala Thr
            420                 425                 430

Asn Thr Trp Leu Phe Val Ser Ser Cys Asn Gly Asn Glu Thr Ser Leu
            435                 440                 445

Trp Asp Cys Lys Asn Trp Gln Trp Gly Gly Leu Ser Cys Asp His Tyr
        450                 455                 460

Asp Glu Ala Lys Ile Thr Cys Ser Ala His Arg Lys Pro Arg Leu Val
465                 470                 475                 480

Gly Gly Asp Ile Pro Cys Ser Gly Arg Val Glu Val Gln His Gly Asp
            485                 490                 495

Thr Trp Gly Thr Val Cys Asp Ser Asp Phe Ser Leu Glu Ala Ala Ser
        500                 505                 510

Val Leu Cys Arg Glu Leu Gln Cys Gly Thr Val Val Ser Leu Leu Gly
            515                 520                 525

Gly Ala His Phe Gly Glu Gly Ser Gly Gln Ile Trp Ala Glu Glu Phe
    530                 535                 540

Gln Cys Glu Gly His Glu Ser His Leu Ser Leu Cys Pro Val Ala Pro
545                 550                 555                 560

Arg Pro Asp Gly Thr Cys Ser His Ser Arg Asp Val Gly Val Val Cys
            565                 570                 575

Ser Arg Tyr Thr Gln Ile Arg Leu Val Asn Gly Lys Thr Pro Cys Glu

```
                        580                 585                 590
Gly Arg Val Glu Leu Asn Ile Leu Gly Ser Trp Gly Ser Leu Cys Asn
            595                 600                 605

Ser His Trp Asp Met Glu Asp Ala His Val Leu Cys Gln Gln Leu Lys
    610                 615                 620

Cys Gly Val Ala Leu Ser Ile Pro Gly Gly Ala Pro Phe Gly Lys Gly
625                 630                 635                 640

Ser Glu Gln Val Trp Arg His Met Phe His Cys Thr Gly Thr Glu Lys
            645                 650                 655

His Met Gly Asp Cys Ser Val Thr Ala Leu Gly Ala Ser Leu Cys Ser
        660                 665                 670

Ser Gly Gln Val Ala Ser Val Ile Cys Ser Gly Asn Gln Ser Gln Thr
            675                 680                 685

Leu Ser Pro Cys Asn Ser Ser Ser Asp Pro Ser Ser Ile Ile
        690                 695                 700

Ser Glu Glu Asn Gly Val Ala Cys Ile Gly Ser Gly Gln Leu Arg Leu
705                 710                 715                 720

Val Asp Gly Gly Gly Arg Cys Ala Gly Arg Val Glu Val Tyr His Glu
                725                 730                 735

Gly Ser Trp Gly Thr Ile Cys Asp Asp Ser Trp Asp Leu Asn Asp Ala
            740                 745                 750

His Val Val Cys Lys Gln Leu Ser Cys Gly Trp Ala Ile Asn Ala Thr
        755                 760                 765

Gly Ser Ala His Phe Gly Glu Gly Thr Gly Pro Ile Trp Leu Asp Glu
    770                 775                 780

Ile Asn Cys Asn Gly Lys Glu Ser His Ile Trp Gln Cys His Ser His
785                 790                 795                 800

Gly Trp Gly Arg His Asn Cys Arg His Lys Glu Asp Ala Gly Val Ile
                805                 810                 815

Cys Ser Glu Phe Met Ser Leu Arg Leu Ile Ser Glu Asn Ser Arg Glu
            820                 825                 830

Thr Cys Ala Gly Arg Leu Glu Val Phe Tyr Asn Gly Ala Trp Gly Ser
        835                 840                 845

Val Gly Arg Asn Ser Met Ser Pro Ala Thr Val Gly Val Val Cys Arg
850                 855                 860

Gln Leu Gly Cys Ala Asp Arg Gly Asp Ile Ser Pro Ala Ser Ser Asp
865                 870                 875                 880

Lys Thr Val Ser Arg His Met Trp Val Asp Asn Val Gln Cys Pro Lys
                885                 890                 895

Gly Pro Asp Thr Leu Trp Gln Cys Pro Ser Ser Pro Trp Lys Lys Arg
            900                 905                 910

Leu Ala Ser Pro Ser Glu Glu Thr Trp Ile Thr Cys Ala Asn Lys Ile
        915                 920                 925

Arg Leu Gln Glu Gly Asn Thr Asn Cys Ser Gly Arg Val Glu Ile Trp
    930                 935                 940

Tyr Gly Gly Ser Trp Gly Thr Val Cys Asp Asp Ser Trp Asp Leu Glu
945                 950                 955                 960

Asp Ala Gln Val Val Cys Arg Gln Leu Gly Cys Gly Ser Ala Leu Glu
                965                 970                 975

Ala Gly Lys Glu Ala Ala Phe Gly Gln Gly Thr Gly Pro Ile Trp Leu
            980                 985                 990

Asn Glu Val Lys Cys Lys Gly Asn  Glu Thr Ser Leu Trp  Asp Cys Pro
                995                 1000                1005
```

```
Ala Arg Ser Trp Gly His Ser Asp Cys Gly His Lys Glu Asp Ala
    1010                1015                1020

Ala Val Thr Cys Ser Glu Ile Ala Lys Ser Arg Glu Ser Leu His
    1025                1030                1035

Ala Thr Gly Arg Ser Ser Phe Val Ala Leu Ala Ile Phe Gly Val
    1040                1045                1050

Ile Leu Leu Ala Cys Leu Ile Ala Phe Leu Ile Trp Thr Gln Lys
    1055                1060                1065

Arg Arg Gln Arg Gln Arg Leu Ser Val Phe Ser Gly Gly Glu Asn
    1070                1075                1080

Ser Val His Gln Ile Gln Tyr Arg Glu Met Asn Ser Cys Leu Lys
    1085                1090                1095

Ala Asp Glu Thr Asp Met Leu Asn Pro Ser Gly Asp His Ser Glu
    1100                1105                1110

Val Gln
    1115

<210> SEQ ID NO 15
<211> LENGTH: 50
<212> TYPE: DNA
<213> ORGANISM: Artificial
<220> FEATURE:
<223> OTHER INFORMATION: PCR Primer

<400> SEQUENCE: 15
caccgcggcc gcgaagttat aaatcgccac catgagcaaa ctcagaatgg          50

<210> SEQ ID NO 16
<211> LENGTH: 40
<212> TYPE: DNA
<213> ORGANISM: Artificial
<220> FEATURE:
<223> OTHER INFORMATION: PCR Primer

<400> SEQUENCE: 16
tgctccggta cctagtccag gtcttcatca aggtatctta                     40

<210> SEQ ID NO 17
<211> LENGTH: 3434
<212> TYPE: DNA
<213> ORGANISM: Homo sapiens

<400> SEQUENCE: 17
atgagcaaac tcagaatggt gctacttgaa gactctggat ctgctgactt cagaagacat    60
tttgtcaacc tgagtccctt caccattact gtggtcttac ttctcagtgc ctgttttgtc   120
accagttctc ttggaggaac agacaaggag ctgaggctag tggatggtga aaacaagtgt   180
agcgggagag tggaagtgaa agtccaggag gagtggggaa cggtgtgtaa taatggctgg   240
agcatggaag cggtctctgt gatttgtaac cagctgggat gtccaactgc tatcaaagcc   300
cctggatggg ctaattccag tgcaggttct ggacgcattt ggatggatca tgtttcttgt   360
cgtgggaatg agtcagctct ttgggattgc aaacatgatg gatggggaaa gcatagtaac   420
tgtactcacc aacaagatgc tggagtgacc tgctcagatg gatccaattt ggaaatgagg   480
ctgacgcgtg agggaatata tgttctggga agaatagaga tcaaattcca aggacggtgg   540
ggaacagtgt gtgatgataa cttcaacata gatcatgcat ctgtcatttg tagacaactt   600
gaatgtggaa gtgctgtcag tttctctggt tcatctcaatt tggagaagg ctctggacca   660 atctggtttg atgatcttat atgcaacgga aatgagtcag ctctctggaa ctgcaaacat   720
```

```
caaggatggg gaaagcataa ctgtgaccat gctgaggatg ctggagtgat ttgctcaaag    780
ggagcagatc tgagcctgag actggtagat ggagtcactg aatgttcagg aagattagaa    840
gtgagattcc aagggaatg ggggacaata tgtgatgacg gctgggacag ttacgatgct     900
gctgtggcat gcaagcaact gggatgtcca actgccgtca cagccattgg tcagttaac    960 gccagtaagg gatttggaca catctggctt gacagcgttt cttgccaggg acatgaacct   1020
gctgtctggc aatgtaaaca ccatgaatgg ggaaagcatt attgcaatca caatgaagat   1080
gctggcgtga catgttctga tggatcagat ctggagctaa gacttagagg tggaggcagc   1140
cgctgtgctg ggacagttga ggtggagatt cagagactgt tagggaaggt gtgtgacaga   1200
ggctggggac tgaaagaagc tgatgtggtt tgcaggcagc tgggatgtgg atctgcactc   1260
aaaacatctt atcaagtgta ctccaaaatc caggcaacaa acacatggct gtttctaagt   1320
agctgtaacg gaaatgaaac ttctctttgg gactgcaaga actggcaatg gggtggactt   1380
acctgtgatc actatgaaga agccaaaatt acctgctcag cccacaggga acccagactg   1440
gttggagggg acattccctg ttctggacgt gttgaagtga agcatggtga cacgtgggc    1500 tccatctgtg attcggactt ctctctggaa gctgccagcg ttctatgcag ggaattacag   1560
tgtggcacag ttgtctctat cctgggggga gctcactttg gagagggaaa tggacagatc   1620
tgggctgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccgtgtgagg gcagagtgga gctcaaaacg   1800
cttggtgcct ggggatccct ctgtaactct cactgggaca tagaagatgc ccatgttctt   1860
tgccagcagc ttaaatgtgg agttgcccct tctaccccag gaggagcacg tttttggaaaa  1920 ggaaatggtc agatctggag gcatatgttt cactgcactg ggactgagca gcacatggga   1980
gattgtcctg taactgctct aggtgcttca ttatgtcctt cagagcaagt ggcctctgta   2040
atctgctcag gaaaccagtc ccaaacactg tcctcgtgca attcatcgtc tttgggccca   2100
acaaggccta ccattccaga gaaagtgct gtggcctgca tagagagtgg tcaacttcgc    2160
ctggtaaatg gaggaggtcg ctgtgctggg agagtagaga tctatcatga gggctcctgg   2220
ggcaccatct gtgatgacag ctgggacctg agtgatgccc acgtggtttg cagacagctg   2280
ggctgtggag aggccattaa tgccactggt tctgctcatt ttggggaagg aacagggccc   2340
atctggctgg atgagatgaa atgcaatgga aaagaatccc gcatttggca gtgccattca   2400
cacggctggg ggcagcaaaa ttgcaggcac aaggaggatg cggagttat ctgctcagaa     2460 ttcatgtctc tgagactgac cagtgaagcc agcagagagg cctgtgcagg gcgtctggaa   2520 gtttttaca atggagcttg gggcactgtt ggcaagagta gcatgtctga aaccactgtg    2580
ggtgtggtgt gcaggcagct gggctgtgca gacaaaggga aaatcaaccc tgcatcttta   2640
gacaaggcca tgtccattcc catgtgggtg gacaatgttc agtgtccaaa aggacctgac   2700
acgctgtggc agtgcccatc atctccatgg gagaagagac tggccagccc ctcggaggag   2760
acctggatca catgtgacaa caagataaga cttcaggaag acccacttc ctgttctgga    2820 cgtgtggaga tctggcatgg aggttcctgg gggacagtgt gtgatgactc ttgggacttg   2880
gacgatgctc aggtggtgtg tcaacaactt ggctgtggtc cagctttgaa agcattcaaa   2940
gaagcagagt ttggtcaggg gactggaccg atatggctca atgaagtgaa gtgcaaaggg   3000
aatgagtctt ccttgtggga ttgtcctgcc agacgctggg gccatagtga gtgtgggcac   3060
aaggaagacg ctgcagtgaa ttgcacagat atttcagtgc agaaaacccc acaaaaagcc   3120
```

```
acaacaggtc gctcatcccg tcagtcatcc tttattgcag tcgggatcct tggggttgtt      3180
ctgttggcca ttttcgtcgc attattcttc ttgactaaaa agcgaagaca gagacagcgg      3240
cttgcagttt cctcaagagg agagaactta gtccaccaaa ttcaataccg ggagatgaat      3300
tcttgcctga atgcagatga tctgaccta atgaattcct caggaggcca ttctgagcca       3360
cactgaaaag gaaaatggga atttataacc cagtgagttc agcctttaag ataccttgat      3420
gaagacctgg acta                                                        3434

<210> SEQ ID NO 18
<211> LENGTH: 3363
<212> TYPE: DNA
<213> ORGANISM: Homo sapiens

<400> SEQUENCE: 18
atgagcaaac tcagaatggt gctacttgaa gactctggat ctgctgactt cagaagacat        60
tttgtcaacc tgagtccctt caccattact gtggtcttac ttctcagtgc ctgttttgtc       120
accagttctc ttggaggaac agacaaggag ctgaggctag tggatggtga aaacaagtgt       180
agcgggagag tggaagtgaa agtccaggag gagtggggaa cggtgtgtaa taatggctgg       240
agcatggaag cggtctctgt gatttgtaac cagctgggat gtccaactgc tatcaaagcc       300
cctggatggg ctaattccag tgcaggttct ggacgcattt ggatggatca tgtttcttgt       360
cgtgggaatg agtcagctct tgggattgc aaacatgatg gatgggaaa gcatagtaac         420 tgtactcacc aacaagatgc tggagtgacc tgctcagatg gatccaattt ggaaatgagg       480
ctgacgcgtg gagggaatat gtgttctgga agaatagaga tcaaattcca aggacggtgg       540
ggaacagtgt gtgatgataa cttcaacata gatcatgcat ctgtcatttg tagacaactt       600
gaatgtggaa gtgctgtcag tttctctggt tcatctaatt ttggagaagg ctctggacca       660
atctggtttg atgatcttat atgcaacgga aatgagtcag ctctctggaa ctgcaaacat       720
caaggatggg gaaagcataa ctgtgaccat gctgaggatg ctggagtgat ttgctcaaag       780
ggagcagatc tgagcctgag actggtagat ggagtcactg aatgttcagg aagattagaa       840
gtgagattcc aaggggaatg ggggacaata tgtgatgacg gctgggacag ttacgatgct       900
gctgtggcat gcaagcaact gggatgtcca actgccgtca cagccattgg tcgagttaac       960
gccagtaagg gatttggaca catctggctt gacagcgttt cttgccaggg acatgaacct      1020
gctgtctggc aatgtaaaca ccatgaatgg ggaaagcatt attgcaatca caatgaagat      1080
gctggcgtga catgttctga tggatcagat ctggagctaa gcttagagg tggaggcagc       1140 cgctgtgctg ggacagttga ggtggagatt cagagactgt agggaaggt gtgtgacaga       1200 ggctggggac tgaaagaagc tgatgtggtt tgcaggcagc tggatgtgg atctgcactc       1260 aaaacatctt atcaagtgta ctccaaaatc caggcaacaa acacatggct gttctaagt        1320 agctgtaacg gaaatgaaac ttctctttgg gactgcaaga actggcaatg gggtggactt      1380
acctgtgatc actatgaaga agccaaaatt acctgctcag cccacaggga acccagactg      1440 gttgagggg acattccctg ttctggacgt gttgaagtga gcatggtga cacgtggggc        1500 tccatctgtg attcggactt ctctctggaa gctgccagcg ttctatgcag ggaattacag      1560
tgtggcacag ttgtctctat cctgggggga gctcactttg gagagggaaa tggacagatc      1620
tgggctgaag aattccagtg tgagggacat gagtcccatc tttcactctg cccagtagca      1680
ccccgcccag aaggaacttg tagccacagc agggatgttg gagtagtctg ctcaagatac      1740
acagaaattc gcttggtgaa tggcaagacc ccgtgtgagg gcagagtgga gctcaaaacg      1800
```

-continued

```
cttggtgcct ggggatccct ctgtaactct cactgggaca tagaagatgc ccatgttctt    1860
tgccagcagc ttaaatgtgg agttgccctt tctaccccag gaggagcacg ttttggaaaa    1920
ggaaatggtc agatctggag gcatatgttt cactgcactg ggactgagca gcacatggga    1980
gattgtcctg taactgctct aggtgcttca ttatgtcctt cagagcaagt ggcctctgta    2040
atctgctcag gaaaccagtc ccaaacactg tcctcgtgca attcatcgtc tttgggccca    2100
acaaggccta ccattccaga gaaagtgct gtggcctgca tagagagtgg tcaacttcgc    2160
ctggtaaatg gaggaggtcg ctgtgctggg agagtagaga tctatcatga gggctcctgg    2220
ggcaccatct gtgatgacag ctgggacctg agtgatgccc acgtggtttg cagacagctg    2280
ggctgtggag aggccattaa tgccactggt tctgctcatt ttggggaagg aacagggccc    2340
atctggctgg atgagatgaa atgcaatgga aaagaatccc gcatttggca gtgccattca    2400
cacggctggg ggcagcaaaa ttgcaggcac aaggaggatg cgggagttat ctgctcagaa    2460
ttcatgtctc tgagactgac cagtgaagcc agcagagagg cctgtgcagg gcgtctggaa    2520
gttttttaca atggagcttg gggcactgtt ggcaagagta gcatgtctga aaccactgtg    2580
ggtgtggtgt gcaggcagct gggctgtgca gacaaaggga aaatcaaccc tgcatcttta    2640
gacaaggcca tgtccattcc catgtgggtg gacaatgttc agtgtccaaa aggacctgac    2700
acgctgtggc agtgcccatc atctccatgg gagaagagac tggccagccc ctcggaggag    2760
acctggatca catgtgacaa caagataaga cttcaggaag acccacttc ctgttctgga    2820
cgtgtggaga tctggcatgg aggttcctgg gggacagtgt gtgatgactc ttgggacttg    2880
gacgatgctc aggtggtgtg tcaacaactt ggctgtggtc cagcttttgaa agcattcaaa    2940
gaagcagagt ttggtcaggg gactggaccg atatggctca atgaagtgaa gtgcaaaggg    3000
aatgagtctt ccttgtggga ttgtcctgcc agacgctggg gccatagtga gtgtgggcac    3060
aaggaagacg ctgcagtgaa ttgcacagat atttcagtgc agaaaacccc acaaaaagcc    3120
acaacaggtc gctcatcccg tcagtcatcc tttattgcag tcgggatcct tggggttgtt    3180
ctgttggcca ttttcgtcgc attattcttc ttgactaaaa agcgaagaca gagacagcgg    3240
cttgcagttt cctcaagagg agagaactta gtccaccaaa ttcaataccg ggagatgaat    3300
tcttgcctga atgcagatga tctggaccta atgaattcct caggaggcca ttctgagcca    3360
cac                                                                 3363
```

<210> SEQ ID NO 19
<211> LENGTH: 1121
<212> TYPE: PRT
<213> ORGANISM: Homo sapiens

<400> SEQUENCE: 19

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Gly Thr Asp
        35                  40                  45

Lys Glu Leu Arg Leu Val Asp Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

```
Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
            115                 120                 125

Asp Cys Lys His Asp Gly Trp Gly Lys His Ser Asn Cys Thr His Gln
            130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Phe Asn Ile Asp His
            180                 185                 190

Ala Ser Val Ile Cys Arg Gln Leu Glu Cys Gly Ser Ala Val Ser Phe
            195                 200                 205

Ser Gly Ser Ser Asn Phe Gly Glu Gly Ser Gly Pro Ile Trp Phe Asp
            210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
            245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
            275                 280                 285

Thr Ile Cys Asp Asp Gly Trp Asp Ser Tyr Asp Ala Ala Val Ala Cys
            290                 295                 300

Lys Gln Leu Gly Cys Pro Thr Ala Val Thr Ala Ile Gly Arg Val Asn
305                 310                 315                 320

Ala Ser Lys Gly Phe Gly His Ile Trp Leu Asp Ser Val Ser Cys Gln
            325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
            355                 360                 365

Ser Asp Leu Glu Leu Arg Leu Arg Gly Gly Gly Ser Arg Cys Ala Gly
            370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
            405                 410                 415

Gly Ser Ala Leu Lys Thr Ser Tyr Gln Val Tyr Ser Lys Ile Gln Ala
            420                 425                 430

Thr Asn Thr Trp Leu Phe Leu Ser Ser Cys Asn Gly Asn Glu Thr Ser
            435                 440                 445

Leu Trp Asp Cys Lys Asn Trp Gln Trp Gly Gly Leu Thr Cys Asp His
            450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
            485                 490                 495

Asp Thr Trp Gly Ser Ile Cys Asp Ser Asp Phe Ser Leu Glu Ala Ala
            500                 505                 510

Ser Val Leu Cys Arg Glu Leu Gln Cys Gly Thr Val Val Ser Ile Leu
            515                 520                 525
```

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
                580                 585                 590

Glu Gly Arg Val Glu Leu Lys Thr Leu Gly Ala Trp Gly Ser Leu Cys
            595                 600                 605

Asn Ser His Trp Asp Ile Glu Asp Ala His Val Leu Cys Gln Gln Leu
        610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Glu Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Thr Val Gly Lys Ser Ser Met Ser Glu Thr Thr Val Gly Val Val Cys
    850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Ser Pro Ser Glu Glu Thr Trp Ile Thr Cys Asp Asn Lys
        915                 920                 925

Ile Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu

```
                        945                 950                 955                 960
Asp Asp Ala Gln Val Val Cys Gln Gln Leu Gly Cys Gly Pro Ala Leu
                965                 970                 975
Lys Ala Phe Lys Glu Ala Glu Phe Gly Gln Gly Thr Gly Pro Ile Trp
            980                 985                 990
Leu Asn Glu Val Lys Cys Lys Gly  Asn Glu Ser Ser Leu  Trp Asp Cys
        995                 1000                1005
Pro Ala Arg Arg Trp Gly His  Ser Glu Cys Gly His  Lys Glu Asp
    1010                1015                1020
Ala Ala Val Asn Cys Thr Asp  Ile Ser Val Gln Lys  Thr Pro Gln
    1025                1030                1035
Lys Ala Thr Thr Gly Arg Ser  Ser Arg Gln Ser Ser  Phe Ile Ala
    1040                1045                1050
Val Gly Ile Leu Gly Val Val  Leu Leu Ala Ile Phe  Val Ala Leu
    1055                1060                1065
Phe Phe Leu Thr Lys Lys Arg  Arg Gln Arg Gln Arg  Leu Ala Val
    1070                1075                1080
Ser Ser Arg Gly Glu Asn Leu  Val His Gln Ile Gln  Tyr Arg Glu
    1085                1090                1095
Met Asn Ser Cys Leu Asn Ala  Asp Asp Leu Asp Leu  Met Asn Ser
    1100                1105                1110
Ser Gly Gly His Ser Glu Pro  His
    1115                1120

<210> SEQ ID NO 20
<211> LENGTH: 37
<212> TYPE: DNA
<213> ORGANISM: Artificial
<220> FEATURE:
<223> OTHER INFORMATION: PCR Primer

<400> SEQUENCE: 20
caccgcggcc gccacacgga gccatcaaaa tcatcaa                              37

<210> SEQ ID NO 21
<211> LENGTH: 46
<212> TYPE: DNA
<213> ORGANISM: Artificial
<220> FEATURE:
<223> OTHER INFORMATION: PCR Primer

<400> SEQUENCE: 21
ggtaccgcga acaagcaaac caatagcaat attgtttaat tccctc                    46

<210> SEQ ID NO 22
<211> LENGTH: 3556
<212> TYPE: DNA
<213> ORGANISM: Mus musculus

<400> SEQUENCE: 22
gctttggaat gggtggacac agaatggttc ttcttggagg tgctggatct cctggttgta     60
aaaggtttgt ccatctaggt ttctttgttg tggctgtgag ctcacttctc agtgcctctg    120
ctgtcactaa cgctcctgga gaaatgaaga aggaactgag actggcgggt ggtgaaaaca    180
actgtagtgg gagagtggaa cttaagatcc atgacaagtg gggcacagtg tgcagtaacg    240
gctggagcat gaatgaagtg tccgtggttt gccagcagct gggatgccca acttctatta    300
aagcccttgg atgggctaac tccagcgccg gctctggata tatctggatg gacaaagttt    360
cttgtacagg gaatgagtca gctctttggg actgcaaaca tgatgggtgg ggaaagcata    420
```

```
actgtaccca tgaaaaagat gctggagtga cctgctcaga tggatctaat ttggagatga      480
gactggtgaa cagtgcgggc caccgatgct taggaagagt agaaataaag ttccagggaa      540
agtgggggac ggtgtgtgac gacaacttca gcaaagatca cgcttctgtg atttgtaaac      600
agcttggatg tggaagtgcc attagtttct ctggctcagc taaattggga gctggttctg      660
gaccaatctg gctcgatgac ctggcatgca atggaaatga gtcagctctc tgggactgca      720
aacaccgggg atggggcaag cataactgtg accatgctga ggatgtcggt gtgatttgct      780
tagagggagc agatctgagc ctgagactag tggatggagt gtccagatgt tcaggaagat      840
tggaagtgag attccaagga gaatggggga ccgtgtgtga tgataactgg gatctccggg      900
atgcttctgt ggtgtgcaag caactgggat gtccaactgc catcagtgcc attggtcgag      960
ttaatgccag tgagggatct ggacagattt ggcttgacaa catttcatgc gaaggacatg     1020
aggcaactct ttgggagtgt aaacaccaag agtggggaaa gcattactgt catcatagag     1080
aagacgctgg cgtgacatgt tctgatggag cagatctgga acttagactt gtaggtggag     1140
gcagtcgctg tgctggcatt gtggaggtgg agattcagaa gctgactggg aagatgtgta     1200
gccgaggctg gacactggca gatgcggatg tggtttgcag acagcttgga tgtggatctg     1260
cgcttcaaac ccaggctaag atctactcta aaactgggggc aacaaatacg tggctctttc     1320
ctggatcttg taatggaaat gaaactactt tttggcaatg caaaaactgg cagtggggcg     1380
gcctttcctg tgataatttc gaagaagcca agttacctg ctcaggccac agggaaccca     1440
gactggttgg aggagaaatc ccatgctctg gtcgtgtgga agtgaaacac ggagacgtgt     1500
ggggctccgt ctgtgatttt gacttgtctc tggaagctgc cagtgtggtg tgcagggaat     1560
tacaatgtgg aacagtcgtc tctatcctag ggggagcaca ttttggagaa ggaagtggac     1620
agatctgggg tgaagaattc cagtgtagtg gggatgagtc ccatctttca ctatgctcag     1680
tggcgccccc gctagacaga acttgtaccc acagcaggga tgtcagcgta gtctgctcac     1740
gatacataga tattcgtctg gcaggcggcg agtcctcctg tgagggaaga gtggagctca     1800
agacactcgg agcctggggt cccctctgca gttctcattg ggacatggaa gatgctcatg     1860
tcttatgtca gcagctgaag tgtgggggttg cccaatctat tccagaagga gcacattttg     1920
ggaaaggagc tggtcaggtc tggagtcaca tgttccactg cactggaact gaggaacata     1980
taggagattg cctcatgact gctctgggtg cgccgacgtg ttccgaagga caggtggcct     2040
ctgtcatctg ctcaggaaac caatcccaga cactattgcc atgtagttca ttgtctccag     2100
tccaaacaac aagctctaca attccaaagg agagtgaagt tccctgcata gcaagtggcc     2160
agcttcgctt ggtaggtgga ggtggtcgct gcgctggaag agtggaggtc taccacgagg     2220
gctcttgggg caccgtctgt gatgacaatt gggatatgac tgatgccaat gtggtgtgca     2280
agcagctgga ctgtggcgtg gcaattaacg ccactggctc tgcttacttc ggggaaggag     2340
caggagctat ctggctagac gaagtcatct gcactgggaa agagtctcat atttggcagt     2400
gccattcaca tggctgggga cgccataact gcaggcacaa agaagatgca ggtgttatct     2460
gctccgagtt catgtctctg aggctgacca acgaagccca caagaaaaac tgcacaggtc     2520
gccttgaagt gttttacaat ggtacatggg gcagtattgg cagtagcaat atgtctccaa     2580
ccactgtggg ggtggtgtgc cgtcagctgg gctgtgcaga caacgggact gtgaaaccca     2640
taccttcaga caagacacca tccaggccca tgtgggtaga tcgtgtgcag tgtccaaaag     2700
gagttgcaca tttgtggcag tgcccctcgt caccttggaa acagagacag gccagccctc     2760
cctcccagga gtcctggatc atctgtgaca acaaaataag actccaggaa gggcatacag     2820
```

```
actgttctgg acgtgtggag atctggcaca aaggttcctg gggaacagtg tgtgatgact    2880
cctgggatct taatgatgct aaggttgtat gtaagcagtt gggctgtggc caagctgtga    2940
aggcactaaa agaagcagca tttggtccag gaactgggcc catatggctc aatgaaatta    3000
agtgtagagg gaatgagtct tccctgtggg attgtcctgc caaaccgtgg agtcacagcg    3060
actgtgggca caaagaagat gcttccatcc agtgcctccc aaaaatgact tcagaatcac    3120
atcatggcac aggtcacccc accctcacgg cactcttggt tgtggagcc attctattgg      3180
tcctcctcat tgtcttcctc ctgtggactc tgaagcgacg acagattcag cgacttacag    3240
tttcctcaag aggagaggtc ttgatacatc aagttcagta ccaagagatg gattcaaagg    3300
cggatgatct ggacttgctg aaatcctcgg gggtcattca gaggcacact gagaaggaaa    3360
atgataattt ataatccact gaggttggag tttaagaagc cttgacagga cagccagcta    3420
aatggaacaa gagcccaggc aacgcacgga tgaccacagc tgcatcttca tgcagtcctt    3480
tgtttcctgg aactctgctg aacctgcaaa aaccatattt gtgaatgtga ccacttaata    3540
gagatgggag actttt                                                    3556

<210> SEQ ID NO 23
<211> LENGTH: 3363
<212> TYPE: DNA
<213> ORGANISM: Mus musculus

<400> SEQUENCE: 23
atgggtggac acagaatggt tcttcttgga ggtgctggat ctcctggttg taaaaggttt      60
gtccatctag gtttctttgt tgtggctgtg agctcacttc tcagtgcctc tgctgtcact     120
aacgctcctg gagaaatgaa gaaggaactg agactggcgg tggtgaaaa caactgtagt     180
gggagagtgg aacttaagat ccatgacaag tggggcacag tgtgcagtaa cggctggagc    240
atgaatgaag tgtccgtggt ttgccagcag ctgggatgcc caacttctat taaagccctt    300
ggatgggcta actccagcgc cggctctgga tatatctgga tggacaaagt ttcttgtaca    360
gggaatgagt cagctctttg ggactgcaaa catgatgggt gggaaaagca taactgtacc    420
catgaaaaag atgctggagt gacctgctca gatggatcta atttggagat gagactggtg    480
aacagtgcgg gccaccgatg cttaggaaga gtagaaataa agttccaggg aaagtggggg    540
acggtgtgtg acgacaactt cagcaaagat cacgcttctg tgatttgtaa acagcttgga    600
tgtggaagtg ccattagttt ctctggctca gctaaattgg gagctggttc tggaccaatc    660
tggctcgatg acctggcatg caatggaaat gagtcagctc tctgggactg caaacaccgg    720
ggatggggca agcataactg tgaccatgct gaggatgtcg gtgtgatttg cttagaggga    780
gcagatctga gcctgagact agtggatgga gtgtccagat gttcaggaag attggaagtg    840
agattccaag gagaatgggg gaccgtgtgt gatgataact gggatctccg ggatgcttct    900
gtggtgtgca agcaactggg atgtccaact gccatcagtg ccattggtcg agttaatgcc    960
agtgagggat ctggacagat ttggcttgac aacatttcat gcgaaggaca tgaggcaact   1020
ctttgggagt gtaaacacca agagtgggga aagcattact gtcatcatag agaagacgct   1080
ggcgtgacat gttctgatgg agcagatctg gaacttagac ttgtaggtgg aggcagtcgc   1140
tgtgctggca ttgtggaggt ggagattcag aagctgactg gaagatgtg tagccgaggc   1200
tggacactgg cagatgcgga tgtggtttgc agacagcttg gatgtggatc tgcgcttcaa   1260
acccaggcta gatctactc taaaactggg gcaacaaata cgtggctctt tcctggatct   1320
tgtaatggaa atgaaactac tttttggcaa tgcaaaaact ggcagtgggg cggcctttcc   1380
```

```
tgtgataatt tcgaagaagc caaagttacc tgctcaggcc acagggaacc cagactggtt    1440
ggaggagaaa tcccatgctc tggtcgtgtg aagtgaaac acggagacgt gtggggctcc      1500
gtctgtgatt ttgacttgtc tctggaagct gccagtgtgg tgtgcaggga attacaatgt    1560
ggaacagtcg tctctatcct aggggagca cattttggag aaggaagtgg acagatctgg     1620
ggtgaagaat tccagtgtag tggggatgag tcccatcttt cactatgctc agtggcgccc    1680
ccgctagaca gaacttgtac ccacagcagg gatgtcagcg tagtctgctc acgatacata    1740
gatattcgtc tggcaggcgg cgagtcctcc tgtgagggaa gagtggagct caagacactc    1800
ggagcctggg gtcccctctg cagttctcat gggacatgg aagatgctca tgtcttatgt     1860
cagcagctga agtgtggggt tgcccaatct attccagaag gagcacattt tgggaaagga    1920
gctggtcagg tctggagtca catgttccac tgcactggaa ctgaggaaca tataggagat    1980
tgcctcatga ctgctctggg tgcgccgacg tgttccgaag acaggtggc ctctgtcatc     2040 tgctcaggaa accaatccca gacactattg ccatgtagtt cattgtctcc agtccaaaca    2100
acaagctcta caattccaaa ggagagtgaa gttccctgca tagcaagtgg ccagcttcgc    2160
ttggtaggtg gaggtggtcg ctgcgctgga agagtggagg tctaccacga gggctcttgg    2220
ggcaccgtct gtgatgacaa ttgggatatg actgatgcca atgtggtgtg caagcagctg    2280
gactgtggcg tggcaattaa cgccactggc tctgcttact tcggggaagg agcaggagct    2340
atctggctag acgaagtcat ctgcactggg aaagagtctc atatttggca gtgccattca    2400
catggctggg gacgccataa ctgcaggcac aaagaagatg caggtgttat ctgctccgag    2460
ttcatgtctc tgaggctgac caacgaagcc cacaaagaaa actgcacagg tcgccttgaa    2520
gtgttttaca atggtacatg gggcagtatt ggcagtagca atatgtctcc aaccactgtg    2580
ggggtggtgt gccgtcagct gggctgtgca gacaacggga ctgtgaaacc cataccttca    2640
gacaagacac catccaggcc catgtgggta gatcgtgtgc agtgtccaaa aggagttgac    2700
actttgtggc agtgcccctc gtcaccttgg aaacagagac aggccagccc ctcctcccag    2760
gagtcctgga tcatctgtga caacaaaata agactccagg aagggcatac agactgttct    2820
ggacgtgtgg agatctggca caaaggttcc tggggaacag tgtgtgatga ctcctgggat    2880
cttaatgatg ctaaggttgt atgtaagcag ttgggctgtg ccaagctgt gaaggcacta     2940 aaagaagcag catttggtcc aggaactggg cccatatggc tcaatgaaat taagtgtaga    3000
gggaatgagt cttccctgtg ggattgtcct gccaaaccgt ggagtcacag cgactgtggg    3060
cacaaagaag atgcttccat ccagtgcctc ccaaaaatga cttcagaatc acatcatggc    3120
acaggtcacc ccaccctcac ggcactcttg gtttgtggag ccattctatt ggtcctcctc    3180
attgtcttcc tcctgtggac tctgaagcga cgacagattc agcgacttac agtttcctca    3240
agaggagagg tcttgataca tcaagttcag taccaagaga tggattcaaa ggcggatgat    3300
ctggacttgc tgaaatcctc gggggtcatt cagaggcaca ctgagaagga aaatgataat    3360
tta                                                                  3363
```

<210> SEQ ID NO 24
<211> LENGTH: 1121
<212> TYPE: PRT
<213> ORGANISM: Mus musculus

<400> SEQUENCE: 24

```
Met Gly Gly His Arg Met Val Leu Leu Gly Gly Ala Gly Ser Pro Gly
1               5                   10                  15
```

```
Cys Lys Arg Phe Val His Leu Gly Phe Phe Val Ala Val Ser Ser
            20              25              30

Leu Leu Ser Ala Ser Ala Val Thr Asn Ala Pro Gly Glu Met Lys Lys
        35              40              45

Glu Leu Arg Leu Ala Gly Gly Glu Asn Asn Cys Ser Gly Arg Val Glu
 50              55              60

Leu Lys Ile His Asp Lys Trp Gly Thr Val Cys Ser Asn Gly Trp Ser
 65              70              75              80

Met Asn Glu Val Ser Val Cys Gln Gln Leu Gly Cys Pro Thr Ser
                85              90              95

Ile Lys Ala Leu Gly Trp Ala Asn Ser Ser Ala Gly Ser Gly Tyr Ile
            100             105             110

Trp Met Asp Lys Val Ser Cys Thr Gly Asn Glu Ser Ala Leu Trp Asp
            115             120             125

Cys Lys His Asp Gly Trp Gly Lys His Asn Cys Thr His Glu Lys Asp
        130             135             140

Ala Gly Val Thr Cys Ser Asp Gly Ser Asn Leu Glu Met Arg Leu Val
145             150             155             160

Asn Ser Ala Gly His Arg Cys Leu Gly Arg Val Glu Ile Lys Phe Gln
                165             170             175

Gly Lys Trp Gly Thr Val Cys Asp Asp Asn Phe Ser Lys Asp His Ala
            180             185             190

Ser Val Ile Cys Lys Gln Leu Gly Cys Gly Ser Ala Ile Ser Phe Ser
        195             200             205

Gly Ser Ala Lys Leu Gly Ala Gly Ser Gly Pro Ile Trp Leu Asp Asp
210             215             220

Leu Ala Cys Asn Gly Asn Glu Ser Ala Leu Trp Asp Cys Lys His Arg
225             230             235             240

Gly Trp Gly Lys His Asn Cys Asp His Ala Glu Asp Val Gly Val Ile
            245             250             255

Cys Leu Glu Gly Ala Asp Leu Ser Leu Arg Leu Val Asp Gly Val Ser
            260             265             270

Arg Cys Ser Gly Arg Leu Glu Val Arg Phe Gln Gly Glu Trp Gly Thr
        275             280             285

Val Cys Asp Asp Asn Trp Asp Leu Arg Asp Ala Ser Val Val Cys Lys
290             295             300

Gln Leu Gly Cys Pro Thr Ala Ile Ser Ala Ile Gly Arg Val Asn Ala
305             310             315             320

Ser Glu Gly Ser Gly Gln Ile Trp Leu Asp Asn Ile Ser Cys Glu Gly
            325             330             335

His Glu Ala Thr Leu Trp Glu Cys Lys His Gln Glu Trp Gly Lys His
            340             345             350

Tyr Cys His His Arg Glu Asp Ala Gly Val Thr Cys Ser Asp Gly Ala
        355             360             365

Asp Leu Glu Leu Arg Leu Val Gly Gly Gly Ser Arg Cys Ala Gly Ile
        370             375             380

Val Glu Val Glu Ile Gln Lys Leu Thr Gly Lys Met Cys Ser Arg Gly
385             390             395             400

Trp Thr Leu Ala Asp Ala Asp Val Val Cys Arg Gln Leu Gly Cys Gly
                405             410             415

Ser Ala Leu Gln Thr Gln Ala Lys Ile Tyr Ser Lys Thr Gly Ala Thr
            420             425             430

Asn Thr Trp Leu Phe Pro Gly Ser Cys Asn Gly Asn Glu Thr Thr Phe
            435             440             445
```

```
Trp Gln Cys Lys Asn Trp Gln Trp Gly Gly Leu Ser Cys Asp Asn Phe
    450                 455                 460
Glu Glu Ala Lys Val Thr Cys Ser Gly His Arg Glu Pro Arg Leu Val
465                 470                 475                 480
Gly Gly Glu Ile Pro Cys Ser Gly Arg Val Glu Val Lys His Gly Asp
                485                 490                 495
Val Trp Gly Ser Val Cys Asp Phe Asp Leu Ser Leu Glu Ala Ala Ser
            500                 505                 510
Val Val Cys Arg Glu Leu Gln Cys Gly Thr Val Val Ser Ile Leu Gly
        515                 520                 525
Gly Ala His Phe Gly Glu Gly Ser Gly Gln Ile Trp Gly Glu Glu Phe
    530                 535                 540
Gln Cys Ser Gly Asp Glu Ser His Leu Ser Leu Cys Ser Val Ala Pro
545                 550                 555                 560
Pro Leu Asp Arg Thr Cys Thr His Ser Arg Asp Val Ser Val Val Cys
                565                 570                 575
Ser Arg Tyr Ile Asp Ile Arg Leu Ala Gly Gly Glu Ser Ser Cys Glu
            580                 585                 590
Gly Arg Val Glu Leu Lys Thr Leu Gly Ala Trp Gly Pro Leu Cys Ser
        595                 600                 605
Ser His Trp Asp Met Glu Asp Ala His Val Leu Cys Gln Gln Leu Lys
    610                 615                 620
Cys Gly Val Ala Gln Ser Ile Pro Glu Gly Ala His Phe Gly Lys Gly
625                 630                 635                 640
Ala Gly Gln Val Trp Ser His Met Phe His Cys Thr Gly Thr Glu Glu
                645                 650                 655
His Ile Gly Asp Cys Leu Met Thr Ala Leu Gly Ala Pro Thr Cys Ser
            660                 665                 670
Glu Gly Gln Val Ala Ser Val Ile Cys Ser Gly Asn Gln Ser Gln Thr
        675                 680                 685
Leu Leu Pro Cys Ser Ser Leu Ser Pro Val Gly Thr Thr Ser Ser Thr
    690                 695                 700
Ile Pro Lys Glu Ser Glu Val Pro Cys Ile Ala Ser Gly Gln Leu Arg
705                 710                 715                 720
Leu Val Gly Gly Gly Gly Arg Cys Ala Gly Arg Val Glu Val Tyr His
                725                 730                 735
Glu Gly Ser Trp Gly Thr Val Cys Asp Asp Asn Trp Asp Met Thr Asp
            740                 745                 750
Ala Asn Val Val Cys Lys Gln Leu Asp Cys Gly Val Ala Ile Asn Ala
        755                 760                 765
Thr Gly Ser Ala Tyr Phe Gly Glu Gly Ala Gly Ile Trp Leu Asp
    770                 775                 780
Glu Val Ile Cys Thr Gly Lys Glu Ser His Ile Trp Gln Cys His Ser
785                 790                 795                 800
His Gly Trp Gly Arg His Asn Cys Arg His Lys Glu Asp Ala Gly Val
                805                 810                 815
Ile Cys Ser Glu Phe Met Ser Leu Arg Leu Thr Asn Glu Ala His Lys
            820                 825                 830
Glu Asn Cys Thr Gly Arg Leu Glu Val Phe Tyr Asn Gly Thr Trp Gly
        835                 840                 845
Ser Ile Gly Ser Ser Asn Met Ser Pro Thr Thr Val Gly Val Val Cys
    850                 855                 860
Arg Gln Leu Gly Cys Ala Asp Asn Gly Thr Val Lys Pro Ile Pro Ser
```

```
                                865                 870                 875                 880
Asp Lys Thr Pro Ser Arg Pro Met Trp Val Asp Arg Val Gln Cys Pro
                    885                 890                 895
Lys Gly Val Asp Thr Leu Trp Gln Cys Pro Ser Ser Pro Trp Lys Gln
                900                 905                 910
Arg Gln Ala Ser Pro Ser Ser Gln Glu Ser Trp Ile Ile Cys Asp Asn
            915                 920                 925
Lys Ile Arg Leu Gln Glu Gly His Thr Asp Cys Ser Gly Arg Val Glu
        930                 935                 940
Ile Trp His Lys Gly Ser Trp Gly Thr Val Cys Asp Asp Ser Trp Asp
945                 950                 955                 960
Leu Asn Asp Ala Lys Val Val Cys Lys Gln Leu Gly Cys Gly Gln Ala
                965                 970                 975
Val Lys Ala Leu Lys Glu Ala Ala Phe Gly Pro Gly Thr Gly Pro Ile
                980                 985                 990
Trp Leu Asn Glu Ile Lys Cys Arg Gly Asn Glu Ser Ser Leu Trp Asp
                995                1000                1005
Cys Pro Ala Lys Pro Trp Ser His Ser Asp Cys Gly His Lys Glu
        1010                1015                1020
Asp Ala Ser Ile Gln Cys Leu Pro Lys Met Thr Ser Glu Ser His
        1025                1030                1035
His Gly Thr Gly His Pro Thr Leu Thr Ala Leu Leu Val Cys Gly
        1040                1045                1050
Ala Ile Leu Leu Val Leu Leu Ile Val Phe Leu Leu Trp Thr Leu
        1055                1060                1065
Lys Arg Arg Gln Ile Gln Arg Leu Thr Val Ser Ser Arg Gly Glu
        1070                1075                1080
Val Leu Ile His Gln Val Gln Tyr Gln Glu Met Asp Ser Lys Ala
        1085                1090                1095
Asp Asp Leu Asp Leu Leu Lys Ser Ser Gly Val Ile Gln Arg His
        1100                1105                1110
Thr Glu Lys Glu Asn Asp Asn Leu
        1115                1120

<210> SEQ ID NO 25
<211> LENGTH: 3639
<212> TYPE: DNA
<213> ORGANISM: Mus musculus

<400> SEQUENCE: 25
gctttggaat gggtggacac agaatggttc ttcttggagg tgctggatct cctggttgta      60
aaaggtttgt ccatctaggt ttctttgttg tggctgtgag ctcacttctc agtgcctctg     120
ctgtcactaa cgctcctgga gaaatgaaga aggaactgag actggcgggt ggtgaaaaca     180
actgtagtgg gagagtggaa cttaagatcc atgacaagtg gggcacagtg tgcagtaacg     240
gctggagcat gaatgaagtg tccgtggttt gccagcagct gggatgccca acttctatta     300
aagcccttgg atgggctaac tccagcgccg gctctggata tatctggatg acaaagttt      360
cttgtacagg gaatgagtca gctctttggg actgcaaaca tgatgggtgg ggaaagcata     420
actgtaccca tgaaaaagat gctggagtga cctgctcaga tggatctaat ttggagatga     480
gactggtgaa cagtgcgggc accgatgct aggaagagt agaaataaag ttccagggaa       540
agtgggggac ggtgtgtgac gacaacttca gcaaagatca cgcttctgtg atttgtaaac     600
agcttggatg tggaagtgcc attagtttct ctggctcagc taaattggga gctggttctg     660
```

```
gaccaatctg gctcgatgac ctggcatgca atggaaatga gtcagctctc tgggactgca    720
aacaccgggg atggggcaag cataactgtg accatgctga ggatgtcggt gtgatttgct    780
tagagggagc agatctgagc ctgagactag tggatggagt gtccagatgt tcaggaagat    840
tggaagtgag attccaagga gaatggggga ccgtgtgtga tgataactgg gatctccggg    900
atgcttctgt ggtgtgcaag caactgggat gtccaactgc catcagtgcc attggtcgag    960
ttaatgccag tgagggatct ggacagattt ggcttgacaa catttcatgc gaaggacatg   1020
aggcaactct ttgggagtgt aaacaccaag agtggggaaa gcattactgt catcatagag   1080
aagacgctgg cgtgacatgt tctgatggag cagatctgga acttagactt gtaggtggag   1140
gcagtcgctg tgctggcatt gtggaggtgg agattcagaa gctgactggg aagatgtgta   1200
gccgaggctg gacactggca gatgcggatg tggtttgcag acagcttgga tgtggatctg   1260
cgcttcaaac ccaggctaag atctactcta aaactggggc aacaaatacg tggctctttc   1320
ctggatcttg taatggaaat gaaactactt tttggcaatg caaaaactgg cagtggggcg   1380
gcctttcctg tgataatttc gaagaagcca agttacctg ctcaggccac agggaaccca   1440
gactggttgg aggagaaatc ccatgctctg gtcgtgtgga atgaaacac ggagacgtgt   1500 ggggctccgt ctgtgatttt gacttgtctc tggaagctgc cagtgtggtg tgcagggaat   1560
tacaatgtgg aacagtcgtc tctatcctag ggggagcaca ttttggagaa ggaagtggac   1620
agatctgggg tgaagaattc cagtgtagtg gggatgagtc ccatctttca ctatgctcag   1680
tggcgccccc gctagacaga acttgtaccc acagcaggga tgtcagcgta gtctgctcac   1740
gatacataga tattcgtctg gcaggcggcg agtcctcctg tgagggaaga gtggagctca   1800
agacactcgg agcctggggt cccctctgca gttctcattg gacatggaa gatgctcatg   1860 tcttatgtca gcagctgaag tgtggggttg cccaatctat tccagaagga gcacatttg   1920 ggaaaggagc tggtcaggtc tggagtcaca tgttccactg cactgaact gaggaacata   1980 taggagattg cctcatgact gctctgggtg cgccgacgtg ttccgaagga caggtggcct   2040
ctgtcatctg ctcaggaaac caatcccaga cactattgcc atgtagttca ttgtctccag   2100
tccaaacaac aagctctaca attccaaagg agagtgaagt ccctgcata gcaagtggcc   2160 agcttcgctt ggtaggtgga ggtggtcgct gcgctggaag agtggaggtc taccacgagg   2220
gctcttgggg caccgtctgt gatgacaatt gggatatgac tgatgccaat gtggtgtgca   2280
agcagctgga ctgtggcgtg gcaattaacg ccactggctc tgcttacttc ggggaaggag   2340
caggagctat ctggctagac gaagtcatct gcactgggaa agagtctcat atttggcagt   2400
gccattcaca tggctgggga cgccataact gcaggcacaa agaagatgca ggtgttatct   2460
gctccgagtt catgtctctg aggctgacca acgaagccca caagaaaac tgcacaggtc   2520 gccttgaagt gttttacaat ggtacatggg gcagtattgg cagtagcaat atgtctccaa   2580
ccactgtggg ggtggtgtgc cgtcagctgg gctgtgcaga caacgggact gtgaaaccca   2640
taccttcaga caagacacca tccaggccca tgtgggtaga tcgtgtgcag tgtccaaaag   2700
gagttgacac tttgtggcag tgcccctcgt caccttggaa acagagacag gccagccccct   2760 cctcccagga gtcctggatc atctgtgaca acaaaataag actccaggaa gggcatacag   2820
actgttctgg acgtgtggag atctggcaca aaggttcctg gggaacagtg tgtgatgact   2880
cctgggatct taatgatgct aaggttgtat gtaagcagtt gggctgtggc caagctgtga   2940
aggcactaaa agaagcagca tttggtccag gaactgggcc catatggctc aatgaaatta   3000
agtgtagagg gaatgagtct tccctgtggg attgtcctgc caaaccgtgg agtcacagcg   3060
```

```
actgtgggca caaagaagat gcttccatcc agtgcctccc caaaatgact tcagaatcac    3120
atcatggcac aggtcacccc accctcacgg cactcttggt ttgtggagcc attctattgg    3180
tcctcctcat tgtcttcctc ctgtggactc tgaagcgacg acagattcag cgacttacag    3240
tttcctcaag aggagaggtc ttgatacatc aagttcagta ccaagagatg gattcaaagg    3300
cggatgatct ggacttgctg aaatcctcgg aaaattccaa caattcatat gattttaatg    3360
atgatggact gacatctttg tctaaatatc ttcctatttc tggaattaaa aagggggtcat   3420 tcagaggcac actgagaagg aaaatgataa tttataatcc actgaggttg gagtttaaga    3480
agccttgaca ggacagccag ctaaatggaa caagagccca ggcaacgcac ggatgaccac    3540
agctgcatct tcatgcagtc ctttgtttcc tggaactctg ctgaacctgc aaaaaccata    3600
tttgtgaatg tgaccactta atagagatgg gagactttt                           3639

<210> SEQ ID NO 26
<211> LENGTH: 3477
<212> TYPE: DNA
<213> ORGANISM: Mus musculus

<400> SEQUENCE: 26
atgggtggac acagaatggt tcttcttgga ggtgctggat ctcctggttg taaaaggttt      60
gtccatctag gtttctttgt tgtggctgtg agctcacttc tcagtgcctc tgctgtcact     120
aacgctcctg gagaaatgaa gaaggaactg agactggcgg gtggtgaaaa caactgtagt     180
gggagagtgg aacttaagat ccatgacaag tggggcacag tgtgcagtaa cggctggagc     240
atgaatgaag tgtccgtggt ttgccagcag ctgggatgcc aacttctat  taaagcccctt    300 ggatgggcta actccagcgc cggctctgga tatatctgga tggacaaagt ttcttgtaca     360
gggaatgagt cagctctttg ggactgcaaa catgatgggt ggggaaagca taactgtacc     420
catgaaaaag atgctggagt gacctgctca gatggatcta atttggagat gagactggtg     480
aacagtgcgg gccaccgatg cttaggaaga gtagaaataa agttccaggg aaagtggggg     540
acggtgtgtg acgacaactt cagcaaagat cacgcttctg tgatttgtaa acagcttgga     600
tgtggaagtg ccattagttt ctctggctca gctaaattgg gagctggttc tggaccaatc     660
tggctcgatg acctggcatg caatggaaat gagtcagctc tctgggactg caaacaccgg     720
ggatggggca agcataactg tgaccatgct gaggatgtcg gtgtgatttg cttagaggga    780
gcagatctga gcctgagact agtggatgga gtgtccagat gttcaggaag attggaagtg     840
agattccaag gagaatgggg gaccgtgtgt gatgataact gggatctccg ggatgcttct     900
gtggtgtgca agcaactggg atgtccaact gccatcagtg ccattggtcg agttaatgcc     960
agtgagggat ctggacagat ttggcttgac aacatttcat gcgaaggaca tgaggcaact    1020
ctttgggagt gtaaacacca agagtgggga aagcattact gtcatcatag agaagacgct    1080
ggcgtgacat gttctgatgg agcagatctg aacttagac  ttgtaggtgg aggcagtcgc    1140
tgtgctggca ttgtggaggt ggagattcag aagctgactg gaagatgtgt agccgaggc     1200 tggacactgg cagatgcgga tgtggttgc agacagcttg gatgtggatc tgcgcttcaa     1260
acccaggcta agatctactc taaaactggg gcaacaaata cgtggctctt tcctggatct     1320
tgtaatggaa atgaaactac ttttggcaa tgcaaaaact ggcagtgggg cggccttttcc    1380 tgtgataatt tcgaagaagc caaagttacc tgctcaggcc acagggaacc cagactggtt     1440
ggaggagaaa tccatgctc tggtcgtgtg gaaatgaaac acggagacgt gtggggctcc     1500
gtctgtgatt ttgacttgtc tctggaagct gccagtgtgg tgtgcaggga attacaatgt     1560
```

```
ggaacagtcg tctctatcct aggggagca catttggag aaggaagtgg acagatctgg    1620
ggtgaagaat tccagtgtag tgggatgag tcccatcttt cactatgctc agtggcgccc    1680
ccgctagaca gaacttgtac ccacagcagg gatgtcagcg tagtctgctc acgatacata    1740
gatattcgtc tggcaggcgg cgagtcctcc tgtgagggaa gagtggagct caagacactc    1800
ggagcctggg gtcccctctg cagttctcat gggacatgg aagatgctca tgtcttatgt     1860
cagcagctga agtgtggggt tgcccaatct attccagaag gagcacattt tgggaaagga    1920
gctggtcagg tctggagtca catgttccac tgcactggaa ctgaggaaca tataggagat    1980
tgcctcatga ctgctctggg tgcgccgacg tgttccgaag acaggtggc ctctgtcatc     2040 tgctcaggaa accaatccca gacactattg ccatgtagtt cattgtctcc agtccaaaca    2100
acaagctcta caattccaaa ggagagtgaa gttccctgca tagcaagtgg ccagcttcgc    2160
ttggtaggtg gaggtggtcg ctgcgctgga agagtggagg tctaccacga gggctcttgg    2220
ggcaccgtct gtgatgacaa ttgggatatg actgatgcca atgtggtgtg caagcagctg    2280
gactgtggcg tggcaattaa cgccactggc tctgcttact tcggggaagg agcaggagct    2340
atctggctag acgaagtcat ctgcactggg aaagagtctc atatttggca gtgccattca    2400
catggctggg gacgccataa ctgcaggcac aaagaagatg caggtgttat ctgctccgag    2460
ttcatgtctc tgaggctgac caacgaagcc cacaaagaaa actgcacagg tcgccttgaa    2520
gtgttttaca atggtacatg gggcagtatt ggcagtagca atatgtctcc aaccactgtg    2580
ggggtggtgt gccgtcagct gggctgtgca gacaacggga ctgtgaaacc catacccttca   2640 gacaagacac catccaggcc catgtgggta gatcgtgtgc agtgtccaaa aggagttgac    2700
actttgtggc agtgccctc gtcacccttgg aaacagagac aggccagccc ctcctcccag    2760
gagtcctgga tcatctgtga caacaaaata agactccagg aagggcatac agactgttct    2820
ggacgtgtgg agatctggca caaggttcc tggggaacag tgtgtgatga ctcctgggat     2880
cttaatgatg ctaaggttgt atgtaagcag ttgggctgtg ccaagctgt gaaggcacta    2940 aaagaagcag catttggtcc aggaactggg cccatatggc tcaatgaaat taagtgtaga    3000
gggaatgagt cttccctgtg ggattgtcct gccaaaccgt ggagtcacag cgactgtggg    3060
cacaaagaag atgcttccat ccagtgcctc cccaaaatga cttcagaatc acatcatggc    3120
acaggtcacc ccaccctcac ggcactcttg gtttgtggag ccattctatt ggtcctcctc    3180
attgtcttcc tcctgtggac tctgaagcga cgacagattc agcgacttac agtttcctca    3240
agaggagagg tcttgataca tcaagttcag taccaagaga tggattcaaa ggcggatgat    3300
ctggacttgc tgaaatcctc ggaaaattcc aacaattcat atgatttaa tgatgatgga    3360 ctgacatctt tgtctaaata tcttcctatt tctggaatta aaaagggtc attcagaggc    3420 acactgagaa ggaaaatgat aatttataat ccactgaggt tggagtttaa gaagcct       3477
```

<210> SEQ ID NO 27
<211> LENGTH: 1159
<212> TYPE: PRT
<213> ORGANISM: Mus musculus

<400> SEQUENCE: 27

Met Gly Gly His Arg Met Val Leu Leu Gly Gly Ala Gly Ser Pro Gly
1               5                   10                  15

Cys Lys Arg Phe Val His Leu Gly Phe Phe Val Ala Val Ser Ser
                20                  25                  30

Leu Leu Ser Ala Ser Ala Val Thr Asn Ala Pro Gly Glu Met Lys Lys
            35                  40                  45

```
Glu Leu Arg Leu Ala Gly Gly Glu Asn Asn Cys Ser Gly Arg Val Glu
     50                  55                  60

Leu Lys Ile His Asp Lys Trp Gly Thr Val Cys Ser Asn Gly Trp Ser
 65                  70                  75                  80

Met Asn Glu Val Ser Val Val Cys Gln Gln Leu Gly Cys Pro Thr Ser
                 85                  90                  95

Ile Lys Ala Leu Gly Trp Ala Asn Ser Ser Ala Gly Ser Gly Tyr Ile
            100                 105                 110

Trp Met Asp Lys Val Ser Cys Thr Gly Asn Glu Ser Ala Leu Trp Asp
            115                 120                 125

Cys Lys His Asp Gly Trp Gly Lys His Asn Cys Thr His Glu Lys Asp
        130                 135                 140

Ala Gly Val Thr Cys Ser Asp Gly Ser Asn Leu Glu Met Arg Leu Val
145                 150                 155                 160

Asn Ser Ala Gly His Arg Cys Leu Gly Arg Val Glu Ile Lys Phe Gln
                165                 170                 175

Gly Lys Trp Gly Thr Val Cys Asp Asp Asn Phe Ser Lys Asp His Ala
            180                 185                 190

Ser Val Ile Cys Lys Gln Leu Gly Cys Gly Ser Ala Ile Ser Phe Ser
        195                 200                 205

Gly Ser Ala Lys Leu Gly Ala Gly Ser Gly Pro Ile Trp Leu Asp Asp
210                 215                 220

Leu Ala Cys Asn Gly Asn Glu Ser Ala Leu Trp Asp Cys Lys His Arg
225                 230                 235                 240

Gly Trp Gly Lys His Asn Cys Asp His Ala Glu Asp Val Gly Val Ile
                245                 250                 255

Cys Leu Glu Gly Ala Asp Leu Ser Leu Arg Leu Val Asp Gly Val Ser
            260                 265                 270

Arg Cys Ser Gly Arg Leu Glu Val Arg Phe Gln Gly Glu Trp Gly Thr
        275                 280                 285

Val Cys Asp Asp Asn Trp Asp Leu Arg Asp Ala Ser Val Val Cys Lys
290                 295                 300

Gln Leu Gly Cys Pro Thr Ala Ile Ser Ala Ile Gly Arg Val Asn Ala
305                 310                 315                 320

Ser Glu Gly Ser Gly Gln Ile Trp Leu Asp Asn Ile Ser Cys Glu Gly
                325                 330                 335

His Glu Ala Thr Leu Trp Glu Cys Lys His Gln Glu Trp Gly Lys His
            340                 345                 350

Tyr Cys His His Arg Glu Asp Ala Gly Val Thr Cys Ser Asp Gly Ala
        355                 360                 365

Asp Leu Glu Leu Arg Leu Val Gly Gly Ser Arg Cys Ala Gly Ile
370                 375                 380

Val Glu Val Glu Ile Gln Lys Leu Thr Gly Lys Met Cys Ser Arg Gly
385                 390                 395                 400

Trp Thr Leu Ala Asp Ala Asp Val Val Cys Arg Gln Leu Gly Cys Gly
                405                 410                 415

Ser Ala Leu Gln Thr Gln Ala Lys Ile Tyr Ser Lys Thr Gly Ala Thr
            420                 425                 430

Asn Thr Trp Leu Phe Pro Gly Ser Cys Asn Gly Asn Glu Thr Thr Phe
        435                 440                 445

Trp Gln Cys Lys Asn Trp Gln Trp Gly Gly Leu Ser Cys Asp Asn Phe
450                 455                 460

Glu Glu Ala Lys Val Thr Cys Ser Gly His Arg Glu Pro Arg Leu Val
```

```
                465                 470                 475                 480
        Gly Gly Glu Ile Pro Cys Ser Gly Arg Val Glu Met Lys His Gly Asp
                            485                 490                 495

Val Trp Gly Ser Val Cys Asp Phe Asp Leu Ser Leu Glu Ala Ala Ser
                        500                 505                 510

Val Val Cys Arg Glu Leu Gln Cys Gly Thr Val Val Ser Ile Leu Gly
                    515                 520                 525

Gly Ala His Phe Gly Glu Gly Ser Gly Gln Ile Trp Gly Glu Glu Phe
                530                 535                 540

Gln Cys Ser Gly Asp Glu Ser His Leu Ser Leu Cys Ser Val Ala Pro
        545                 550                 555                 560

Pro Leu Asp Arg Thr Cys Thr His Ser Arg Asp Val Ser Val Val Cys
                            565                 570                 575

Ser Arg Tyr Ile Asp Ile Arg Leu Ala Gly Gly Glu Ser Ser Cys Glu
                        580                 585                 590

Gly Arg Val Glu Leu Lys Thr Leu Gly Ala Trp Gly Pro Leu Cys Ser
                    595                 600                 605

Ser His Trp Asp Met Glu Asp Ala His Val Leu Cys Gln Gln Leu Lys
                610                 615                 620

Cys Gly Val Ala Gln Ser Ile Pro Glu Gly Ala His Phe Gly Lys Gly
        625                 630                 635                 640

Ala Gly Gln Val Trp Ser His Met Phe His Cys Thr Gly Thr Glu Glu
                            645                 650                 655

His Ile Gly Asp Cys Leu Met Thr Ala Leu Gly Ala Pro Thr Cys Ser
                        660                 665                 670

Glu Gly Gln Val Ala Ser Val Ile Cys Ser Gly Asn Gln Ser Gln Thr
                    675                 680                 685

Leu Leu Pro Cys Ser Ser Leu Ser Pro Val Gln Thr Thr Ser Ser Thr
                690                 695                 700

Ile Pro Lys Glu Ser Glu Val Pro Cys Ile Ala Ser Gly Gln Leu Arg
        705                 710                 715                 720

Leu Val Gly Gly Gly Arg Cys Ala Gly Arg Val Glu Val Tyr His
                            725                 730                 735

Glu Gly Ser Trp Gly Thr Val Cys Asp Asp Asn Trp Asp Met Thr Asp
                        740                 745                 750

Ala Asn Val Val Cys Lys Gln Leu Asp Cys Gly Val Ala Ile Asn Ala
                    755                 760                 765

Thr Gly Ser Ala Tyr Phe Gly Glu Gly Ala Gly Ala Ile Trp Leu Asp
                770                 775                 780

Glu Val Ile Cys Thr Gly Lys Glu Ser His Ile Trp Gln Cys His Ser
        785                 790                 795                 800

His Gly Trp Gly Arg His Asn Cys Arg His Lys Glu Asp Ala Gly Val
                            805                 810                 815

Ile Cys Ser Glu Phe Met Ser Leu Arg Leu Thr Asn Glu Ala His Lys
                        820                 825                 830

Glu Asn Cys Thr Gly Arg Leu Glu Val Phe Tyr Asn Gly Thr Trp Gly
                    835                 840                 845

Ser Ile Gly Ser Ser Asn Met Ser Pro Thr Thr Val Gly Val Val Cys
                850                 855                 860

Arg Gln Leu Gly Cys Ala Asp Asn Gly Thr Val Lys Pro Ile Pro Ser
        865                 870                 875                 880

Asp Lys Thr Pro Ser Arg Pro Met Trp Val Asp Arg Val Gln Cys Pro
                            885                 890                 895
```

Lys Gly Val Asp Thr Leu Trp Gln Cys Pro Ser Ser Pro Trp Lys Gln
               900                 905                 910

Arg Gln Ala Ser Pro Ser Ser Gln Glu Ser Trp Ile Ile Cys Asp Asn
               915                 920                 925

Lys Ile Arg Leu Gln Glu Gly His Thr Asp Cys Ser Gly Arg Val Glu
               930                 935                 940

Ile Trp His Lys Gly Ser Trp Gly Thr Val Cys Asp Ser Trp Asp
945                 950                 955                 960

Leu Asn Asp Ala Lys Val Val Cys Lys Gln Leu Gly Cys Gly Gln Ala
               965                 970                 975

Val Lys Ala Leu Lys Glu Ala Ala Phe Gly Pro Gly Thr Gly Pro Ile
               980                 985                 990

Trp Leu Asn Glu Ile Lys Cys Arg Gly Asn Glu Ser Ser Leu Trp Asp
               995                1000                1005

Cys Pro Ala Lys Pro Trp Ser His Ser Asp Cys Gly His Lys Glu
               1010                1015                1020

Asp Ala Ser Ile Gln Cys Leu Pro Lys Met Thr Ser Glu Ser His
               1025                1030                1035

His Gly Thr Gly His Pro Thr Leu Thr Ala Leu Leu Val Cys Gly
               1040                1045                1050

Ala Ile Leu Leu Val Leu Leu Ile Val Phe Leu Leu Trp Thr Leu
               1055                1060                1065

Lys Arg Arg Gln Ile Gln Arg Leu Thr Val Ser Ser Arg Gly Glu
               1070                1075                1080

Val Leu Ile His Gln Val Gln Tyr Gln Glu Met Asp Ser Lys Ala
               1085                1090                1095

Asp Asp Leu Asp Leu Leu Lys Ser Ser Glu Asn Ser Asn Asn Ser
               1100                1105                1110

Tyr Asp Phe Asn Asp Asp Gly Leu Thr Ser Leu Ser Lys Tyr Leu
               1115                1120                1125

Pro Ile Ser Gly Ile Lys Lys Gly Ser Phe Arg Gly Thr Leu Arg
               1130                1135                1140

Arg Lys Met Ile Ile Tyr Asn Pro Leu Arg Leu Glu Phe Lys Lys
               1145                1150                1155

Pro

<210> SEQ ID NO 28
<211> LENGTH: 26
<212> TYPE: DNA
<213> ORGANISM: Artificial
<220> FEATURE:
<223> OTHER INFORMATION: PCR Primer

<400> SEQUENCE: 28
caccggaatg agcaaactca gaatgg                                  26

<210> SEQ ID NO 29
<211> LENGTH: 40
<212> TYPE: DNA
<213> ORGANISM: Artificial
<220> FEATURE:
<223> OTHER INFORMATION: PCR Primer

<400> SEQUENCE: 29
tgctccggta cctagtccag gtcttcatca aggtatctta                   40

<210> SEQ ID NO 30
<211> LENGTH: 3414

```
<212> TYPE: DNA
<213> ORGANISM: African green monkey

<400> SEQUENCE: 30
atgagcaaac tcagaatggt gctacttgaa gactctggat ctgctgacgt cagaagacat      60
tttgtcaact tgagtcccct cactattgct gtggtcttac ttctccgtgc ctgttttgtc     120
accagttctc ttggaggaac aaccaaggag ctgaggctag tggatggtga aaacaagtgt     180
agtgggagag tggaagtgaa aatccaggag gagtggggaa cggtgtgtaa taatggctgg     240
agcatggaag cagtctctgt gatttgtaac cagctgggat gtccaactgc tatcaaagcc     300
actggatggg ctaattccag tgcaggttct ggacgcattt ggatggatca tgtttcttgt     360
cgtgggaatg agtcagctct ttgggactgc aaacatgatg gatggggaaa gcatagtaac     420
tgtactcacc aacaagatgc tggagtgact tgctcagatg gatccgattt ggaaatgagg     480
ctgacgaatg gagggaatat gtgttctgga agaatagaga tcaaattcca aggacagtgg     540
ggaacagtgt gtgatgataa cttcaacatc aatcatgcat ctgtggtttg taaacaactt     600
gaatgtggaa gtgctgtcag tttctctggt tcagctaatt ttggagaagg ctctggacca     660
atctggtttg atgatcttat atgcaacgga atgagtcag ctctctggaa ctgcaaacat     720
caaggatggg gaaagcataa ctgtgatcat gctgaggatg ctggagtgat ttgctcaaag     780
ggagcagatc tgagcctgag actggtagat ggagtcactg aatgttcagg aagattagaa     840
gtgagattcc aaggagaatg ggggacaata tgtgatgacg ctgggacag tcatgatgct     900
gctgtggcat gcaagcaact gggatgtcca actgctatca ccgccattgg tcgagttaac     960
gccagtgagg gatttggaca catctggctt gacagtgttt cttgccaggg acatgaacct    1020
gcggtctggc aatgtaaaca ccatgaatgg ggaaagcatt attgcaatca caatgaagat    1080
gctggcgtaa catgttctga tggatcagat ctggagctaa gacttagagg tggaggcagc    1140
cgctgtgctg ggacagttga ggtggagatt cagagactgt tagggaaggt gtgtgacaga    1200
ggctggggac tgaaagaagc tgatgtggtt tgcaggcagc tgggatgtgg atctgcactc    1260
aaaacatcct atcaagtata ctccaaaatc caggcaacaa acatgtggct gtttctaagt    1320
agctgtaacg gaaatgaaac ttctctttgg gactgcaaga actggcaatg gggtggactt    1380
acctgtgatc actatgaaga agccaaaatt acctgctcag cccacaggga acccagactg    1440
gttggaggag acattccctg ttctggacgc gttgaagtga agcatggtga cacatggggc    1500
tccgtctgtg attcggattt ctctctggaa gctgccagcg ttctatgcag ggaattacag    1560
tgtggcacag tcgtctctat cctgggggga gctcactttg gagagggaaa tggacagatc    1620
tgggctgaag aattccagtg tgagggacat gagtcccatc tttcactctg cccagtagca    1680
ccccgcccag aaggaacttg tagccacagc agggatgttg agtagtctg ctcaagatac     1740
acagaaattc gcttggtgaa tgcaagacc ccatgtgagg gcagagtgga gctcaaaacg     1800
cttaatgcct ggggatccct ctgcaactct cactgggaca tagaagatgc ccacgttctt    1860
tgccaacaac ttaaatgtgg agttgccctt tctaccccag aggagcaca ttttggaaaa     1920
ggaaatggtc aggtctggag gcatatgttt cactgcactg gactgagca gcacatggga     1980
gattgtcctg taactgctct gggtgcttca ctatgtcctt cagggcaagt ggcctctgta    2040
atttgctcag gaaaccagtc ccaaacactg tcctcgtgca attcatcatc tctgggccca    2100
acaaggccta ccattccaga gaaagtgct gtggcctgca tagagagtgg tcaacttcgc     2160
ttggtaaatg gaggaggtcg ctgtgctggg agagtagaga tttatcatga gggctcctgg    2220
ggcaccatct gtgatgacag ctgggaccct agcgatgccc acgtggtgtg cagacagctg    2280
```

```
ggctgtggag aggccattaa tgccactggt tctgctcatt ttggagaagg aacagggccc   2340
atctggctgg atgagatgaa atgcaatgga aaagaatccc gcatttggca gtgccattca   2400
catggctggg ggcagcaaaa ctgcaggcac aaggaggatg caggagttat ctgctcagag   2460
ttcatgtctc tgagactgac cagtgaagcc agcagagagg cctgtgcagg gcgtctagaa   2520 gtttttaca acggagcttg gggcagtgtt ggcaggagta acatgtctga aaccactgtg    2580
ggtgtggtgt gcaggcagct gggctgtgca gacaaaggga aaatcaaccc tgcatcttta   2640
gacaaggcca tgtccattcc catgtgggtg acaatgttc agtgtccaaa aggacctgac     2700
acgctgtggc agtgcccatc atctccatgg gagaagagac tggccaggcc ctcggaggag   2760
acctggatca catgtgacaa caagatgaga ctacaagaag acccacttc ctgttctgga     2820 cgtgtggaga tctggcacgg aggttcctgg gggacagtgt gtgatgactc ctgggacttg    2880
aacgatgctc aggtggtgtg tcaacaactt ggctgtggtc cagctttgaa agcattcaaa    2940
gaagcagagt ttggtcaggg gactggaccc atatggctca atgaagtgaa gtgcaaaggg    3000
aatgagtctt ccttgtggga ttgtcctgcc agacgctggg gccacagtga gtgtggacac    3060
aaggaagacg ctgcagtgaa ttgcacagat atttcaacga acaaaacccc acaaaaagcc    3120
acaacaggtc agtcatccct tattgcagtc ggaatccttg gagttgttct cttggtcatt    3180
ttcgtcgcat tattcttgac tcaaaagcga agacagagac agcggcttac agtttcctca    3240
agaggagaga acttagtcca ccaaattcaa taccgggaga tgaattcttg cctgaatgca    3300
gatgatctgg acctaatgaa ttcctcagga ggccattctg aggcacactg aaaaggaaaa    3360
tgggaattta aacccagtg agccttgaag ataccttgat gaagacctgg acta            3414
```

<210> SEQ ID NO 31
<211> LENGTH: 3348
<212> TYPE: DNA
<213> ORGANISM: African green monkey

<400> SEQUENCE: 31

```
atgagcaaac tcagaatggt gctacttgaa gactctggat ctgctgacgt cagaagacat     60
tttgtcaact tgagtcccTT cactattgct gtggtcttac ttctccgtgc ctgttttgtc    120
accagttctc ttggaggaac aaccaaggag ctgaggctag tggatggtga aaacaagtgt     180
agtgggagag tggaagtgaa atccaggag agtggggaa cggtgtgtaa taatggctgg      240
agcatggaag cagtctctgt gatttgtaac cagctgggat gtccaactgc tatcaaagcc    300
actggatggg ctaattccag tgcaggttct ggacgcattt ggatggatca tgtttcttgt    360
cgtgggaatg agtcagctct ttgggactgc aaacatgatg gatggggaaa gcatagtaac    420
tgtactcacc aacaagatgc tggagtgact tgctcagatg gatccgattt ggaaatgagg    480
ctgacgaatg gagggaatat gtgttctgga agaatagaga tcaaattcca aggacagtgg    540
ggaacagtgt gtgatgataa cttcaacatc aatcatgcat ctgtggtttg taaacaactt    600
gaatgtggaa gtgctgtcag ttttctctggt tcagctaatt ttggagaagg ctctggacca    660
atctggtttg atgatcttat atgcaacgga aatgagtcag ctctctggaa ctgcaaacat    720
caaggatggg gaaagcataa ctgtgatcat gctgaggatg ctggagtgat tgctcaaag     780 ggagcagatc tgagcctgag actggtagat ggagtcactg aatgttcagg aagattagaa    840
gtgagattcc aaggagaatg ggggacaata tgtgatgacg ctgggacag tcatgatgct    900 gctgtggcat gcaagcaact gggatgtcca actgctatca ccgccattgg tcgagttaac    960
gccagtgagg gatttggaca catctggctt gacagtgttt cttgccaggg acatgaacct    1020
```

```
gcggtctggc aatgtaaaca ccatgaatgg ggaaagcatt attgcaatca caatgaagat   1080
gctggcgtaa catgttctga tggatcagat ctggagctaa gacttagagg tggaggcagc   1140
cgctgtgctg ggacagttga ggtggagatt cagagactgt tagggaaggt gtgtgacaga   1200
ggctggggac tgaaagaagc tgatgtggtt tgcaggcagc tgggatgtgg atctgcactc   1260
aaaacatcct atcaagtata ctccaaaatc caggcaacaa acatgtggct gtttctaagt   1320
agctgtaacg gaaatgaaac ttctctttgg gactgcaaga actggcaatg gggtggactt   1380
acctgtgatc actatgaaga agccaaaatt acctgctcag cccacaggga acccagactg   1440
gttggaggag acattccctg ttctggacgc gttgaagtga agcatggtga cacatggggc   1500
tccgtctgtg attcggattt ctctctggaa gctgccagcg ttctatgcag ggaattacag   1560
tgtggcacag tcgtctctat cctgggggga gctcactttg gagagggaaa tggacagatc   1620
tgggctgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccatgtgagg gcagagtgga gctcaaaacg   1800
cttaatgcct ggggatccct ctgcaactct cactgggaca tagaagatgc ccacgttctt   1860
tgccaacaac ttaaatgtgg agttgccctt tctaccccag gaggagcaca ttttggaaaa   1920
ggaaatggtc aggtctggag gcatatgttt cactgcactg gactgagcag cacatggga   1980
gattgtcctg taactgctct gggtgcttca ctatgtcctt cagggcaagt ggcctctgta   2040
atttgctcag gaaccagtc ccaaacactg tcctcgtgca attcatcatc tctgggccca   2100
acaaggccta ccattccaga gaaagtgct gtggcctgca tagagagtgg tcaacttcgc   2160
ttggtaaatg gaggaggtcg ctgtgctggg agagtagaga tttatcatga gggctcctgg   2220
ggcaccatct gtgatgacag ctgggacctg agcgatgccc acgtggtgtg cagacagctg   2280
ggctgtggag aggccattaa tgccactggt tctgctcatt ttggagaagg aacagggccc   2340
atctggctgg atgagatgaa atgcaatgga aaagaatccc gcatttggca gtgccattca   2400
catggctggg gcagcaaaaa ctgcaggcac aaggaggatg caggagttat ctgctcagag   2460
ttcatgtctc tgagactgac cagtgaagcc agcagagagg cctgtgcagg gcgtctagaa   2520
gttttttaca acggagcttg gggcagtgtt ggcaggagta acatgtctga aaccactgtg   2580
ggtgtggtgt gcaggcagct gggctgtgca gacaaaggga aaatcaaccc tgcatcttta   2640
gacaaggcca tgtccattcc catgtgggtg gacaatgttc agtgtccaaa aggacctgac   2700
acgctgtggc agtgcccatc atctccatgg gagaagagac tggccaggcc ctcggaggag   2760
acctggatca catgtgacaa caagatgaga ctacaagaag acccacttc ctgttctgga   2820
cgtgtggaga tctggcacgg aggttcctgg gggacagtgt gtgatgactc ctgggactgg   2880
aacgatgctc aggtggtgtg tcaacaactt ggctgtggtc cagctttgaa agcattcaaa   2940
gaagcagagt ttggtcaggg gactggaccc atatggctca atgaagtgaa gtgcaaaggg   3000
aatgagtctt ccttgtggga ttgtcctgcc agacgctggg gccacagtga gtgtggacac   3060
aaggaagacg ctgcagtgaa ttgcacagat atttcaacga acaaaacccc acaaaaagcc   3120
acaacaggtc agtcatccct tattgcagtc ggaatccttg gagttgttct cttggtcatt   3180
ttcgtcgcat tattcttgac tcaaaagcga agacagagac agcggcttac agtttcctca   3240
agaggagaga acttagtcca ccaaattcaa taccgggaga tgaattcttg cctgaatgca   3300
gatgatctgg acctaatgaa ttcctcagga ggccattctg aggcacac                3348
```

```
<210> SEQ ID NO 32
<211> LENGTH: 1116
<212> TYPE: PRT
<213> ORGANISM: African green monkey

<400> SEQUENCE: 32

Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
                20                  25                  30

Leu Leu Leu Arg Ala Cys Phe Val Thr Ser Ser Leu Gly Gly Thr Thr
            35                  40                  45

Lys Glu Leu Arg Leu Val Asp Gly Glu Asn Lys Cys Ser Gly Arg Val
50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Ser Arg Cys Ala Gly
370                 375                 380

Thr Val Glu Val Glu Ile Gln Arg Leu Leu Gly Lys Val Cys Asp Arg
```

```
                385                 390                 395                 400
Gly Trp Gly Leu Lys Glu Ala Asp Val Val Cys Arg Gln Leu Gly Cys
                405                 410                 415
Gly Ser Ala Leu Lys Thr Ser Tyr Gln Val Tyr Ser Lys Ile Gln Ala
                420                 425                 430
Thr Asn Met Trp Leu Phe Leu Ser Ser Cys Asn Gly Asn Glu Thr Ser
                435                 440                 445
Leu Trp Asp Cys Lys Asn Trp Gln Trp Gly Gly Leu Thr Cys Asp His
                450                 455                 460
Tyr Glu Glu Ala Lys Ile Thr Cys Ser Ala His Arg Glu Pro Arg Leu
465                 470                 475                 480
Val Gly Gly Asp Ile Pro Cys Ser Gly Arg Val Glu Val Lys His Gly
                485                 490                 495
Asp Thr Trp Gly Ser Val Cys Asp Ser Asp Phe Ser Leu Glu Ala Ala
                500                 505                 510
Ser Val Leu Cys Arg Glu Leu Gln Cys Gly Thr Val Val Ser Ile Leu
                515                 520                 525
Gly Gly Ala His Phe Gly Glu Gly Asn Gly Gln Ile Trp Ala Glu Glu
                530                 535                 540
Phe Gln Cys Glu Gly His Glu Ser His Leu Ser Leu Cys Pro Val Ala
545                 550                 555                 560
Pro Arg Pro Glu Gly Thr Cys Ser His Ser Arg Asp Val Gly Val Val
                565                 570                 575
Cys Ser Arg Tyr Thr Glu Ile Arg Leu Val Asn Gly Lys Thr Pro Cys
                580                 585                 590
Glu Gly Arg Val Glu Leu Lys Thr Leu Asn Ala Trp Gly Ser Leu Cys
                595                 600                 605
Asn Ser His Trp Asp Ile Glu Asp Ala His Val Leu Cys Gln Gln Leu
                610                 615                 620
Lys Cys Gly Val Ala Leu Ser Thr Pro Gly Gly Ala His Phe Gly Lys
625                 630                 635                 640
Gly Asn Gly Gln Val Trp Arg His Met Phe His Cys Thr Gly Thr Glu
                645                 650                 655
Gln His Met Gly Asp Cys Pro Val Thr Ala Leu Gly Ala Ser Leu Cys
                660                 665                 670
Pro Ser Gly Gln Val Ala Ser Val Ile Cys Ser Gly Asn Gln Ser Gln
                675                 680                 685
Thr Leu Ser Ser Cys Asn Ser Ser Ser Leu Gly Pro Thr Arg Pro Thr
                690                 695                 700
Ile Pro Glu Glu Ser Ala Val Ala Cys Ile Glu Ser Gly Gln Leu Arg
705                 710                 715                 720
Leu Val Asn Gly Gly Gly Arg Cys Ala Gly Arg Val Glu Ile Tyr His
                725                 730                 735
Glu Gly Ser Trp Gly Thr Ile Cys Asp Asp Ser Trp Asp Leu Ser Asp
                740                 745                 750
Ala His Val Val Cys Arg Gln Leu Gly Cys Gly Glu Ala Ile Asn Ala
                755                 760                 765
Thr Gly Ser Ala His Phe Gly Glu Gly Thr Gly Pro Ile Trp Leu Asp
                770                 775                 780
Glu Met Lys Cys Asn Gly Lys Glu Ser Arg Ile Trp Gln Cys His Ser
785                 790                 795                 800
His Gly Trp Gly Gln Gln Asn Cys Arg His Lys Glu Asp Ala Gly Val
                805                 810                 815
```

```
Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                 1005

Pro Ala  Arg Arg Trp Gly His  Ser Glu Cys Gly His  Lys Glu Asp
    1010                 1015                 1020

Ala Ala  Val Asn Cys Thr Asp  Ile Ser Thr Asn Lys  Thr Pro Gln
    1025                 1030                 1035

Lys Ala  Thr Thr Gly Gln Ser  Ser Leu Ile Ala Val  Gly Ile Leu
    1040                 1045                 1050

Gly Val  Val Leu Leu Val Ile  Phe Val Ala Leu Phe  Leu Thr Gln
    1055                 1060                 1065

Lys Arg  Arg Gln Arg Gln Arg  Leu Thr Val Ser Ser  Arg Gly Glu
    1070                 1075                 1080

Asn Leu  Val His Gln Ile Gln  Tyr Arg Glu Met Asn  Ser Cys Leu
    1085                 1090                 1095

Asn Ala  Asp Asp Leu Asp Leu  Met Asn Ser Ser Gly  Gly His Ser
    1100                 1105                 1110

Glu Ala  His
    1115

<210> SEQ ID NO 33
<211> LENGTH: 3348
<212> TYPE: DNA
<213> ORGANISM: African green monkey

<400> SEQUENCE: 33
atgagcaaac tcagaatggt gctacttgaa gactctggat ctgctgacgt cagaagacat      60
tttgtcaact tgagtcccct cactattgct gtggtcttac ttctccgtgc ctgttttgtc     120
accagttctc ttggaggaac aaccaaggag ctgaggctag tggatggtga aaacaagtgt     180
agtgggagag tggaagtgaa aatccaggag gagtggggaa cggtgtgtaa taatggctgg     240
agcatggaag cagtctctgt gatttgtaac cagctgggat gtccaactgc tatcaaagcc     300
actggatggg ctaattccag tgcaggttct ggacgcattt ggatggatca tgtttcttgt     360
```

```
cgtgggaatg agtcagctct ttgggactgc aaacatgatg gatggggaaa gcatagtaac        420
tgtactcacc aacaagatgc tggagtaact tgctcagatg gatccgattt ggaaatgagg        480
ctgacgaatg gagggaatat gtgttctgga agaatagaga tcaaattcca aggacagtgg        540
ggaacagtgt gtgatgataa cttcaacatc aatcatgcat ctgtggtttg taaacaactt        600
gaatgtggaa gtgctgtcag tttctctggt tcagctaatt ttggagaagg ctctggacca        660
atctggtttg atgatcttat atgcaacgga aatgagtcag ctctctggaa ctgcaaacat        720
caaggatggg gaaagcataa ctgtgatcat gctgaggatg ctggagtgat tgctcaaag         780 ggagcagatc tgagcctgag actggtagat ggagtcactg aatgttcagg aagattagaa        840
gtgagattcc aaggagaatg ggggacaata tgtgatgacg ctgggacag tcatgatgct         900 gctgtggcat gcaagcaact gggatgtcca actgctatca ccgccattgg tcagttaac         960 gccagtgagg gatttggaca catctggctt gacagtgttt cttgccaggg acatgaacct       1020
gcggtctggc aatgtaaaca ccatgaatgg ggaaagcatt attgcaatca caatgaagat       1080
gctggcgtaa catgttctga tggatcaggt ctggagctaa gacttagagg tggaggcagc       1140
cgctgtgctg ggacagttga ggtggagatt cagagactgt tagggaaggt gtgtgacaga       1200
ggctggggac tgaaagaagc tgatgtggtt tgcaggcagc tgggatgtgg atctgcactc       1260
aaaacatcct atcaagtata ctccaaaatc caggcaacaa acatgtggct gtttctaagt       1320
agctgtaacg gaaatgaaac ttctctttgg gactgcaaga actggcaatg gggtggactt       1380
acctgtgatc actatgaaga agccaaaatt acctgctcag cccacaggga acccagactg       1440
gttggaggag acattccctg ttctggacgc gttgaagtga agcatggtga cacatggggc       1500
tccgtctgtg attcggattt ctctctggaa gctgccagcg ttctatgcag gaattacag        1560 tgtggcacag tcgtctctat cctgggggga gctcactttg gagagggaaa tggacagatc       1620
tggactgaag aattccagtg tgagggacat gagtcccatc tttcactctg cccagtagca       1680
ccccgcccag aaggaacttg tagccacagc agggatgttg gagtagtctg ctcaagatac       1740
acagaaattc gcttggtgaa tggcaagacc ccatgtgagg gcagagtgga gctcaaaacg       1800
cttaatgcct ggggatccct ctgcaactct cactgggaca tagaagatgc ccacgttctt       1860
tgccaacaac ttaaatgtgg agttgccctt tctaccccag gaggagcaca ttttggaaaa       1920
ggaaatggtc aggtctggag gcatatgttt cactgcactg gactgagca gcacatggga       1980 gattgtcctg taactgctct gggtgcttca ctatgtcctt cagggcaagt ggcctctgta       2040
atttgctcag gaaaccagtc ccaaacactg tcctcgcgca attcatcatc tctgggccca       2100
acaaggccta ccattccaga agaaagtgct gtggcctgca tagagagtgg tcaacttcgc       2160
ttggtaaatg gaggaggtcg ctgtgctggg agagtagaga tttatcatga gggctcctgg       2220
ggcaccatct gtgatgacag ctgggaccctg agcgatgccc acgtggtgtg cagacagctg       2280
ggctgtggag aggccattaa tgccactggt tctgctcatt ttggagaagg aacagggccc       2340
atctggctgg atgagatgaa atgcaatgga aaagaatccc gcatttggca gtgccattca       2400
catgctgggg gcagcaaaaa ctgcaggcac aaggaggatg caggagttat ctgctcagag       2460
ttcatgtctc tgagactgac cagtgaagcc agcagagagg cctgtgcagg gcgtctagaa       2520
gttttttaca cggagcttg gggcagtgtt ggcaggagta acatgtctga aaccactgtg       2580
ggtgtagtgt gcaggcagct gggctgtgca gacaaaggga aaatcaactc tgcatcttta       2640
gacaaggcca tgtccattcc catgggggtg gacaatgttc agtgtccaaa aggacctgac       2700
acgctgtggc agtgcccatc atctccatgg gagaagagac tggccaggcc ctcggaggag       2760
```

-continued

```
acctggatca catgtgacaa caagatgaga ctacaagaag gacccacttc ctgttctgga    2820
cgtgtgagga tctggcacgg aggttcctgg gggacagtgt gtgatgactc ctgggacttg    2880
aacgatgctc aggtggtgtg tcaacaactt ggctgtggtc cagctttgaa agcattcaaa    2940
gaagcagagt ttggtcaggg gactggaccc atatggctca atgaagtgaa gtgcgaaggg    3000
aatgagtctt ccttgtggga ttgtcctgcc agacgctggg ccacagtga gtgtggacac    3060 aaggaagacg ctgcagtgaa ttgcacagat atttcaacgc gcaaaacccc acaaaaagcc    3120
acaacaggtc agtcatccct tattgcagtc ggaatccttg gagttgttct cttggccatt    3180
ttcgtcgcat tattcttgac tcaaaagcga gacagagac agcggcttac agtttcctca    3240
agaggagaga acttagtcca ccaaattcaa taccgggaga tgaattcttg cctgaatgca    3300
gatgatctgg acctaatgaa ttcctcagga ggccattctg aggcacac                3348
```

<210> SEQ ID NO 34
<211> LENGTH: 1116
<212> TYPE: PRT
<213> ORGANISM: African Green Monkey

<400> SEQUENCE: 34

```
Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
                20                  25                  30

Leu Leu Leu Arg Ala Cys Phe Val Thr Ser Ser Leu Gly Gly Thr Thr
            35                  40                  45

Lys Glu Leu Arg Leu Val Asp Gly Glu Asn Lys Cys Ser Gly Arg Val
        50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Phe Asn Ile Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
```

-continued

```
            275                 280                 285
Thr Ile Cys Asp Asp Gly Trp Asp Ser His Asp Ala Val Ala Cys
290                 295                 300
Lys Gln Leu Gly Cys Pro Thr Ala Ile Thr Ala Ile Gly Arg Val Asn
305                 310                 315                 320
Ala Ser Glu Gly Phe Gly His Ile Trp Leu Asp Ser Val Ser Cys Gln
                325                 330                 335
Gly His Glu Pro Ala Val Trp Gln Cys Lys His His Glu Trp Gly Lys
                340                 345                 350
His Tyr Cys Asn His Asn Glu Asp Ala Gly Val Thr Cys Ser Asp Gly
            355                 360                 365
Ser Gly Leu Glu Leu Arg Leu Arg Gly Gly Ser Arg Cys Ala Gly
370                 375                 380
Thr Val Glu Val Glu Ile Gln Arg Leu Leu Gly Lys Val Cys Asp Arg
385                 390                 395                 400
Gly Trp Gly Leu Lys Glu Ala Asp Val Val Cys Arg Gln Leu Gly Cys
                405                 410                 415
Gly Ser Ala Leu Lys Thr Ser Tyr Gln Val Tyr Ser Lys Ile Gln Ala
                420                 425                 430
Thr Asn Met Trp Leu Phe Leu Ser Ser Cys Asn Gly Asn Glu Thr Ser
            435                 440                 445
Leu Trp Asp Cys Lys Asn Trp Gln Trp Gly Gly Leu Thr Cys Asp His
450                 455                 460
Tyr Glu Glu Ala Lys Ile Thr Cys Ser Ala His Arg Glu Pro Arg Leu
465                 470                 475                 480
Val Gly Gly Asp Ile Pro Cys Ser Gly Arg Val Glu Val Lys His Gly
                485                 490                 495
Asp Thr Trp Gly Ser Val Cys Asp Ser Asp Phe Ser Leu Glu Ala Ala
                500                 505                 510
Ser Val Leu Cys Arg Glu Leu Gln Cys Gly Thr Val Val Ser Ile Leu
            515                 520                 525
Gly Gly Ala His Phe Gly Glu Gly Asn Gly Gln Ile Trp Thr Glu Glu
530                 535                 540
Phe Gln Cys Glu Gly His Glu Ser His Leu Ser Leu Cys Pro Val Ala
545                 550                 555                 560
Pro Arg Pro Glu Gly Thr Cys Ser His Ser Arg Asp Val Gly Val Val
                565                 570                 575
Cys Ser Arg Tyr Thr Glu Ile Arg Leu Val Asn Gly Lys Thr Pro Cys
                580                 585                 590
Glu Gly Arg Val Glu Leu Lys Thr Leu Asn Ala Trp Gly Ser Leu Cys
            595                 600                 605
Asn Ser His Trp Asp Ile Glu Asp Ala His Val Leu Cys Gln Gln Leu
            610                 615                 620
Lys Cys Gly Val Ala Leu Ser Thr Pro Gly Gly Ala His Phe Gly Lys
625                 630                 635                 640
Gly Asn Gly Gln Val Trp Arg His Met Phe His Cys Thr Gly Thr Glu
                645                 650                 655
Gln His Met Gly Asp Cys Pro Val Thr Ala Leu Gly Ala Ser Leu Cys
                660                 665                 670
Pro Ser Gly Gln Val Ala Ser Val Ile Cys Ser Gly Asn Gln Ser Gln
            675                 680                 685
Thr Leu Ser Ser Arg Asn Ser Ser Leu Gly Pro Thr Arg Pro Thr
690                 695                 700
```

```
Ile Pro Glu Glu Ser Ala Val Ala Cys Ile Glu Ser Gly Gln Leu Arg
705                 710                 715                 720

Leu Val Asn Gly Gly Arg Cys Ala Gly Arg Val Glu Ile Tyr His
            725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
            755                 760                 765

Thr Gly Ser Ala His Phe Gly Glu Gly Thr Gly Pro Ile Trp Leu Asp
770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
                820                 825                 830

Glu Ala Cys Ala Gly Arg Leu Glu Val Phe Tyr Asn Gly Ala Trp Gly
                835                 840                 845

Ser Val Gly Arg Ser Asn Met Ser Glu Thr Thr Val Gly Val Val Cys
850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
                900                 905                 910

Arg Leu Ala Arg Pro Ser Glu Glu Thr Trp Ile Thr Cys Asp Asn Lys
                915                 920                 925

Met Arg Leu Gln Glu Gly Pro Thr Ser Cys Ser Gly Arg Val Glu Ile
                930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
                980                 985                 990

Leu Asn Glu Val Lys Cys Glu Gly Asn Glu Ser Ser Leu Trp Asp Cys
                995                 1000                1005

Pro Ala Arg Arg Trp Gly His Ser Glu Cys Gly His Lys Glu Asp
    1010                1015                1020

Ala Ala Val Asn Cys Thr Asp Ile Ser Thr Arg Lys Thr Pro Gln
    1025                1030                1035

Lys Ala Thr Thr Gly Gln Ser Ser Leu Ile Ala Val Gly Ile Leu
    1040                1045                1050

Gly Val Val Leu Leu Ala Ile Phe Val Ala Leu Phe Leu Thr Gln
    1055                1060                1065

Lys Arg Arg Gln Arg Gln Arg Leu Thr Val Ser Ser Arg Gly Glu
    1070                1075                1080

Asn Leu Val His Gln Ile Gln Tyr Arg Glu Met Asn Ser Cys Leu
    1085                1090                1095

Asn Ala Asp Asp Leu Asp Leu Met Asn Ser Ser Gly Gly His Ser
    1100                1105                1110

Glu Ala His
    1115
```

<210> SEQ ID NO 35
<211> LENGTH: 3453
<212> TYPE: DNA
<213> ORGANISM: African Green Monkey

<400> SEQUENCE: 35

| | | | | | |
|---|---|---|---|---|---|
| atgagcaaac | tcagaatggt | gctacttgaa | gactctggat | ctgctgacgt | cagaagacat | 60 |
| tttgtcaact | tgagtccctt | cactattgct | gtggtcttac | ttctccgtgc | ctgttttgtc | 120 |
| accagttctc | ttggaggaac | aaccaaggag | ctgaggctag | tggatggtga | aaacaagtgt | 180 |
| agtgggagag | tggaagtgaa | aatccaggag | gagtggggaa | cggtgtgtaa | taatggctgg | 240 |
| agcatggaag | cagtctctgt | gatttgtaac | cagctgggat | gtccaactgc | tatcaaagcc | 300 |
| actggatggg | ctaattccag | tgcaggttct | ggacgcattt | ggatggatca | tgtttcttgt | 360 |
| cgtgggaatg | agtcagctct | ttgggactgc | aaacatgatg | gatggggaaa | gcatagtaac | 420 |
| tgtactcacc | aacaagatgc | tggagtaact | tgctcagatg | gatccgattt | ggaaatgagg | 480 |
| ctgacgaatg | gagggaatat | gtgttctgga | agaatagaga | tcaaattcca | aggacagtgg | 540 |
| ggaacagtgt | gtgatgataa | cttcaacatc | aatcatgcat | ctgtggtttg | taaacaactt | 600 |
| gaatgtggaa | gtgctgtcag | tttctctggt | tcagctaatt | ttggagaagg | ctctggacca | 660 |
| atctggtttg | atgatcttat | atgcaacgga | atgagtcag | ctctctggaa | ctgcaaacat | 720 |
| caaggatggg | gaaagcataa | ctgtgatcat | gctgaggatg | ctggagtgat | tgctcaaag | 780 |
| ggagcagatc | tgagcctgag | actggtagat | ggagtcactg | aatgttcagg | aagattagaa | 840 |
| gtgagattcc | aaggagaatg | ggggacaata | tgtgatgacg | gctgggacag | tcatgatgct | 900 |
| gctgtggcat | gcaagcaact | gggatgtcca | actgctatca | ccgccattgg | tcgagttaac | 960 |
| gccagtgagg | gatttggaca | catctggctt | gacagtgttt | cttgccaggg | acatgaacct | 1020 |
| gcggtctggc | aatgtaaaca | ccatgaatgg | ggaaagcatt | attgcaatca | caatgaagat | 1080 |
| gctggcgtaa | catgttctga | tggatcagat | ctggagctaa | gacttagagg | tggaggcagc | 1140 |
| cgctgtgctg | ggacagttga | ggtggagatt | cagagactgt | tagggaaggt | gtgtgacaga | 1200 |
| ggctggggac | tgaaagaagc | tgatgtggtt | tgcaggcagc | tgggatgtgg | atctgcactc | 1260 |
| aaaacatcct | atcaagtata | ctccaaaatc | caggcaacaa | acatgtggct | gtttctaagt | 1320 |
| agctgtaacg | gaaatgaaac | ttctcttgg | gactgcaaga | actggcaatg | gggtggactt | 1380 |
| acctgtgatc | actatgaaga | agccaaaatt | acctgctcag | cccacaggga | acccagactg | 1440 |
| gttggaggag | acattccctg | ttctggacgc | gttgaagtga | agcatggtga | cacatggggc | 1500 |
| tccgtctgtg | attcggattt | ctctctggaa | gctgccagcg | ttctatgcag | ggaattacag | 1560 |
| tgtggcacag | tcgtctctat | cctgggggga | gctcactttg | gagagggaaa | tggacagatc | 1620 |
| tggactgaag | aattccagtg | tgagggacat | gagtcccatc | tttcactctg | cccagtagca | 1680 |
| ccccgcccag | aaggaacttg | tagccacagc | agggatgttg | gagtagtctg | ctcaagatac | 1740 |
| acagaaattc | gcttggtgaa | tggcaagacc | ccatgtgagg | gcagagtgga | gctcaaaacg | 1800 |
| cttaatgcct | ggggatccct | ctgcaactct | cactgggaca | tagaagatgc | ccacgttctt | 1860 |
| tgccaacaac | ttaaatgtgg | agttgccctt | tctaccccag | gaggagcaca | ttttggaaaa | 1920 |
| ggaaatggtc | aggtctggag | gcatatgttt | cactgcactg | ggactgagca | gcacatggga | 1980 |
| gattgtcctg | taactgctct | gggtgcttca | ctatgtcctt | cagggcaagt | ggcctctgta | 2040 |
| atttgctcag | gaaccagtc | ccaaacactg | tcctcgtgca | attcatcatc | tctgggccca | 2100 |
| acaaggccta | ccattccaga | agaaagtgct | gtggcctgca | tagagagtgg | tcaacttcgc | 2160 |

```
ttggtaaatg aggaggtcg ctgtgctggg agagtagaga tttatcatga gggctcctgg    2220
ggcaccatct gtgatgacag ctgggacctg agcgatgccc acgtggtgtg cagacagctg    2280
ggctgtggag aggccattaa tgccactggt tctgctcatt ttggagaagg aacagggccc    2340
atctggctgg atgagatgaa atgcaatgga aaagaatccc gcatttggca gtgccattca    2400
catggctggg ggcagcaaaa ctgcaggcac aaggaggatg caggagttat ctgctcagag    2460
ttcatgtctc tgagactgac cagtgaagcc agcagagagg cctgtgcagg gcgtctagaa    2520
gttttttaca acggagcttg gggcagtgtt ggcaggagta acatgtctga aaccactgtg    2580
ggtgtagtgt gcaggcagct gggctgtgca gacaaaggga aaatcaactc tgcatctta    2640 gacaaggcca tgtccattcc catgtgggtg gacaatgttc agtgtccaaa aggacctgac    2700
acgctgtggc agtgcccatc atctccatgg gagaagagac tggccaggcc ctcggaggag    2760
acctggatca catgtgacaa caagatgaga ctacaagaag gacccacttc ctgttctgga    2820
cgtgtggaga tctggcacgg aggttcctgg gggacagtgt gtgatgactc ctgggacttg    2880
aacgatgctc aggtggtgtg tcaacaactt ggctgtggtc cagctttgaa agcattcaaa    2940
gaagcagagt ttggtcaggg gactggaccc atatggctca atgaagtgaa gtgcaaaggg    3000
aatgagtctt ccttgtggga ttgtcctgcc agacgctggg ccacagtga gtgtggacac    3060 aaggaagacg ctgcagtgaa ttgcacagat atttcaacgc gcaaaacccc acaaaaagcc    3120
acaacaggtc agtcatccct tattgcagtc ggaatccttg gagttgttct cttggccatt    3180
ttcgtcgcat tattcttgac tcaaaagcga agacagagac agcggcttac agtttcctca    3240
agaggagaga acttagtcca ccaaattcaa taccgggaga tgaattcttg cctgaatgca    3300
gatgatctgg acctaatgaa ttcctcagaa aattccaatg agtcagctga tttcaatgct    3360
gctgaactaa tttctgtgtc taaatttctt cctatttctg gaatggaaaa ggaggccatt    3420
ctgaggcaca ctgaaaagga aaatgggaat tta                                 3453
```

<210> SEQ ID NO 36
<211> LENGTH: 1151
<212> TYPE: PRT
<213> ORGANISM: African Green Monkey

<400> SEQUENCE: 36

```
Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140
```

-continued

```
Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
            165                 170                 175

Gln Gly Gln Trp Gly Thr Val Cys Asp Asp Asn Phe Asn Ile Asn His
        180                 185                 190

Ala Ser Val Val Cys Lys Gln Leu Glu Cys Gly Ser Ala Val Ser Phe
    195                 200                 205

Ser Gly Ser Ala Asn Phe Gly Glu Gly Ser Gly Pro Ile Trp Phe Asp
210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
            245                 250                 255

Ile Cys Ser Lys Gly Ala Asp Leu Ser Leu Arg Leu Val Asp Gly Val
        260                 265                 270

Thr Glu Cys Ser Gly Arg Leu Glu Val Arg Phe Gln Gly Glu Trp Gly
    275                 280                 285

Thr Ile Cys Asp Asp Gly Trp Asp Ser His Asp Ala Ala Val Ala Cys
290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
            325                 330                 335

Gly His Glu Pro Ala Val Trp Gln Cys Lys His His Glu Trp Gly Lys
        340                 345                 350

His Tyr Cys Asn His Asn Glu Asp Ala Gly Val Thr Cys Ser Asp Gly
    355                 360                 365

Ser Asp Leu Glu Leu Arg Leu Arg Gly Gly Ser Arg Cys Ala Gly
370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
            405                 410                 415

Gly Ser Ala Leu Lys Thr Ser Tyr Gln Val Tyr Ser Lys Ile Gln Ala
        420                 425                 430

Thr Asn Met Trp Leu Phe Leu Ser Ser Cys Asn Gly Asn Glu Thr Ser
    435                 440                 445

Leu Trp Asp Cys Lys Asn Trp Gln Trp Gly Gly Leu Thr Cys Asp His
450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
            485                 490                 495

Asp Thr Trp Gly Ser Val Cys Asp Ser Asp Phe Ser Leu Glu Ala Ala
        500                 505                 510

Ser Val Leu Cys Arg Glu Leu Gln Cys Gly Thr Val Val Ser Ile Leu
    515                 520                 525

Gly Gly Ala His Phe Gly Glu Gly Asn Gly Gln Ile Trp Thr Glu Glu
530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
            565                 570                 575
```

```
Cys Ser Arg Tyr Thr Glu Ile Arg Leu Val Asn Gly Lys Thr Pro Cys
                580                 585                 590

Glu Gly Arg Val Glu Leu Lys Thr Leu Asn Ala Trp Gly Ser Leu Cys
            595                 600                 605

Asn Ser His Trp Asp Ile Glu Asp Ala His Val Leu Cys Gln Gln Leu
        610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly Asn Glu Ser Ser Leu Trp Asp Cys
```

|  |  | 995 |  |  | 1000 |  |  | 1005 |  |
|---|---|---|---|---|---|---|---|---|---|

Pro Ala Arg Arg Trp Gly His Ser Glu Cys Gly His Lys Glu Asp
    1010                    1015                    1020

Ala Ala Val Asn Cys Thr Asp Ile Ser Thr Arg Lys Thr Pro Gln
    1025                    1030                    1035

Lys Ala Thr Thr Gly Gln Ser Ser Leu Ile Ala Val Gly Ile Leu
    1040                    1045                    1050

Gly Val Val Leu Leu Ala Ile Phe Val Ala Leu Phe Leu Thr Gln
    1055                    1060                    1065

Lys Arg Arg Gln Arg Gln Leu Thr Val Ser Ser Arg Gly Glu
    1070                    1075                    1080

Asn Leu Val His Gln Ile Gln Tyr Arg Glu Met Asn Ser Cys Leu
    1085                    1090                    1095

Asn Ala Asp Asp Leu Asp Leu Met Asn Ser Ser Glu Asn Ser Asn
    1100                    1105                    1110

Glu Ser Ala Asp Phe Asn Ala Ala Glu Leu Ile Ser Val Ser Lys
    1115                    1120                    1125

Phe Leu Pro Ile Ser Gly Met Glu Lys Glu Ala Ile Leu Arg His
    1130                    1135                    1140

Thr Glu Lys Glu Asn Gly Asn Leu
    1145                    1150

<210> SEQ ID NO 37
<211> LENGTH: 3273
<212> TYPE: DNA
<213> ORGANISM: African Green Monkey

<400> SEQUENCE: 37

| | | |
|---|---|---|
| atgagcaaac tcagaatggt gctacttgaa gactctggat ctgctgacgt cagaagacat | 60 |
| tttgtcaact tgagtccctt cactattgct gtggtcttac ttctccgtgc ctgttttgtc | 120 |
| accagttctc ttggaggaac aaccaaggag ctgaggctag tggatggtga aaacaagtgt | 180 |
| agtgggagag tggaagtgaa atccaggag gagtggggaa cggtgtgtaa taatggctgg | 240 |
| agcatggaag cagtctctgt gatttgtaac cagctggat gtccaactgc tatcaaagcc | 300 |
| actggatggg ctaattccag tgcaggttct ggacgcattt ggatggatca tgtttcttgt | 360 |
| cgtgggaatg agtcagctct tgggactgc aaacatgatg gatggggaaa gcatagtaac | 420 |
| tgtactcacc aacaagatgc tggagtaact tgctcagatg gatccgattt ggaaatgagg | 480 |
| ctgacgaatg gagggaatat gtgttctgga agaatagaga tcaaattcca aggacagtgg | 540 |
| ggaacagtgt gtgatgataa cttcaacatc aatcatgcat ctgtggtttg taaacaactt | 600 |
| gaatgtggaa gtgctgtcag tttctctggt tcagctaatt ttggagaagg ctctggacca | 660 |
| atctggttg atgatcttat atgcaacgga aatgagtcag ctctctggaa ctgcaaacat | 720 |
| caaggatggg aaagcataa ctgtgatcat gctgaggatg ctggagtgat tgctcaaag | 780 |
| ggagcagatc tgagcctgag actggtagat ggagtcactg aatgttcagg aagattagaa | 840 |
| gtgagattcc aaggagaatg ggggacaata tgtgatgacg gctgggacag tcatgatgct | 900 |
| gctgtggcat gcaagcaact gggatgtcca actgctatca ccgccattgg tcgagttaac | 960 |
| gccagtgagg gatttggaca catctggctt gacagtgttt cttgccaggg acatgaacct | 1020 |
| gcggtctggc aatgtaaaca ccatgaatgg ggaaagcatt attgcaatca caatgaagat | 1080 |
| gctggcgtaa catgttctga tggatcagat ctggagctaa gacttagagg tggaggcagc | 1140 |
| cgctgtgctg ggacagttga ggtggagatt cagagactgt tagggaaggt gtgtgacaga | 1200 |

```
ggctggggac tgaaagaagc tgatgtggtt tgcaggcagc tgggatgtgg atctgcactc   1260
aaaacatcct atcaagtata ctccaaaatc caggcaacaa acatgtggct gtttctaagt   1320
agctgtaacg gaaatgaaac ttctctttgg gactgcaaga actggcaatg gggtggactt   1380
acctgtgatc actatgaaga agccaaaatt acctgctcag cccacaggga acccagactg   1440
gttggaggag acattccctg ttctggacgc gttgaagtga agcatggtga cacatggggc   1500
tccgtctgtg attcggattt ctctctggaa gctgccagcg ttctatgcag ggaattacag   1560
tgtggcacag tcgtctctat cctgggggga gctcactttg agagggaaa tggacagatc    1620
tggactgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tgcaagacc ccatgtgagg gcagagtgga gctcaaaacg    1800
cttaatgcct ggggatccct ctgcaactct cactgggaca tagaagatgc ccacgttctt   1860
tgccaacaac ttaaatgtgg agttgcccct tctaccccag gaggagcaca ttttggaaaa   1920
ggaaatggtc aggtctggag gcatatgttt cactgcactg ggactgagca gcacatggga   1980
gattgtcctg taactgctct gggtgcttca ctatgtcctt cagggcaagt ggcctctgta   2040
atttgctcag gaaccagtc ccaaacactg tcctcgtgca attcatcatc tctgggccca    2100
acaaggccta ccattccaga gaaagtgct gtggcctgca tagagagtgg tcaacttcgc    2160
ttggtaaatg aggaggtcg ctgtgctggg agagtagaga tttatcatga gggctcctgg    2220
ggaccatct gtgatgacag ctgggacctg agcgatgccc acgtggtgtg cagacagctg    2280
ggctgtggag aggccattaa tgccactggt tctgctcatt ttggagaagg aacagggccc   2340
atctggctgg atgagatgaa atgcaatgga aagaatccc gcatttggca gtgccattca    2400
catggctggg ggcagcaaaa ctgcaggcac aaggaggatg caggagttat ctgctcagag   2460
ttcatgtctc tgagactgac cagtgaagcc agcagagagg cctgtgcagg gcgtctagaa   2520
gttttttaca acggagcttg gggcagtgtt ggcaggagta acatgtctga aaccactgtg   2580
ggtgtagtgt gcaggcagct gggctgtgca gacaaaggga aaatcaactc tgcatcttta   2640
gacaaggcca tgtccattcc catgtgggtg acaatgttcc agtgtccaaa aggacctgac   2700
acgctgtggc agtgcccatc atctccatgg gagaagagac tggccaggcc ctcggaggag   2760
acctggatca catgtgacaa caagatgaga ctacaagaag acccacttc ctgttctgga    2820
cgtgtggaga tctggcacgg aggttcctgg ggacagtgt gtgatgactc ctgggacttg    2880
aacgatgctc aggtggtgtg tcaacaactt ggctgtggtc cagctttgaa agcattcaaa   2940
gaagcagagt ttggtcaggg gactggaccc atatggctca tgaagtgaa gtgcaaaggg    3000
aatgagtctt ccttgtggga ttgtcctgcc agacgctggg gccacagtga gtgtggacac   3060
aaggaagacg ctgcggtgaa ttgcacagat atttcaacgc gcaaaacccc acaaaaagcc   3120
acaacggttt cctcaagagg agagaactta gtccaccaaa ttcaataccg ggagatgaat   3180
tcttgcctga atgcagatga tctgaaccta atgaattcct caggaggcca ttctgaggca   3240
cactgaaaag gaaaatggga atttataacc cag                                3273
```

<210> SEQ ID NO 38
<211> LENGTH: 1081
<212> TYPE: PRT
<213> ORGANISM: African Green Monkey

<400> SEQUENCE: 38

```
Met Ser Lys Leu Arg Met Val Leu Leu Glu Asp Ser Gly Ser Ala Asp
1               5                   10                  15
```

-continued

```
Val Arg Arg His Phe Val Asn Leu Ser Pro Phe Thr Ile Ala Val Val
             20                  25                  30

Leu Leu Leu Arg Ala Cys Phe Val Thr Ser Ser Leu Gly Gly Thr Thr
         35                  40                  45

Lys Glu Leu Arg Leu Val Asp Gly Glu Asn Lys Cys Ser Gly Arg Val
50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
             85                  90                  95

Ala Ile Lys Ala Thr Gly Trp Ala Asn Ser Ser Ala Gly Ser Gly Arg
                100                 105                 110

Ile Trp Met Asp His Val Ser Cys Arg Gly Asn Glu Ser Ala Leu Trp
                115                 120                 125

Asp Cys Lys His Asp Gly Trp Gly Lys His Ser Asn Cys Thr His Gln
            130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
                180                 185                 190

Ala Ser Val Val Cys Lys Gln Leu Glu Cys Gly Ser Ala Val Ser Phe
            195                 200                 205

Ser Gly Ser Ala Asn Phe Gly Glu Gly Ser Gly Pro Ile Trp Phe Asp
        210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
                260                 265                 270

Thr Glu Cys Ser Gly Arg Leu Glu Val Arg Phe Gln Gly Glu Trp Gly
            275                 280                 285

Thr Ile Cys Asp Asp Gly Trp Asp Ser His Asp Ala Ala Val Ala Cys
        290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
```

```
                435              440              445
Leu Trp Asp Cys Lys Asn Trp Gln Trp Gly Leu Thr Cys Asp His
450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
                500                 505                 510

Ser Val Leu Cys Arg Glu Leu Gln Cys Gly Thr Val Val Ser Ile Leu
                515                 520                 525

Gly Gly Ala His Phe Gly Glu Gly Asn Gly Gln Ile Trp Thr Glu Glu
530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
                580                 585                 590

Glu Gly Arg Val Glu Leu Lys Thr Leu Asn Ala Trp Gly Ser Leu Cys
                595                 600                 605

Asn Ser His Trp Asp Ile Glu Asp Ala His Val Leu Cys Gln Gln Leu
                610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
                660                 665                 670

Pro Ser Gly Gln Val Ala Ser Val Ile Cys Ser Gly Asn Gln Ser Gln
                675                 680                 685

Thr Leu Ser Ser Cys Asn Ser Ser Ser Leu Gly Pro Thr Arg Pro Thr
690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
                740                 745                 750

Ala His Val Val Cys Arg Gln Leu Gly Cys Gly Glu Ala Ile Asn Ala
                755                 760                 765

Thr Gly Ser Ala His Phe Gly Glu Gly Thr Gly Pro Ile Trp Leu Asp
770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
                820                 825                 830

Glu Ala Cys Ala Gly Arg Leu Glu Val Phe Tyr Asn Gly Ala Trp Gly
                835                 840                 845

Ser Val Gly Arg Ser Asn Met Ser Glu Thr Thr Val Gly Val Val Cys
850                 855                 860
```

```
Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                 1005

Pro Ala Arg Arg Trp Gly His  Ser Glu Cys Gly His  Lys Glu Asp
    1010                 1015                 1020

Ala Ala Val Asn Cys Thr Asp  Ile Ser Thr Arg Lys  Thr Pro Gln
    1025                 1030                 1035

Lys Ala Thr Thr Val Ser Ser  Arg Gly Glu Asn Leu  Val His Gln
    1040                 1045                 1050

Ile Gln Tyr Arg Glu Met Asn  Ser Cys Leu Asn Ala  Asp Asp Leu
    1055                 1060                 1065

Asn Leu Met Asn Ser Ser Gly  Gly His Ser Glu Ala  His
    1070                 1075                 1080

<210> SEQ ID NO 39
<211> LENGTH: 3279
<212> TYPE: DNA
<213> ORGANISM: African Green Monkey

<400> SEQUENCE: 39
atgagcaaac tcagaatggt gctacttgaa gactctggat ctgctgacgt cagaagacat      60
tttgtcaact tgagtcccct cactattgct gtggtcttac ttctccgtgc ctgttttgtc     120
accagttctc ttggaggaac aaccaaggag ctgaggctag tggatggtga aaacaagtgt     180
agtgggagag tggaagtgaa atccaggag gagtggggaa cggtgtgtaa taatggctgg     240
agcatggaag cagtctctgt gatttgtaac cagctgggat gtccaactgc tatcaaagcc     300
actgatgggg ctaattccag tgcaggttct ggacgcattt ggatggatca tgtttcttgt     360
cgtgggaatg agtcagctct ttgggactgc aaacatgatg gatggggaaa gcatagtaac     420
tgtactcacc aacaagatgc tggagtgact tgctcagatg gatccgattt ggaaatgagg     480
ctgacgaatg gagggaatat gtgttctgga agaatagaga tcaaattcca aggacagtgg     540
ggaacagtgt gtgatgataa cttcaacgtc aatcatgcat ctgtggtttg taaacaactt     600
gaatgtggaa gtgctgtcag tttctctggt tcagctaatt ttggagaagg ctctggacca     660
atctggtttg atgatcttat atgcaacgga aatgagtcag ctctctggaa ctgcaaacat     720
caaggatggg gaaagcataa ctgtgatcat gctgaggatg ctggagtgat tgctcaaag     780
ggagcagatc tgagcctgag actggtagat ggagtcactg aatgttcagg aagattagaa     840
gtgagattcc aaggagaatg ggggacaata tgtgatgacg gctgggacag tcatgatgct     900
```

```
gctgtggcat gcaagcaact gggatgtcca actgctatca ccgccattgg tcgagttaac    960
gccagtgagg gatttggaca catctggctt gacagtgttt cttgccaggg acatgaacct   1020
gcggtctggc aatgtaaaca ccatgaatgg ggaaagcatt attgcaatca caatgaagat   1080
gctggcgtaa catgttctga tggatcagat ctggagctaa gacttagagg tggaggcagc   1140
cgctgtgctg ggacagttga ggtggagatt cagagactgt tagggaaggt gtgtgacaga   1200
ggctggggac tgaaagaagc tgatgtggtt tgcaggcagc tgggatgtgg atctgcactc   1260
aaaacatcct atcaagtata ctccaaaatc caggcaacaa acatgtggct gtttctaagt   1320
agctgtaacg gaaatgaaac ttctctttgg gactgcaaga actggcaatg gggtggactt   1380
acctgtgatc actatgaaga agccaaaatt acctgctcag cccacaggga acccagactg   1440
gttggaggag acattccctg ttctggacgc gttgaagtga agcatggtga cacatggggc   1500
tccgtctgtg attcggattt ctctctggaa gctgccagcg ttctatgcag ggaattacag   1560
tgtggcacag tcgtctctat cctgggggga gctcactttg gagagggaaa tggacagatc   1620
tgggctgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccatgtgagg gcagagtgga gctcaaaacg   1800
cttaatgcct ggggatccct ctgcaactct cactgggaca tagaagatgc ccacgttctt   1860
tgccaacaac ttaaatgtgg agttgccctt tctaccccag gaggagcaca ttttggaaaa   1920
ggaaatggtc aggtctggag gcatatgttt cactgcactg ggactgagca gcacatggga   1980
gattgtcctg taactgctct gggtgcttca ctatgtcctt cagggcaagt ggcctctgta   2040
atttgctcag gaaccagtc ccaaacactg tcctcgtgca attcatcatc tctgggccca   2100
acaaggccta ccattccaga gaaagtgct gtggcctgca tagagagtgg tcaacttcgc   2160
ttggtaaatg gaggaggtcg ctgtgctggg agagtagaga tttatcatga gggctcctgg   2220
ggcaccatct gtgatgacag ctgggacctg agcgatgccc acgtggtgtg cagacagctg   2280
ggctgtggag aggccattaa tgccactggt tctgctcatt ttggagaagg aacagggccc   2340
atctggctgg atgagatgaa atgcaatgga aagaatcccg tatttggca gtgccattca   2400 catggctggg ggcagcaaaa ctgcaggcac aaggaggatg caggagttat ctgctcagag   2460
ttcatgtctc tgagactgac cagtgaagcc agcagagagg cctgtgcagg gcgtctagaa   2520
gttttttaca acggagcttg gggcagtgtt ggcaggagta acatgtctga aaccactgtg   2580
ggtgtggtgt gcaggcagct gggctgtgca gacaaaggga aaatcaactc tgcatcttta   2640
gacaaggcca tgtccattcc catgtgggtg acaatgttcc agtgtccaaa aggacctgac   2700
acgctgtggc agtgcccatc atctccatgg agaagagac tggccaggcc ctcggaggag   2760
acctggatca catgtgacaa caagatgaga ctacaagaag acccacttc ctgttctgga   2820 cgtgtggaga tctggcacgg aggttcctgg ggacagtgt gtgatgactc ctgggacttg   2880
aacgatgctc aggtggtgtg tcaacaactt ggctgtggtc cagctttgaa agcattcaaa   2940
gaagcagagt ttggtcaggg gactggaccc atatggctca atgaagtgaa gtgcaaaggg   3000
aatgagtctt ccttgtggga ttgtcctgcc agacgctggg gccacagtga gtgtggacac   3060
aaggaagacg ctgcagtgaa ttgcacagca caaaaaattt caacgcacaa accccacaa   3120 aaagccacaa cagtttcctc aagaggagag aacttagtcc accaaattca ataccgggag   3180
atgaattctt gcctgaatgc agatgatctg gacctaatga attcctcagg aggccattct   3240
gaggcacact gaaaaggaaa atgggaattt ataacccag                          3279
```

<210> SEQ ID NO 40
<211> LENGTH: 1083
<212> TYPE: PRT
<213> ORGANISM: African Green Monkey

<400> SEQUENCE: 40

```
Met Ser Lys Leu Arg Met Val Leu Glu Asp Ser Gly Ser Ala Asp
1               5                   10                  15

Val Arg Arg His Phe Val Asn Leu Ser Pro Phe Thr Ile Ala Val
                20                  25                  30

Leu Leu Leu Arg Ala Cys Phe Val Thr Ser Ser Leu Gly Gly Thr Thr
                35                  40                  45

Lys Glu Leu Arg Leu Val Asp Gly Glu Asn Lys Cys Ser Gly Arg Val
50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ala Gly Ser Gly Arg
                100                 105                 110

Ile Trp Met Asp His Val Ser Cys Arg Gly Asn Glu Ser Ala Leu Trp
            115                 120                 125

Asp Cys Lys His Asp Gly Trp Gly Lys His Ser Asn Cys Thr His Gln
        130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Val Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380
```

-continued

```
Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
            405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815
```

| | | | | | | | | | | | |
|---|---|---|---|---|---|---|---|---|---|---|---|
|Ile|Cys|Ser|Glu|Phe|Met|Ser|Leu|Arg|Leu|Thr|Ser|Glu|Ala|Ser|Arg|
| | | |820| | | |825| | | |830|

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
            835                 840                 845

Ser Val Gly Arg Ser Asn Met Ser Glu Thr Thr Val Gly Val Val Cys
        850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Thr Trp Ile Thr Cys Asp Asn Lys
            915                 920                 925

Met Arg Leu Gln Glu Gly Pro Thr Ser Cys Ser Gly Arg Val Glu Ile
        930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly Asn Glu Ser Ser Leu Trp Asp Cys
        995                 1000                1005

Pro Ala Arg Arg Trp Gly His Ser Glu Cys Gly His Lys Glu Asp
    1010                1015                1020

Ala Ala Val Asn Cys Thr Ala Gln Lys Ile Ser Thr His Lys Thr
    1025                1030                1035

Pro Gln Lys Ala Thr Thr Val Ser Ser Arg Gly Glu Asn Leu Val
    1040                1045                1050

His Gln Ile Gln Tyr Arg Glu Met Asn Ser Cys Leu Asn Ala Asp
    1055                1060                1065

Asp Leu Asp Leu Met Asn Ser Ser Gly Gly His Ser Glu Ala His
    1070                1075                1080

```
<210> SEQ ID NO 41
<211> LENGTH: 3354
<212> TYPE: DNA
<213> ORGANISM: African Green Monkey

<400> SEQUENCE: 41
atgagcaaac tcagaatggt gctacttgaa gactctggat ctgctgacgt cagaagacat      60
tttgtcaact tgagtccctt cactattgct gtggtcttac ttctccgtgc ctgttttgtc     120
accagttctc ttggaggaac aaccaaggag ctgaggctag tggatggtga aaacaagtgt     180
agtgggagag tggaagtgaa atccaggag gagtggggaa cggtgtgtaa taatggctgg     240
agcatggaag cagtctctgt gatttgtaac cagctgggat gtccaactgc tatcaaagcc     300
actggatggg ctaattccag tgcaggttct ggacgcattt ggatggatca tgtttcttgt     360
cgtgggaatg agtcagctct ttgggactgc aaacatgatg gatggggaaa gcatagtaac     420
tgtactcacc aacaagatgc tggagtgact tgctcagatg gatccgattt ggaaatgagg     480
ctgacgaatg gagggaatat gtgttctgga gaatagaga tcaaattcca aggacagtgg     540
ggaacagtgt gtgatgataa cttcaacatc aatcatgcat ctgtggtttg taaacaactt     600
```

```
gaatgtggaa gtgctgtcag tttctctggt tcagctaatt ttggagaagg ctctggacca      660
atctggtttg atgatcttat atgcaacgga aatgagtcag ctctctggaa ctgcaaacat      720
caaggatggg gaaagcataa ctgtgatcat gctgaggatg ctggagtgat ttgctcaaag      780
ggagcagatc tgagcctgag actggtagat ggagtcactg aatgttcagg aagattagaa      840
gtgagattcc aaggagaatg ggggacaata tgtgatgacg ctgggacag tcatgatgct       900
gctgtggcat gcaagcaact gggatgtcca actgctatca ccgccattgg tcgagttaac      960
gccagtgagg gatttggaca catctggctt gacagtgttt cttgccaggg acatgaacct     1020
gcggtctggc aatgtaaaca ccatgaatgg ggaaagcatt attgcaatca caatgaagat     1080
gctggcgtaa catgttctga tggatcagat ctggagctaa gacttagagg tggaggcagc     1140
cgctgtgctg ggacagttga ggtggagatt cagagactgt tagggaaggt gtgtgacaga     1200
ggctggggac tgaaagaagc tgatgtggtt tgcaggcagc tgggatgtgg atctgcactc     1260
aaaacatcct atcaagtata ctccaaaatc caggcaacaa acatgtggct gtttctaagt     1320
agctgtaacg gaaatgaaac ttctctttgg gactgcaaga actggcaatg gggtggactt     1380
acctgtgatc actatgaaga agccaaaatt acctgctcag cccacaggga acccagactg     1440
gttggaggag acattccctg ttctggacgc gttgaagtga agcatggtga cacatggggc     1500
tccgtctgtg attcggattt ctctctggaa gctgccagcg ttctatgcag ggaattacag     1560
tgtggcacag tcgtctctat cctgggggga gctcactttg gagagggaaa tggacagatc     1620
tgggctgaag aattccagtg tgagggacat gagtcccatc tttcactctg cccagtagca     1680
ccccgcccag aaggaacttg tagccacagc agggatgttg agtagtctg ctcaagatac      1740
acagaaattc gcttggtgaa tggcaagacc ccatgtgagg gcagagtgga gctcaaaacg     1800
cttaatgcct ggggatccct ctgcaactct cactgggaca tagaagatgc ccacgttctt     1860
tgccaacaac ttaaatgtgg agttgccctt tctaccccag gaggagcaca ttttggaaaa     1920
ggaaatggtc aggtctggag gcatatgttt cactgcactg gactgagca gcacatggga      1980
gattgtcctg taactgctct gggtgcttca ctatgtcctt cagggcaagt ggcctctgta     2040
atttgctcag gaaaccagtc ccaaacactg tcctcgtgca attcatcatc tctgggccca     2100
acaaggccta ccattccaga gaaagtgct gtggcctgca tagagagtgg tcaacttcgc      2160
ttggtaaatg gaggaggtcg ctgtgctggg agagtagaga tttatcatga gggctcctgg     2220
ggcaccatct gtgatgacag ctgggaccta gcgatgccc acgtggtgtg cagacagctg      2280
ggctgtggag aggccattaa tgccactggt tctgctcatt ttggagaagg aacagggccc     2340
atctggctgg atgagatgaa atgcaatgga aaagaatccc gtatttggca gtgccattca     2400
catggctggg ggcagcaaaa ctgcaggcac aaggaggatg caggagttat ctgctcagag     2460
ttcatgtctc tgagactgac cagtgaagcc agcagagagg cctgtgcagg gcgtctagaa     2520
gtttttttaca acggagcttg gggcagtgtt ggcaggagta acatgtctga aaccactgtg     2580
ggtgtggtgt gcaggcagct gggctgtgca gacaaaggga aaatcaactc tgcatcttta     2640
gacaaggcca tgtccattcc catgtgggtg gacaatgttc agtgtccaaa aggacctgac     2700
acgctgtggc agtgcccatc atctccatgg gagaagagac tggccaggcc ctcggaggag     2760
acctggatca catgtgacaa caagatgaga ctacaagaag acccacttc ctgttctgga      2820
cgtgtggaga tctggcacgg aggttcctgg gggacagtgt gtgatgactc ctgggactg      2880
aacgatgctc aggtggtgtg tcaacaactt ggctgtggtc cagctttgaa agcattcaaa     2940
gaagcagagt ttggtcaggg gactggaccc atatggctca tgaagtgaa gtgcaaaggg      3000
```

```
aatgagtctt ccttgtggga ttgtcctgcc agacgctggg gccacagtga gtgtggacac    3060
aaggaagacg ctgcagtgaa ttgcacagca caaaaatttt caacgcacaa aaccccacaa    3120
aaagccacaa caggtcggtc attccttatt gcattcggaa tccttggagt tgttctcttg    3180
gccattttcg tcgcattatt cttgactcaa aagcgaagac agagacagcg gcttacagtt    3240
tcctcaagag gagagaactt agtccaccaa attcaatacc gggagatgaa ttcttgcctg    3300
aatgcagatg atctggacct aatgaattcc tcaggaggcc attctgaggc acac          3354
```

<210> SEQ ID NO 42
<211> LENGTH: 1118
<212> TYPE: PRT
<213> ORGANISM: African Green Monkey

<400> SEQUENCE: 42

```
Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
                20                  25                  30

Leu Leu Leu Arg Ala Cys Phe Val Thr Ser Ser Leu Gly Gly Thr Thr
            35                  40                  45

Lys Glu Leu Arg Leu Val Asp Gly Glu Asn Lys Cys Ser Gly Arg Val
    50                  55                  60

Glu Val Lys Ile Gln Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Phe Asn Ile Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320
```

-continued

```
Ala Ser Glu Gly Phe Gly His Ile Trp Leu Asp Ser Val Ser Cys Gln
            325                 330                 335

Gly His Glu Pro Ala Val Trp Gln Cys Lys His His Glu Trp Gly Lys
        340                 345                 350

His Tyr Cys Asn His Asn Glu Asp Ala Gly Val Thr Cys Ser Asp Gly
            355                 360                 365

Ser Asp Leu Glu Leu Arg Leu Arg Gly Gly Ser Arg Cys Ala Gly
370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
            405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
            435                 440                 445

Leu Trp Asp Cys Lys Asn Trp Gln Trp Gly Gly Leu Thr Cys Asp His
        450                 455                 460

Tyr Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
        530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
            595                 600                 605

Asn Ser His Trp Asp Ile Glu Asp Ala His Val Leu Cys Gln Gln Leu
        610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Leu Gly Pro Thr Arg Pro Thr
        690                 695                 700

Ile Pro Glu Glu Ser Ala Val Ala Cys Ile Glu Ser Gly Gln Leu Arg
705                 710                 715                 720

Leu Val Asn Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750
```

Ala His Val Val Cys Arg Gln Leu Gly Cys Gly Glu Ala Ile Asn Ala
                755                 760                 765

Thr Gly Ser Ala His Phe Gly Glu Gly Thr Gly Pro Ile Trp Leu Asp
        770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly Asn Glu Ser Ser Leu Trp Asp Cys
        995                 1000                1005

Pro Ala Arg Arg Trp Gly His Ser Glu Cys Gly His Lys Glu Asp
    1010                1015                1020

Ala Ala Val Asn Cys Thr Ala Gln Lys Ile Ser Thr His Lys Thr
    1025                1030                1035

Pro Gln Lys Ala Thr Thr Gly Arg Ser Phe Leu Ile Ala Phe Gly
    1040                1045                1050

Ile Leu Gly Val Val Leu Leu Ala Ile Phe Val Ala Leu Phe Leu
    1055                1060                1065

Thr Gln Lys Arg Arg Gln Arg Gln Arg Leu Thr Val Ser Ser Arg
    1070                1075                1080

Gly Glu Asn Leu Val His Gln Ile Gln Tyr Arg Glu Met Asn Ser
    1085                1090                1095

Cys Leu Asn Ala Asp Asp Leu Asp Leu Met Asn Ser Ser Gly Gly
    1100                1105                1110

His Ser Glu Ala His
    1115

<210> SEQ ID NO 43
<211> LENGTH: 3459
<212> TYPE: DNA
<213> ORGANISM: African Green Monkey

<400> SEQUENCE: 43

```
atgagcaaac tcagaatggt gctacttgaa gactctggat ctgctgacgt cagaagacat      60
tttgtcaact tgagtccctt cactattgct gtggtcttac ttctccgtgc ctgttttgtc     120
accagttctc ttggaggaac aaccaaggag ctgaggctag tggatggtga aaacaagtgt     180
agtgggagag tggaagtgaa aatccaggag gagtggggaa cggtgtgtaa taatggctgg     240
agcatggaag cagtctctgt gatttgtaac cagctgggat gtccaactgc tatcaaagcc     300
actggatggg ctaattccag tgcaggttct ggacgcattt ggatggatca tgtttcttgt     360
cgtgggaatg agtcagctct ttgggactgc aaacatgatg gatggggaaa gcatagtaac     420
tgtactcacc aacaagatgc tggagtgact tgctcagatg gatccgattt ggaaatgagg     480
ctgacgaatg gagggaatat gtgttctgga agaatagaga tcaaattcca aggacagtgg     540
ggaacagtgt gtgatgataa cttcaacatc aatcatgcat ctgtggtttg taaacaactt     600
gaatgtggaa gtgctgtcag tttctctggt tcagctaatt ttggagaagg ctctggacca     660
atctggtttg atgatcttat atgcaacgga aatgagtcag ctctctggaa ctgcaaacat     720
caaggatggg gaaagcataa ctgtgatcat gctgaggatg ctggagtgat tgctcaaag      780
ggagcagatc tgagcctgag actggtagat ggagtcactg aatgttcagg aagattagaa     840
gtgagattcc aaggagaatg ggggacaata tgtgatgacg ctgggacag tcatgatgct      900
gctgtggcat gcaagcaact gggatgtcca actgctatca ccgccattgg tcagttaac      960
gccagtgagg gatttggaca catctggctt gacagtgttt cttgccaggg acatgaacct    1020
gcggtctggc aatgtaaaca ccatgaatgg ggaaagcatt attgcaatca caatgaagat    1080
gctggcgtaa catgttctga tggatcagat ctggagctaa gacttagagg tggaggcagc    1140
cgctgtgctg ggacagttga ggtggagatt cagagactgt tagggaaggt gtgtgacaga    1200
ggctggggac tgaaagaagc tgatgtggtt tgcaggcagc tgggatgtgg atctgcactc    1260
aaaacatcct atcaagtata ctccaaaatc caggcaacaa acatgtggct gtttctaagt    1320
agctgtaacg gaaatgaaac ttctctttgg gactgcaaga actggcaatg gggtggactt    1380
acctgtgatc actatgaaga agccaaaatt acctgctcag cccacaggga acccagactg    1440
gttggaggag acattccctg ttctggacgc gttgaagtga agcatggtga cacatggggc    1500
tccgtctgtg attcggattt ctctctggaa gctgccagcg ttctatgcag ggaattacag    1560
tgtggcacag tcgtctctat cctgggggga gctcactttg gagagggaaa tggacagatc    1620
tgggctgaag aattccagtg tgagggacat gagtcccatc tttcactctg cccagtagca    1680
ccccgcccag aaggaacttg tagccacagc agggatgttg gagtagtctg ctcaagatac    1740
acagaaattc gcttggtgaa tggcaagacc ccatgtgagg gcagagtgga gctcaaaacg    1800
cttaatgcct ggggatccct ctgcaactct cactgggaca tagaagatgc ccacgttctt    1860
tgccaacaac ttaaatgtgg agttgcccct tctaccccag gaggagcaca ttttggaaaa    1920
ggaaatggtc aggtctggag gcatatgttt cactgcactg ggactgagca gcacatggga    1980
gattgtcctg taactgctct gggtgcttca ctatgtcctt cagggcaagt ggcctctgta    2040
atttgctcag gaaaccagtc ccaaacactg tcctcgtgca ttcatcatc tctgggccca     2100
acaaggccta ccattccaga gaaaagtgct gtggcctgca tagagagtgg tcaacttcgc    2160
ttggtaaatg gaggaggtcg ctgtgctggg agagtagaga tttatcatga gggctcctgg    2220
ggcaccatct gtgatgacag ctgggaccct agcgatgccc acgtggtgtg cagacagctg    2280
ggctgtggag aggccattaa tgccactggt tctgctcatt ttgagaagg aacagggcc     2340
atctggctgg atgagatgaa atgcaatgga aaagaatccc gtatttggca gtgccattca    2400
```

-continued

```
catggctggg ggcagcaaaa ctgcaggcac aaggaggatg caggagttat ctgctcagag    2460
ttcatgtctc tgagactgac cagtgaagcc agcagagagg cctgtgcagg gcgtctagaa    2520
gttttttaca acggagcttg gggcagtgtt ggcaggagta acatgtctga aaccactgtg    2580
ggtgtggtgt gcaggcagct gggctgtgca gacaaaggga aaatcaactc tgcatcttta    2640
gacaaggcca tgtccattcc catgtgggtg acaatgttca gtgtccaaa aggacctgac    2700 acgctgtggc agtgcccatc atctccatgg gagaagagac tggccaggcc ctcggaggag    2760
acctggatca catgtgacaa caagatgaga ctacaagaag acccacttc ctgttctgga    2820 cgtgtggaga tctggcacgg aggttcctgg gggacagtgt gtgatgactc ctgggacttg    2880
aacgatgctc aggtggtgtg tcaacaactt ggctgtggtc cagctttgaa agcattcaaa    2940
gaagcagagt ttggtcaggg gactggaccc atatggctca atgaagtgaa gtgcaaaggg    3000
aatgagtctt ccttgtggga ttgtcctgcc agacgctggg gccacagtga gtgtggacac    3060
aaggaagacg ctgcagtgaa ttgcacagca caaaaaattt caacgcacaa acccccacaa    3120
aaagccacaa caggtcagtc attccttatt gcattcggaa tccttggagt tgttctcttg    3180
gccattttcg tcgcattatt cttgactcaa aagcgaagac agagacagcg gcttacagtt    3240
tcctcaagag gagagaactt agtccaccaa attcaatacc gggagatgaa ttcttgcctg    3300
aatgcagatg atctggacct aatgaattcc tcagaaaatt ccaatgagtc agctgatttc    3360
aatgctgctg aactaatttc tgtgtctaaa tttcttccta tttctggaat ggaaaaggag    3420
gccattctga ggcacactga aaggaaaat gggaattta                            3459
```

<210> SEQ ID NO 44
<211> LENGTH: 1153
<212> TYPE: PRT
<213> ORGANISM: African Green Monkey

<400> SEQUENCE: 44

```
Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
            180                 185                 190
```

```
Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
        210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                    245                 250                 255

Ile Cys Ser Lys Gly Ala Asp Leu Ser Leu Arg Leu Val Asp Gly Val
                260                 265                 270

Thr Glu Cys Ser Gly Arg Leu Glu Val Arg Phe Gln Gly Glu Trp Gly
            275                 280                 285

Thr Ile Cys Asp Asp Gly Trp Asp Ser His Asp Ala Ala Val Ala Cys
        290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                    325                 330                 335

Gly His Glu Pro Ala Val Trp Gln Cys Lys His His Glu Trp Gly Lys
                340                 345                 350

His Tyr Cys Asn His Asn Glu Asp Ala Gly Val Thr Cys Ser Asp Gly
            355                 360                 365

Ser Asp Leu Glu Leu Arg Leu Arg Gly Gly Gly Ser Arg Cys Ala Gly
        370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                    405                 410                 415

Gly Ser Ala Leu Lys Thr Ser Tyr Gln Val Tyr Ser Lys Ile Gln Ala
                420                 425                 430

Thr Asn Met Trp Leu Phe Leu Ser Ser Cys Asn Gly Asn Glu Thr Ser
            435                 440                 445

Leu Trp Asp Cys Lys Asn Trp Gln Trp Gly Gly Leu Thr Cys Asp His
        450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                    485                 490                 495

Asp Thr Trp Gly Ser Val Cys Asp Ser Asp Phe Ser Leu Glu Ala Ala
                500                 505                 510

Ser Val Leu Cys Arg Glu Leu Gln Cys Gly Thr Val Val Ser Ile Leu
            515                 520                 525

Gly Gly Ala His Phe Gly Glu Gly Asn Gly Gln Ile Trp Ala Glu Glu
        530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                    565                 570                 575

Cys Ser Arg Tyr Thr Glu Ile Arg Leu Val Asn Gly Lys Thr Pro Cys
                580                 585                 590

Glu Gly Arg Val Glu Leu Lys Thr Leu Asn Ala Trp Gly Ser Leu Cys
            595                 600                 605

Asn Ser His Trp Asp Ile Glu Asp Ala His Val Leu Cys Gln Gln Leu
```

```
                610                 615                 620
Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
                660                 665                 670

Pro Ser Gly Gln Val Ala Ser Val Ile Cys Ser Gly Asn Gln Ser Gln
                675                 680                 685

Thr Leu Ser Ser Cys Asn Ser Ser Leu Gly Pro Thr Arg Pro Thr
690                 695                 700

Ile Pro Glu Glu Ser Ala Val Ala Cys Ile Glu Ser Gly Gln Leu Arg
705                 710                 715                 720

Leu Val Asn Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
                740                 745                 750

Ala His Val Val Cys Arg Gln Leu Gly Cys Gly Glu Ala Ile Asn Ala
                755                 760                 765

Thr Gly Ser Ala His Phe Gly Glu Gly Thr Gly Pro Ile Trp Leu Asp
770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
                820                 825                 830

Glu Ala Cys Ala Gly Arg Leu Glu Val Phe Tyr Asn Gly Ala Trp Gly
                835                 840                 845

Ser Val Gly Arg Ser Asn Met Ser Glu Thr Thr Val Gly Val Val Cys
                850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
                900                 905                 910

Arg Leu Ala Arg Pro Ser Glu Glu Thr Trp Ile Thr Cys Asp Asn Lys
                915                 920                 925

Met Arg Leu Gln Glu Gly Pro Thr Ser Cys Ser Gly Arg Val Glu Ile
930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
                980                 985                 990

Leu Asn Glu Val Lys Cys Lys Gly Asn Glu Ser Ser Leu Trp Asp Cys
                995                1000                1005

Pro Ala Arg Arg Trp Gly His Ser Glu Cys Gly His Lys Glu Asp
   1010                1015                1020

Ala Ala Val Asn Cys Thr Ala Gln Lys Ile Ser Thr His Lys Thr
   1025                1030                1035
```

```
Pro Gln Lys Ala Thr Thr Gly Gln Ser Phe Leu Ile Ala Phe Gly
    1040                1045                1050

Ile Leu Gly Val Val Leu Leu Ala Ile Phe Val Ala Leu Phe Leu
    1055                1060                1065

Thr Gln Lys Arg Arg Gln Gln Arg Leu Thr Val Ser Ser Arg
    1070                1075                1080

Gly Glu Asn Leu Val His Gln Ile Gln Tyr Arg Glu Met Asn Ser
    1085                1090                1095

Cys Leu Asn Ala Asp Asp Leu Asp Leu Met Asn Ser Ser Glu Asn
    1100                1105                1110

Ser Asn Glu Ser Ala Asp Phe Asn Ala Ala Glu Leu Ile Ser Val
    1115                1120                1125

Ser Lys Phe Leu Pro Ile Ser Gly Met Glu Lys Glu Ala Ile Leu
    1130                1135                1140

Arg His Thr Glu Lys Glu Asn Gly Asn Leu
    1145                1150

<210> SEQ ID NO 45
<211> LENGTH: 3345
<212> TYPE: DNA
<213> ORGANISM: Canis familiaris

<400> SEQUENCE: 45
atgagcaaac tcagaatggt cccacatgga aactctggat ctgctgactt tagaagatgt    60
tttgccctct tgtgtccctc tgctgtggct gtggtctcca ttctcagtac ctgtttgatg   120
accaattctc ttgggagagc agataaagag atgaggctaa cggatggtga agacaattgc   180
tccgggagag tggaagtgaa agtccaggag gagtggggaa cggtgtgtaa taatggctgg   240
ggcatggatg aagtctctgt gatttgcagg cagctgggat gtcccactgc tatcaaagcc   300
gctggatggg ccaattccag gcaggctct ggacgaatct ggatggatca tgtttcttgt   360
cgagggaatg aatctgctct ctgggactgc aaacatgatg gatgggggaa gcacaactgc   420
agtcatcaac aggatgctgg agtaacctgt tcagatggat ccagtttgga tgaggttg    480 atgaacggcg gaaaccagtg ttctggcaga atagaagtca agttccaggg acagtgggga   540
acagtgtgtg atgacaactt caacatagat catgcttctg tggtttgtaa acagctcgaa   600
tgtggaagtg ctgtcagttt ctctggttca gctaattttg gagaaggttc tgggccaatc   660
tggtttgatg atcttgtgtg cagtggaaat gagtcagctc tctggaactg caagcatgaa   720
ggatggggaa agcataactg tgatcacgct gaggatgttg gagtgatttg cttggatgga   780
gcagatctga gcctgagact ggtagatgga gtcactgaat gttcaggaag attagaagta   840
aaattccaag gggaatgggg acagtgtgt gatgatggct gggatagtaa tgatgctgct   900
gtggtatgta acaactggg atgcccaact gctgtcaccg ccattggtcg agttaacgcc   960
agtgagggaa gtggacacat ttggcttgac aatctttcct gccaaggaga cgaatctgct  1020
ctctggcagt gtagacacca tgaatgggga agcattatt gcaatcataa tgaagatgct  1080
ggtgtgacat gttctgatgg atcagacctg agctgagac ttgtcggtgg aggcagccgc  1140
tgtgctggga cagtggaggt tgaaattcag aaactgctag ggaaagtatg tgatagaggc  1200
tggggactga agaagccga tgtggttgc aagcagttgg gatgtggatc tgctctcaaa  1260
acgtcctatc agcgttattc caaagttaag gcaacaaaca catggctgtt tttaagccgc  1320
tgtagtggca atgaaacttc cctttgggac tgcaagaact ggcagtgggg tggactgagc  1380
tgtgatcact atgaagaagc taaagttacc tgctcagccc acagggaacc cagactagtt  1440
```

-continued

```
ggaggagata ttccctgctc tggtcgtgtt gaagtgaaac atggtgacac atggggcacc      1500
gtctgtgatt ccgacttctc tttggaagct gccagtgtgc tgtgcagaga gttacagtgt      1560
ggcacagtca tctccatcct agggggagct cactttggag aaggaaatgg acagatctgg      1620
gctgaagaat tccagtgtga ggggcaggag tcccatcttt cactctgttc agtagcctct      1680
cgcccagatg ggacctgtag ccacagcagg gatgttggag tcgtctgctc aagatacacg      1740
gaaatccgct tggtgaatgg ccagtccccg tgtgaaggaa gagtggagct caagatactt      1800
gggaactggg gatccctctg caactctcac tgggacatag aagatgccca tgttttctgt      1860
cagcagctca aatgtggagt tgcccttcct attccgggag gagcacattt tgggaaagga      1920
agtggtcaga tctggaggca catgtttcac tgcactggga ctgagcagca catgggagat      1980
tgccctgtaa ctgctctggg cgcgacgctg tgttctgctg ggcaagtggc ctctgtaatc      2040
tgctcaggaa atcagagcca gacgctatcc ccatgcaatt caacatctct ggacccaaca      2100
agatctacca cttcggaaga aagtgctgtt gcttgtattg cgagtgggca acttcgcctg      2160
gtaaatggag gcggtcgctg tgctgggaga atagaggtct accatgaggg ctcctggggc      2220
accatctgtg atgacagctg ggacctgagt gatgcccatg tggtgtgcag acagctgggc      2280
tgtggagtgg ccattaatgc cactggctct gctcattttg gggaaggaac agggcccatc      2340
tggctggacg aggtgaactg taatggaaag gaatctcata tctggcaatg ccgctcacac      2400 ggctggggc aacacaactg cagacataag gaggatgcag gagttatctg ctcagagttc      2460
atgtctctca gactgattga tgaaaccagc agagacatct gtgcagggcg tcttgaagtt      2520
ttttacaatg gagcttgggg cagcgttggc aagagtaata tgtctgcaac cactgtggag      2580
gtggtatgca ggcaactggg ttgtgcagac aaggggagca tcaaccctgc atcttcagac      2640
aagcccatgt ccaggcacat gtgggtggac aatgtccagt gtccaaaagg acctgacacc      2700
ttatggcagt gcccatcttc tccatggaaa cagagagtgg ccagttcttc agaggagacc      2760
tggatcacat gtgccaacaa gataagactt caagaaggaa cctctaattg ttctggacgt      2820
gtggagctct ggcacggagg ttcctggggg acagtgtgcg atgactcctg ggaccttgaa      2880
gatgcacaag tggtgtgtcg acagctgggc tgtggcccag cattagaagc actaaaagag      2940
gcagcatttg gtcaggggac tgggcctata tggctcaatg acgtgaagtg caaagggaat      3000
gagtcttcct gtgggattg tcctgctaga ccctgggggc acagtgactg tggccacaag      3060
gaagatgctg ctgtgaggtg ctcagaaatt gcaatggccc aaagatcatc aaatcctaga      3120
ggtcactcat cccttgttgc attggggatc tttggtgtca ttcttctggc ctttctcatc      3180
gctctcctct gtggactca aaggcgaaga cagcaacagc ggcttacagt tccttgaga      3240 ggagagaatt ctgtccacca aattcaatac cgggaaatga attcttccct gaaagcagat      3300
gatctggacg tgctgacttc ctcagaagac cattttgagg tacac                       3345
```

<210> SEQ ID NO 46
<211> LENGTH: 1115
<212> TYPE: PRT
<213> ORGANISM: Canis familiaris

<400> SEQUENCE: 46

Met Ser Lys Leu Arg Met Val Pro His Gly Asn Ser Gly Ser Ala Asp
1               5                   10                  15

Phe Arg Arg Cys Phe Ala Leu Leu Cys Pro Ser Ala Val Ala Val Val
                20                  25                  30

Ser Ile Leu Ser Thr Cys Leu Met Thr Asn Ser Leu Gly Arg Ala Asp
            35                  40                  45

```
Lys Glu Met Arg Leu Thr Asp Gly Glu Asp Asn Cys Ser Gly Arg Val
 50                  55                  60

Glu Val Lys Val Gln Glu Trp Gly Thr Val Cys Asn Asn Gly Trp
 65                  70                  75                  80

Gly Met Asp Glu Val Ser Val Ile Cys Arg Gln Leu Gly Cys Pro Thr
                     85                  90                  95

Ala Ile Lys Ala Ala Gly Trp Ala Asn Ser Arg Ala Gly Ser Gly Arg
                100                 105                 110

Ile Trp Met Asp His Val Ser Cys Arg Gly Asn Glu Ser Ala Leu Trp
            115                 120                 125

Asp Cys Lys His Asp Gly Trp Gly Lys His Asn Cys Ser His Gln Gln
            130                 135                 140

Asp Ala Gly Val Thr Cys Ser Asp Gly Ser Ser Leu Glu Met Arg Leu
145                 150                 155                 160

Met Asn Gly Gly Asn Gln Cys Ser Gly Arg Ile Glu Val Lys Phe Gln
                165                 170                 175

Gly Gln Trp Gly Thr Val Cys Asp Asp Asn Phe Asn Ile Asp His Ala
                180                 185                 190

Ser Val Val Cys Lys Gln Leu Glu Cys Gly Ser Ala Val Ser Phe Ser
            195                 200                 205

Gly Ser Ala Asn Phe Gly Glu Gly Ser Gly Pro Ile Trp Phe Asp Asp
            210                 215                 220

Leu Val Cys Ser Gly Asn Glu Ser Ala Leu Trp Asn Cys Lys His Glu
225                 230                 235                 240

Gly Trp Gly Lys His Asn Cys Asp His Ala Glu Asp Val Gly Val Ile
                245                 250                 255

Cys Leu Asp Gly Ala Asp Leu Ser Leu Arg Leu Val Asp Gly Val Thr
                260                 265                 270

Glu Cys Ser Gly Arg Leu Glu Val Lys Phe Gln Gly Glu Trp Gly Thr
            275                 280                 285

Val Cys Asp Asp Gly Trp Asp Ser Asn Asp Ala Ala Val Val Cys Lys
            290                 295                 300

Gln Leu Gly Cys Pro Thr Ala Val Thr Ala Ile Gly Arg Val Asn Ala
305                 310                 315                 320

Ser Glu Gly Ser Gly His Ile Trp Leu Asp Asn Leu Ser Cys Gln Gly
                325                 330                 335

Asp Glu Ser Ala Leu Trp Gln Cys Arg His His Glu Trp Gly Lys His
                340                 345                 350

Tyr Cys Asn His Asn Glu Asp Ala Gly Val Thr Cys Ser Asp Gly Ser
            355                 360                 365

Asp Leu Glu Leu Arg Leu Val Gly Gly Ser Arg Cys Ala Gly Thr
            370                 375                 380

Val Glu Val Glu Ile Gln Lys Leu Leu Gly Lys Val Cys Asp Arg Gly
385                 390                 395                 400

Trp Gly Leu Lys Glu Ala Asp Val Val Cys Lys Gln Leu Gly Cys Gly
                405                 410                 415

Ser Ala Leu Lys Thr Ser Tyr Gln Arg Tyr Ser Lys Val Lys Ala Thr
            420                 425                 430

Asn Thr Trp Leu Phe Leu Ser Arg Cys Ser Gly Asn Glu Thr Ser Leu
            435                 440                 445

Trp Asp Cys Lys Asn Trp Gln Trp Gly Gly Leu Ser Cys Asp His Tyr
            450                 455                 460

Glu Glu Ala Lys Val Thr Cys Ser Ala His Arg Glu Pro Arg Leu Val
```

```
                465                 470                 475                 480
Gly Gly Asp Ile Pro Cys Ser Gly Arg Val Glu Val Lys His Gly Asp
                    485                 490                 495
Thr Trp Gly Thr Val Cys Asp Ser Asp Phe Ser Leu Glu Ala Ala Ser
                500                 505                 510
Val Leu Cys Arg Glu Leu Gln Cys Gly Thr Val Ile Ser Ile Leu Gly
            515                 520                 525
Gly Ala His Phe Gly Glu Gly Asn Gly Gln Ile Trp Ala Glu Glu Phe
        530                 535                 540
Gln Cys Glu Gly Gln Glu Ser His Leu Ser Leu Cys Ser Val Ala Ser
545                 550                 555                 560
Arg Pro Asp Gly Thr Cys Ser His Ser Arg Asp Val Gly Val Val Cys
                565                 570                 575
Ser Arg Tyr Thr Glu Ile Arg Leu Val Asn Gly Gln Ser Pro Cys Glu
            580                 585                 590
Gly Arg Val Glu Leu Lys Ile Leu Gly Asn Trp Gly Ser Leu Cys Asn
        595                 600                 605
Ser His Trp Asp Ile Glu Asp Ala His Val Phe Cys Gln Gln Leu Lys
    610                 615                 620
Cys Gly Val Ala Leu Ser Ile Pro Gly Gly Ala His Phe Gly Lys Gly
625                 630                 635                 640
Ser Gly Gln Ile Trp Arg His Met Phe His Cys Thr Gly Thr Glu Gln
                645                 650                 655
His Met Gly Asp Cys Pro Val Thr Ala Leu Gly Ala Thr Leu Cys Ser
                660                 665                 670
Ala Gly Gln Val Ala Ser Val Ile Cys Ser Gly Asn Gln Ser Gln Thr
            675                 680                 685
Leu Ser Pro Cys Asn Ser Thr Ser Leu Asp Pro Thr Arg Ser Thr Thr
        690                 695                 700
Ser Glu Glu Ser Ala Val Ala Cys Ile Ala Ser Gly Gln Leu Arg Leu
705                 710                 715                 720
Val Asn Gly Gly Gly Arg Cys Ala Gly Arg Ile Glu Val Tyr His Glu
                725                 730                 735
Gly Ser Trp Gly Thr Ile Cys Asp Asp Ser Trp Asp Leu Ser Asp Ala
                740                 745                 750
His Val Val Cys Arg Gln Leu Gly Cys Gly Val Ala Ile Asn Ala Thr
            755                 760                 765
Gly Ser Ala His Phe Gly Glu Gly Thr Gly Pro Ile Trp Leu Asp Glu
        770                 775                 780
Val Asn Cys Asn Gly Lys Glu Ser His Ile Trp Gln Cys Arg Ser His
785                 790                 795                 800
Gly Trp Gly Gln His Asn Cys Arg His Lys Glu Asp Ala Gly Val Ile
                805                 810                 815
Cys Ser Glu Phe Met Ser Leu Arg Leu Ile Asp Glu Thr Ser Arg Asp
                820                 825                 830
Ile Cys Ala Gly Arg Leu Glu Val Phe Tyr Asn Gly Ala Trp Gly Ser
            835                 840                 845
Val Gly Lys Ser Asn Met Ser Ala Thr Thr Val Glu Val Val Cys Arg
        850                 855                 860
Gln Leu Gly Cys Ala Asp Lys Gly Ser Ile Asn Pro Ala Ser Ser Asp
865                 870                 875                 880
Lys Pro Met Ser Arg His Met Trp Val Asp Asn Val Gln Cys Pro Lys
                885                 890                 895
```

```
Gly Pro Asp Thr Leu Trp Gln Cys Pro Ser Ser Pro Trp Lys Gln Arg
            900                 905                 910
Val Ala Ser Ser Glu Glu Thr Trp Ile Thr Cys Ala Asn Lys Ile
        915                 920                 925
Arg Leu Gln Glu Gly Thr Ser Asn Cys Ser Gly Arg Val Glu Leu Trp
    930                 935                 940
His Gly Gly Ser Trp Gly Thr Val Cys Asp Asp Ser Trp Asp Leu Glu
945                 950                 955                 960
Asp Ala Gln Val Val Cys Arg Gln Leu Gly Cys Gly Pro Ala Leu Glu
                965                 970                 975
Ala Leu Lys Glu Ala Ala Phe Gly Gln Gly Thr Gly Pro Ile Trp Leu
            980                 985                 990
Asn Asp Val Lys Cys Lys Gly Asn Glu Ser Ser Leu Trp Asp Cys Pro
        995                 1000                1005
Ala Arg Pro Trp Gly His Ser Asp Cys Gly His Lys Glu Asp Ala
    1010                1015                1020
Ala Val Arg Cys Ser Glu Ile Ala Met Ala Gln Arg Ser Ser Asn
    1025                1030                1035
Pro Arg Gly His Ser Ser Leu Val Ala Leu Gly Ile Phe Gly Val
    1040                1045                1050
Ile Leu Leu Ala Phe Leu Ile Ala Leu Leu Leu Trp Thr Gln Arg
    1055                1060                1065
Arg Arg Gln Gln Gln Arg Leu Thr Val Ser Leu Arg Gly Glu Asn
    1070                1075                1080
Ser Val His Gln Ile Gln Tyr Arg Glu Met Asn Ser Ser Leu Lys
    1085                1090                1095
Ala Asp Asp Leu Asp Val Leu Thr Ser Ser Glu Asp His Phe Glu
    1100                1105                1110
Val His
    1115

<210> SEQ ID NO 47
<211> LENGTH: 3399
<212> TYPE: DNA
<213> ORGANISM: Canis familiaris

<400> SEQUENCE: 47
atgagcaaac tcagaatggt cccacatgga aactctggat ctgctgactt tagaagatgt      60
tttgccctct tgtgtccctc tgctgtggct gtggtctcca ttctcagtac ctgtttgatg     120
accaattctc ttgggagagc agataaagag atgaggctaa cggatggtga agacaattgc     180
tccgggagag tggaagtgaa agtccaggag gagtggggaa cggtgtgtaa taatggctgg     240
ggcatggatg aagtctctgt gatttgcagg cagctgggat gtcccactgc tatcaaagcc     300
gctggatggg ccaattccag gcaggctct ggacgaatct ggatggatca tgtttcttgt     360
cgagggaatg aatctgctct ctgggactgc aaacatgatg gatggggaaa gcacaactgc     420
agtcatcaac aggatgctgg agtaacctgt tcagatggat ccagtttgga gatgaggttg     480
atgaacggcg gaaaccagtg ttctggcaga atagaagtca agttccaggg acagtgggga     540
acagtgtgtg atgacaactt caacatagat catgcttctg tggtttgtaa acagctcgaa     600
tgtggaagtg ctgtcagttt ctctggttca gctaattttg gagaaggttc tgggccaatc     660
tggtttgatg atcttgtgtg cagtggaaat gagtcagctc tctgaaactg caagcatgaa     720
ggatggggaa agcataactg tgatcacgct gaggatgttg gagtgatttg cttggatgga     780
gcagatctga gcctgagact ggtagatgga gtcactgaat gttcaggaag attagaagta     840
```

```
aaattccaag gggaatgggg gacagtgtgt gatgatggct gggatagtaa tgatgctgct    900
gtggtatgta aacaactggg atgcccaact gctgtcaccg ccattggtcg agttaacgcc    960
agtgagggaa gtggacacat ttggcttgac aatctttcct gccaaggaga cgaatctgct   1020
ctctggcagt gtagacacca tgaatgggga agcattatt gcaatcataa tgaagatgct    1080
ggtgtgacat gttctgatgg atcagacctg gagctgagac ttgtcggtgg aggcagccgc   1140
tgtgctggga cagtggaggt tgaaattcag aaactgctag ggaaagtatg tgatagaggc   1200
tggggactga agaagccga tgtggtttgc aagcagttgg gatgtggatc tgctctcaaa    1260
acgtcctatc agcgttattc caaagttaag gcaacaaaca catggctgtt tttaagccgc   1320
tgtagtggca atgaaacttc cctttgggac tgcaagaact ggcagtgggg tggactgagc   1380
tgtgatcact atgaagaagc taagttacc tgctcagccc acagggaacc cagactagtt    1440
ggaggagata ttccctgctc tggtcgtgtt gaagtgaaac atggtgacac atggggcacc   1500
gtctgtgatt ccgacttctc tttggaagct gccagtgtgc tgtgcagaga gttacagtgt   1560
ggcacagtca tctccatcct aggggagct cactttggag aaggaaatgg acagatctgg    1620
gctgaagaat ccagtgtga ggggcaggag tcccatcttt cactctgttc agtagcctct    1680
cgcccagatg ggacctgtag ccacagcagg gatgttggag tcgtctgctc aagatacacg   1740
gaaatccgct tggtgaatgg ccagtccccg tgtgaaggaa gagtggagct caagatactt   1800
gggaactggg gatccctctg caactctcac tgggacatag aagatgccca tgttttctgt   1860
cagcagctca aatgtggagt tgccctttct attccgggag gagcacattt tgggaaagga   1920
agtggtcaga tctggaggca catgtttcac tgcactggga ctgagcagca catgggagat   1980
tgccctgtaa ctgctctggg cgcgacgctg tgttctgctg ggcaagtggc ctctgtaatc   2040
tgctcaggaa atcagagcca gacgctatcc ccatgcaatt caacatctct ggacccaaca   2100
agatctacca cttcggaaga aagtgctgtt gcttgtattg cgagtgggca acttcgcctg   2160
gtaaatggag gcggtcgctg tgctgggaga atagaggtct accatgaggg ctcctggggc   2220
accatctgtg atgacagctg ggacctgagt gatgcccatg tggtgtgcag acagctgggc   2280
tgtggagtgg ccattaatgc cactggctct gctcattttg gggaaggaac agggcccatc   2340
tggctggacg aggtgaactg taatggaaag gaatctcata tctggcaatg ccgctcacac   2400
ggctgggggc aacacaactg cagacataag gaggatgcag gagttatctg ctcagagttc   2460
atgtctctca gactgattga tgaaaccagc agagacatct gtgcagggcg tcttgaagtt   2520
ttttacaatg gagcttgggg cagcgttggc aagagtaata tgtctgcaac cactgtggag   2580
gtggtatgca ggcaactggg ttgtgcagac aaggggagca tcaaccctgc atcttcagac   2640
aagcccatgt ccaggcacat gtgggtggac aatgtccagt gtccaaaagg acctgacacc   2700
ttatggcagt gcccatcttc tccatggaaa cagagagtgg ccagttcttc agaggagacc   2760
tggatcacat gtgccaacaa gataagactt caagaaggaa cctctaattg ttctggacgt   2820
gtggagctct ggcacggagg ttcctggggg acagtgtgcg atgactcctg gaccttgaa    2880
gatgcacaag tggtgtgtcg acagctggc tgtggcccag cattagaagc actaaaagag    2940
gcagcatttg gtcagggac tgggcctata tggctcaatg acgtgaagtg caaagggaat   3000
gagtcttcct gtgggattg tcctgctaga ccctgggggc acagtgactg tggccacaag   3060
gaagatgctg ctgtgaggtg ctcagaaatt gcaatggccc aaagatcatc aaatcctaga   3120
ggtcactcat cccttgttgc attggggatc tttggtgtca ttcttctggc ctttctcatc   3180
gctctcctct tgtggactca aaggcgaaga cagcaacagc ggcttacagt ttccttgaga   3240
```

-continued

```
ggagagaatt ctgtccacca aattcaatac cgggaaatga attcttccct gaaagcagat    3300
gatctggacg tgctgacttc ctcagaatat cccaatgagt cagatgattt taatgatgct    3360
gggctaattt ctgtgtctaa atctcttcct atttctgga                           3399
```

<210> SEQ ID NO 48
<211> LENGTH: 1133
<212> TYPE: PRT
<213> ORGANISM: Canis familiaris

<400> SEQUENCE: 48

```
Met Ser Lys Leu Arg Met Val Pro His Gly Asn Ser Gly Ser Ala Asp
 1               5                  10                  15

Phe Arg Arg Cys Phe Ala Leu Leu Cys Pro Ser Ala Val Ala Val Val
                20                  25                  30

Ser Ile Leu Ser Thr Cys Leu Met Thr Asn Ser Leu Gly Arg Ala Asp
            35                  40                  45

Lys Glu Met Arg Leu Thr Asp Gly Glu Asp Asn Cys Ser Gly Arg Val
        50                  55                  60

Glu Val Lys Val Gln Glu Glu Trp Gly Thr Val Cys Asn Asn Gly Trp
 65                  70                  75                  80

Gly Met Asp Glu Val Ser Val Ile Cys Arg Gln Leu Gly Cys Pro Thr
                85                  90                  95

Ala Ile Lys Ala Ala Gly Trp Ala Asn Ser Arg Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Asn Cys Ser His Gln Gln
    130                 135                 140

Asp Ala Gly Val Thr Cys Ser Asp Gly Ser Ser Leu Glu Met Arg Leu
145                 150                 155                 160

Met Asn Gly Gly Asn Gln Cys Ser Gly Arg Ile Glu Val Lys Phe Gln
                165                 170                 175

Gly Gln Trp Gly Thr Val Cys Asp Asp Asn Phe Asn Ile Asp His Ala
            180                 185                 190

Ser Val Val Cys Lys Gln Leu Glu Cys Gly Ser Ala Val Ser Phe Ser
        195                 200                 205

Gly Ser Ala Asn Phe Gly Glu Gly Ser Gly Pro Ile Trp Phe Asp Asp
    210                 215                 220

Leu Val Cys Ser Gly Asn Glu Ser Ala Leu Trp Asn Cys Lys His Glu
225                 230                 235                 240

Gly Trp Gly Lys His Asn Cys Asp His Ala Glu Asp Val Gly Val Ile
                245                 250                 255

Cys Leu Asp Gly Ala Asp Leu Ser Leu Arg Leu Val Asp Gly Val Thr
            260                 265                 270

Glu Cys Ser Gly Arg Leu Glu Val Lys Phe Gln Gly Glu Trp Gly Thr
        275                 280                 285

Val Cys Asp Asp Gly Trp Asp Ser Asn Asp Ala Ala Val Val Cys Lys
    290                 295                 300

Gln Leu Gly Cys Pro Thr Ala Val Thr Ala Ile Gly Arg Val Asn Ala
305                 310                 315                 320

Ser Glu Gly Ser Gly His Ile Trp Leu Asp Asn Leu Ser Cys Gln Gly
                325                 330                 335

Asp Glu Ser Ala Leu Trp Gln Cys Arg His His Glu Trp Gly Lys His
            340                 345                 350
```

```
Tyr Cys Asn His Asn Glu Asp Ala Gly Val Thr Cys Ser Asp Gly Ser
        355                 360                 365
Asp Leu Glu Leu Arg Leu Val Gly Gly Ser Arg Cys Ala Gly Thr
    370                 375                 380
Val Glu Val Glu Ile Gln Lys Leu Leu Gly Lys Val Cys Asp Arg Gly
385                 390                 395                 400
Trp Gly Leu Lys Glu Ala Asp Val Val Cys Lys Gln Leu Gly Cys Gly
                405                 410                 415
Ser Ala Leu Lys Thr Ser Tyr Gln Arg Tyr Ser Lys Val Lys Ala Thr
                420                 425                 430
Asn Thr Trp Leu Phe Leu Ser Arg Cys Ser Gly Asn Glu Thr Ser Leu
            435                 440                 445
Trp Asp Cys Lys Asn Trp Gln Trp Gly Gly Leu Ser Cys Asp His Tyr
    450                 455                 460
Glu Glu Ala Lys Val Thr Cys Ser Ala His Arg Glu Pro Arg Leu Val
465                 470                 475                 480
Gly Gly Asp Ile Pro Cys Ser Gly Arg Val Glu Val Lys His Gly Asp
                485                 490                 495
Thr Trp Gly Thr Val Cys Asp Ser Asp Phe Ser Leu Glu Ala Ala Ser
            500                 505                 510
Val Leu Cys Arg Glu Leu Gln Cys Gly Thr Val Ile Ser Ile Leu Gly
        515                 520                 525
Gly Ala His Phe Gly Glu Gly Asn Gly Gln Ile Trp Ala Glu Glu Phe
    530                 535                 540
Gln Cys Glu Gly Gln Glu Ser His Leu Ser Leu Cys Ser Val Ala Ser
545                 550                 555                 560
Arg Pro Asp Gly Thr Cys Ser His Ser Arg Asp Val Gly Val Val Cys
                565                 570                 575
Ser Arg Tyr Thr Glu Ile Arg Leu Val Asn Gly Gln Ser Pro Cys Glu
            580                 585                 590
Gly Arg Val Glu Leu Lys Ile Leu Gly Asn Trp Gly Ser Leu Cys Asn
        595                 600                 605
Ser His Trp Asp Ile Glu Asp Ala His Val Phe Cys Gln Gln Leu Lys
    610                 615                 620
Cys Gly Val Ala Leu Ser Ile Pro Gly Gly Ala His Phe Gly Lys Gly
625                 630                 635                 640
Ser Gly Gln Ile Trp Arg His Met Phe His Cys Thr Gly Thr Glu Gln
                645                 650                 655
His Met Gly Asp Cys Pro Val Thr Ala Leu Gly Ala Thr Leu Cys Ser
            660                 665                 670
Ala Gly Gln Val Ala Ser Val Ile Cys Ser Gly Asn Gln Ser Gln Thr
        675                 680                 685
Leu Ser Pro Cys Asn Ser Thr Ser Leu Asp Pro Thr Arg Ser Thr Thr
    690                 695                 700
Ser Glu Glu Ser Ala Val Ala Cys Ile Ala Ser Gly Gln Leu Arg Leu
705                 710                 715                 720
Val Asn Gly Gly Gly Arg Cys Ala Gly Arg Ile Glu Val Tyr His Glu
                725                 730                 735
Gly Ser Trp Gly Thr Ile Cys Asp Asp Ser Trp Asp Leu Ser Asp Ala
            740                 745                 750
His Val Val Cys Arg Gln Leu Gly Cys Gly Val Ala Ile Asn Ala Thr
        755                 760                 765
Gly Ser Ala His Phe Gly Glu Gly Thr Gly Pro Ile Trp Leu Asp Glu
```

-continued

```
            770              775              780
Val Asn Cys Asn Gly Lys Glu Ser His Ile Trp Gln Cys Arg Ser His
785                 790                  795                 800

Gly Trp Gly Gln His Asn Cys Arg His Lys Glu Asp Ala Gly Val Ile
                805                  810                 815

Cys Ser Glu Phe Met Ser Leu Arg Leu Ile Asp Glu Thr Ser Arg Asp
                820                  825                 830

Ile Cys Ala Gly Arg Leu Glu Val Phe Tyr Asn Gly Ala Trp Gly Ser
                835                  840                 845

Val Gly Lys Ser Asn Met Ser Ala Thr Thr Val Glu Val Val Cys Arg
850                 855                  860

Gln Leu Gly Cys Ala Asp Lys Gly Ser Ile Asn Pro Ala Ser Ser Asp
865                 870                  875                 880

Lys Pro Met Ser Arg His Met Trp Val Asp Asn Val Gln Cys Pro Lys
                885                  890                 895

Gly Pro Asp Thr Leu Trp Gln Cys Pro Ser Ser Pro Lys Gln Arg
                900                  905                 910

Val Ala Ser Ser Glu Glu Thr Trp Ile Thr Cys Ala Asn Lys Ile
                915                  920                 925

Arg Leu Gln Glu Gly Thr Ser Asn Cys Ser Gly Arg Val Glu Leu Trp
930                 935                  940

His Gly Gly Ser Trp Gly Thr Val Cys Asp Asp Ser Trp Asp Leu Glu
945                 950                  955                 960

Asp Ala Gln Val Val Cys Arg Gln Leu Gly Cys Gly Pro Ala Leu Glu
                965                  970                 975

Ala Leu Lys Glu Ala Ala Phe Gly Gln Gly Thr Gly Pro Ile Trp Leu
                980                  985                 990

Asn Asp Val Lys Cys Lys Gly Asn Glu Ser Ser Leu Trp Asp Cys Pro
                995                 1000                1005

Ala Arg Pro Trp Gly His Ser Asp Cys Gly His Lys Glu Asp Ala
    1010                1015                1020

Ala Val Arg Cys Ser Glu Ile Ala Met Ala Gln Arg Ser Ser Asn
    1025                1030                1035

Pro Arg Gly His Ser Ser Leu Val Ala Leu Gly Ile Phe Gly Val
    1040                1045                1050

Ile Leu Leu Ala Phe Leu Ile Ala Leu Leu Leu Trp Thr Gln Arg
    1055                1060                1065

Arg Arg Gln Gln Gln Arg Leu Thr Val Ser Leu Arg Gly Glu Asn
    1070                1075                1080

Ser Val His Gln Ile Gln Tyr Arg Glu Met Asn Ser Ser Leu Lys
    1085                1090                1095

Ala Asp Asp Leu Asp Val Leu Thr Ser Ser Glu Tyr Pro Asn Glu
    1100                1105                1110

Ser Asp Asp Phe Asn Asp Ala Gly Leu Ile Ser Val Ser Lys Ser
    1115                1120                1125

Leu Pro Ile Ser Gly
    1130
```